US007932252B2

(12) United States Patent
Ungashe et al.

(10) Patent No.: US 7,932,252 B2
(45) Date of Patent: Apr. 26, 2011

(54) ARYL SULFONAMIDES

(75) Inventors: Solomon Ungashe, Fremont, CA (US); John Jessen Wright, Sandringham (AU); Andrew Pennell, San Francisco, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 542 days.

(21) Appl. No.: 11/596,147

(22) PCT Filed: May 12, 2005

(86) PCT No.: PCT/US2005/016544
§ 371 (c)(1),
(2), (4) Date: Nov. 7, 2007

(87) PCT Pub. No.: WO2005/113513
PCT Pub. Date: Dec. 1, 2005

(65) Prior Publication Data
US 2008/0161345 A1   Jul. 3, 2008

Related U.S. Application Data

(60) Provisional application No. 60/570,569, filed on May 12, 2004, provisional application No. 60/570,568, filed on May 12, 2004, provisional application No. 60/570,710, filed on May 12, 2004, provisional application No. 60/571,868, filed on May 17, 2004.

(51) Int. Cl.
*A61K 31/18* (2006.01)
*A61K 31/335* (2006.01)
*A61K 31/44* (2006.01)
*A61K 31/47* (2006.01)
*A61K 31/535* (2006.01)
*C07D 211/82* (2006.01)
*C07D 213/00* (2006.01)
*C07D 217/02* (2006.01)
*C07D 233/54* (2006.01)
*C07D 317/00* (2006.01)
*C07D 413/00* (2006.01)

(52) U.S. Cl. ............ 514/235.5; 514/307; 514/352; 514/467; 514/604; 544/131; 546/144; 546/307; 546/328; 546/333; 548/341.1; 549/451; 564/92

(58) Field of Classification Search .................. None
See application file for complete search history.

(56) References Cited

U.S. PATENT DOCUMENTS

| 6,403,607 | B1 | 6/2002 | Hidaka et al. |
| 6,939,885 | B2 | 9/2005 | Ungashe et al. |
| 7,227,035 | B2 | 6/2007 | Ungashe et al. |
| 7,718,683 | B2 | 5/2010 | Charvat et al. |
| 7,776,877 | B2 | 8/2010 | Charvat et al. |
| 2004/0167113 | A1 | 8/2004 | Ungashe et al. |
| 2004/0171654 | A1 | 9/2004 | Ungashe et al. |
| 2005/0137193 | A1 | 6/2005 | Ungashe et al. |
| 2005/0165067 | A1 | 7/2005 | Ungashe et al. |
| 2006/0111351 | A1 | 5/2006 | Ungashe et al. |
| 2006/0173019 | A1 | 8/2006 | Ungashe et al. |
| 2007/0021466 | A1 | 1/2007 | Ungashe et al. |
| 2007/0037794 | A1 | 2/2007 | Ungashe et al. |
| 2007/0203131 | A1 | 8/2007 | Ungashe et al. |
| 2008/0039465 | A1 | 2/2008 | Charvat et al. |
| 2008/0039504 | A1 | 2/2008 | Charvat et al. |
| 2009/0048301 | A1 | 2/2009 | Chen et al. |
| 2010/0190762 | A1 | 7/2010 | Charvat et al. |
| 2010/0234364 | A1* | 9/2010 | Basak et al. ............... 514/227.5 |

FOREIGN PATENT DOCUMENTS

| DE | 3544409 A1 | 12/1985 |
| GB | 2376691 | * 12/2002 |
| WO | WO 93/09780 | 5/1993 |
| WO | WO 01/77087 A1 | 10/2001 |
| WO | WO 02/092585 A | 11/2002 |
| WO | WO 03/045393 | * 6/2003 |
| WO | WO 03/068732 A | 8/2003 |
| WO | WO 03/099773 A1 | 12/2003 |
| WO | WO 2004/016221 A | 2/2004 |
| WO | WO 2004/058741 A1 | 7/2004 |
| WO | WO 2004/073634 A2 | 9/2004 |
| WO | WO 2004/085384 A2 | 10/2004 |
| WO | WO 2005/004810 A2 | 1/2005 |
| WO | WO 2005/004818 A2 | 1/2005 |
| WO | WO 2005/007621 A | 1/2005 |
| WO | WO 2005/080335 A | 9/2005 |
| WO | WO 2005/113513 A2 | 12/2005 |
| WO | WO 2007/014008 A2 | 1/2007 |
| WO | WO 2007/014054 A2 | 1/2007 |
| WO | WO 2008/008374 A2 | 1/2008 |
| WO | WO 2008/008375 A2 | 1/2008 |
| WO | WO 2008/008431 A2 | 1/2008 |

OTHER PUBLICATIONS

Registry No. 349404-57-5, entered into Registry file on STN on Jul. 29, 2001.*
Cook, A. H. et al., "Sulfonamides Derived from Substituted Anilines", Journal of the Chemical Society, 182-185, 1945.*
Registry No. 460334-45-6, entered into Registry file on STN on Oct. 10, 2002.*
PCT International Search Report; Mailing Date: Nov. 16, 2005; 7 pp.
PCT Written Opinion of the International Searching Authority; Mailing Date: Nov. 16, 2005; 8 pp.
International Application No. PCT/US2007/015808—Search Report; Jan. 30, 2008.
Science IP Jun. 29, 2007—Search Report.
Notice of Allowance U.S. Appl. No. 11/775,585, mailed Jan. 27, 2010, 9 pages.
Maquestiau et al., Rapid Communications in Mass Spectrometry (1989), 3(9), 320-2.
Charvat et al., U.S. Appl. No. 12/753,342, filed Apr. 2, 2010.
Charvat et al., U.S. Appl. No. 12/832,374, filed Jul. 8, 2010.

* cited by examiner

*Primary Examiner* — Fiona T Powers
(74) *Attorney, Agent, or Firm* — Brinks Hofer Gilson & Lione

(57) ABSTRACT

The present invention relates to compounds that modulate various chemokine receptors. These compounds are useful for treating inflammatory and immune diseases.

4 Claims, No Drawings

ARYL SULFONAMIDES

This application is a §371 filing based on International Application No. PCT/US2005/016544, filed May 12, 2005, and present patent document claims the benefit of the filing date under 35 U.S.C. §119(e) of Provisional U.S. Patent Applications Ser. No. 60/570,569, filed May 12, 2004; Ser. No. 60/570,568, filed May 12, 2004; Ser. No. 60/570,710, filed May 12, 2004; and Ser. No. 60/571,868, filed May 17, 2004. The disclosure of each of these applications is incorporated by reference herein in their entirety.

BACKGROUND OF THE INVENTION

The present invention provides compounds, pharmaceutical compositions containing one or more of those compounds or their pharmaceutically acceptable salts, which are effective in inhibiting the binding or function of various chemokines, such as TECK (thymus-expressed chemokine), to the CCR9 receptor. As antagonists or modulators for the CCR9 receptor, the compounds and compositions have utility in treating inflammatory and immune disorder conditions and diseases.

Chemokines are chemotactic cytokines that are released by a wide variety of cells and attract various types of immune system cells, such as macrophages, T cells, eosinophils, basophils and neutrophils, to sites of inflammation (reviewed in Schall, *Cytokine*, 3:165-183 (1991), Schall, et al., *Curr. Opin. Immunol.*, 6:865 873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ($[Ca^{2+}]$), granule exocytosis, integrin up-regulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

T lymphocyte (T cell) infiltration into the small intestine and colon has been linked to the pathogenesis of Coeliac diseases, food allergies, rheumatoid arthritis, human inflammatory bowel diseases (IBD) which include Crohn's disease and ulcerative colitis. Blocking trafficking of relevant T cell populations to the intestine can lead to an effective approach to treat human IBD. More recently, chemokine receptor 9 (CCR9) has been noted to be expressed on gut-homing T cells in peripheral blood, elevated in patients with small bowel inflammation such as Crohn's disease and celiac disease. The only CCR9 ligand identified to date, TECK (thymus-expressed chemokine) is expressed in the small intestine and the ligand receptor pair is now thought to play a pivotal role in the development of IBD. In particular, this pair mediates the migration of disease-causing T cells to the intestine. See for example, Zaballos, et al., *J. Immunol.*, 162(10):5671-5675 (1999); Kunkel, et al., *J. Exp. Med.* 192(5):761-768 (2000); Papadakis, et al., *J. Immunol.*, 165(9):5069-5076 (2000); Papadakis, et al., *Gastroenterology*, 121(2):246-254 (2001); Campbell, et al., *J. Exp. Med.*, 195(1):135-141 (2002); Wurbel, et al., *Blood*, 98(9):2626-2632 (2001); and Uehara, et al., *J. Immunol*, 168(6):2811-2819 (2002).

The identification of compounds that modulate the function of CCR9 represents an attractive new family of therapeutic agents for the treatment of inflammatory and other conditions and diseases associated with CCR9 activation, such as inflammatory bowel disease.

U.S. Pat. No. 6,403,607 discloses sulfonamide derivatives useful as treatment for peptic ulcers.

PCT Published Application WO03/099773 discloses sulfonamide derivatives as CCR9 inhibitors.

PCT Published Application WO05/004810 discloses arylsuflonamide derivatives as useful in the management of inflammation.

PCT Published Applications WO04/085384 and WO04/046092, assigned to ChemoCentryx, disclose sulfonamide derivatives as CCR9 modulators.

BRIEF SUMMARY OF THE INVENTION

The present invention is directed to compounds and pharmaceutically acceptable salts thereof, compositions, and methods useful in modulating CCR9 chemokine activity. The compounds and salts thereof, compositions, and methods described herein are useful in treating or preventing CCR9-mediated conditions or diseases, including certain inflammatory and immunoregulatory disorders and diseases.

In one embodiment, the inventive compounds are of the formula (I):

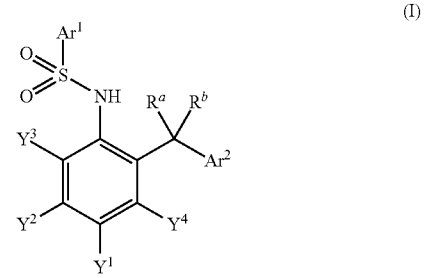

(I)

where $Ar^1, Y^1, Y^2, Y^3, Y^4, R^a, R^b$ and $Ar^2$ are as defined below. Salts and N-oxides of these compounds are also within the scope of the invention.

In another embodiment, the inventive compounds are of the formula (III):

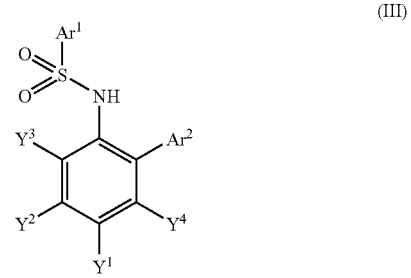

(III)

where $Ar^1, Ar^2, Y^1, Y^2, Y^3,$ and $Y^4$ are as defined below. Salts and N-oxides of these compounds are also within the scope of the invention.

In another embodiment, the inventive compounds are of the formula (VI):

(VI)

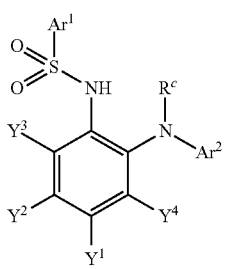

where $Ar^1$, $Ar^2$, $R^c$, $Y^1$, $Y^2$, $Y^3$, and $Y^4$ are as defined below. Salts and N-oxides of these compounds are also within the scope of the invention.

In another embodiment, the inventive compounds are of the formula (VIII):

(VIII)

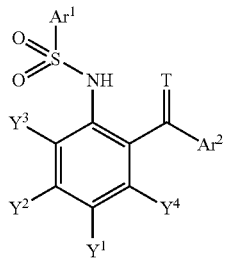

where $Ar^1$, $Ar^2$, T, $Y^1$, $Y^2$, $Y^3$, and $Y^4$ are as defined below. Salts and N-oxides of these compounds are also within the scope of the invention.

In another aspect, the present invention provides compositions useful in modulating CCR9 chemokine activity. In one embodiment, a composition according to the present invention comprises a compound according to the invention and a pharmaceutically acceptable carrier or excipient.

In yet another aspect, the present invention provides a method of modulating CCR9 function in a cell, comprising contacting the cell with a therapeutically effective amount of a compound or composition according to the invention.

In still another aspect, the present invention provides a method for modulating CCR9 function, comprising contacting a CCR9 protein with a therapeutically effective amount of a compound or composition according to the invention.

In still another aspect, the present invention provides a method for treating a CCR9-mediated condition or disease, comprising administering to a subject a safe and effective amount of a compound or composition according to the invention.

In addition to the compounds provided herein, the present invention further provides pharmaceutical compositions containing one or more of these compounds, as well as methods for the use of these compounds in therapeutic methods, primarily to treat diseases associated with CCR9 signaling activity.

DETAILED DESCRIPTION OF THE INVENTION

General

The present invention is directed to compounds and salts thereof, compositions and methods useful in the modulation of chemokine receptor function, particularly CCR9 function. Modulation of chemokine receptor activity, as used herein in its various forms, is intended to encompass antagonism, agonism, partial antagonism, inverse agonism and/or partial agonism of the activity associated with a particular chemokine receptor, preferably the CCR9 receptor. Accordingly, the compounds of the present invention are compounds which modulate at least one function or characteristic of mammalian CCR9, for example, a human CCR9 protein. The ability of a compound to modulate the function of CCR9, can be demonstrated in a binding assay (e.g., ligand binding or agonist binding), a migration assay, a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

Abbreviations and Definitions

When describing the compounds, compositions, methods and processes of this invention, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, thioalkyl, aminoalkyl, and the like.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Aryl" refers to a polyunsaturated, aromatic hydrocarbon group having a single ring (bicyclic) or multiple rings (preferably bicyclic) which can be fused together or linked covalently. Aryl groups with 6-10 carbon atoms are preferred. Examples of aryl groups include phenyl and naphthalene-1-yl, naphthalene-2-yl, biphenyl and the like. Aryl groups can be substituted or unsubstituted, unless otherwise indicated.

"Halo" or "halogen", by itself or as part of a substituent refers to a chlorine, bromine, iodine, or fluorine atom. Additionally, "haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic group containing at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

In one preferred embodiment, heterocyclic groups may be represented by formula (AA) below:

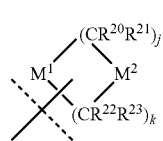

(AA)

where formula (AA) is attached via a free valence on either $M^1$ or $M^2$; $M^1$ represents O, $NR^{24}$, or $S(O)_j$; $M^2$ represents $CR^{25}R^{26}$, O, $S(O)_j$, or $NR^{24}$; I is 0, 1 or 2; j is 1, 2 or 3; and k is 1, 2 or 3, with the proviso that j+k is 3, 4, or 5; and $R^{20}$, $R^{21}$, $R^{22}$, $R^{23}$, $R^{24}$, $R^{25}$, and $R^{26}$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, —C(O)$R^{27}$, —CO$_2R^{27}$, —C(O)NR$^{27}R^{28}$, —NR$^{27}$C(O)$R^{28}$, —S(O)$_2R^{28}$, —S(O)$_2$NR$^{28}R^{29}$, —NS(O)$_2R^{28}R^{29}$, —NR$^{28}R^{29}$, —OR$^{28}$, —V$^1$C(O)$R^{28}$, —V$^1$CO$_2R^{28}$, —V$^1$C(O)NR$^{28}R^{29}$, —V$^1$NR$^{28}$C(O)$R^{29}$, —V$^1$S(O)$_2R^{28}$, —V$^1$S(O)$_2$NR$^{28}R^{29}$, —V$^1$NS(O)$_2R^{28}R^{29}$, —V$^1$NR$^{28}R^{29}$, and —V$^1$OR$^{28}$, wherein $V^1$ is a member selected from the group consisting of $C_{1-4}$ alkylene, $C_{2-4}$ alkenylene and $C_{2-4}$ alkynylene, and $R^{27}$, $R^{28}$ and $R^{29}$ are independently selected from the group consisting of hydrogen and $C_{1-8}$ alkyl, and wherein the aliphatic portions of each of the $R^{20}$, $R^{21}$, $R^{22}$, $R^{23}$, $R^{24}$, $R^{25}$, $R^{26}$, $R^{27}$, $R^{28}$ and $R^{29}$ substituents are optionally substituted with from one to three members selected from the group consisting of halogen, —OH, —OR$^{30}$, —OC(O)NHR$^{30}$, —OC(O)NR$^{30}R^{31}$, —SH, —SR$^{30}$, —S(O)$R^{30}$, —S(O)$_2R^{30}$, —S(O)$_2$NH$_2$, —S(O)$_2$NHR$^{30}$, —S(O)$_2$NR$^{30}R^{31}$, —NHS(O)$_2R^{30}$, —NR$^{30}$S(O)$_2R^{31}$, —C(O)NH$_2$, —C(O)NHR$^{30}$, —C(O)NR$^{30}R^{31}$, —C(O)$R^{30}$, —NHC(O)$R^{30}$, —NR$^{30}$C(O)$R^{31}$, —NHC(O)NH$_2$, —NR$^{30}$C(O)NH$_2$, —NR$^{30}$C(O)NHR$^{31}$, —NHC(O)NHR$^{30}$, —NR$^{30}$C(O)NR$^{30}R^{31}$, —NHC(O)NR$^{30}R^{31}$, —NHC(O)NR$^{30}R^{31}$, —CO$_2$H, —CO$_2R^{30}$, —NHCO$_2R^{30}$, —NR$^{30}$CO$_2R^{31}$, —CN, —NO$_2$, —NH$_2$, —NHR$^{30}$, —NR$^{30}R^{31}$, —NR$^{30}$S(O)NH$_2$ and —NR$^{30}$C(O)$_2$NHR$^{31}$, wherein $R^{30}$ and $R^{31}$ are independently an unsubstituted $C_{1-6}$ alkyl. Additionally, any two of $R^{20}$, $R^{21}$, $R^{22}$, $R^{23}$, $R^{24}$, $R^{25}$, and $R^{26}$ may be combined to form a bridged or spirocyclic ring system.

In one preferred embodiment, the number of $R^{20}$+$R^{21}$+$R^{22}$+$R^{23}$ groups that are other than hydrogen is 0, 1 or 2. In a more preferred embodiment, $R^{20}$, $R^{21}$, $R^{22}$, $R^{23}$, $R^{24}$, $R^{25}$, and $R^{26}$ are independently selected from the group consisting of hydrogen, halogen, unsubstituted or substituted $C_{1-8}$ alkyl, —C(O)$R^{28}$, —CO$_2R^{28}$, —C(O)NR$^{28}R^{29}$, —NR$^{28}$C(O)$R^{29}$, —S(O)$_2R^{28}$, —S(O)$_2$NR$^{28}R^{29}$, —NS(O)$_2R^{28}R^{29}$, —NR$^{28}R^{29}$, and —OR$^{28}$, wherein $R^{28}$ and $R^{29}$ are independently selected from the group consisting of hydrogen, unsubstituted $C_{1-8}$ alkyl and wherein the aliphatic portions of each of the $R^{20}$, $R^{21}$, $R^{22}$, $R^{23}$, $R^{24}$, $R^{25}$ and $R^{26}$ substituents are optionally substituted with from one to three members selected from the group consisting of halogen, —OH, —OR$^{30}$, —OC(O)NHR$^{30}$, —OC(O)NR$^{30}R^{31}$, —SH, —SR$^{30}$, —S(O)$R^{30}$, —S(O)$_2R^{30}$, —S(O)$_2$NH$_2$, —S(O)$_2$NHR$^{30}$, —S(O)$_2$NR$^{30}R^{31}$, —NHS(O)$_2R^{30}$, —NR$^{30}$S(O)$_2R^{31}$, —C(O)NH$_2$, —C(O)NHR$^{30}$, —C(O)NR$^{30}R^{31}$, —C(O)$R^{30}$, —NHC(O)$R^{30}$, —NR$^{30}$C(O)$R^{31}$, —NHC(O)NH$_2$, —NR$^{30}$C(O)NH$_2$, —NR$^{30}$C(O)NHR$^{31}$, —NHC(O)NHR$^{30}$, —NR$^{30}$C(O)NR$^{30}R^{31}$, —NHC(O)NR$^{30}R^{31}$, —CO$_2$H, —CO$_2R^{30}$, —NHCO$_2R^{30}$, —NR$^{30}$CO$_2R^{31}$, —CN, —NO$_2$, —NH$_2$, —NHR$^{30}$, —NR$^{30}R^{31}$, —NR$^{30}$S(O)NH$_2$ and —NR$^{30}$S(O)$_2$NHR$^{31}$, wherein $R^{30}$ and $R^{31}$ are independently an unsubstituted $C_{1-6}$ alkyl.

In a more preferred embodiment, $R^{20}$, $R^{21}$, $R^{22}$, $R^{23}$, $R^{24}$, $R^{25}$, and $R^{26}$ are independently hydrogen or $C_{1-4}$alkyl. In another preferred embodiment, at least three of $R^{20}$, $R^{21}$, $R^{22}$, $R^{23}$, $R^{24}$, $R^{25}$, and $R^{26}$ are hydrogen.

"Heteroaryl" refers to an aromatic group containing at least one heteroatom. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is =O, the resulting group may have either a carbonyl (—C(O)—) or a N-oxide (—N$^+$—O$^-$).

Suitable substituents for substituted alkyl, substituted alkenyl, and substituted alkynyl include halogen, —CN, —CO$_2$R', —C(O)R', —C(O)NR'R", oxo (=O or —O$^-$), —OR', —OC(O)R', —OC(O)NR'R"—NO$_2$, —NR'C(O)R", —NR'''C(O)NR'R", —NR'R", —NR'CO$_2$R", —NR'S(O)$_2$R''', —SR', —S(O)R', —S(O)$_2$R', —S(O)$_2$NR'R", —SiR'R"R''', —N$_3$, substituted or unsubstituted $C_{6-10}$ aryl, substituted or unsubstituted 5- to 10-membered heteroaryl, and substituted or unsubstituted 3- to 10-membered heterocyclyl, in a number ranging from zero to (2m'+1), where m' is the total number of carbon atoms in such radical.

Suitable substituents for substituted aryl, substituted heteroaryl and substituted heterocyclyl include halogen, —CN, —CO$_2$R', —C(O)R', —C(O)NR'R", oxo (=O or —O$^-$), —OR', —OC(O)R', —OC(O)NR'R", —NO$_2$, —NR'C(O)R", —NR'C(O)NR"R''', —NR'R", —NR'CO$_2$R", —NR'S(O)$_2$R", —SR', —S(O)R', —S(O)$_2$R', —S(O)$_2$NR'R", —NR'—C(NHR")=NR''', —SiR'R"R''', —N$_3$, substituted or unsubstituted C$_{1-8}$ alkyl group, substituted or unsubstituted C$_{6-10}$ aryl group, substituted or unsubstituted 5- to 10-membered heteroaryl, and substituted or unsubstituted 3- to 10-membered heterocyclyl, in a number ranging from zero to the total number of open valences on the aromatic ring system.

As used above, R', R" and R''' each independently refer to a variety of groups including hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, and substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl).

Two of the substituents on adjacent atoms of an aryl or heteroaryl ring may optionally be replaced with a substituent of the formula -T-C(O)—(CH$_2$)$_q$—U—, wherein T and U are independently —NR""—, —O—, —CH$_2$— or a single bond, and q is an integer of from 0 to 2. Alternatively, two of the substituents on adjacent atoms of the aryl or heteroaryl ring may optionally be replaced with a substituent of the formula -A'-(CH$_2$)$_r$—B'—, wherein A' and B' are independently —CH$_2$—, —O—, —NR""—, —S—, —S(O)—, —S(O)$_2$—, —S(O)$_2$NR""— or a single bond, and r is an integer from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers from 0 to 3, and X is —O—, —NR""—, —S—, —S(O)—, —S(O)$_2$—, or —S(O)$_2$NR'—. The substituent R"" in —NR""— and —S(O)$_2$NR""— is hydrogen or unsubstituted C$_{1-6}$ alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M., et al, "Pharmaceutical Salts", *J. Pharmaceutical Science,* 1977, 66:1-19) Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

"Therapeutically effective amount" refers to an amount sufficient to effect treatment when administered to a patient in need of treatment.

"Treating" or "treatment" as used herein refers to the treating or treatment of a disease or medical condition (such as a bacterial infection) in a patient, such as a mammal (particularly a human or a companion animal) which includes:

ameliorating the disease or medical condition, i.e., eliminating or causing regression of the disease or medical condition in a patient;

suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Compounds that Modulate CCR9 Activity

The present invention provides compounds that modulate CCR9 activity. Specifically, the invention provides compounds having anti-inflammatory or immunoregulatory activity. The compounds of the invention are thought to interfere with inappropriate T cell trafficking by specifically modulating or inhibiting a chemokine receptor function. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR9 and a CCR9 ligand, such as TECK. Compounds contemplated by the invention include, but are not limited to, the exemplary compounds provided herein and salts thereof.

For example, compounds of this invention act as potent CCR9 antagonists. Accordingly, the compounds provided herein are useful in pharmaceutical compositions, methods for the treatment of CCR9-mediated diseases, and as controls in assays for the identification of competitive CCR9 antagonists.

CCR9 Antagonists as Treatments of Cancer

In additional to inflammatory diseases, cancers that are caused by uncontrolled proliferation of T cells may be treated with a CCR9 antagonist. Certain types of cancer are caused by T cells expressing chemokine receptor CCR9. For example, thymoma and thymic carcinoma are diseases in which cancer cells are found in the tissues of the thymus, an organ where lymphocyte development occurs. T cells in the thymus, called thymocytes, are known to express functional CCR9; its ligand is highly expressed in the thymus. Another example is the acute lymphocytic leukemia (ALL), also called acute lymphoblastic leukemia and acute, is a common leukemia, which can occur in children as well as adults. Recent studies have shown that T cells in patients with ALL selectively express high level of CCR9 (Qiuping Z et al., Cancer Res. 2003, 1; 63(19):6469-77)

Chemokine receptors have been implicated in cancer. Although the exact mechanisms of chemokine receptors' involvements have yet to be fully understood, such receptors are known to promote the growth of cancer cells (proliferation), facilitate the spread of cancer cells (metastasis) or help them resist program cell death (apoptosis). For example, CCR9 in a cancer T cell line MOLT-4 provides the cells with a survival signal, allowing them to resist apoptosis (Youn B S, et al., Apoptosis. 2002 June; 7(3):271-6). In the cases of thymoma, thymic carcinoma and acute lymphocytic leukemia, it is likely that CCR9 plays a key in the survival and proliferation of these cells. Thus, blocking the signaling of CCR9 should help prevent their expansion and metastasis.

Compounds of the Invention

The present invention provides compounds of the formula (I) and pharmaceutically acceptable salts and N-oxides thereof:

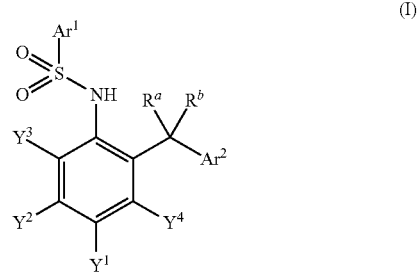

(I)

where:

$R^a$ and $R^b$ are each independently hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, —OR$^1$, —NR$^1$R$^2$, —NHC(O)R$^1$, —NHSO$^2$R$^1$, —S(O)R$^1$, or —S(O)$_2$R$^2$; or where $R^a$ and $R^b$, together with the atom to which they are attached are combined to form substituted or unsubstituted $C_{3-8}$ cycloalkyl or substituted or unsubstituted 3- to 10-membered heterocyclic ring;

where $R^1$ and $R^2$ are each independently selected from the group consisting of hydrogen, $C_{1-8}$ alkyl, $C_{2-8}$ alkenyl, $C_{2-8}$ alkynyl, $C_{6-10}$ aryl, 5- to 10-membered heteroaryl, and 3- to 10-membered heterocycle, or when attached to the same nitrogen atom, can be combined with the nitrogen atom to form a 5- or 6-membered heterocyclyl; and where the aliphatic and aromatic portions of R$^1$, R$^2$, R$^a$ and R$^b$ can be substituted with from 1 to 3 substituents selected from the group consisting of halogen, —OH, —OR'", —OC(O)NHR'", —OC(O)NR'"R", —SH, —SR'", —S(O)R'", —S(O)$_2$R'", —S(O)$_2$NH$_2$, —S(O)$_2$NHR'", —S(O)$_2$NR'"R", —NHS(O)$_2$R'", —NR'"S(O)$_2$R", —C(O)NH$_2$, —C(O)NHR'", —C(O)N(R'")$_2$, —C(O)R'", —NHC(O)R'", —NR'"C(O)R", —NHC(O)NH$_2$, —NR'"C(O)NH$_2$, —NR'"C(O)NHR", —NHC(O)NHR'", —NR°C(O)NR'"R", —NHC(O)N (R'")$_2$, —CO$_2$H, —CO$_2$R'", —NHCO$_2$R", —NR'"CO$_2$R", —CN, —NO$_2$, —NH$_2$, —NHR", —NR'"R", —NR'"S(O)NH$_2$ and —NR'"S(O)$_2$NHR", where R'", R", and R° are each independently unsubstituted $C_{1-6}$ alkyl.

Ar$^1$ is a substituted or unsubstituted $C_{6-10}$ aryl or substituted or unsubstituted 5- to 10-membered heteroaryl; each having 0 to 5 substituents selected from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, =O, —C(O)R$^3$, —CO$_2$R$^3$, —C(O)NR$^3$R$^4$, —OR$^3$, —OC(O)R$^3$, —OC(O)NR$^3$R$^4$, —NR$^5$C(O)R$^3$, —NR$^5$C(O)NR$^3$R$^4$, —NR$^3$R$^4$, —NR$^5$CO$_2$R$^3$, —NR$^5$S(O)$_2$R$^3$, —SR$^3$, —S(O)R$^3$, —S(O)$_2$R$^3$, —S(O)$_2$NR$^3$R$^4$, substituted or unsubstituted $C_{6-10}$ aryl, substituted or unsubstituted 5- to 10-membered heteroaryl, and substituted or unsubstituted 3- to 10-membered heterocyclyl;

suitable substituted $C_{1-8}$ alkyl, substituted $C_{2-8}$ alkenyl, or substituted $C_{2-8}$ alkynyl may have from 1-5 substituents independently selected from the group consisting of halogen, —OH, —CN, —NO$_2$, =O, —OC(O)R$^3$, —OR$^3$, —C(O)R$^3$, —C(O)NR$^3$R$^4$, —OC(O)NR$^3$R$^4$, —NR$^4$C(O)R$^3$, —NR$^3$C(O)NR$^4$R$^5$, —CO$_2$R$^3$, —NR$^3$R$^4$, —NR$^4$CO$_2$R$^3$, —SR$^3$, —S(O)R$^3$, —S(O)$_2$R$^3$, —S(O)$_2$NR$^3$R$^4$, —NR$^3$S(O)$_2$R$^4$, unsubstituted or substituted aryl, unsubstituted or substituted heteroaryl, and unsubstituted or substituted heterocyclyl;

suitable substituted $C_{6-10}$ aryl, substituted 5- to 10-membered heteroaryl, or substituted 3- to 10-membered heterocyclyl, may have from 1-4 substituents independently selected from the group consisting of halogen, unsubstituted $C_{1-8}$ alkyl, unsubstituted $C_{1-8}$ haloalkyl, —CN, —NO$_2$, —OR$^3$, =O, —OC(O)R$^3$, —CO$_2$R$^3$, —C(O)R$^3$, —C(O)NR$^3$R$^4$, —OC(O)NR$^3$R$^4$, —NR$^4$C(O)R$^3$, —NR$^3$C(O)NR$^4$R$^5$, —NR$^3$R$^4$, —NR$^4$CO$_2$R$^3$, —SR$^3$, —S(O)R$^3$, —S(O)$_2$R$^3$, —S(O)$_2$NR$^3$R$^4$, and —NR$^3$S(O)$_2$R$^4$;

where R$^3$, R$^4$, and R$^5$ are each independently selected from the group consisting of hydrogen, $C_{1-8}$ alkyl, $C_{2-8}$ alkenyl, $C_{2-8}$ alkynyl, $C_{6-10}$ aryl, 5- to 10-membered heteroaryl, and 3- to 10-membered heterocycle, or where R$^3$ and R$^4$, together with the atom(s) to which they are attached, form an substituted or unsubstituted 5-, 6-, or 7-membered ring;

where the aliphatic and aromatic portions of R$^3$, R$^4$ and R$^5$ can be substituted with from 1 to 3 substituents selected from the group consisting of halogen, —OH, —OR$'''$, —OC(O)NHR$'''$, —OC(O)NR$'''$R$''$, —SH, —SR$'''$, —S(O)R$'''$, —S(O)$_2$R$'''$, —S(O)$_2$NH$_2$, —S(O)$_2$NHR$'''$, —S(O)$_2$NR$'''$R$''$, —NHS(O)$_2$R$'''$, —NR$'''$S(O)$_2$R$''$, —C(O)NH$_2$, —C(O)NHR$'''$, —C(O)N(R$'''$)$_2$, —C(O)R$'''$, —NHC(O)R$'''$, —NR$'''$C(O)R$''$, —NHC(O)NH$_2$, —NR$'''$C(O)NH$_2$, —NR$'''$C(O)NHR$''$, —NHC(O)NHR$'''$, —NR$°$C(O)NR$'''$R$''$, —NHC(O)N(R$'''$)$_2$, —CO$_2$H, —CO$_2$R$'''$, —NHCO$_2$R$'''$, —NR$'''$CO$_2$R$''$, —CN, —NO$_2$, —NH$_2$, —NHR$''$, —NR$'''$R$''$, —NR$'''$S(O)NH$_2$ and —NR$'''$S(O)$_2$NHR$''$, where R$'''$, R$''$, and R$°$ are each independently unsubstituted $C_{1-6}$ alkyl.

Y$^1$, Y$^2$, Y$^3$, and Y$^4$ are each independently selected from the group consisting of hydrogen, halogen, substituted or unsubstituted $C_{1-4}$ alkyl, —CN, —C(O)R$^6$, —CO$_2$R$^6$, —OR$^6$, —NO$_2$, —SR$^6$, —S(O)R$^6$, and —S(O)$_2$R$^6$;

where substituted $C_{1-4}$ alkyl can have from 1 to 3 substituents independently selected from the group consisting of halogen, —OH, —OR$^6$, —CN, —NO$_2$, =O, —OC(O)R$^6$, —CO$_2$R$^6$, —C(O)R$^6$, —C(O)NR$^6$R$^{13}$, —OC(O)NR$^6$R$^{13}$, —NR$^{13}$C(O)R$^6$, —NR$^6$C(O)NR$^{13}$R$^{14}$, —NR$^6$R$^{13}$, —NR$^{13}$CO$_2$R$^6$, —SR$^6$, —S(O)R$^6$, —S(O)$_2$R$^6$, —S(O)$_2$NR$^6$R$^{13}$, and —NR$^{13}$S(O)$_2$R$^6$;

where R$^6$, R$^{13}$, and R$^{14}$ are independently selected from the group consisting of hydrogen, $C_{1-8}$ alkyl, $C_{2-8}$ alkenyl, $C_{2-8}$ alkynyl, $C_{6-10}$ aryl, and 5- to 10-membered heteroaryl; and where the aliphatic and aromatic portions of R$^6$, R$^{13}$, and R$^{14}$ can be substituted with from 1 to 3 substituents selected from the group consisting of halogen, —OH, —OR$'''$, —OC(O)NHR$'''$, —OC(O)NR$'''$R$''$, —SH, —SR$'''$, —S(O)R$'''$, —S(O)$_2$R$'''$, —S(O)$_2$NH$_2$, —S(O)$_2$NHR$'''$, —S(O)$_2$NR$'''$R$''$, —NHS(O)$_2$R$'''$, —NR$'''$S(O)$_2$R$''$, —C(O)NH$_2$, —C(O)NHR$'''$, —C(O)N(R$'''$)$_2$, —C(O)R$'''$, —NHC(O)R$'''$, —NR$'''$C(O)R$''$, —NHC(O)NH$_2$, —NR$'''$C(O)NH$_2$, —NR$'''$C(O)NHR$''$, —NHC(O)NHR$'''$, —NR$°$C(O)NR$'''$R$''$, —NHC(O)N(R$'''$)$_2$, —CO$_2$H, —CO$_2$R$'''$, —NHCO$_2$R$'''$, —NR$'''$CO$_2$R$''$, —CN, —NO$_2$, —NH$_2$, —NHR$''$, —NR$'''$R$''$, —NR$'''$S(O)NH$_2$ and —NR$'''$S(O)$_2$NHR$''$, where R$'''$, R$''$, and R$°$ are each independently unsubstituted $C_{1-6}$ alkyl.

Ar$^2$ is a substituted or unsubstituted $C_{6-10}$ aryl, a substituted or unsubstituted 5- to 10-membered heteroaryl, or a substituted or unsubstituted 3- to 10-membered heterocyclyl; each having 0 to 4 substituents selected from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, =O, —NO$_2$, —OR$^7$, —OC(O)R$^7$, —CO$_2$R$^7$, —C(O)R$^7$, —C(O)NR$^8$R$^9$, —OC(O)NR$^8$R$^9$, —NR$^7$C(O)R$^8$, —NR$^7$C(O)NR$^8$R$^9$, —NR$^8$R$^9$, —NR$^7$CO$_2$R$^8$, —SR$^7$, —S(O)R$^7$, —S(O)$_2$R$^7$, —S(O)$_2$NR$^8$R$^9$, —NR$^7$S(O)$_2$R$^8$, substituted or unsubstituted $C_{6-10}$ aryl, substituted or unsubstituted 5- to 10-membered heteroaryl and substituted or unsubstituted 3- to 10-membered heterocyclyl;

suitable substituted $C_{1-8}$ alkyl, $C_{2-8}$ alkenyl, $C_{2-8}$ alkynyl may have from 1 to 5 substituents independently selected from the group consisting of halogen, —OH, —OR$^7$, —CN, —NO$_2$, =O, —OC(O)R$^7$, —CO$_2$R$^7$, —C(O)R$^7$, —C(O)NR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —S(O)R$^7$, —S(O)$_2$R$^7$, —S(O)$_2$NR$^7$R$^8$, —NR$^7$S(O)$_2$R$^8$, unsubstituted or substituted phenyl, unsubstituted or substituted $C_{5-6}$ heteroaryl, or unsubstituted or substituted $C_{3-6}$ heterocyclyl;

suitable substituted aryl, heteroaryl and heterocyclyl substituents may have from 1 to 5 substituents independently selected from the group consisting of halogen, —OR$^7$, —CN, —NO$_2$, =O, —OC(O)R$^7$, —CO$_2$R$^7$, —C(O)R$^7$, —C(O)NR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —S(O)R$^7$, —S(O)$_2$R$^7$, —S(O)$_2$NR$^7$R$^8$, —NR$^7$S(O)$_2$R$^8$, unsubstituted $C_{3-6}$ heterocyclyl, unsubstituted $C_{1-8}$ alkyl, and unsubstituted $C_{1-8}$ haloalkyl;

where R$^7$, R$^8$ and R$^9$ are each independently selected from the group consisting of hydrogen, $C_{1-8}$ alkyl, $C_{2-8}$ alkenyl, $C_{2-8}$ alkynyl, $C_{6-10}$ aryl, 5 to 10 membered heteroaryl and 3- to 10-membered heterocycle, or R$^7$, R$^8$ and R$^9$, may together with the atom(s) to which they are attached, form a substituted or unsubstituted 5-, 6-, or 7-membered ring, and where the aliphatic and aromatic portions of R$^7$, R$^8$ and R$^9$ can be substituted with 1 to 3 substituents selected from the group consisting of halogen, —OH, —OR$'''$, —OC(O)NHR$'''$, —OC(O)NR$'''$R$''$, —SH, —SR$'''$, —S(O)R$'''$, —S(O)$_2$R$'''$, —S(O)$_2$NH$_2$, —S(O)$_2$NHR$'''$, —S(O)$_2$NR$'''$R$''$, —NHS(O)$_2$R$'''$, —NR$'''$S(O)$_2$R$''$, —C(O)NH$_2$, —C(O)NHR$'''$, —C(O)N(R$'''$)$_2$, —C(O)R$'''$, —NHC(O)R$'''$, —NR$'''$C(O)R$''$, —NHC(O)NH$_2$, —NR$'''$C(O)NH$_2$, —NR$'''$C(O)NHR$''$, —NHC(O)NHR$'''$, —NR$°$C(O)NR$'''$R$''$, —NHC(O)N(R$'''$)$_2$, —CO$_2$H, —CO$_2$R$'''$, —NHCO$_2$R$'''$, —NR$'''$CO$_2$R$''$, —CN, —NO$_2$, —NH$_2$, —NHR$''$, —NR$'''$R$''$, —NR$'''$S(O)NH$_2$ and —NR$'''$S(O)$_2$NHR$''$, where R$'''$, R$''$, and R$°$ are each independently unsubstituted $C_{1-6}$ alkyl.

In another embodiment, the present invention provides compounds of the formula (II) and pharmaceutically acceptable salts and N-oxides thereof:

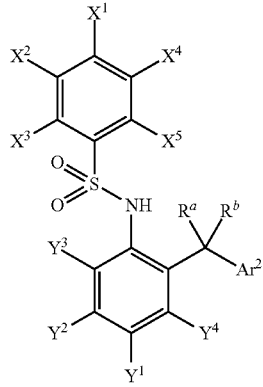
(II)

where $Ar^2, Y^1, Y^2, Y^3, Y^4, R^a$, and $R^b$ are as defined in formula (I); and $X^1, X^2, X^3, X^4, X^5$ are each independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, —C(O)R$^3$, —CO$_2$R$^3$, —C(O)NR$^3$R$^4$, —OR$^3$, —OC(O)R$^3$, —OC(O)NR$^3$R$^4$, —NO$_2$, —NR$^5$C(O)R$^3$, —NR$^5$C(O) NR$^3$R$^4$, —NR$^3$R$^4$, —NR$^5$CO$_2$R$^3$, —NR$^5$S(O)$_2$R$^3$, —SR$^3$, —S(O)R$^3$, —S(O)$_2$R$^3$, —S(O)$_2$NR$^3$R$^4$, substituted or unsubstituted $C_{6-10}$ aryl, substituted or unsubstituted 5- to 10-membered heteroaryl, and substituted or unsubstituted 3- to 10-membered heterocyclyl;

where $R^3, R^4$, and $R^5$ and substituted $C_{1-8}$ alkyl, substituted $C_{2-8}$ alkenyl, substituted $C_{2-8}$ alkynyl, substituted $C_{6-10}$ aryl, substituted 5- to 10-membered heteroaryl, and substituted 3- to 10-membered heterocyclyl are as defined for formula (I).

In another embodiment, the present invention provides compounds of the formula (III) and pharmaceutically acceptable salts and N-oxides thereof:

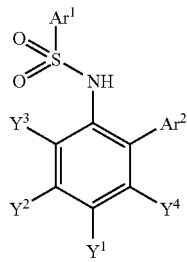
(III)

where $Ar^1, Ar^2, Y^1, Y^2, Y^3$, and $Y^4$ are as defined in formula (I).

In another embodiment, the present invention provides compounds of the formula (IV) and pharmaceutically acceptable salts and N-oxides thereof:

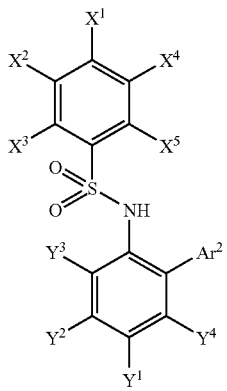
(IV)

where $Ar^2, Y^1, Y^2, Y^3$, and $Y^4$ are as defined in formula (I) and $X^1, X^2, X^3$, and $X^4$, are as defined in formula (II).

In another embodiment, the present invention provides compounds of the formula (V) and pharmaceutically acceptable salts and N-oxides thereof,

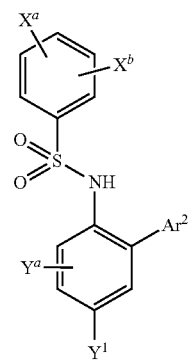
(V)

where $X^a$ and $X^b$ are each independently as defined for $X^1$ in formula (II); $Y^1$ and $Y^a$ are each independently as defined for $Y^1$ in formula (IV); and $Ar^2$ is as defined for formula (I).

The present invention provides compounds of the formula (VI) and pharmaceutically acceptable salts and N-oxides thereof:

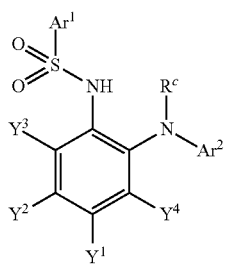
(VI)

where $Ar^1, Ar^2, Y^1, Y^2, Y^3$, and $Y^4$ are as defined in formula (I); and $R^c$ is hydrogen, substituted or unsubstituted $C_{1-8}$ alkyl, —C(O)R$^1$, —C(O)$_2$R$^1$, or —S(O)$_2$R$^1$; where $R^1$ is as defined for formula (I).

In another embodiment, the present invention provides compounds of the formula (VII) and pharmaceutically acceptable salts and N-oxides thereof:

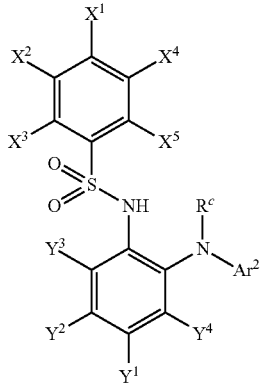

(VII)

where $Ar^2, Y^1, Y^2, Y^3$, and $Y^4$ are as defined in formula (I); $X^1, X^2, X^3$, and $X^4$ are as defined in formula (II); and $R^c$ is as defined in formula (VI).

The present invention provides compounds of the formula (VIII) and pharmaceutically acceptable salts and N-oxides thereof:

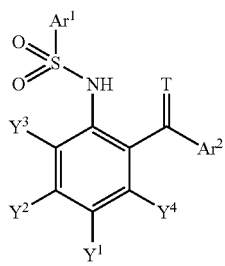

(VIII)

where $Ar^1, Ar^2, Y^1, Y^2, Y^3$, and $Y^4$ are as defined in formula (I); and

T is selected from the group consisting of $=CR^dR^e$, $=NOR^d$, and $=NR^d$;

$R^d$ and $R^e$ are each independently selected from the group consisting of hydrogen, halogen (only for $=CR^dR^e$), substituted or unsubstituted $C_{1-8}$ alkyl, —CN, —OR$^{41}$ (only for $=CR^dR^e$), —C(O)R$^{41}$, —C(O)$_2$R$^{41}$, —C(O)NR$^{41}$R$^{42}$, —SR$^{41}$ (only for $=CR^dR^e$); —NR$^{41}$R$^{42}$ (only for $=CR^eR^e$), —S(O)R$^{41}$ (only for $=CR^dR^e$), and —S(O)$_2$R$^{42}$ (only for $=CR^dR^e$); or where $R^d$ and $R^e$, together with the atom to which they are attached, form substituted or unsubstituted $C_{3-8}$ cycloalkyl or substituted or unsubstituted 3- to 10-membered heterocyclic ring (only for $=CR^dR^e$);

$R^{41}$ and $R^{42}$ are each independently hydrogen, $C_{1-8}$ alkyl, 5- to 10-membered heteroaryl, 3 to 10 membered heterocycle, or when attached to the same nitrogen atom, can be combined with the nitrogen atom to form a 5- or 6-membered heterocyclyl, and substituted $C_{1-8}$ alkyl, substituted 3- to 10-membered heterocyclic ring, substituted 5- to 10-membered heteroaryl, and the aliphatic portions of $R^{41}$ and $R^{42}$ can be substituted with from 1 to 3 substituents selected from the group consisting of halogen, —OH, —OR$^m$, —OC(O)NHR$^m$, —OC(O) NR$^m$R$^n$, —SH, —SR$^m$, —S(O)R$^m$, —S(O)$_2$R$^m$, —S(O)$_2$NH$_2$, —S(O)$_2$NHR$^m$, —S(O)$_2$NR$^m$R$^n$, —NHS(O)$_2$R$^m$, —NR$^m$S(O)$_2$R$^n$, —C(O)NH$_2$, —C(O)NHR$^m$, —C(O)N(R$^m$)$_2$, —C(O)R$^m$, —NHC(O)R$^m$, —NR$^m$C(O)R$^n$, —NHC(O)NH$_2$, —NR$^m$C(O)NH$_2$, —NR$^m$C(O)NHR$^n$, —NHC(O) NHR$^m$, —NR$^o$C(O)NR$^m$R$^n$, —NHC(O)N(R$^m$)$_2$, —CO$_2$H, —CO$_2$R$^m$, —NHCO$_2$R$^m$, —NR$^m$CO$_2$R$^n$, —CN, —NO$_2$, —NH$_2$, —NHR$^n$, —NR$^m$R$^n$, —NR$^m$S(O)NH$_2$ and —NR$^m$S(O)$_2$ NHR$^n$, where R$^m$, R$^n$, and R$^o$ are each independently unsubstituted $C_{1-6}$ alkyl.

In another embodiment, the present invention provides compounds of the formula (IX) and pharmaceutically acceptable salts and N-oxides thereof:

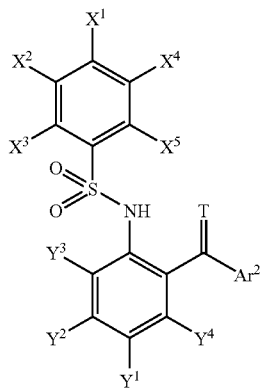

(IX)

where $Ar^2, Y^1, Y^2, Y^3$, and $Y^4$ are as defined in formula (I); T is as defined for formula (VIII); and $X^1, X^2, X^3, X^4$, and $X^5$ are as defined in formula (II).

In another embodiment, the present invention provides compounds of the formula (X) and pharmaceutically acceptable salts and N-oxides thereof:

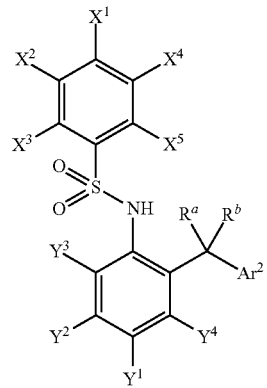

(X)

where $Ar^2, Y^1, Y^2, Y^3, Y^4, R^a$, and $R^b$ are as defined in formula (I); $X^1, X^2, X^3, X^4$, and $X^5$ are as defined in formula (II), with the proviso that $X^1$ is not —NR$^5$C(O)R$^3$, —NR$^5$C(O)NR$^3$R$^4$, —NR$^5$CO$_2$R$^3$, —NR$^5$S(O)$_2$R$^3$. In another embodiment, Ar$^2$, $Y^1, Y^2, Y^3, Y^4, R^a$, and $R^b$ are as defined in formula (I); $X^1, X^2$, $X^3, X^4$, and $X^5$ are as defined in formula (II), with the proviso that $X^1$ is not butyrolactam, valerolactam, imidazolidinone, hydantoin, phthalimide, and pyridone.

In another embodiment, the present invention provides compounds of the formula (XI) and pharmaceutically acceptable salts and N-oxides thereof:

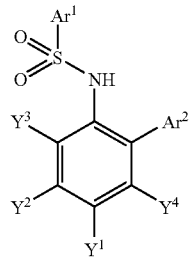

(XI)

where $Ar^2$, $Y^1$, $Y^2$, $Y^3$, and $Y^4$ are as defined for formula (I); and $X^1$, $X^2$, $X^3$, $X^4$, and $X^5$ are as defined in formula (II), with the proviso that at least one of $Y^1$, $Y^2$, $Y^3$ and $Y^4$ is other than hydrogen, and that when three of $Y^1$, $Y^2$, $Y^3$ and $Y^4$ are hydrogen, the other is not —$OR^6$.

In another embodiment, the present invention provides compounds of the formula (XII) and pharmaceutically acceptable salts and N-oxides thereof:

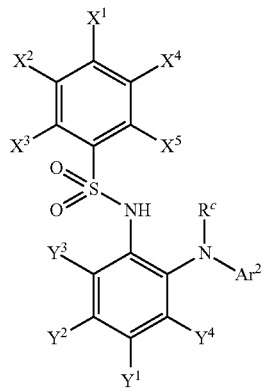

(XII)

where $Ar^2$, $Y^1$, $Y^2$, $Y^3$, and $Y^4$ are as defined in formula (I); $R^c$ is as defined in formula (VI); and $X^1$, $X^2$, $X^3$, and $X^4$ are as defined in formula (II) with the proviso that $X^1$ is not —$NR^5C(O)R^3$, —$NR^5C(O)NR^3R^4$, —$NR^5CO_2R^3$, —$NR^5S(O)_2R^3$. In another embodiment, $Ar^2$, $Y^1$, $Y^2$, $Y^3$, and $Y^4$ are as defined in formula (I); $R^c$ is as defined in formula (VI); and $X^1$, $X^2$, $X^3$, and $X^4$ are as defined in formula (II) with the proviso that $X^1$ is not butyrolactam, valerolactam, imidazolidinone, hydantoin, phthalimide, and pyridone.

In another embodiment, the present invention provides compounds of the formula (XIII) and pharmaceutically acceptable salts and N-oxides thereof:

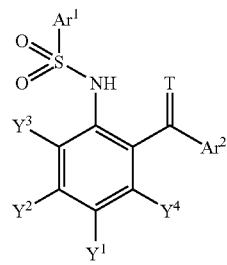

(XIII)

where $Ar^2$, $Y^1$, $Y^2$, $Y^3$, and $Y^4$ are as defined for formula (I); T is =$NR^d$; and $X^1$, $X^2$, $X^3$, $X^4$, and $X^5$ are as defined in formula (II), with the proviso that at least one of $Y^1$, $Y^2$, $Y^3$ and $Y^4$ is other than hydrogen, and that when three of $Y^1$, $Y^2$, $Y^3$ and $Y^4$ are hydrogen, the other is not —$OR^6$.

In other embodiments, the present invention provides compounds of the formula (XX-CXXXVI) and pharmaceutically acceptable salts and N-oxides thereof:

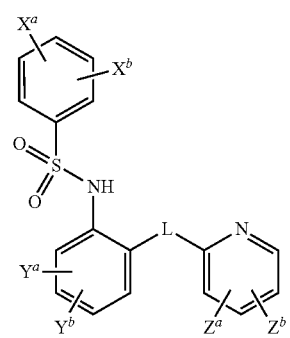

(XX)

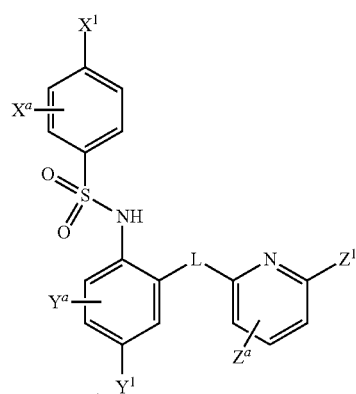

(XXI)

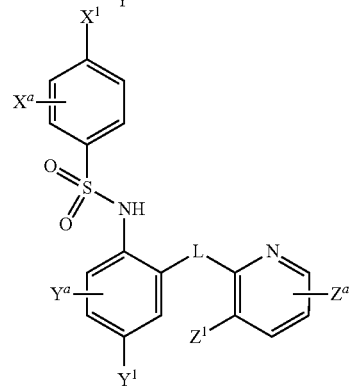

(XXII)

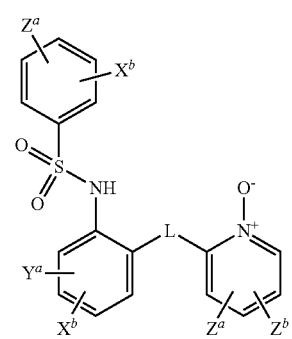
(XXIII)
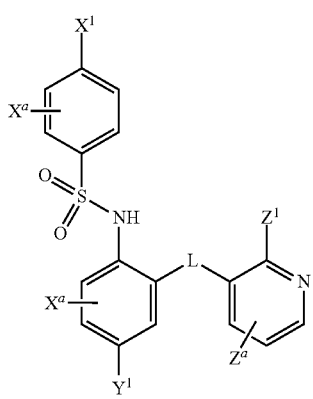
(XXVII)
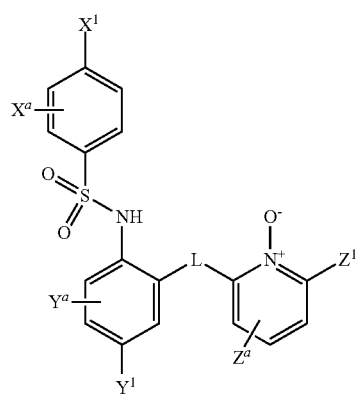
(XXIV)
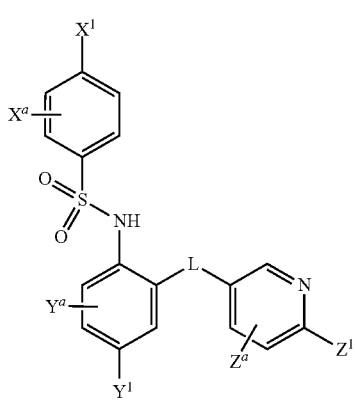
(XXVIII)
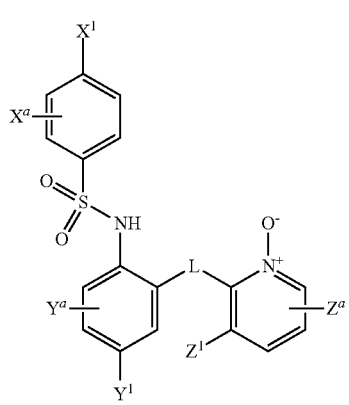
(XXV)
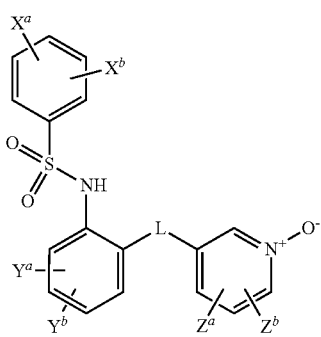
(XXIX)
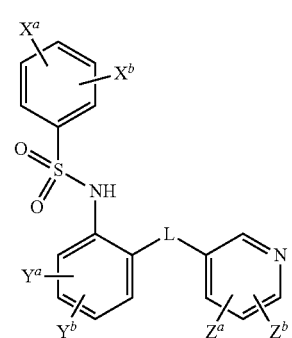
(XXVI)
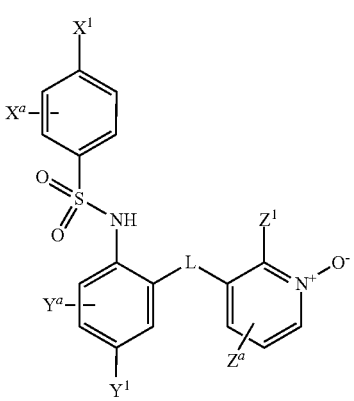
(XXX)

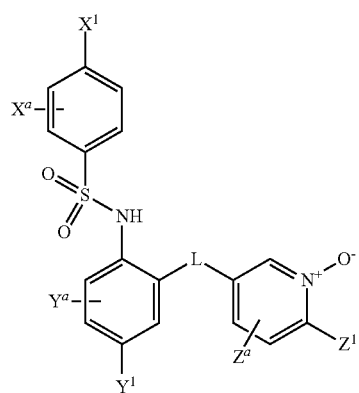
(XXXI)
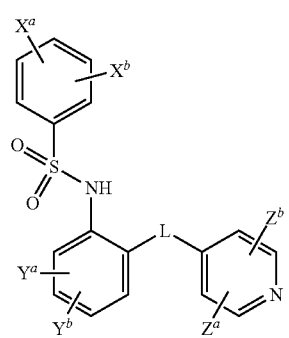
(XXXII)
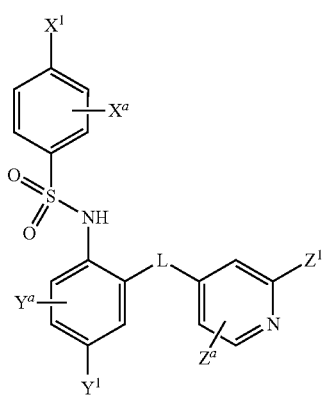
(XXXIII)
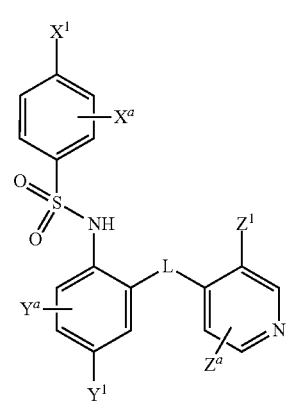
(XXXIV)
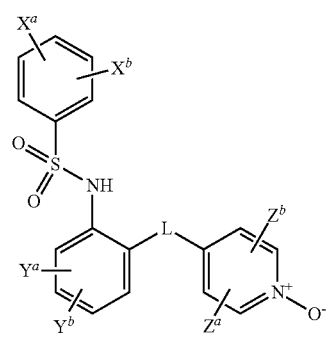
(XXXV)
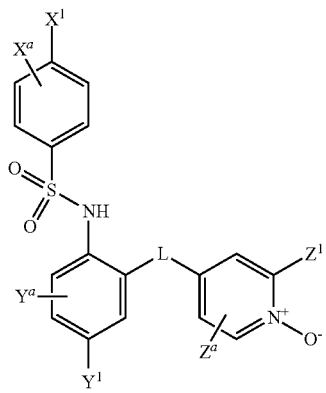
(XXXVI)
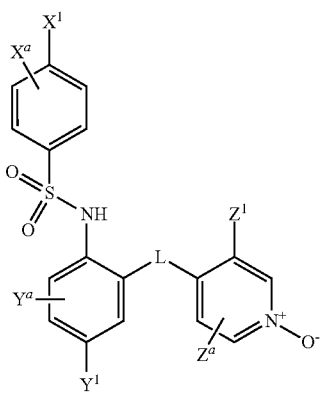
(XXXVII)
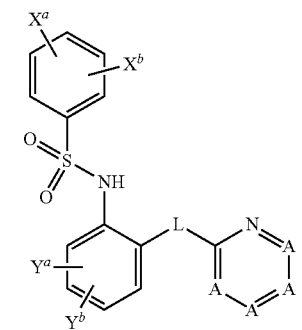
(XXXVIII)

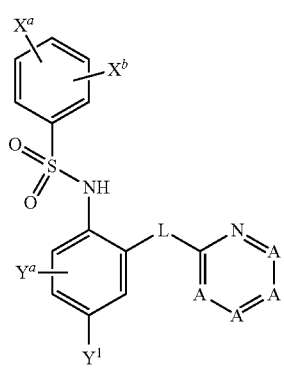
(XXXIX)
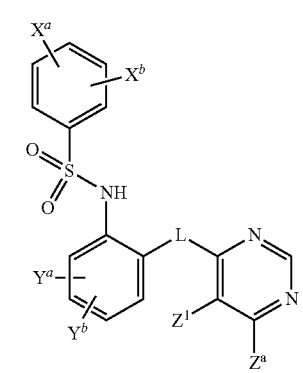
(XL)
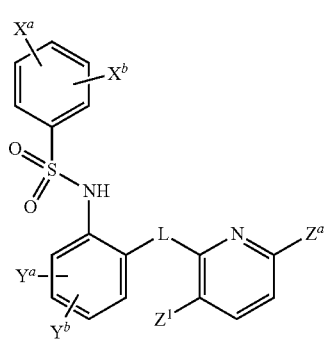
(XLI)
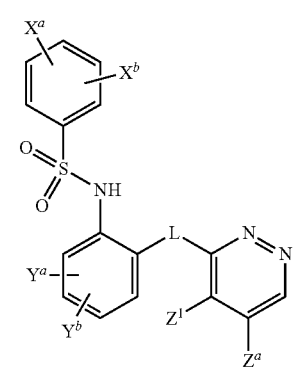
(XLII)
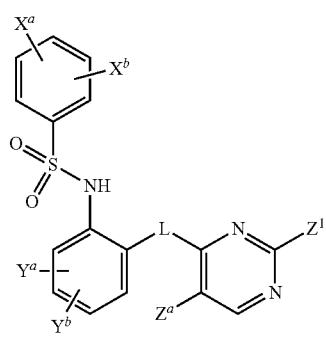
(XLIII)
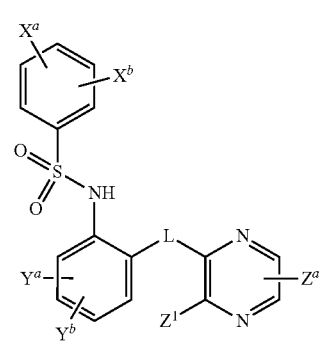
(XLIV)
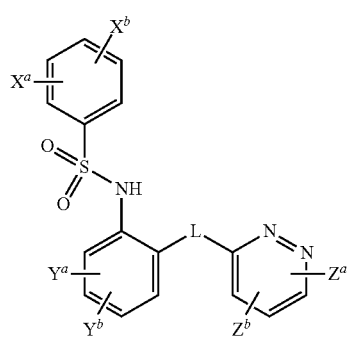
(XLV)
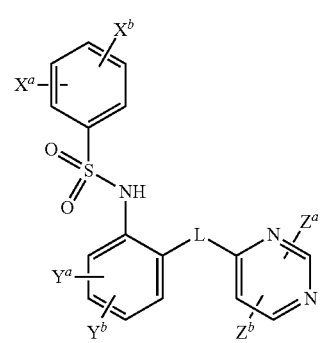
(XLVI)

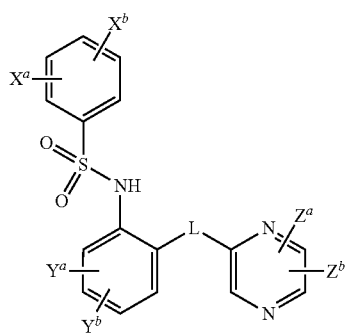
(XLVII)
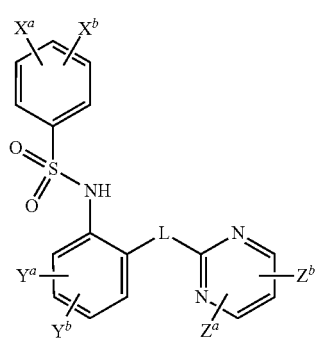
(XLVIII)
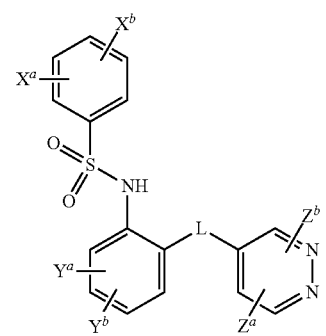
(XLIX)
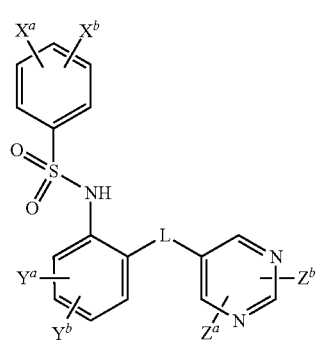
(L)
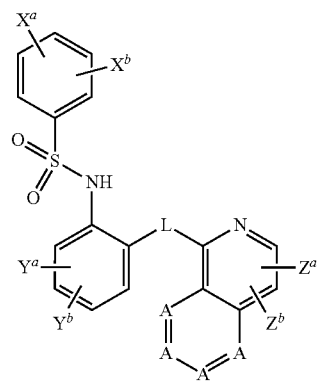
(LI)
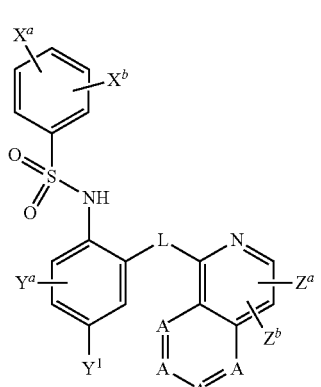
(LII)
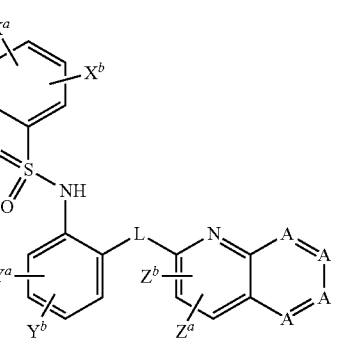
(LIII)
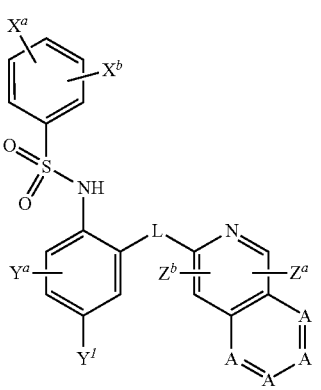
(LIV)

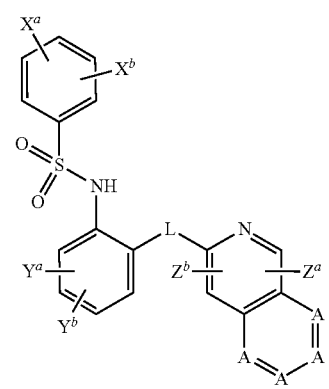
(LV)
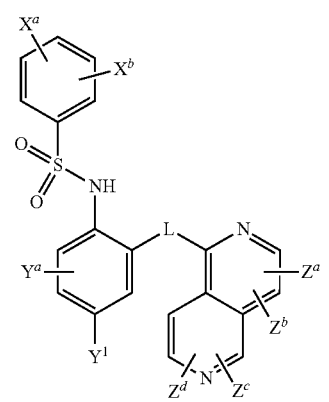
(LVI)
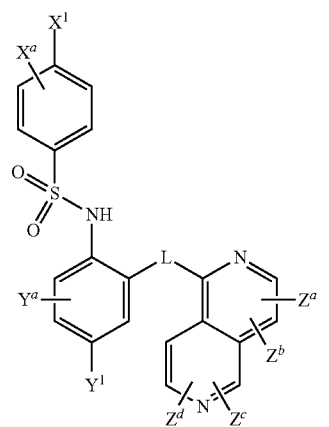
(LVII)
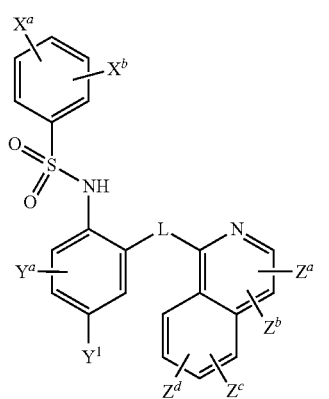
(LVIII)
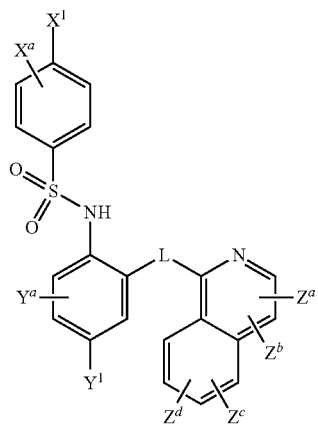
(LIX)
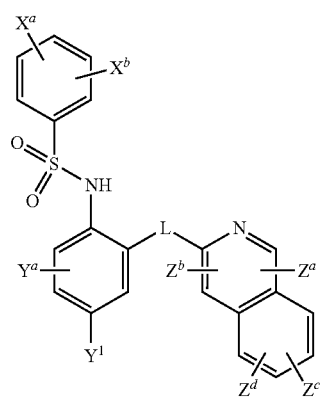
(LX)
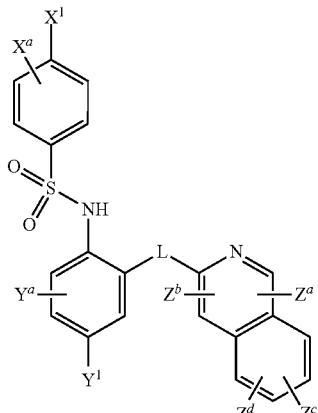
(LXI)
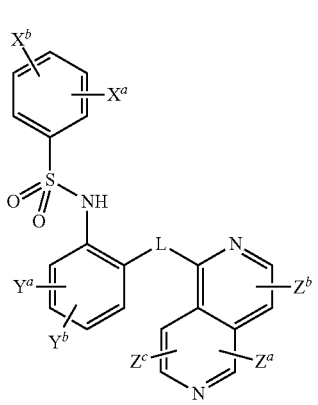
(LXII)

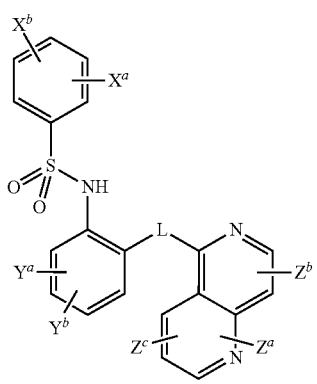
(LXIII)
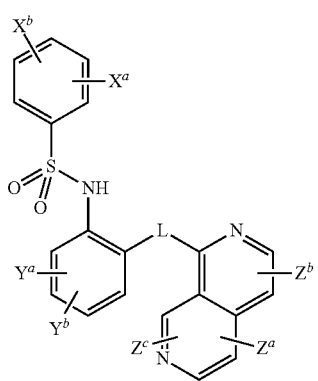
(LXIV)
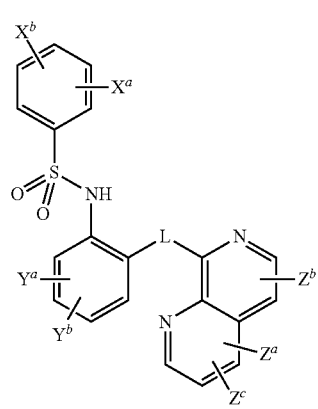
(LXV)
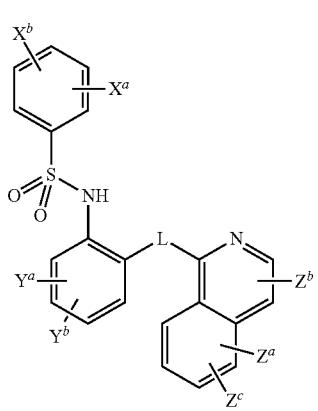
(LXVI)
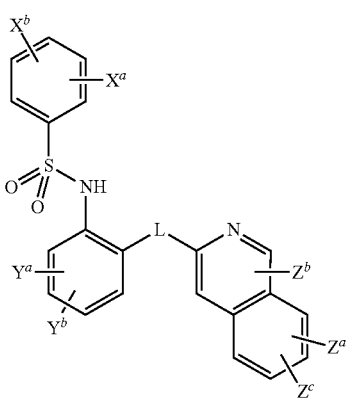
(LXVII)
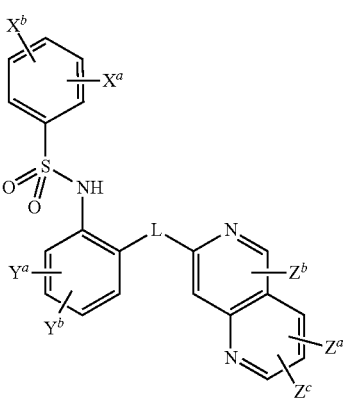
(LXVIII)
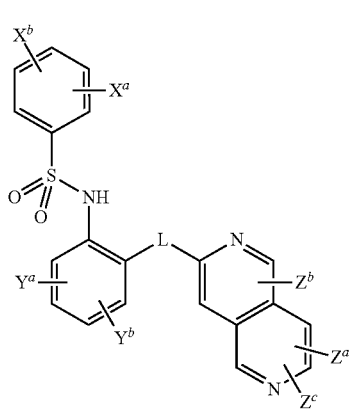
(LXIX)
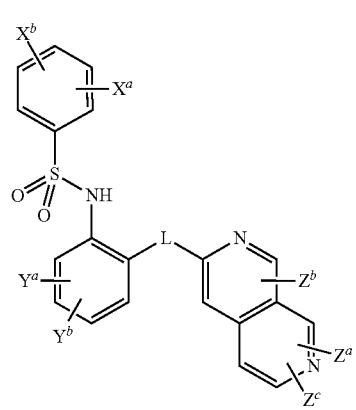
(LXX)

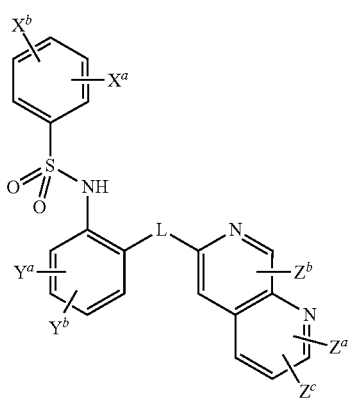 (LXXI)
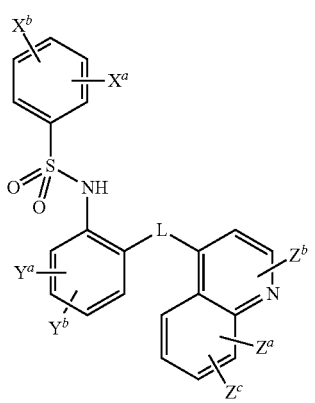 (LXXII)
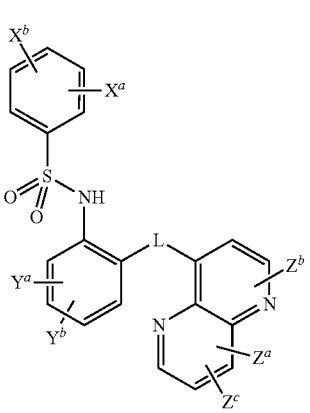 (LXXIII)
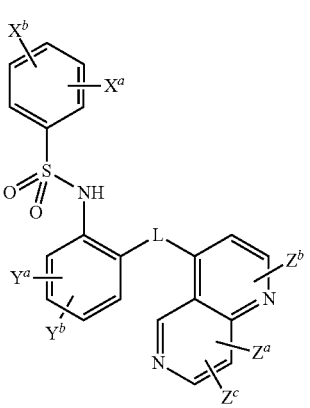 (LXXIV)
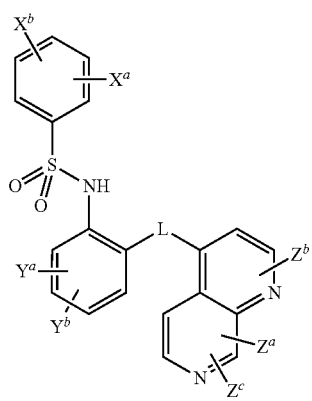 (LXXV)
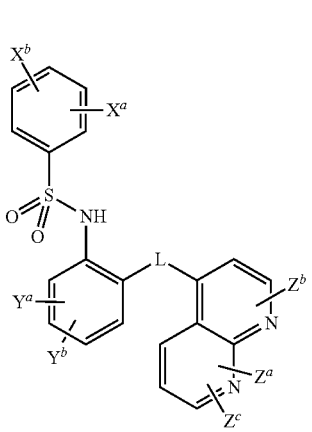 (LXXVI)
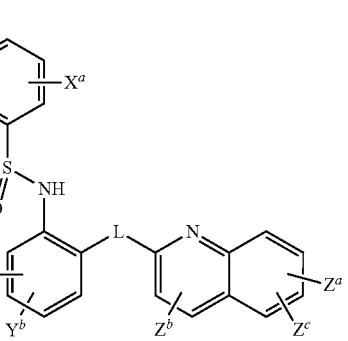 (LXXVII)
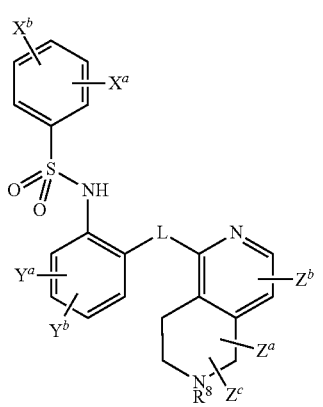 (LXXVIII)

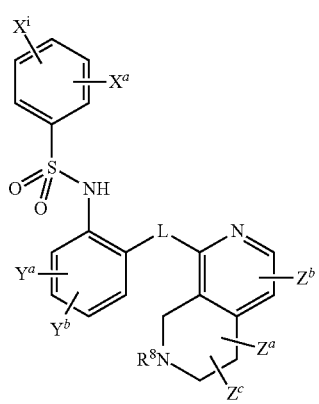
(LXXIX)
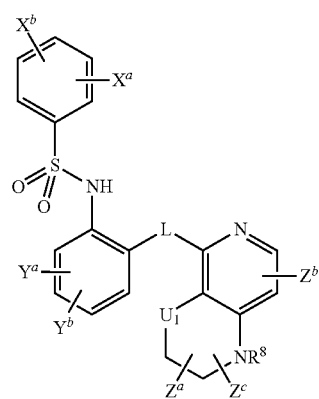
(LXXX)
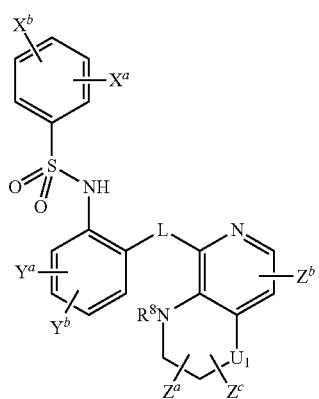
(LXXXI)
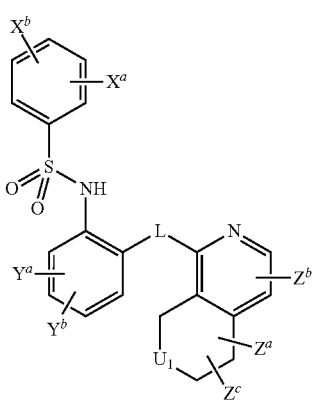
(LXXXII)
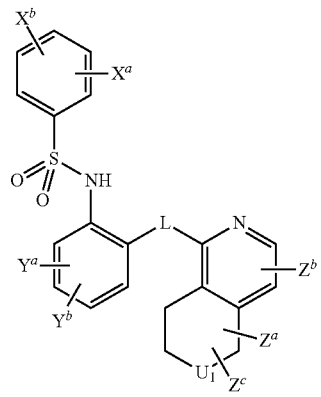
(LXXXIII)
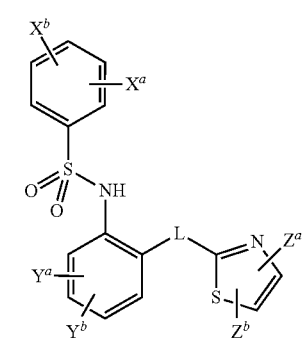
(LXXXIV)
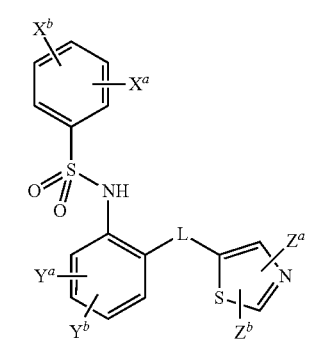
(LXXXV)
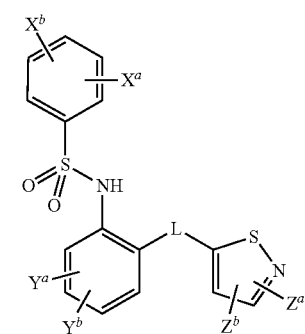
(LXXXVI)

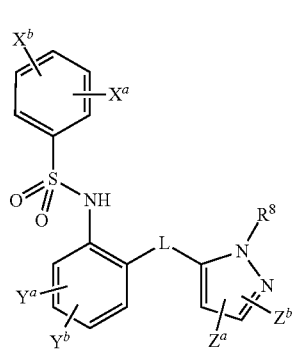 (LXXXVII)
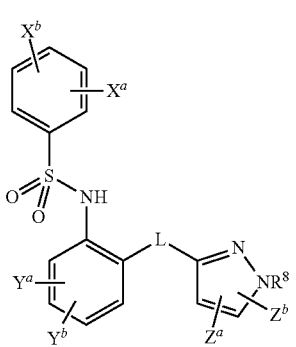 (LXXXVIII)
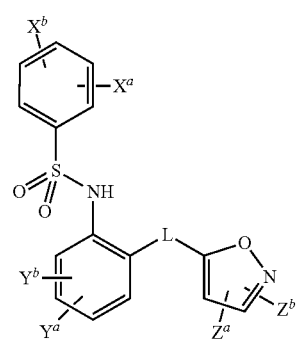 (LXXXIX)
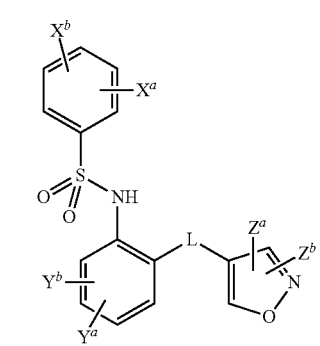 (XC)
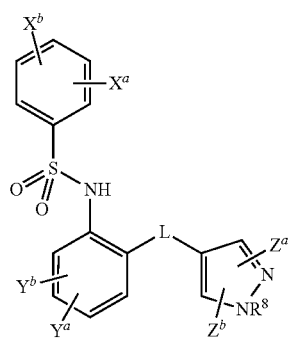 (XCI)
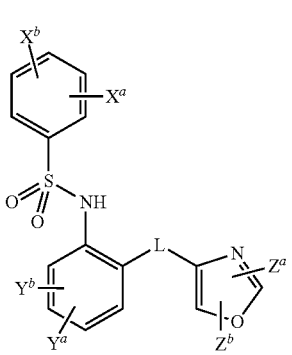 (XCII)
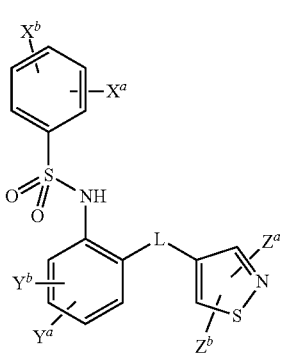 (XCIII)
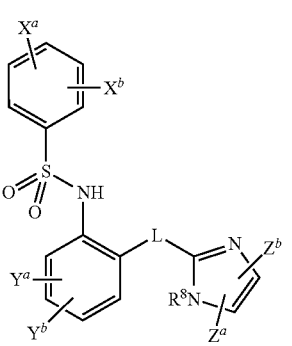 (XCIV)

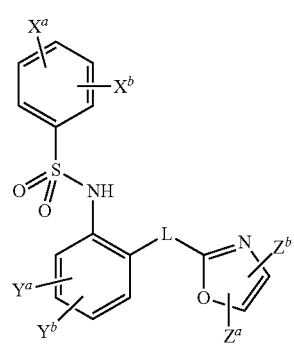
(XCV)
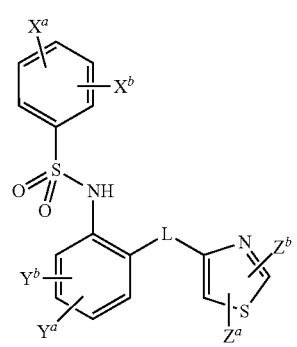
(XCIX)
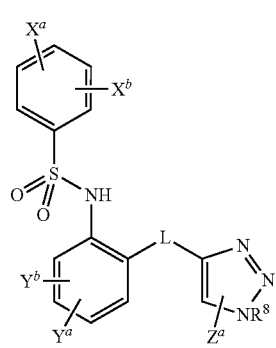
(C)
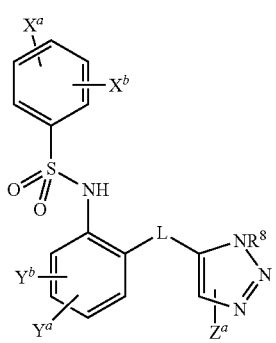
(CI)
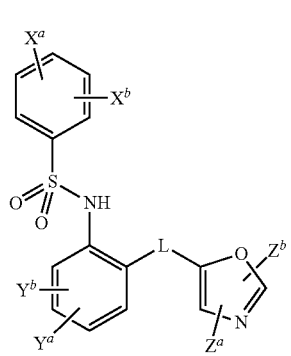
(XCVIII)

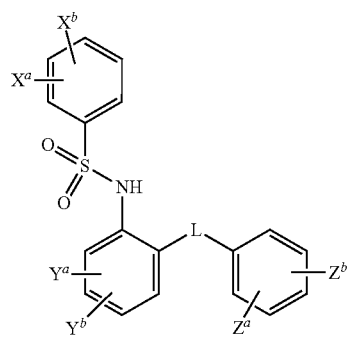
(CIII)
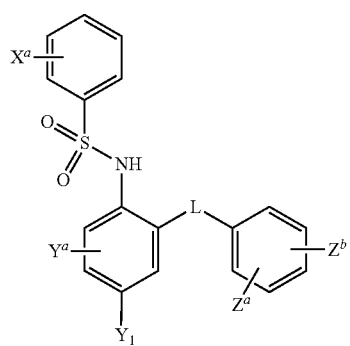
(CIV)
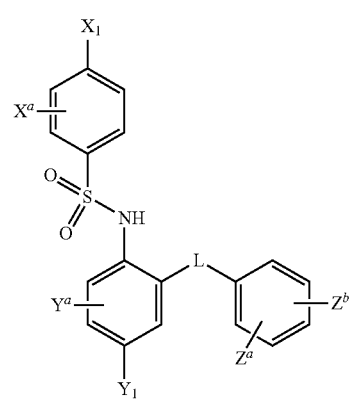
(CV)
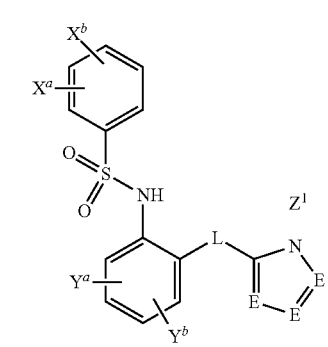
(CVI)
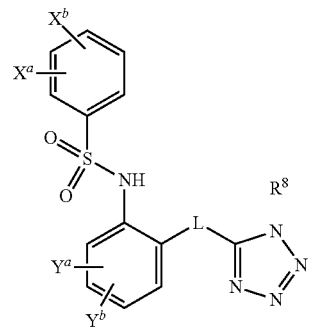
(CVII)
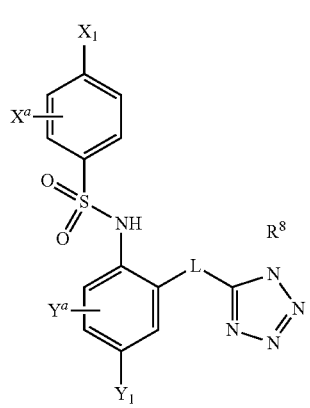
(CVIII)
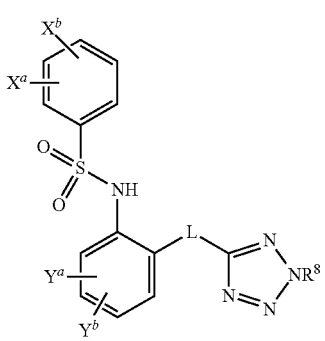
(CIX)
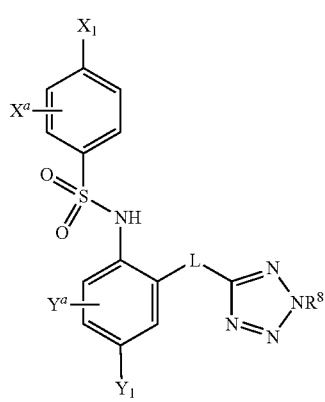
(CX)

-continued
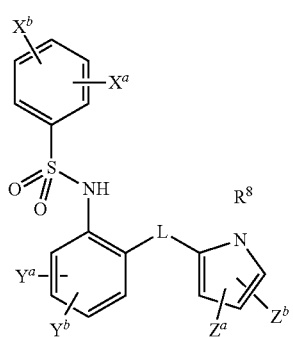
(CXI)
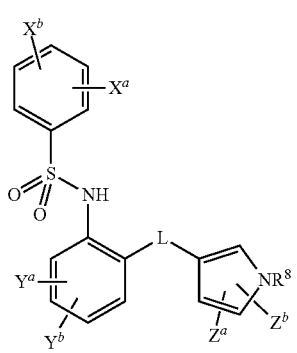
(CXII)
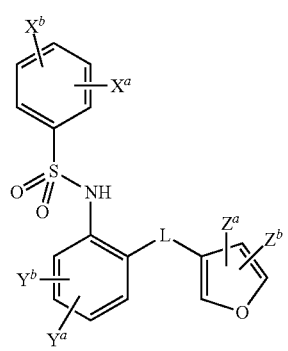
(CXIII)
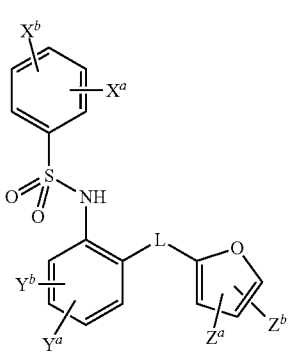
(CXIV)
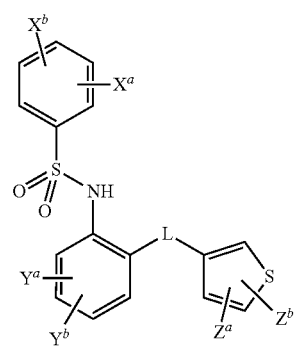
(CXV)
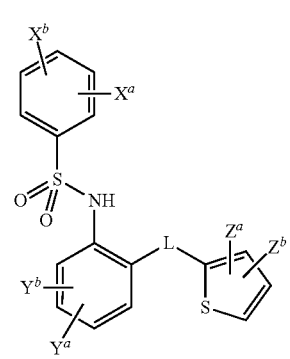
(CXVI)
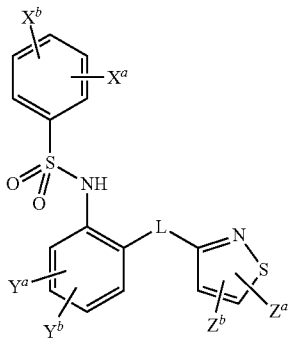
(CXVII)
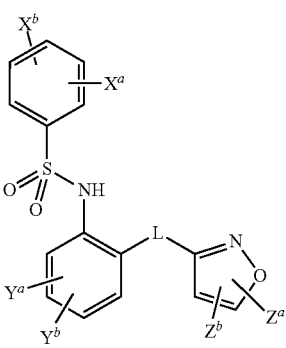
(CXVIII)

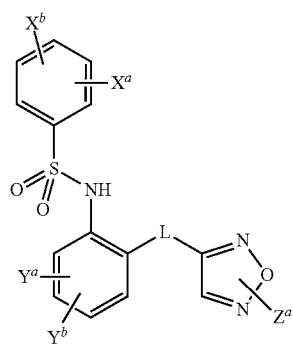
(CXIX)
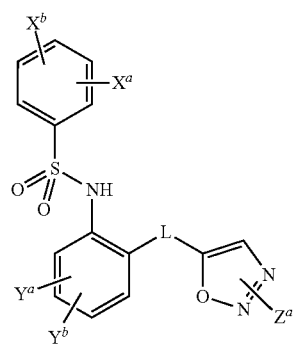
(CXXIII)
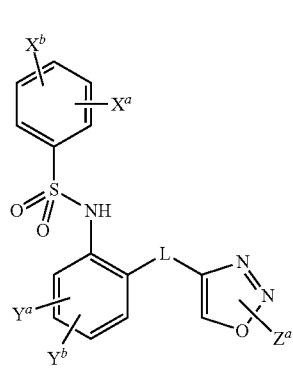
(CXX)
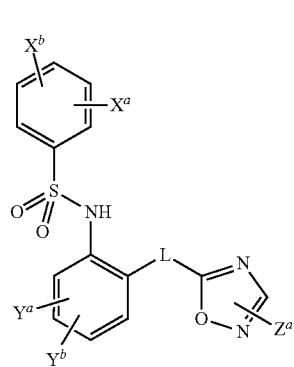
(CXXIV)
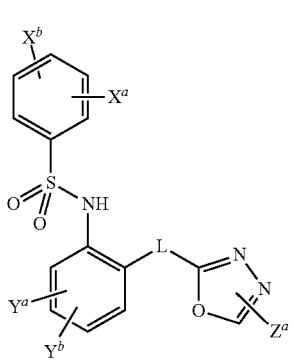
(CXXI)
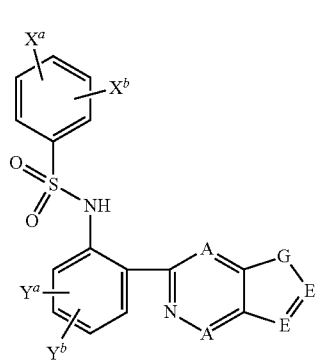
(CXXV)
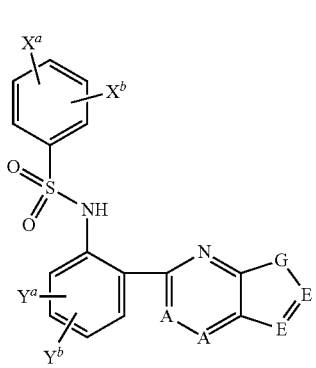
(CXXII)
(CXXVI)

(CCXXVII)
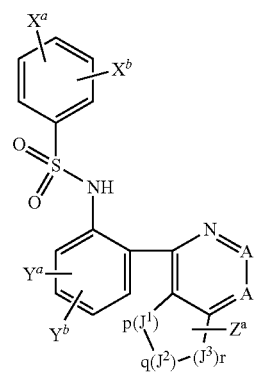
(CXXXI)
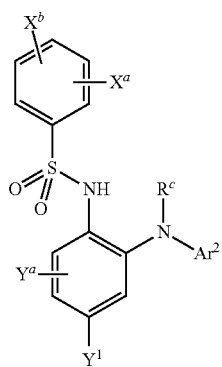
(CXXVIII)
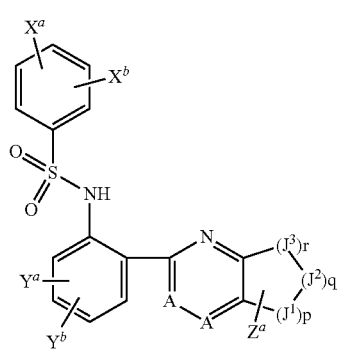
(CXXXII)
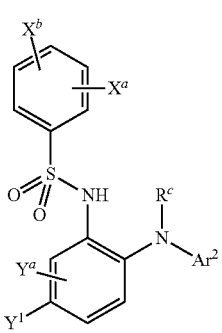
(CXXIX)
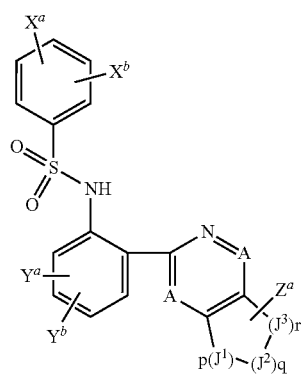
(CXXXIII)
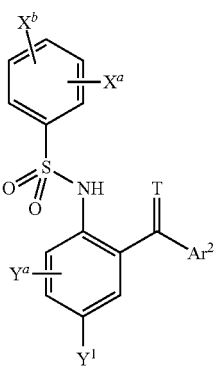
(CXXX)
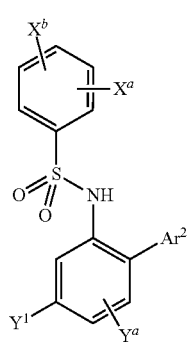
(CXXXIV)
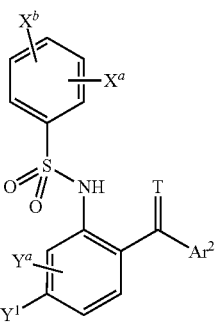

-continued

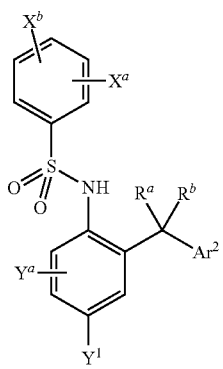

(CXXXV)

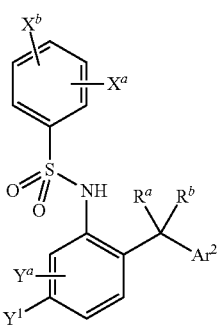

(CXXXVI)

The following descriptions and embodiments only refer to those formulae (I-CXXXVI) that are applicable (i.e., those formulae with the applicable substituents). In the following embodiments, when one substituent is specified, the remaining substituents remain as defined during their first appearance, unless otherwise specified. For example, if $X^1$ is defined, then $X^2$, $X^3$, $X^4$, and $X^5$ remain as defined in formula (II).

In each of the formula (XX-CXXXVI), L is selected from the group consisting of —$NR^c$—, $CR^aR^b$, C=T, and a bond;
$R^c$ is defined as in formula (VI);
$R^a$ and $R^b$ are defined as in formula (I);
T is defined as in formula (VIII);
$X^1$, $X^a$ and $X^b$ are each independently as defined for $X^1$ in formula (II);
$Y^1$, $Y^a$, and $Y^b$ are each independently as defined for $Y^1$ in formula (I); and
$Z^1$, $Z^a$, $Z^b$ and $Z^c$ are each independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —$NO_2$, —$OR^{10}$, —$OC(O)R^{10}$, —$CO_2R^{10}$, —$C(O)R^{10}$, —$C(O)NR^{11}R^{12}$, —$OC(O)NR^{11}R^{12}$, —$NR^{10}C(O)R^{11}$, —$NR^{10}C(O)NR^{11}R^{12}$, —$NR^{11}R^{12}$, —$NR^{10}CO_2R^{11}$, —$SR^{10}$, —$S(O)R^{10}$, —$S(O)_2R^{10}$, —$S(O)_2NR^{11}R^{12}$, —$NR^{10}S(O)_2R^{11}$, substituted or unsubstituted $C_{6-10}$ aryl, substituted or unsubstituted 5- to 10-membered heteroaryl and substituted or unsubstituted 3- to 10-membered heterocyclyl;
where suitable substituted $C_{1-8}$ alkyl, $C_{2-8}$ alkenyl, $C_{2-8}$ alkynyl may have from 1 to 3 substituents independently selected from the group consisting of halogen, —$OR^{10}$, —CN, —$NO_2$, =O, —$OC(O)R^{10}$, —$CO_2R^{10}$, —$C(O)R^{10}$, —$C(O)NR^{10}R^{11}$, —$OC(O)NR^{10}R^{11}$, —$NR^{10}C(O)R^{11}$, —$NR^{10}C(O)NR^{11}R^{12}$, —$NR^{10}R^{11}$, —$NR^{10}CO_2R^{11}$, —$SR^{10}$, —$S(O)R^{10}$, —$S(O)_2R^{10}$, —$S(O)_2NR^{10}R^{11}$, —$NR^{10}S(O)_2R^{11}$, unsubstituted or substituted phenyl, unsubstituted or substituted $C_{5-6}$ heteroaryl, and unsubstituted or substituted $C_{3-6}$ heterocyclyl;
where suitable substituted aryl, heteroaryl and heterocyclyl substituents may have from 1 to 3 substituents independently selected from the group consisting of halogen, —$OR^{10}$, —CN, —$NO_2$, =O, —$OC(O)R^{10}$, —$OC(O)R^{10}$, —$CO_2R^{10}$, —$C(O)R^{10}$, —$C(O)NR^{10}R^{11}$, —$OC(O)NR^{10}R^{11}$, —$NR^{10}C(O)R^{11}$, —$NR^{10}C(O)NR^{11}R^{12}$, —$NR^{10}R^{11}$, —$NR^{10}CO_2R^{11}$, —$SR^{10}$, —$S(O)R^{10}$, —$S(O)_2R^{10}$, —$S(O)_2NR^{10}R^{11}$, —$NR^{10}S(O)_2R^{11}$, unsubstituted 4- to 7-membered ring heterocyclyl, unsubstituted $C_{1-8}$ alkyl and unsubstituted $C_{1-8}$ haloalkyl; with the proviso that when L is C=T where the substituent $Z^1$, $Z^a$, $Z^b$ and $Z^c$ is a heterocycle, suitable substituents on this heterocycle preferably do not include another heterocycle;
$R^{10}$, $R^{11}$ and $R^{12}$ are each hydrogen, $C_{1-8}$ alkyl, $C_{2-8}$ alkenyl, $C_{2-8}$ alkynyl, aryl, or heteroaryl; or $R^{10}$ and $R^{11}$, or $R^{11}$ and $R^{12}$, or $R^{10}$ and $R^{12}$, together with the atom(s) to which they are attached, form a substituted or unsubstituted 5-, 6-, or 7-membered ring; and
the aliphatic and aromatic portions of $R^{10}$, $R^{11}$ and $R^{12}$ are optionally further substituted with from 1 to 3 substituents selected from the group consisting of halogen, —OH, —$OR'''$, —$OC(O)NHR'''$, —$OC(O)NR'''R''$, —SH, —$SR'''$, —$S(O)R'''$, —$S(O)_2R'''$, —$S(O)_2NH_2$, —$S(O)_2NHR'''$, —$S(O)_2NR'''R''$, —$NHS(O)_2R'''$, —$NR'''S(O)_2R''$, —$C(O)NH_2$, —$C(O)NHR'''$, —$C(O)N(R''')_2$, —$C(O)R'''$, —$NHC(O)R'''$, —$NR'''C(O)R''$, —$NHC(O)NH_2$, —$NR'''C(O)NH_2$, —$NR'''C(O)NHR''$, —$NHC(O)NHR'''$, —$NR^oC(O)NR'''R''$, —$NHC(O)N(R''')_2$, —$CO_2H$, —$CO_2R'''$, —$NHCO_2R'''$, —$NR'''CO_2R''$, —CN, —$NO_2$, —$NH_2$, —$NHR''$, —$NR'''R''$, —$NR'''S(O)NH_2$, and —$NR'''S(O)_2NHR''$, where $R'''$, $R''$, and $R^o$ are each independently unsubstituted $C_{1-6}$ alkyl.
$J^1$, $J^2$ and $J^3$ are each independently selected from the group consisting of $CR^{25}R^{26}$, O, $S(O)_f$, and $NR^{24}$, where I is 0, 1 or 2 with the proviso that p+q+r is 3, 4 or 5; and with the proviso that the resulting ring system does not contain a hydrazine functionality, a peroxide functionality nor a hydroxylamine derived functionality, and where $R^{24}$, $R^{25}$ and $R^{26}$ are as defined for formula (AA) in [0029] in the section describing abbreviations. In one preferred embodiment, $R^{24}$, $R^{25}$ and $R^{26}$ are independently hydrogen or unsubstituted $C_{1-6}$ alkyl.
Each A is independently $CZ^1$, N or $N^+$—$O^-$, where $Z^1$ is an $Ar^2$ substituent, as defined for formula (III), independently selected from the group consisting of: halogen, substituted or unsubstituted $C_{1-8}$ alkyl, substituted or unsubstituted $C_{2-8}$ alkenyl, substituted or unsubstituted $C_{2-8}$ alkynyl, —CN, =O, —$NO_2$, —$OR^7$, —$OC(O)R^7$, —$CO_2R^7$, —$C(O)R^7$, —$C(O)NR^8R^9$, —$OC(O)NR^8R^9$, —$NR^7C(O)R^8$, —$NR^7C(O)NR^8R^9$, —$NR^8R^9$, —$NR^7CO_2R^8$, —$SR^7$, —$S(O)R^7$, —$S(O)_2R^7$, —$S(O)_2NR^8R^9$, —$NR^7S(O)_2R^8$, substituted or unsubstituted $C_{6-10}$ aryl, substituted or unsubstituted 5- to 10-membered heteroaryl and substituted or unsubstituted 3- to 10-membered heterocyclyl;
where $R^7$, $R^8$, $R^9$, substituted $C_{1-8}$ alkyl, substituted $C_{2-8}$ alkenyl, substituted $C_{2-8}$ alkynyl, substituted $C_{6-10}$ aryl, substituted 5- to 10-membered heteroaryl, and substituted 3- to 10-membered heterocyclyl are as defined for formula (III).
Each E is independently $CZ^1$, or N, where $Z^1$ is defined as in [0072].
Each G is independently O, S, or $NZ^1$, where $Z^1$ is defined as in [0072].

Each $U_1$ is independently selected from the group consisting of $CH_2$, $O$, $NR^8$, where $R^8$ is as defined in formula (I).

The following preferred embodiments of formulae (I-XIII and XX-CXXXVI) are applicable to [0082-00355]:

In one embodiment where L is $CR^aR^b$ or $NR^c$, the substituents $Ar^2$, $Y^1$, $Y^2$, $Y^3$, $Y^4$, $R^a$, and $R^b$ are as defined in formula (I); $X^1$, $X^2$, $X^3$, $X^4$, and $X^5$ are as defined in formula (II), with the proviso that $X^1$ is not $-NR^5C(O)R^3$, $-NR^5C(O)NR^3R^4$, $-NR^5CO_2R^3$, $-NR^5S(O)_2R^3$.

In another embodiment where L is $CR^aR^b$ or $NR^c$, $Ar^2$, $Y^1$, $Y^2$, $Y^3$, $Y^4$, $R^a$, and $R^b$ are as defined in formula (I); $X^1$, $X^2$, $X^3$, $X^4$, and $X^5$ are as defined in formula (II), with the proviso that $X^1$ is not butyrolactam, valerolactam, imidazolidinone, hydantoin, phthalimide, and pyridone.

In another embodiment where L is a bond or $C=NR^d$, $Ar^2$, $Y^1$, $Y^2$, $Y^3$, and $Y^4$ are as defined for formula (I); and $X^1$, $X^2$, $X^3$, $X^4$, and $X^5$ are as defined in formula (II), with the proviso that at least one of $Y^1$, $Y^2$, $Y^3$ and $Y^4$ is other than hydrogen.

In another embodiment where L is a bond or $C=NR^d$, $Ar^2$, $Y^1$, $Y^2$, $Y^3$, and $Y^4$ are as defined for formula (I); and $X^1$, $X^2$, $X^3$, $X^4$, and $X^5$ are as defined in formula (II), with the proviso and that when three of $Y^1$, $Y^2$, $Y^3$ and $Y^4$ are hydrogen, the other is not $-OR^6$.

In formulae (XX-CXXIX, CXXXIII, and CXXXIV) where L is $C=T$, $R^8$ is as defined in formula (I). In one preferred embodiment, $R^8$ is hydrogen or unsubstituted $C_{1-6}$ alkyl.

In one embodiment of any of formulae (I, II, X, XX-CXXIX, CXXXV, and CXXXVI) where L is $CR^aR^b$, $R^a$ is hydrogen, halogen, $-OR^1$ (where $R^1$ is as defined in formula (I) and preferably is hydrogen or $C_{1-4}$ alkyl), substituted or unsubstituted $C_{1-4}$ alkyl, or substituted or unsubstituted $C_{1-4}$ alkenyl.

In one embodiment of any of formulae (I, II, X, XX-CXXIX, CXXXV, and CXXXVI) where L is $CR^aR^b$, $R^b$ is hydrogen, halogen, or $-OR^1$ (where $R^1$ is as defined in formula (I) and preferably is hydrogen or $C_{1-4}$ alkyl).

In one embodiment of any of formulae (I, II, X, XX-CXXIX, CXXXV, and CXXXVI) where L is $CR^aR^b$, one of $R^a$ and $R^b$ is other than hydrogen.

In one embodiment of any of formulae (I, II, X, XX-CXXIX, CXXXV, and CXXXVI) where L is $CR^aR^b$, $R^a$ and $R^b$ are both halogen, and more preferably, are both fluorine.

In one embodiment of any of formulae (I, II, X, XX-CXXIX, CXXXV, and CXXXVI) where L is $CR^aR^b$, $R^a$ is hydrogen and $R^b$ is $-OR^1$ (where $R^1$ is as defined in formula (I) and is preferably hydrogen or $C_{1-4}$ alkyl).

In one embodiment of any of formulae (I, II, X, XX-CXXIX, CXXXV, and CXXXVI) where L is $CR^aR^b$, $R^a$ and $R^b$ are both $-OR^1$ (where $R^1$ is as defined in formula (I)) and where both $R^1$ groups are combined together with the atoms to which they are attached to form a 5-7 membered heterocyclic acetal ring system.

In one embodiment of any of formulae (I, II, X, XX-CXXIX, CXXXV, and CXXXVI) where L is $CR^aR^b$, $R^a$ is $C_{1-4}$ alkyl or $C_{1-4}$ alkenyl and $R^b$ is $-OR^1$ (where $R^1$ is as defined in formula (I) and is preferably hydrogen or $C_{1-4}$ alkyl).

In one preferred embodiment of any of formulae (VI, VII, XII, XX-CXXIX and CXXXI, and CXXXII) where L is $NR^c$, $R^c$ is hydrogen, $-S(O)_2R^1$ or $-C(O)R^1$.

In one preferred embodiment of formula (XXXII) or formula (XXXIII) where L is $NR^c$, $R^c$ is hydrogen or $-CO_2R^1$, $Y^a$ is hydrogen, $Y^1$ is chlorine, $Z^a$ and $Z^1$ are hydrogen, $X^a$ is hydrogen, and $X^1$ is substituted or unsubstituted $C_{1-8}$alkyl.

In one preferred embodiment of formula (XXXII) or formula (XXXIII) where L is $NR^c$, $R^c$ is hydrogen or $-CO_2R^1$, $Y^a$ is hydrogen, $Y^1$ or $Y^b$ is halogen, preferably chlorine, $Z^a$, $Z^b$ and $Z^1$ are hydrogen, $X^a$ and $X^a$ are hydrogen, and $X^1$ is substituted or unsubstituted $C_{1-8}$alkyl.

In another preferred embodiment, in each of the formulae (VI, VII, XII, XX-CXXIX and CXXXI, and CXXXII) where L is $NR^c$, $R^c$ is hydrogen or $-C(O)Me$.

In one embodiment of formula (I, III, VI, VIII, XI and XIII), $Ar^1$ is a substituted or unsubstituted $C_{6-10}$ aryl. Preferably, $Ar^1$ is a substituted or unsubstituted phenyl.

In one embodiment of formulae (I, III, VI, VIII, XI and XIII), $Ar^1$ is a substituted or unsubstituted 5- to 10-membered heteroaryl selected from pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

In one embodiment of formulae (I, III, VI, VIII, XI and XIII), $Ar^1$ is substituted or unsubstituted 5- to 10-membered heteroaryl and comprises from 0 to 2 sulfur atoms, 0 to 2 oxygen atoms and 0 to 5 nitrogen atoms.

In one embodiment of formula (I, III, VI, VIII, XI and XIII), heterocycle groups as substituents on $Ar^1$ can include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S, S-dioxide, piperazine, pyran, pyridone, 3-pyrroline, thiopyran, pyrone, tetrahydrofuran, or tetrahydrothiophene.

In one embodiment of formula (I, III, VI, VIII, XI and XIII), 6-membered heteroaryl systems as substituents on $Ar^1$ include pyridyl, pyridazinyl, pyrazinyl, pyrimidinyl and triazinyl.

In one embodiment of formula (I, III, VI, VIII, XI and XIII), 5-ring heteroaryl systems as substituents on $Ar^1$ include isothiazolyl, pyrazolyl, imidazolyl, triazolyl, tetrazolyl, oxazolyl, isoxazolyl, oxadiazolyl, thiadiazolyl, pyrrolyl and thiazolyl.

In one embodiment of formula (I, III, VI, VIII, XI and XIII), $Ar^1$ is a substituted or unsubstituted 5- or 6-membered heteroaryl or substituted or unsubstituted phenyl, each optionally having 1 to 5 substituents as defined in formula (I).

In one embodiment of formula (I, III, VI, VIII, XI and XIII), $Ar^1$ is substituted or unsubstituted phenyl, having 1 to 5 substituents ($X^1$, $X^2$, $X^3$, $X^4$, $X^5$) as defined in formula (II).

In one embodiment of formula (I, III, VI, and VIII), $Ar^1$ is a substituted or unsubstituted phenyl and $Ar^2$ is substituted or unsubstituted 5- to 10-membered monocyclic or bicyclic heteroaryl, phenyl or naphthalenyl, each with 0 to 4 substituents.

In one embodiment of formula (I, III, VI, and VIII), $Ar^1$ is a substituted or unsubstituted phenyl and $Ar^2$ is substituted or unsubstituted phenyl, or a substituted or unsubstituted 5- or 6-membered heteroaryl.

In one embodiment of formula (III), $Ar^1$ is substituted or unsubstituted phenyl and $Ar^2$ is a substituted or unsubstituted fused 5,6-ring and 6,6-ring heteroaryl.

In one embodiment of formula (III and XI), $Ar^1$ is substituted or unsubstituted phenyl and $Ar^2$ is 5- to 10-membered monocyclic or bicyclic heteroaryl ring system, where one ring heteroatom is located alpha (ortho) to the biaryl bond.

In one embodiment of formula (III and XI), $Ar^1$ is substituted or unsubstituted phenyl and $Ar^2$ is 5- to 10-membered monocyclic or bicyclic heteroaryl ring system containing one or more ring nitrogen atoms, and where one or more ring nitrogen atoms is located alpha (ortho) to the biaryl bond.

In one embodiment of formula (I), $Ar^1$ is substituted or unsubstituted phenyl; $Ar^2$ is substituted or unsubstituted phenyl, or a substituted or unsubstituted 5- or 6-membered heteroaryl; and $R^a$ and $R^b$ are both halogen, and more preferably, are both fluorine.

In one embodiment of formula (I), $Ar^1$ is substituted or unsubstituted phenyl; $Ar^2$ is substituted or unsubstituted phenyl, or a substituted or unsubstituted 5- or 6-membered heteroaryl; $R^a$ is hydrogen, halogen, $-OR^1$ (where $R^1$ is as defined in formula (I) and preferably is hydrogen or $C_{1-4}$ alkyl), substituted or unsubstituted $C_{1-4}$ alkyl, or substituted or unsubstituted $C_{1-4}$ alkenyl; and $R^b$ is hydrogen, halogen, or $-OR^1$ (where $R^1$ is as defined in formula (I) and preferably is hydrogen or $C_{1-4}$ alkyl).

In one embodiment of formula (VI), $Ar^1$ is a substituted or unsubstituted phenyl and $Ar^2$ is substituted or unsubstituted phenyl, or a substituted or unsubstituted 5- or 6-membered heteroaryl, where $R^c$ is hydrogen or $-CO_2R^1$.

In one embodiment of formula (VI), $Ar^1$ is a substituted or unsubstituted phenyl and $Ar^2$ is substituted or unsubstituted phenyl, or a substituted or unsubstituted 5- or 6-membered heteroaryl, where $R^c$ is hydrogen or $-CO_2Me$.

In one embodiment of any of formulae (I-XIII), $Ar^2$ is a substituted or unsubstituted phenyl, having 0 to 5 substituents as defined in formula (I).

In one preferred embodiment of formulae (VIII, IX, and XIII), $Ar^2$ is a substituted or unsubstituted phenyl.

In one embodiment of any of formulae (I-XIII), $Ar^2$ is a substituted or unsubstituted naphthalyl, having 0 to 5 substituents as defined in formula (I).

In one embodiment of any of formulae (I-XIII), $Ar^2$ is a substituted or unsubstituted 5- to 10-membered heteroaryl, having 0 to 5 substituents as defined in formula (I).

In one embodiment of any of formulae (III, IV, V, and XI), $Ar^2$ is substituted or unsubstituted 5- to 10-membered monocyclic or bicyclic heteroaryl with 0 to 4 substituents.

In one embodiment of any of the formulae (III-V, XI, XX-CXXIX and CXXX) where L is a bond, $Ar^2$ is 5- to 10-membered monocyclic or bicyclic heteroaryl ring system, where one ring heteroatom is located alpha (ortho) to the biaryl bond.

In one embodiment of any of the formulae (III-V, XI, XX-CXXIX and CXXX) where L is a bond, $Ar^2$ is 5- to 10-membered monocyclic or bicyclic heteroaryl ring system containing one or more ring nitrogen atoms, and where one or more ring nitrogen atoms is located alpha (ortho) to the biaryl bond.

In one embodiment, in any of the formulae (I-XIII), $Ar^2$ is a substituted or unsubstituted 5- to 10-membered heteroaryl selected from the group consisting of pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl and thienyl.

In one embodiment, in any of the formulae (I-XIII), $Ar^2$ is substituted or unsubstituted 6-membered heteroaryl with 1 to 2 nitrogen atoms and with 0 to 2 substituents independently selected from the group consisting of halogen, unsubstituted or substituted $C_{1-6}$ alkyl, unsubstituted or substituted $C_{1-6}$ alkenyl, unsubstituted or substituted $C_{1-6}$ alkynyl, $=O$, $-CN$, $-NO_2$$-OR^{10}$, $-C(O)R^{10}$, $-C(O)NR^{10}R^{11}$, $-NR^{10}C(O)R^{11}$, $-NR^{11}R^{12}$, $-SR^{10}$, $-S(O)R^{10}$, $-S(O)_2R^{10}$, $-S(O)_2NR^{11}R^{12}$, $-NR^{10}S(O)_2R^{11}$, $-OC(O)R^{10}$, $-CO_2R^{10}$, $-OC(O)NR^{11}R^{12}$, $-NR^{10}C(O)NR^{11}R^{12}$, $-NR^{10}CO_2R^{11}$, unsubstituted or substituted 5- or 6-membered heteroaryl and unsubstituted or substituted 3- to 7-membered heterocyclyl. In this embodiment, $Ar^2$ can be any chemically allowed regioisomer of pyridyl, pyrimidinyl, pyridazinyl, pyrazinyl and the like, and their respective N-oxides.

In one embodiment in any of the formulae (I-XIII), $Ar^2$ is a substituted or unsubstituted 6-membered heteroaryl with 1 to 2 nitrogen atoms and with 0 to 2 substituents independently selected from the group consisting of halogen, substituted $C_{1-6}$ alkyl (but not $C_{1-6}$ haloalkyl), unsubstituted or substituted $C_{1-6}$ alkenyl, unsubstituted or substituted $C_{1-6}$ alkynyl, $=O$, $-CN$, $-C(O)R^{10}$, $-C(O)NR^{10}R^{11}$, $-NR^{10}C(O)R^1$, $-NR^{11}R^{12}$, $-SR^{10}$, $-S(O)R^{10}$, $-S(O)_2R^{10}$, $-S(O)_2NR^{11}R^{12}$, $-NR^{10}S(O)_2R^{11}$, $-OC(O)R^{10}$, $-CO_2R^{10}$ (but not $-CO_2H$), $-OC(O)NR^{11}R^{12}$, $-NR^{10}C(O)NR^{11}R^{12}$, $-NR^{10}CO_2R^{11}$, unsubstituted or substituted 5- or 6-membered heteroaryl and a unsubstituted or substituted 3- to 7-membered heterocyclyl. Preferred substituents include chlorine, $=O$, $-CN$, $-SCH_3$, $-SO_2CH_3$. In this embodiment, $Ar^2$ can be any chemically allowed regioisomer of pyridyl, pyrimidinyl, pyridazinyl, pyrazinyl and the like, and their respective N-oxides.

In one embodiment, in any of the formulae (I-XIII), $Ar^2$ is substituted or unsubstituted 6-membered heteroaryl with 1 to 2 nitrogen atoms and optionally with 1 or 2 substituents independently selected from the group consisting of halogen, unsubstituted or substituted $C_{1-6}$ alkyl, unsubstituted or substituted $C_{1-6}$ alkenyl, unsubstituted or substituted $C_{1-6}$ alkynyl, $=O$, $-CN$, $-NO_2$, $-OR^{10}$, $-C(O)R^{10}$, $-C(O)NR^{10}R^{11}$, $-NR^{10}C(O)R^{11}$, $-NR^{11}R^{12}$, $-SR^{10}$, $-S(O)R^{10}$, $-S(O)_2R^{10}$, $-S(O)_2NR^{11}R^{12}$, $-NR^{10}S(O)_2R^{11}$, $-OC(O)R^{10}$, $-CO_2R^{10}$, $-OC(O)NR^{11}R^{12}$, $-NR^{10}C(O)NR^{11}R^{12}$, $-NR^{10}CO_2R^{11}$, 5- or 6-membered heteroaryl and a 3- to 7-membered heterocyclyl. In this embodiment, $Ar^2$ can be any chemically allowed regioisomer of pyridyl, pyrimidinyl, pyridazinyl, pyrazinyl and the like, and their respective N-oxides.

In one embodiment in any of the formulae (I-XIII), $Ar^2$ is substituted or unsubstituted 6-membered heteroaryl with 1 to 2 nitrogen atoms and with 0 to 2 substituents independently selected from the group consisting of unsubstituted $C_{1-6}$ alkyl, $=O$, $C_{1-6}$ haloalkyl, $-COOH$, $-NO_2$, or $-OR^{10}$. In this embodiment, $Ar^2$ can be any chemically allowed regioisomer of pyridyl, pyrimidinyl, pyridazinyl, pyrazinyl and the like, and their respective N-oxides.

In one embodiment in any of the formulae (I-XIII), $Ar^2$ is substituted or unsubstituted 6-membered heteroaryl with 1 to 2 nitrogen atoms and with 0 to 2 substituents independently selected from the group consisting of $-CH_3$, $=O$, $-CH_3$, $-OCH_3$. In this embodiment, $Ar^2$ can be any chemically allowed regioisomer of pyridyl, pyrimidinyl, pyridazinyl, pyrazinyl and the like, and their respective N-oxides.

In one embodiment of formula (I-XIII), $Ar^2$ is a substituted or unsubstituted fused 5,6-ring and 6,6-ring heteroaryl selected from the group which includes isoquinolinyl, quinolizinyl, pyrrolizinyl, quinoxalinyl, quinazolinyl, cinnolinyl, phthalazinyl, benzotriazinyl, purinyl, benzimidazolyl, benzopyrazolyl, isoquinolinyl, quinolizinyl, benzotriazolyl, benzisoxazolyl, isobenzofuryl, isoindolyl, indolizinyl, thienopyridinyl, thienopyrimidinyl, pyrazolopyrimidinyl, pyrazolopyridinyl, imidazopyridinyl, pyridinopyridinyl, pyridinopyrimidinyl, pyridinopyridizinyl, pyridinopyrazinyl, pyrazolopyridinyl, triazolopyridinyl, pyrrolopyrazinyl, imidazotriazinyl, imidazopyrimidinyl, naphthyridinyl, benzothiazolyl, benzofuranyl, benzothienyl, indolyl, azaindolyl, benzopyrrolyl, benzisoxazolyl, benzisothiazolyl, quinolyl, isoquinolyl, indazolyl, pteridinyl, azaindolyl, benzopyrrolyl, benzisoxazolyl, benzisothiazolyl, and the like.

In one embodiment of each of the formulae (I-XIII), $Ar^2$ is a substituted or unsubstituted 5- to 10-membered heteroaryl with 1 to 4 nitrogen atoms and with 0 to 4 substituents independently selected from the group consisting of halogen, unsubstituted or substituted $C_{1-6}$ alkyl, unsubstituted or substituted $C_{2-6}$ alkenyl, unsubstituted or substituted $C_{2-6}$ alkynyl, =O, —CN, —NO$_2$—OR$^{10}$, —C(O)R$^{10}$, —C(O)NR$^{10}$R$^{11}$, —NR$^{10}$C(O)R$^{11}$, —NR$^{11}$R$^{12}$, —SR$^{10}$, —S(O)R$^{10}$, —S(O)$_2$R$^{10}$, —S(O)$_2$NR$^{11}$R$^{12}$, —NR$^{10}$S(O)$_2$R$^{11}$, —OC(O)R$^{10}$, —CO$_2$R$^{10}$, —OC(O)NR$^{11}$R$^{12}$, —NR$^{10}$C(O)NR$^{11}$R$^{12}$, —NR$^{10}$CO$_2$R$^{11}$, unsubstituted or substituted 5- or 6-membered heteroaryl and a unsubstituted or substituted 3- to 7-membered heterocyclyl.

In one embodiment of any of formulae (I-XIII), $Ar^2$ is a substituted or unsubstituted 6-membered heteroaryl selected from the group consisting of pyridyl, pyridazinyl, pyrazinyl, pyrimidinyl, and triazinyl.

In one embodiment of any of formulae (I-XIII), $Ar^2$ is a substituted or unsubstituted 5-membered heteroaryl selected from the group consisting of isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl.

In one embodiment in formulae (VIII, IX, and XIII), suitable 6-membered ring heteroaryl systems as substituents on $Ar^2$ include pyridyl, pyridazinyl, pyrazinyl, pyrimidinyl and triazinyl.

In one embodiment in formulae (VIII, IX, and XIII), suitable 5-membered ring heteroaryl systems as substituents on $Ar^2$ include isothiazolyl, pyrazolyl, imidazolyl, triazolyl, tetrazolyl, oxazolyl, isoxazolyl, oxadiazolyl, thiadiazolyl, pyrrolyl and thiazolyl.

In one embodiment of any of formulae (I-XIII), $Ar^2$ is any substituted or unsubstituted chemically allowed regioisomers of pyridyl, pyrimidinyl, pyridazinyl, pyrazinyl and the like and their respective N-oxides.

In one embodiment of any of formulae (I-XIII), $Ar^2$ is a substituted or unsubstituted 2-pyridyl.

In one embodiment of any of formulae (I-XIII), $Ar^2$ is a substituted or unsubstituted 2-pyridyl-N-oxide.

In one embodiment of any of formulae (I-XIII), $Ar^2$ is a substituted or unsubstituted 3-pyridyl.

In one embodiment of any of formulae (I-XIII), $Ar^2$ is a substituted or unsubstituted 3-pyridyl-N-oxide.

In one embodiment of any of formulae (I-XIII), $Ar^2$ is a substituted or unsubstituted 4-pyridyl.

In one embodiment of any of formulae (I-XIII), $Ar^2$ is a substituted or unsubstituted 4-pyridyl-N-oxide.

In one preferred embodiment of any of formulae (I-XIII), $Ar^2$ is a substituted or unsubstituted 2-pyridyl, 3-pyridyl or 4-pyridyl ring.

In one preferred embodiment of each of formulae (I-XIII), $Ar^2$ is a substituted or unsubstituted 3-pyridazinyl, 4-pyridazinyl, 5-pyridazinyl, 6-pyridazinyl, 2-pyrazinyl, 3-pyrazinyl, 5-pyrazinyl, 6-pyrazinyl, 2-pyrimidinyl, 4-pyrimidinyl, 5-pyrimidinyl or 6-pyrimidinyl ring.

In one embodiment of any of formulae (I-XIII), $Ar^2$ is pyridinyl with from 0 to 3 substituents; pyrimidinyl with from 0 to 3 substituents; pyrazinyl with from 0 to 3 substituents; or pyridazinyl with from 0 to 3 substituents (especially, where one ring nitrogen has a =O substituent).

In one embodiment of any of formulae (I-XIII), $Ar^2$ has from 0 to 3 substituents; (and in one particular embodiment, one ring nitrogen has a =O substituent).

In one embodiment of any of formulae (I-XIII), $Ar^2$ is pyrazolyl with from 0 to 3 substituents; or imidazolyl with from 0 to 3 substituents.

In one preferred embodiment of each of formulae (I-XIII), $Ar^2$ is a substituted or unsubstituted N-pyrazolyl, 3-pyrazolyl, 4-pyrazolyl, 5-pyrazolyl, 2-imidazolyl, 4-imidazolyl or 5-imidazolyl.

In one embodiment of any of formulae (I-XIII), $Ar^2$ is a substituted or unsubstituted pyrazolyl.

In one embodiment of any of formulae (I-XIII), $Ar^2$ is tetrazolyl with 0 or 1 substituents.

In one embodiment of any of formulae (I-XIII), $Ar^2$ is a substituted or unsubstituted imidazolyl.

In one embodiment of any of formulae (I-XIII), $Ar^2$ is imidazolyl with 0 or 1 substituents.

In one embodiment of any of formulae (I-XIII), $Ar^2$ is a substituted or unsubstituted thiazolyl.

In one embodiment of any of formulae (I-XIII), $Ar^2$ is a substituted or unsubstituted triazolyl.

In one embodiment of any of formulae (I-XIII), $Ar^2$ is a substituted or unsubstituted $C_{6-10}$ aryl or substituted or unsubstituted 5- to 10-membered heteroaryl selected from pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

In one embodiment of any of formulae (I-XIII), $Ar^2$ is a substituted or unsubstituted $C_{6-10}$ aryl selected from phenyl or naphthalenyl or is a substituted or unsubstituted 5- to 10-membered heteroaryl selected from the group which includes isoquinolinyl, quinolizinyl, pyrrolizinyl, quinoxalinyl, quinazolinyl, cinnolinyl, phthalazinyl, benzotriazinyl, purinyl, benzimidazolyl, benzopyrazolyl, isoquinolinyl, quinolizinyl, benzotriazolyl, benzisoxazolyl, isobenzofuryl, isoindolyl, indolizinyl, thienopyridinyl, thienopyrimidinyl, pyrazolopyridinyl, pyrazolopyrimidinyl, imidazopyridinyl, pyridinopyridinyl, pyridinopyrimidinyl, pyridinopyridizinyl, pyridinopyrazinyl, pyrrolopyrazinyl, imidazotriazinyl, imidazopyrimidinyl, triazolopyridinyl, naphthyridinyl, benzothiazolyl, benzofuranyl, benzothienyl, indolyl, azaindolyl, benzopyrrolyl, benzisoxazolyl, benzisothiazolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl, thienyl, azaindolyl, benzopyrrolyl, benzisoxazolyl, benzisothiazolyl, and the like.

In one embodiment of any of formulae (I-XIII), $Ar^2$ is monocyclic.

In one embodiment of any of formulae (I-XIII), $Ar^2$ is a fused bicyclic.

In one embodiment in any of the formulae (I-XIII), at least one substituent on the group $Ar^2$ is cyano.

In one embodiment in any of the formulae (I-XIII), at least one substituent on the group $Ar^2$ is —S(O)$_2$R$^7$. In one particular embodiment, $R^7$ is methyl.

In one embodiment in any of the formulae (I-XIII), at least one substituent on the group $Ar^2$ is halogen, particularly chlorine.

In one embodiment in any of the formulae (I-XIII), at least one substituent on the group $Ar^2$ is —$OR^7$. In one particular embodiment, $R^7$ is methyl.

In one embodiment in any of the formulae (I-XIII), at least one substituent on the group $Ar^2$ is —$SR^7$. In one particular embodiment, $R^7$ is methyl.

In one embodiment in any of the formulae (I-XIII), at least one substituent on the group $Ar^2$ is unsubstituted $C_{1-6}$ alkyl (in particular methyl) or $C_{1-6}$ haloalkyl (in particular —$CF_3$).

In one embodiment in any of the formulae (I-XIII), at least one substituent on the group $Ar^2$ is substituted $C_{1-6}$ alkyl (preferably not $C_{1-6}$ haloalkyl).

In one embodiment of any of the formulae (I-XIII), at least one substituent on the group $Ar^2$ is a heterocyclyl selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment in any of the formulae (I-XIII), no substituents, except hydrogen, exist on the group $Ar^2$.

In one embodiment of any of the formulae (I-XIII), $Ar^2$ is a substituted or unsubstituted 3- to 10-membered heterocycle, having 0 to 3 substituents as defined in formula (I).

In one embodiment of any of the formulae (I-XIII), $Ar^2$ is a substituted or unsubstituted 3- to 10-membered heterocycle selected from the group consisting of pyrimidine, pyrrolidine, piperidine, imidazolidine, pyrazolidine, butyrolactam, valerolactam, imidazolidinone, hydantoin, dioxolane, phthalimide, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of any of the formulae (I-XIII), $Ar^2$ is a substituted or unsubstituted 3- to 10-membered heterocycle selected from the group consisting of pyrimidine, pyrrolidine, piperidine, imidazolidine, pyrazolidine, dioxolane, 1,4-dioxane, morpholine, thiomorpholine, thiomorpholine-S-oxide, thiomorpholine-S,S-dioxide, piperazine, pyran, 3-pyrroline, thiopyran, pyrone, tetrahydrofuran, and tetrahydrothiophene.

In one embodiment of any of the formulae (I-XIII), $Ar^2$ is a substituted or unsubstituted heterocyclic ring system selected from pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S, S-dioxide, piperazine, pyran, pyridone, 3-pyrroline, thiopyran, pyrone, tetrahydrofuran or tetrahydrothiophene. Preferably, $Ar^2$ is selected from substituted and unsubstituted piperidine, substituted and unsubstituted piperazine, and substituted and unsubstituted morpholine.

In one embodiment of any of the formulae (I-XIII), $Ar^2$ is a substituted or unsubstituted heterocyclic ring system selected from pyrrolidine, piperidine, imidazolidine, pyrazolidine, dioxolane, piperidine, 1,4-dioxane, morpholine, thiomorpholine, thiomorpholine-S-oxide, thiomorpholine-S,S-dioxide, piperazine, pyran, 3-pyrroline, thiopyran, pyrone, tetrahydrofuran or tetrahydrothiophene.

In one embodiment of any of formulae (I-XIII), $Ar^2$ is pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S, S-dioxide, piperazine, pyran, pyridone, 3-pyrroline, thiopyran, pyrone, tetrahydrofuran, tetrahydrothiophene.

In one embodiment of any of formulae (I-XIII), $Ar^2$ is pyrrolidine, piperidine, imidazolidine, pyrazolidine, dioxolane, piperidine, 1,4-dioxane, morpholine, thiomorpholine, thiomorpholine-S-oxide, thiomorpholine-S,S-dioxide, piperazine, pyran, 3-pyrroline, thiopyran, pyrone, tetrahydrofuran, tetrahydrothiophene.

In one embodiment of any of formulae (I-XIII), $Ar^2$ is a heterocyclic group represented by formula (AA) below, where formula (AA) is attached via a free valence on either $M^1$ or $M^2$, and where formula AA and the substituents therein are defined in [0029].

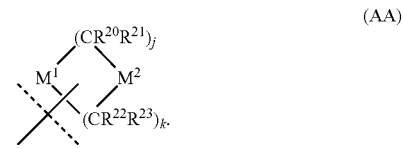

(AA)

In one embodiment of any of formulae (I-XIII), heterocycle groups as substituents on $Ar^2$ include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of any of formulae (I-XIII), heterocycle groups as substituents on $Ar^2$ include pyrrolidine, piperidine, imidazolidine, pyrazolidine, dioxolane, piperidine, 1,4-dioxane, morpholine, thiomorpholine, thiomorpholine-S-oxide, thiomorpholine-S,S-dioxide, piperazine, pyran, 3-pyrroline, thiopyran, pyrone, tetrahydrofuran, and tetrahydrothiophene.

In one embodiment of the formulae (I-IX), $Ar^2$ has one or more substituents selected from the group consisting of:

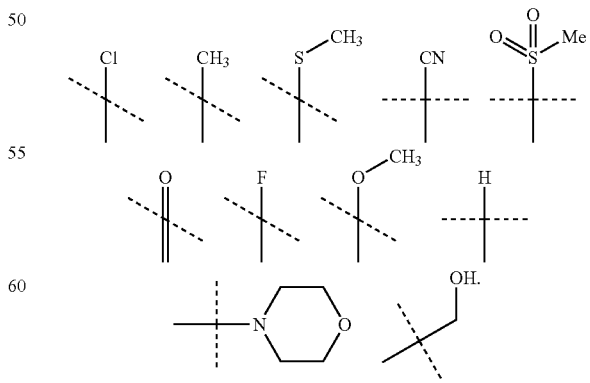

In one embodiment of any of formulae (I-XIII), $Ar^2$ is the following residue:

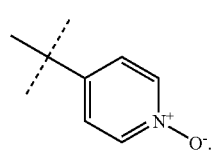

In another embodiment of any of formulae (I-XIII), Ar² is selected from one of the following residues:

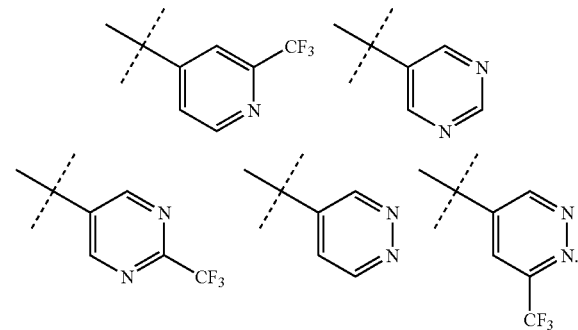

In another embodiment of any of formulae (I-XIII), Ar² is selected from one of the following residues:

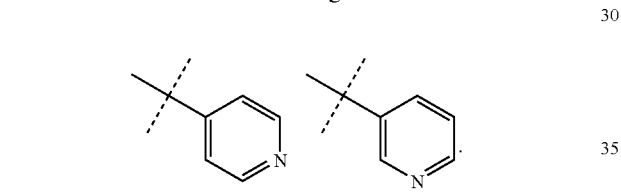

In another embodiment of any of formulae (I-XIII), Ar² is selected from one of the following residues:

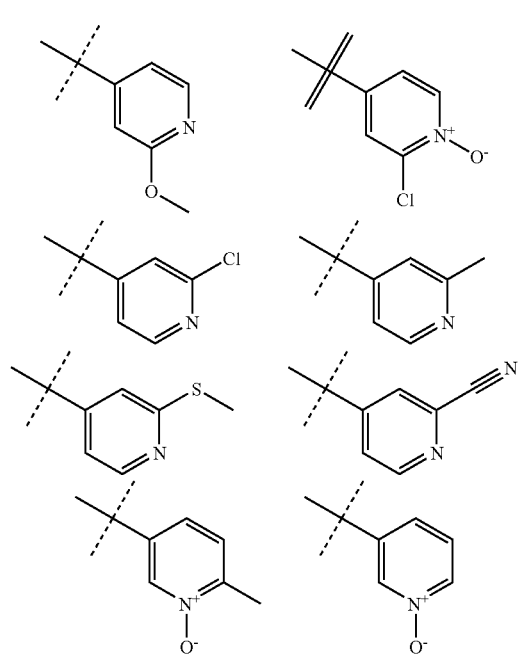

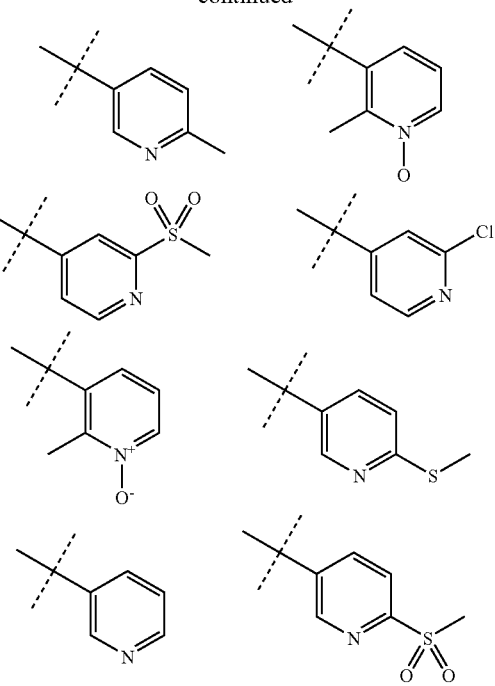

In other embodiments for each of the formulae (I-XIII, and XX-CXXXVI), Ar² is selected from the group consisting of:

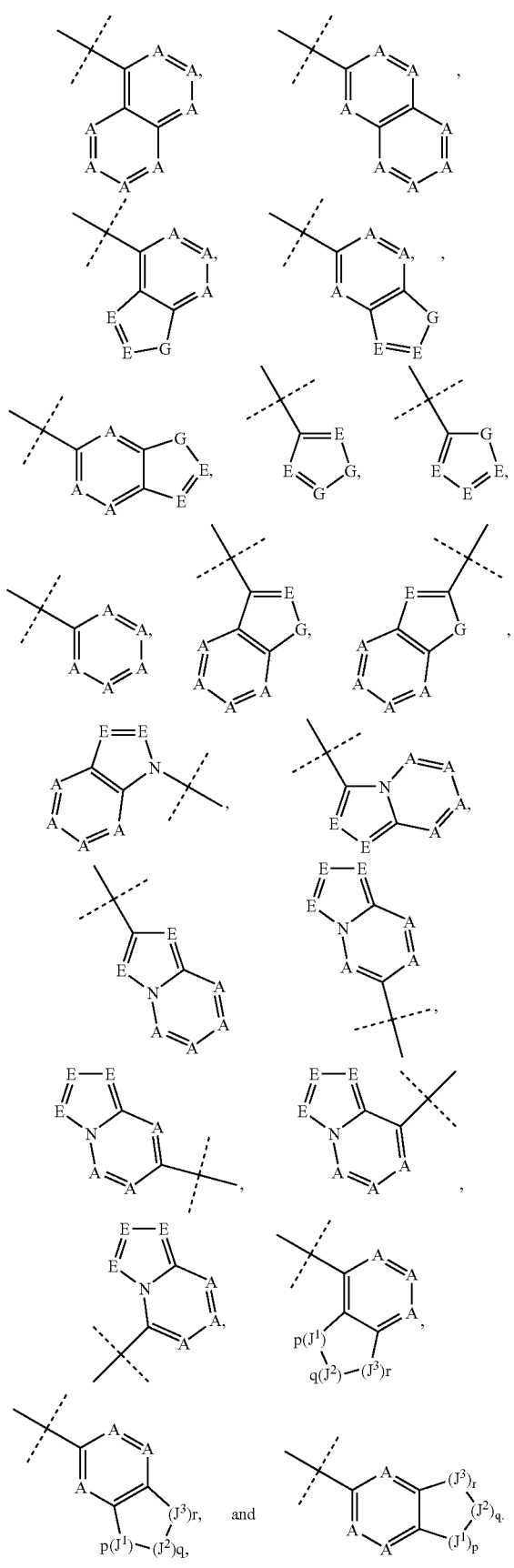
In other embodiments for each of the formulae (I-XIII and XX-CXXXVI), Ar² is selected from the group consisting of:
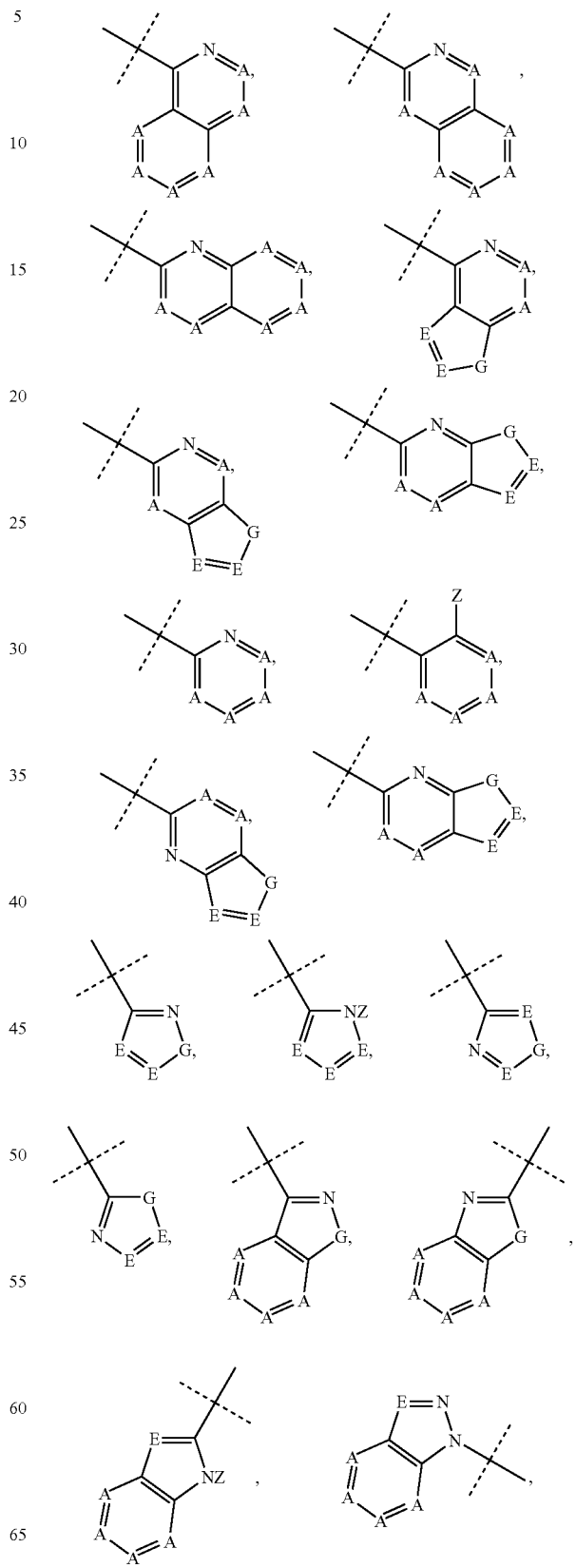

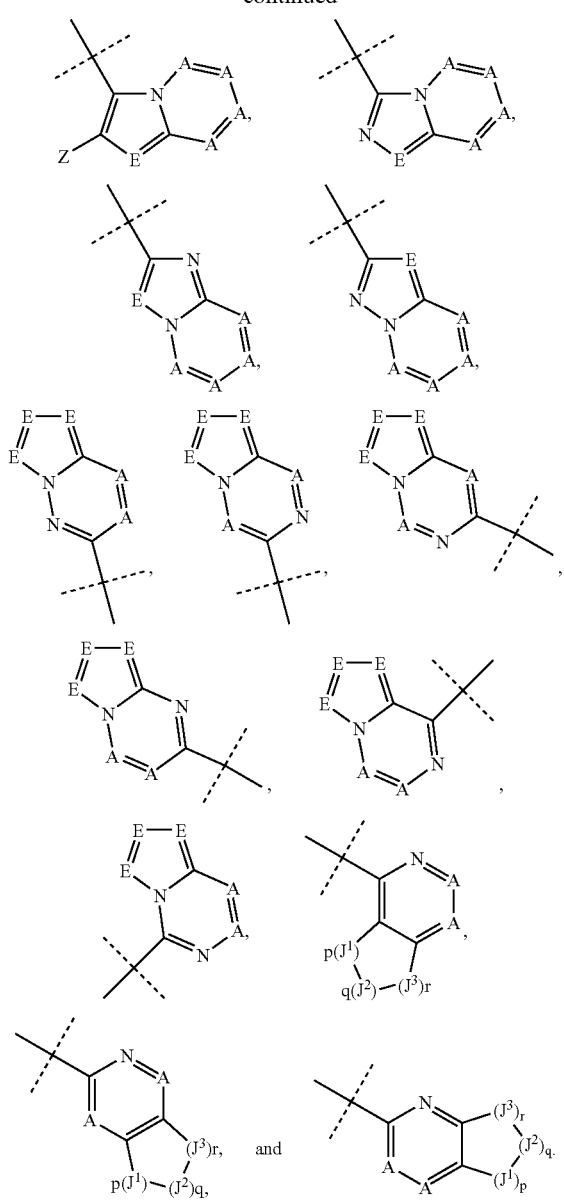

In one embodiment of any of formulae (I-XIII), Ar² has one or more substituents selected from the group consisting of:

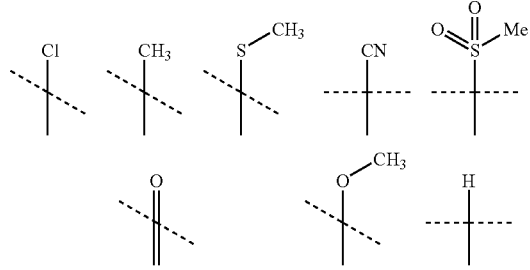

(e.g. N=O, C=O, S=O)

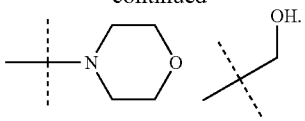

with the proviso that at least one substituent is other than hydrogen. In another embodiment, all substituents on Ar² are hydrogen.

In one embodiment of formula (II, IV, VII, and IX), at least one of $X^1$, $X^2$, $X^3$, $X^4$, and $X^5$ is other than hydrogen.

In one embodiment of formula (II, IV, VII, and IX), $X^1$ is other than hydrogen and at least 2 of $X^2$, $X^3$, $X^4$, and $X^5$ are hydrogen. Preferably, at least 3 of $X^2$, $X^3$, $X^4$, and $X^5$ are hydrogen; more preferably, $X^2$, $X^3$, $X^4$, and $X^5$ are hydrogen; also more preferably $X^2$, $X^3$, and $X^5$ are hydrogen.

In one embodiment of any of formulae (II, IV, V, VII, IX and XX-CXXXVI), any one of $X^1$, $X^2$, $X^3$, $X^4$, $X^5$, $X^a$, and $X^b$ may be a heterocyclic group represented by formula (AA) below, where formula (AA) is attached via a free valence on either $M^1$ or $M^2$, and where formula (AA) and the substituents therein are defined in [0029].

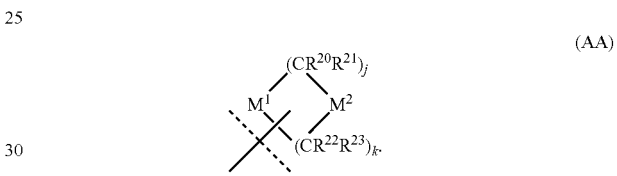

(AA)

In one embodiment, in each of formulae (II, IV, V, VII, IX and XX-CXXXVI), $X^1$, $X^2$, $X^3$, $X^4$, $X^5$, $X^a$, and $X^b$ are each independently selected from the group consisting of hydrogen, halogen, —CN, —NO₂, —OH, —OR³, —C(O)R³, —CO₂R³, —O(CO)R³, —OC(O)NR³R⁴, —SR³, —S(O)R³, —S(O)₂R³, —NR³R³, —NR⁵C(O)R³, —NR⁵C(O)₂R³, —NR⁵C(O)NR³R⁴, —NR⁵S(O)₂R³, —S(O)₂NR³R⁴, substituted or unsubstituted C₁₋₈ alkyl, substituted or unsubstituted C₂₋₈ alkenyl, substituted or unsubstituted C₂₋₈ alkynyl, substituted or unsubstituted phenyl, substituted or unsubstituted 5- or 6-membered heteroaryl, and substituted or unsubstituted 4- to 7-membered heterocyclyl.

In one embodiment, in each of formulae (II, IV, V, VII, IX and XX-CXXXVI), $X^1$, $X^2$, $X^3$, $X^4$, $X^5$, $X^a$, and $X^b$ are each independently selected from the group consisting of hydrogen, halogen, —CN, —NO₂, —OH, —OR³, —C(O)R³, —CO₂R³, —O(CO)R³, —OC(O)NR³R⁴, —SR³, —S(O)R³, —S(O)₂R³, —NR³R³, —S(O)₂NR³R⁴, substituted or unsubstituted C₁₋₈ alkyl, substituted or unsubstituted C₂₋₈ alkenyl, substituted or unsubstituted C₂₋₈ alkynyl, substituted or unsubstituted phenyl, substituted or unsubstituted 5- or 6-membered heteroaryl, and substituted or unsubstituted 4- to 7-membered heterocyclyl.

In one embodiment of any of formulae (II, IV, V, VII, IX and XX-CXXXVI), $X^1$, $X^a$, and $X^b$ are each independently selected from the group consisting of hydrogen, halogen, —NO₂, —OR³, —C(O)R³, —S(O)₂R³, —NR³R⁴, substituted or unsubstituted C₁₋₈ alkyl, substituted or unsubstituted phenyl, substituted or unsubstituted 5- or 6-membered heteroaryl, and substituted or unsubstituted 5- or 6-membered heterocyclyl. In one preferred embodiment, $X^a$ or $X^2$ is hydrogen. In another, $X^a$ or $X^2$ is fluorine, chlorine, —CN, or —CF₃.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is substituted or unsubstituted heterocyclic group selected from the group consisting of pyrrolidinyl, piperidinyl, piperazinyl, morpholinyl, 1,3-dioxalanyl, thiomorpholinyl, thiomorpholinyl-S,S-dioxide, piperazinyl and pyranyl.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is a substituted $C_{1-8}$ alkyl, where suitable substituents are as defined for formula (II). Preferably, the substituent is a substituted or unsubstituted heterocyclic group of the formula (AA) as defined in paragraph [0029], [0030] and [0031]. More preferably, the substituent is selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of each of the formulae (II, IV, V, VII, IX and XX-CXXXVI), when a heterocyclic group represented by formula (AA) is present, $R^{20}$, $R^{21}$, $R^{22}$, $R^{23}$, $R^{24}$, $R^{25}$, and $R^{26}$ are independently hydrogen or $C_{1-4}$alkyl. In another preferred embodiment, at least three of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4. In another preferred embodiments, at least five of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is a substituted $C_{1-8}$ alkyl, where suitable substituents are as defined for formula (II). In one preferred embodiment, the substituted $C_{1-8}$ alkyl is substituted with a 5- or 6-membered heteroaryl selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl. More preferably, the substituted $C_{1-8}$ alkyl is substituted with oxazolyl.

In one embodiment of each of the formulae (II, IV, V, VII, IX and XX-CXXXVI), a suitable substituent for substituted $C_{1-8}$ alkyl (as X, $X^1$, $X^2$, $X^3$, $X^4$, $X^5$, $X^a$, $X^b$, or X) can be selected from the group consisting of —CN, —$OR^1$, —C(O)$R^1$, —$CO_2R^1$, —O(CO)$R^1$, —$SO_2R^1$ and halogen.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is an unsubstituted $C_{1-8}$ alkyl.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is t-butyl.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is oxazolyl.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is trifluoromethoxy.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is —$SO_2R^3$.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is isopropyl.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is a cyano, halogen or trifluoromethyl group.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is —$C(Me)_2CH_2OH$.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is —C(O)Me.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is —$(CH_2)_2CO_2Me$.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is isoamyl.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is 1-3,dioxalanyl.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is furyl.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is pyrazolyl.

In one embodiment of each of the formulae (II, IV, V, VII, IX and XX-CXXXVI), at least one of $X^a$, $X^b$, $X^1$, $X^2$, $X^3$, $X^4$, $X^5$ or at least one X is thienyl.

In one embodiment of paragraphs [0165] to [00179], the remaining substituents are hydrogen. In another embodiment, the remaining substituents are selected from the group consisting of hydrogen, halogen, cyano, or trifluoromethyl.

In one embodiment of formula (II, IV, V, VII, IX and XX-CXXXVI), at least one of $X^1$, $X^2$, $X^3$, $X^4$, and $X^5$ is other than hydrogen.

In one embodiment of formula (II, IV, V, VII, IX and XX-CXXXVI), $X^1$ is other than hydrogen and at least 2 of $X^2$, $X^3$, $X^4$, and $X^5$ are hydrogen. Preferably, at least 3 of $X^2$, $X^3$, $X^4$, and $X^5$ are hydrogen; more preferably, $X^2$, $X^3$, $X^4$, and $X^5$ are hydrogen.

In one embodiment of each of the formulae (II, IV, V, VII, IX and XX-CXXXVI), at least one of $X^1$, $X^a$, and $X^b$ is a substituted or unsubstituted 5- or 6-membered heteroaryl ring selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl.

In one embodiment of each of the formulae (II, IV, V, VII, IX and XX-CXXXVI), at least one of $X^1$, $X^a$, and $X^b$ is a substituted or unsubstituted 5- or 6-membered heterocyclic ring, and the heterocycle is selected from the group consisting of pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of each of the formulae (II, IV, V, VII, IX and XX-CXXXVI), at least one of X, $X^1$, $X^2$, $X^3$, $X^4$, $X^5$, $X^a$, and $X^b$ are independently selected from the group consisting of:

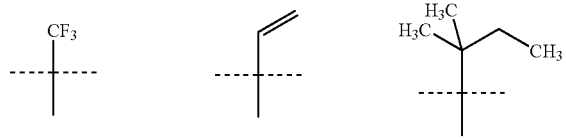

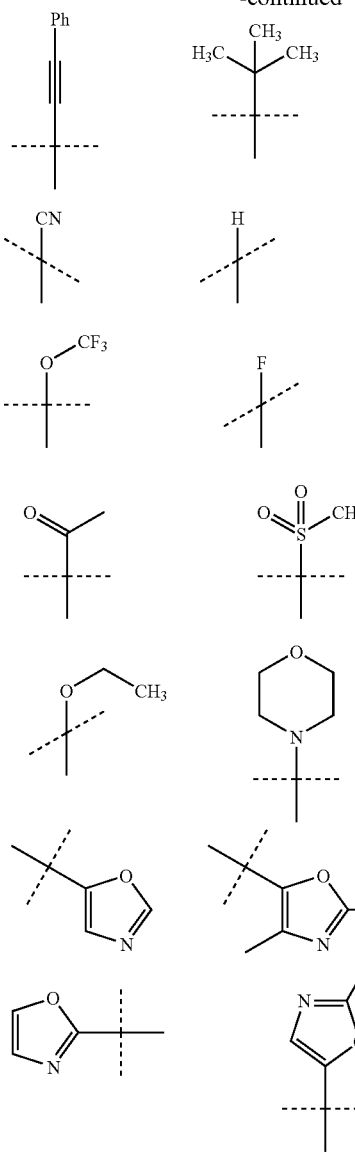
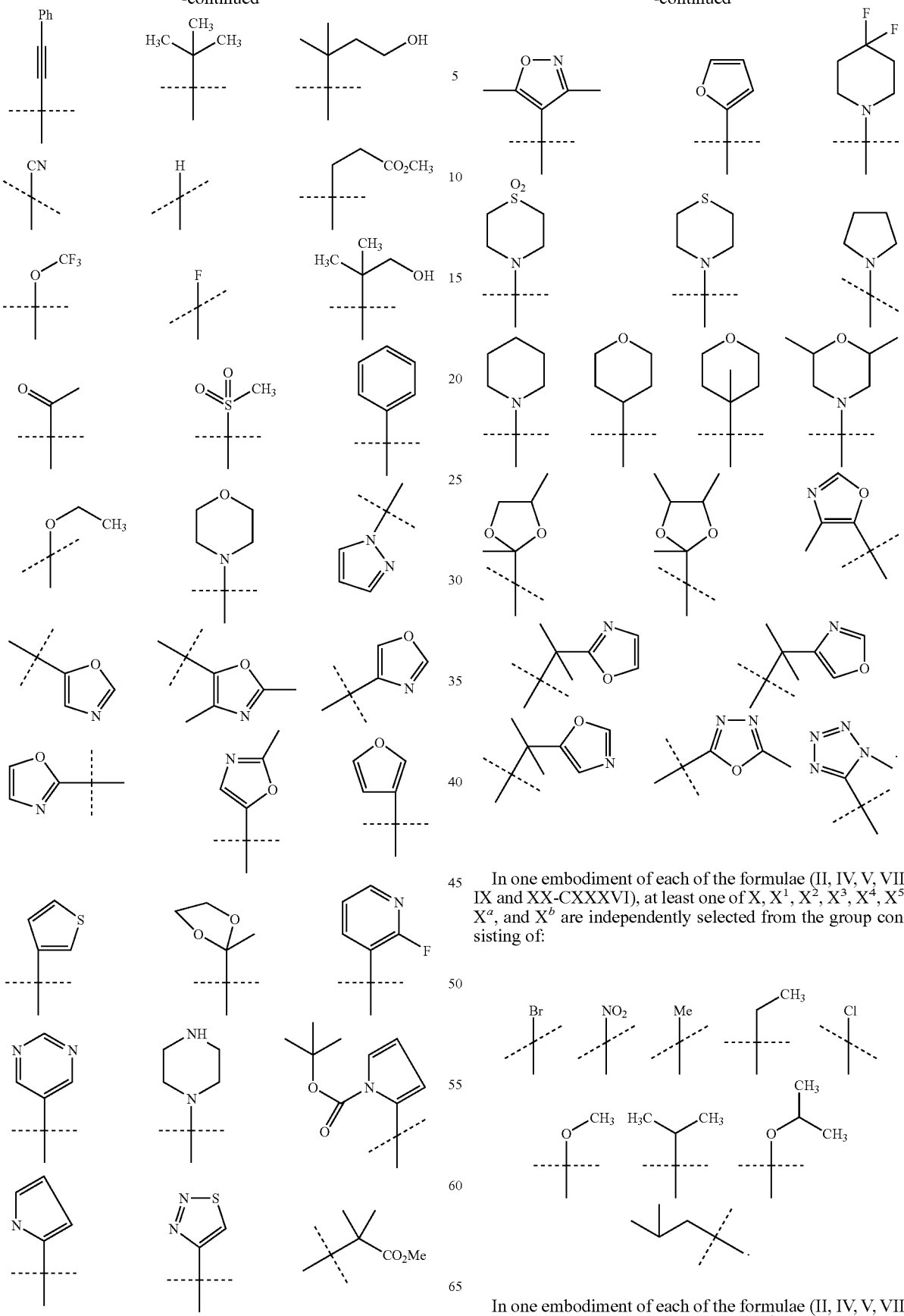
In one embodiment of each of the formulae (II, IV, V, VII, IX and XX-CXXXVI), at least one of X, $X^1$, $X^2$, $X^3$, $X^4$, $X^5$, $X^a$, and $X^b$ are independently selected from the group consisting of:
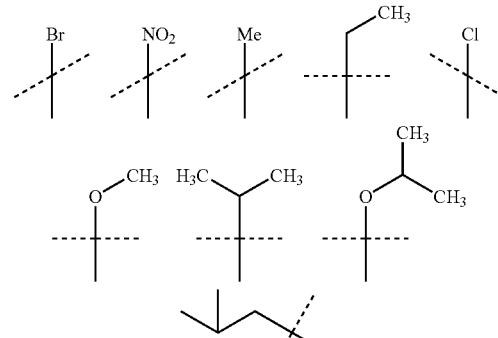
In one embodiment of each of the formulae (II, IV, V, VII, IX and XX-CXXXVI), X, $X^1$, $X^a$, and $X^b$ are independently selected from the group consisting hydrogen, —OMe, —O$^i$Pr, —OEt, ethyl, methyl, iso-propyl, isoamyl, or —CF$_3$ with the proviso that at least one substituent is other than hydrogen.

In one embodiment of each of the formulae (II, IV, V, VII, IX and XX-CXXXVI), $X^1$, $X^a$, and $X^b$ are independently selected from the group consisting of hydrogen, —S(O)$_2$R$^3$, —NR$^5$C(O)NR$^3$R$^4$, —NR$^5$S(O)$_2$R$^3$, —S(O)$_2$NR$^3$R$^4$, substituted C$_{1-8}$ alkyl (but not C$_{1-8}$ haloalkyl), substituted C$_{2-8}$ alkenyl, substituted C$_{2-8}$ alkynyl, substituted or unsubstituted 5- or 6-membered heteroaryl, or substituted or unsubstituted 4- to 7-membered heterocyclyl, with the proviso that at least one substituent is other than hydrogen.

In one embodiment of each of the formulae (II, IV, V, VII, IX and XX-CXXXVI), $X^1$, $X^a$, and $X^b$ are independently selected such that at least one substituent is unsubstituted C$_{1-8}$ alkyl.

In one embodiment of each of the formulae (II, IV, V, VII, IX and XX-CXXXVI), $X^1$, $X^a$, and $X^b$ are independently selected from the group consisting of hydrogen, —NO$_2$, —OR$^3$, —C(O)R$^3$, —S(O)$_2$R$^3$, —NR$^3$R$^4$, substituted or unsubstituted C$_{1-8}$ alkyl, substituted or unsubstituted phenyl, substituted or unsubstituted 5- or 6-membered heteroaryl, or substituted or unsubstituted 5- or 6-membered heterocyclyl. Preferably, $X^a$ is hydrogen. In another preferred embodiment, $X^a$ is fluorine, chlorine, —CN, —CF$_3$.

In one embodiment of each of the formulae (II, IV, V, VII, IX and XX-CXXXVI), $X^a$ is hydrogen, and $X^b$ is other than hydrogen.

In one embodiment, in each of formulae (II, IV, V, VII, IX, X, XII and XX-CXXXVI), at least one of $X^1$, $X^a$, and $X^b$ is a substituted or unsubstituted C$_{1-8}$ alkyl as defined for formula (VIII). In certain preferred embodiments, $X^a$ or $X^2$ is hydrogen, and $X^1$ and $X^b$ are substituted C$_{1-8}$ alkyl. In certain other preferred embodiments, $X^a$ or $X^2$ is hydrogen, and $X^1$ and $X^b$ are unsubstituted C$_{1-8}$ alkyl.

In one embodiment, in each of formulae (II, IV, V, VII, IX and XX-CXXXVI), at least one of $X^1$, $X^a$, and $X^b$ is a halogen atom, —CF$_3$, —CN, substituted or unsubstituted C$_{1-8}$ alkyl, substituted or unsubstituted 5- or 6-membered heteroaryl, or substituted or unsubstituted 4- to 7-membered heterocyclyl and when an additional $X^1$, $X^a$, and $X^b$ group is present, it is a halogen atom or CF$_3$.

In one embodiment of any of formulae (II, IV, V, VII, IX, X, XII, and XX-CXXXVI), at least one of $X^1$, $X^a$, and $X^b$ is a substituted or unsubstituted 5- or 6-membered heteroaryl ring selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl; and wherein additional $X^1$, $X^2$, $X^3$, $X^4$, $X^5$, $X^a$, and $X^b$, when present, are defined as for formula (II).

In one embodiment of any of formulae (II, IV, V, VII, IX, X, XII, and XX-CXXXVI), at least one of $X^1$, $X^a$, and $X^b$ is a substituted or unsubstituted oxazolyl.

In one embodiment of any of formulae (II, IV, V, VII, IX, X, XII, and XX-CXXXVI), at least one of $X^1$, $X^a$, and $X^b$ is a substituted or unsubstituted morpholinyl.

In one embodiment of any of formulae (II, IV, V, VII, IX and XX-CXXXVI), at least one of $X^1$, $X^a$, and $X^b$ is a substituted or unsubstituted 5- or 6-membered heterocyclic ring, and the heterocycle is selected from the group consisting of pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene; and wherein additional $X^1$, $X^2$, $X^3$, $X^4$, $X^5$, $X^a$, and $X^b$, when present, are defined as for formula (II).

In one embodiment of any of formulae (II, IV, V, VII, IX and XX-CXXXVI), at least one of $X^1$, $X^a$, and $X^b$ is a substituted or unsubstituted 5- or 6-membered heterocyclic ring, and the heterocycle is selected from the group consisting of pyrrolidine, piperidine, imidazolidine, pyrazolidine, dioxolane, piperidine, 1,4-dioxane, morpholine, thiomorpholine, thiomorpholine-S-oxide, thiomorpholine-S,S-dioxide, piperazine, pyran, 3-pyrroline, thiopyran, pyrone, tetrahydrofuran, and tetrahydrothiophene; and wherein additional $X^1$, $X^2$, $X^3$, $X^4$, $X^5$, $X^a$, and $X^b$, when present, are defined as for formula (II).

In one embodiment of any of formulae (II, IV, V, VII, IX, X, XII, and XX-CXXXVI), $X^1$, $X^a$, and $X^b$ are independently selected from the group consisting of:

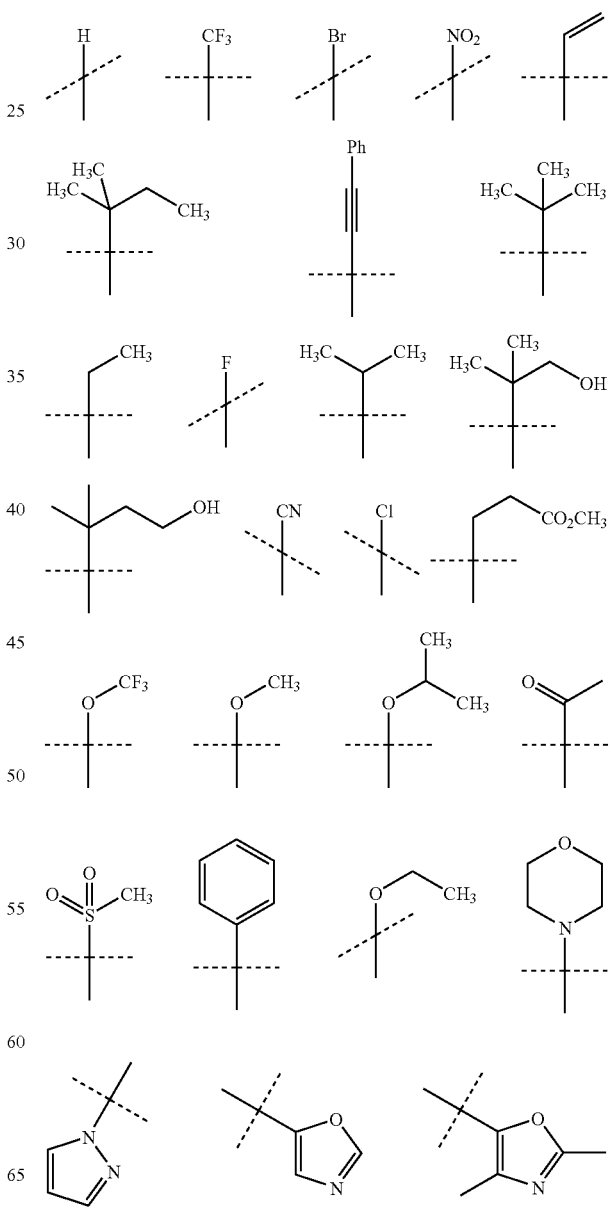

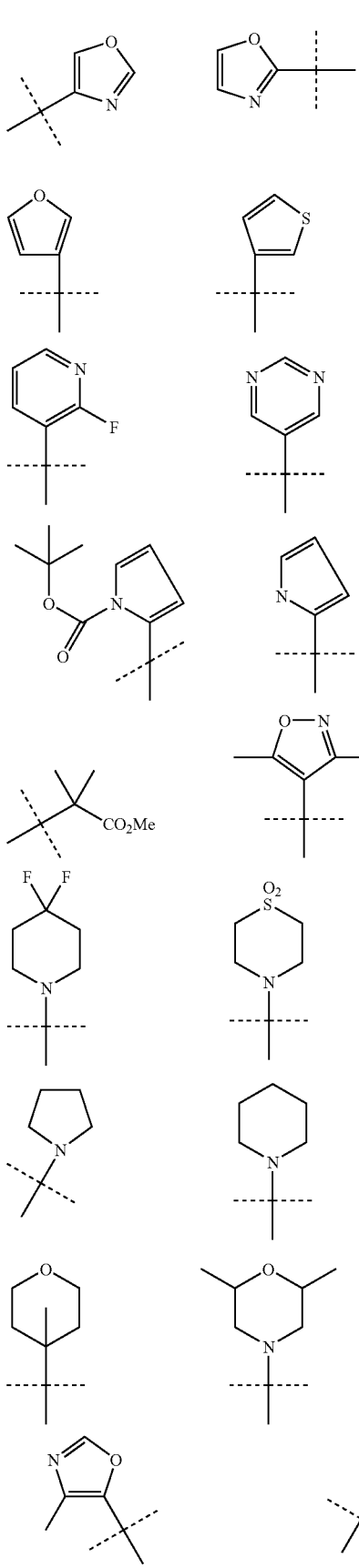
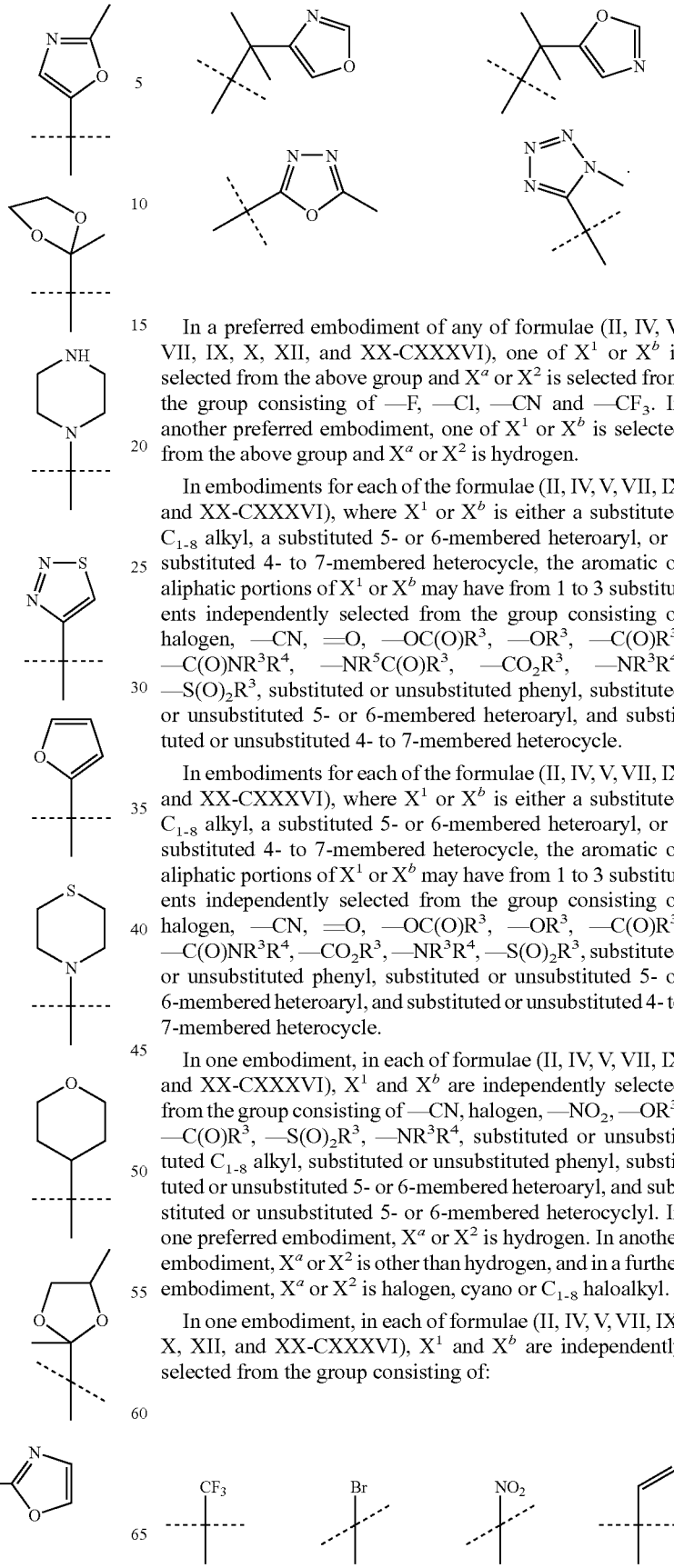

In a preferred embodiment of any of formulae (II, IV, V, VII, IX, X, XII, and XX-CXXXVI), one of $X^1$ or $X^b$ is selected from the above group and $X^a$ or $X^2$ is selected from the group consisting of —F, —Cl, —CN and —CF$_3$. In another preferred embodiment, one of $X^1$ or $X^b$ is selected from the above group and $X^a$ or $X^2$ is hydrogen.

In embodiments for each of the formulae (II, IV, V, VII, IX and XX-CXXXVI), where $X^1$ or $X^b$ is either a substituted $C_{1-8}$ alkyl, a substituted 5- or 6-membered heteroaryl, or a substituted 4- to 7-membered heterocycle, the aromatic or aliphatic portions of $X^1$ or $X^b$ may have from 1 to 3 substituents independently selected from the group consisting of halogen, —CN, =O, —OC(O)R$^3$, —OR$^3$, —C(O)R$^3$, —C(O)NR$^3$R$^4$, —NR$^5$C(O)R$^3$, —CO$_2$R$^3$, —NR$^3$R$^4$, —S(O)$_2$R$^3$, substituted or unsubstituted phenyl, substituted or unsubstituted 5- or 6-membered heteroaryl, and substituted or unsubstituted 4- to 7-membered heterocycle.

In embodiments for each of the formulae (II, IV, V, VII, IX and XX-CXXXVI), where $X^1$ or $X^b$ is either a substituted $C_{1-8}$ alkyl, a substituted 5- or 6-membered heteroaryl, or a substituted 4- to 7-membered heterocycle, the aromatic or aliphatic portions of $X^1$ or $X^b$ may have from 1 to 3 substituents independently selected from the group consisting of halogen, —CN, =O, —OC(O)R$^3$, —OR$^3$, —C(O)R$^3$, —C(O)NR$^3$R$^4$, —CO$_2$R$^3$, —NR$^3$R$^4$, —S(O)$_2$R$^3$, substituted or unsubstituted phenyl, substituted or unsubstituted 5- or 6-membered heteroaryl, and substituted or unsubstituted 4- to 7-membered heterocycle.

In one embodiment, in each of formulae (II, IV, V, VII, IX and XX-CXXXVI), $X^1$ and $X^b$ are independently selected from the group consisting of —CN, halogen, —NO$_2$, —OR$^3$, —C(O)R$^3$, —S(O)$_2$R$^3$, —NR$^3$R$^4$, substituted or unsubstituted $C_{1-8}$ alkyl, substituted or unsubstituted phenyl, substituted or unsubstituted 5- or 6-membered heteroaryl, and substituted or unsubstituted 5- or 6-membered heterocyclyl. In one preferred embodiment, $X^a$ or $X^2$ is hydrogen. In another embodiment, $X^a$ or $X^2$ is other than hydrogen, and in a further embodiment, $X^a$ or $X^2$ is halogen, cyano or $C_{1-8}$ haloalkyl.

In one embodiment, in each of formulae (II, IV, V, VII, IX, X, XII, and XX-CXXXVI), $X^1$ and $X^b$ are independently selected from the group consisting of:

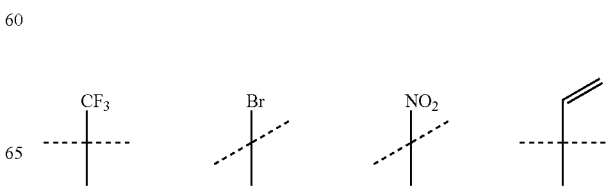

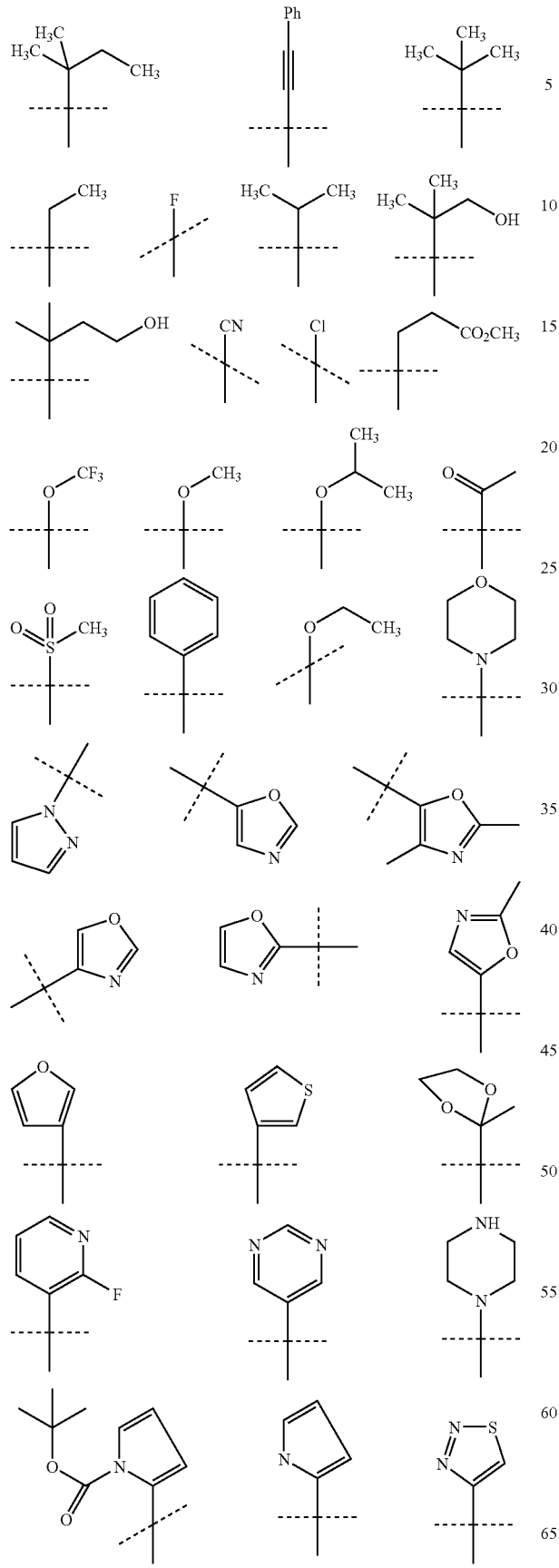
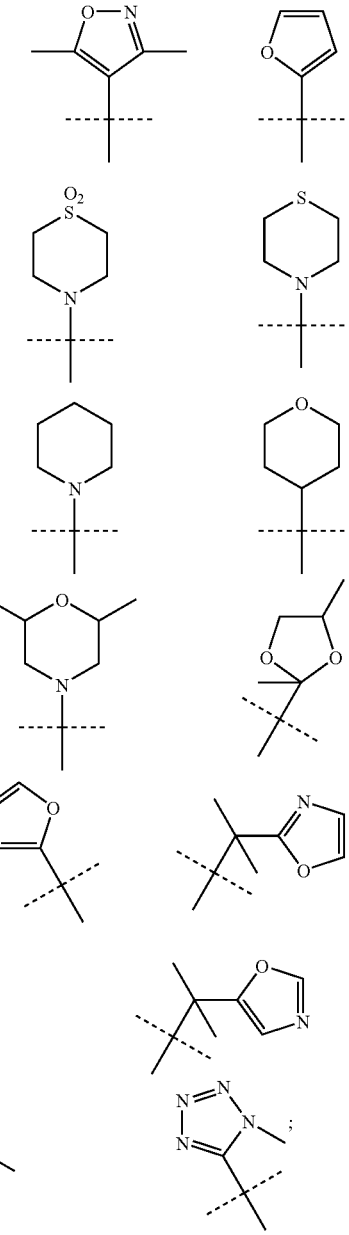

$X^2$ and $X^a$ are selected from either hydrogen or fluorine; and $X^3$, $X^4$ and $X^5$ are hydrogen.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is other than hydrogen.

In one embodiment, in each of formulae (II, IV, V, VII, IX and XX-CXXXVI), each of $X^a$, $X^2$, $X^3$, $X^4$ and $X^5$ is hydrogen and $X^1$ or $X^b$ is hydrogen and the other is $C_{1-8}$ alkyl, optionally having from 1 to 3 substituents independently selected from the group consisting of halogen, —CN, =O, —OC(O)R$^3$, —OR$^3$, —C(O)R$^3$, —C(O)NR$^3$R$^4$, —NR$^4$C(O)R$^3$, —CO$_2$R$^3$, —NR$^3$R$^4$, —SR$^3$, —S(O)R$^3$, —S(O)$_2$R$^3$, —NR$^3$S(O)$_2$R$^4$, substituted or unsubstituted phenyl, and substituted or unsubstituted 5- or 6-membered heteroaryl, and substituted or unsubstituted 4- to 7-membered heterocycle. In other embodiments, one of $X^a$ and $X^2$ is selected from the group consisting of halogen, cyano or $C_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen and $X^1$ or $X^b$ is hydrogen and the other is $C_{1-8}$ alkyl, optionally having from 1 to 3 substituents independently selected from the group consisting of halogen, —CN, =O, —OC(O)R$^3$, —OR$^3$, —C(O)R$^3$, —C(O)NR$^3$R$^4$, —CO$_2$R$^3$, —NR$^3$R$^4$, —SR$^3$, —S(O)R$^3$, —S(O)$_2$R$^3$, substituted or unsubstituted phenyl, and substituted or unsubstituted 5- or 6-membered heteroaryl, and substituted or unsubstituted 4- to 7-membered heterocycle. In other embodiments, one of $X^a$ and $X^2$ is selected from the group consisting of halogen, cyano or $C_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen and $X^1$ or $X^b$ is $C_{6-10}$ aryl or a heteroaryl, optionally having from 1 to 3 substituents independently selected from the group consisting of halogen, —CN, —OH, —OR$^3$, =O, —OC(O)R$^3$, —CO$_2$R$^3$, —C(O)R$^3$, —C(O)NR$^3$R$^4$, —NR$^5$C(O)R$^3$, —NR$^3$R$^4$, —SR$^3$, —S(O)R$^3$, —S(O)$_2$R$^3$, —NR$^5$S(O)$_2$R$^3$, and substituted or unsubstituted $C_{1-8}$ alkyl. In other embodiments, one of $X^a$ and $X^1$ is selected from the group consisting of halogen, cyano and $C_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen and $X^1$ or $X^b$ is $C_{6-10}$ aryl or a heteroaryl, optionally having from 1 to 3 substituents independently selected from the group consisting of halogen, —CN, —OH, —OR$^3$, =O, —OC(O)R$^3$, —CO$_2$R$^3$, —C(O)R$^3$, —C(O)NR$^3$R$^4$, —NR$^3$R$^4$, —SR$^3$, —S(O)R$^3$, —S(O)$_2$R$^3$ and substituted or unsubstituted $C_{1-8}$ alkyl. In other embodiments, one of $X^a$ and $X^1$ is selected from the group consisting of halogen, cyano and $C_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen and $X^1$ or $X^b$ is a 5- or 6-membered heterocyclyl, optionally having 1 to 2 substituents independently selected from the group consisting of substituted or unsubstituted $C_{1-8}$ alkyl, —OR$^3$, —C(O)R$^3$, —C(O)NR$^3$R$^4$, —NR$^3$R$^4$, and —S(O)$_2$R$^3$. In other embodiments, one of $X^a$ and $X^2$ is selected from the group consisting of halogen, cyano and $C_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is substituted phenyl or substituted 5- or 6-membered heteroaryl, optionally having from 1 to 3 substituents independently selected from the group consisting of halogen, —OR$^3$, —NO$_2$, =O—C(O)R$^3$, —C(O)NR$^3$R$^4$, —NR$^5$C(O)R$^3$, —NR$^3$R$^4$, —SR$^3$, —NR$^5$S(O)$_2$R$^3$, —S(O)$_2$R$^3$, and substituted or unsubstituted $C_{1-8}$ alkyl. In other embodiments, one of $X^a$ and $X^2$ is selected from the group consisting of halogen, cyano and $C_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is substituted phenyl or substituted 5- or 6-membered heteroaryl, optionally having from 1 to 3 substituents independently selected from the group consisting of halogen, —OR$^3$, —NO$_2$, =O—C(O)R$^3$, —C(O)NR$^3$R$^4$, —NR$^3$R$^4$, —SR$^3$, —S(O)$_2$R$^3$, and substituted or unsubstituted $C_{1-8}$ alkyl. In other embodiments, one of $X^a$ and $X^2$ is selected from the group consisting of halogen, cyano and $C_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is a 4- to 7-membered heterocyclyl, optionally having from 1 to 3 substituents independently selected from the group consisting of substituted or unsubstituted $C_{1-8}$ alkyl, —OR$^3$, —OC(O)R$^3$, —CO$_2$R$^3$, —C(O)R$^3$, —CONR$^3$R$^4$, —NR$^3$R$^4$, —NR$^5$C(O)R$^3$, —S(O)$_2$R$^3$, —SR$^3$ and —NR$^5$S(O)$_2$R$^3$. In other embodiments, one of $X^a$ and $X^1$ is selected from the group consisting of halogen, cyano and $C_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is a 4- to 7-membered heterocyclyl, optionally having from 1 to 3 substituents independently selected from the group consisting of substituted or unsubstituted $C_{1-8}$ alkyl, —OR$^3$, —OC(O)R$^3$, —CO$_2$R$^3$, —C(O)R$^3$, —CONR$^3$R$^4$, —NR$^3$R$^4$, —S(O)$_2$R$^3$, and —SR$^3$. In other embodiments, one of $X^a$ and $X^1$ is selected from the group consisting of halogen, cyano and $C_{1-8}$ haloalkyl.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is other than hydrogen.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is $C_{1-8}$ alkyl, optionally having from 1 to 3 substituents independently selected from the group consisting of halogen, —OH, —CN, =O, —OC(O)R$^3$, —OR$^3$, —C(O)R$^3$, —C(O)NR$^3$R$^4$, —NR$^5$C(O)R$^3$, —CO$_2$R$^3$, —NR$^3$R$^4$, —S(O)$_2$R$^3$, substituted or unsubstituted phenyl, substituted or unsubstituted 5- or 6-membered heteroaryl, and substituted or unsubstituted 4- to 7-membered heterocycle. In other embodiments, $X^a$ or $X^2$ is selected from the group consisting of halogen, cyano and $C_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is $C_{1-8}$ alkyl, optionally having from 1 to 3 substituents independently selected from the group consisting of halogen, —OH, —CN, =O, —OC(O)R$^3$, —OR$^3$, —C(O)R$^3$, —C(O)NR$^3$R$^4$, —CO$_2$R$^3$, —NR$^3$R$^4$, —S(O)$_2$R$^3$, substituted or unsubstituted phenyl, substituted or unsubstituted 5- or 6-membered heteroaryl, and substituted or unsubstituted 4- to 7-membered heterocycle. In other embodiments, $X^a$ or $X^2$ is selected from the group consisting of halogen, cyano and $C_{1-8}$ haloalkyl.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is $C_{1-8}$ alkyl, having 1 to 3 substituents independently selected from the group consisting of halogen, —CN, =O, —OC(O)R$^3$, —OR$^3$, —C(O)R$^3$, —C(O)NR$^3$R$^4$, —NR$^4$C(O)R$^3$, —CO$_2$R$^3$, —NR$^3$R$^4$, —SR$^3$, —S(O)R$^3$, —S(O)$_2$R$^3$, —NR$^3$S(O)$_2$R$^4$, substituted or unsubstituted phenyl, and substituted or unsubstituted 5- or 6-membered heteroaryl, and substituted or unsubstituted 4- to 7-membered heterocycle. In certain other preferred embodiments, $X^a$, $X^2$, $X^3$, $X^4$ and $X^5$ is hydrogen, and $X^1$ and $X^b$ are unsubstituted $C_{1-8}$ alkyl.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is $C_{1-8}$ alkyl, having 1 to 3 substituents independently selected from the group consisting of halogen, —CN, =O, —OC(O)R$^3$, —OR$^3$, —C(O)R$^3$, —C(O)NR$^3$R$^4$, —CO$_2$R$^3$, —NR$^3$R$^4$, —SR$^3$, —S(O)R$^3$, —S(O)$_2$R$^3$, substituted or unsubstituted phenyl, and substituted or unsubstituted 5- or 6-membered heteroaryl, and substituted or unsubstituted 4- to 7-membered heterocycle. In certain other preferred embodiments, $X^a$, $X^2$, $X^3$, $X^4$ and $X^5$ is hydrogen, and $X^1$ and $X^b$ are unsubstituted $C_{1-8}$ alkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is selected from the group consisting of —CN, —CF$_3$, halogen, —OR$^3$, —S(O)$_2$R$^3$, —C(O)R$^3$, a substituted or unsubstituted $C_{1-8}$ alkyl, a substituted or unsubstituted 5- or 6-membered heteroaryl, and a substituted or unsubstituted 4- to 7-membered heterocycle.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is selected from the group consisting of —CN, halogen, —OR$^3$, —SO$_2$R$^3$, —C(O)R$^3$, substituted or unsubstituted C$_{1-8}$ alkyl, substituted or unsubstituted 5- or 6-membered heteroaryl, and substituted or unsubstituted 4- to 7-membered heterocycle. In other embodiments, $X^a$ and $X^2$ is selected from the group consisting of halogen, cyano and C$_{1-8}$ haloalkyl.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is unsubstituted C$_{1-8}$ alkyl.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is a t-butyl group.

In another embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is selected from the group consisting of halogen, —CN, —CF$_3$, unsubstituted or substituted C$_{1-6}$ alkyl, substituted or unsubstituted 5- or 6-membered heteroaryl, and substituted or unsubstituted 4- to 7-membered heterocyclyl. In another embodiment, one of $X^a$ and $X^2$ is other than hydrogen.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is C$_{6-10}$ aryl or a heteroaryl, having from 0 to 3 substituents independently selected from the group consisting of halogen, —CN, —OH, —OR$^3$, =O, —OC(O)R$^3$, —CO$_2$R$^3$, —C(O)R$^3$, —C(O)NR$^3$R$^4$, —NR$^3$R$^4$, —SR$^3$, —S(O)R$^3$, —S(O)$_2$R$^3$, and substituted or unsubstituted C$_{1-8}$ alkyl. In other embodiments, $X^a$ or $X^2$ is halogen, —CN, or —CF$_3$.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is C$_{6-10}$ aryl or a heteroaryl, having from 0 to 3 substituents independently selected from the group consisting of halogen, —CN, —OH, —OR$^3$, =O, —OC(O)R$^3$, —CO$_2$R$^3$, —C(O)R$^3$, —C(O)NR$^3$R$^4$, —NR$^5$C(O)R$^3$, —NR$^3$R$^4$, —SR$^3$, —S(O)R$^3$, —S(O)$_2$R$^3$, —NR$^5$S(O)$_2$R$^3$, and substituted or unsubstituted C$_{1-8}$ alkyl. In other embodiments, $X^a$ or $X^2$ is halogen, —CN, or —CF$_3$.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is substituted phenyl or substituted 5- or 6-membered heteroaryl, having from 0 to 3 substituents independently selected from the group consisting of halogen, —OR$^3$, —NO$_2$, =O—C(O)R$^3$, —C(O)NR$^3$R$^4$, —NR$^5$C(O)R$^3$, —NR$^3$R$^4$, —SR$^3$, —NR$^5$S(O)$_2$R$^3$, —S(O)$_2$R$^3$, and substituted or unsubstituted C$_{1-8}$ alkyl. In other embodiments, $X^a$ or $X^2$ is halogen, —CN, or —CF$_3$.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is substituted phenyl or substituted 5- or 6-membered heteroaryl, having from 0 to 3 substituents independently selected from the group consisting of halogen, —OR$^3$, —NO$_2$, =O—C(O)R$^3$, —C(O)NR$^3$R$^4$, —NR$^3$R$^4$, —SR$^3$, —S(O)$_2$R$^3$, and substituted or unsubstituted C$_{1-8}$ alkyl. In other embodiments, $X^a$ or $X^2$ is halogen, —CN, or —CF$_3$.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is a 4- to 7-membered heterocyclyl, having 0 to 3 substituents independently selected from the group consisting of substituted or unsubstituted C$_{1-8}$ alkyl, —OR$^3$, —OC(O)R$^3$, —CO$_2$R$^3$, —C(O)R$^3$, —C(O)NR$^3$R$^4$, —NR$^3$R$^4$, —NR$^5$C(O)R$^3$, —S(O)$_2$R$^3$, —SR$^3$ and —NR$^5$S(O)$_2$R$^3$. In other embodiments, $X^a$ or $X^2$ is halogen, —CN, or —CF$_3$.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is a 4- to 7-membered heterocyclyl, having 0 to 3 substituents independently selected from the group consisting of substituted or unsubstituted C$_{1-8}$ alkyl, —OR$^3$, —OC(O)R$^3$, —CO$_2$R$^3$, —C(O)R$^3$, —C(O)NR$^3$R$^4$, —NR$^3$R$^4$, —S(O)$_2$R$^3$, and —SR$^3$. In other embodiments, $X^a$ or $X^2$ is halogen, —CN, or —CF$_3$.

In one embodiment of any of formulae (II, IV, V, VII, IX and XX-CXXXVI), each of $X^a$, $X^2$, $X^3$, $X^4$ and $X^5$ is hydrogen, and $X^1$ or $X^b$ is a 5- or 6-membered heterocyclyl, having 0 to 2 substituents independently selected from the group consisting of substituted or unsubstituted C$_{1-8}$ alkyl, —OR$^3$, —C(O)R$^3$, —C(O)NR$^3$R$^4$, —NR$^3$R$^4$, and —S(O)$_2$R$^3$. In other embodiments, $X^a$ or $X^2$ is halogen, —CN, or —CF$_3$ In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is C$_{6-10}$ aryl or a heteroaryl, optionally having from 1 to 3 substituents independently selected from the group consisting of halogen, —CN, —OH, —OR$^3$, =O, —NO$_2$, —OC(O)R$^3$, —CO$_2$R$^3$, —C(O)R$^3$, —C(O)NR$^3$R$^4$, —NR$^5$C(O)R$^3$, —NR$^3$R$^4$, —SR$^3$, —S(O)R$^3$, —S(O)$_2$R$^3$, —NR$^5$S(O)$_2$R$^3$, and substituted or unsubstituted C$_{1-8}$ alkyl. In other embodiments, $X^a$ or $X^2$ is selected from the group consisting of halogen, cyano and C$_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is C$_{6-10}$ aryl or a heteroaryl, optionally having from 1 to 3 substituents independently selected from the group consisting of halogen, —CN, —OH, —OR$^3$, =O, —NO$_2$, —OC(O)R$^3$, —CO$_2$R$^3$, —C(O)R$^3$, —C(O)NR$^3$R$^4$, —NR$^3$R$^4$, —SR$^3$, —S(O)R$^3$, —S(O)$_2$R$^3$, and substituted or unsubstituted C$_{1-8}$ alkyl. In other embodiments, $X^a$ or $X^2$ is selected from the group consisting of halogen, cyano and C$_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is phenyl or 5- or 6-membered heteroaryl, optionally having from 1 to 3 substituents independently selected from the group consisting of halogen, —OR$^3$, =O, —NO$_2$, —C(O)R$^3$, —C(O)NR$^3$R$^4$, —NR$^5$C(O)R$^3$, —NR$^3$R$^4$, —SR$^3$, —NR$^5$S(O)$_2$R$^3$, —S(O)$_2$R$^3$, and substituted or unsubstituted C$_{1-8}$ alkyl. In other embodiments, $X^a$ or $X^2$ is selected from the group consisting of halogen, cyano and C$_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is phenyl or 5- or 6-membered heteroaryl, optionally having from 1 to 3 substituents independently selected from the group consisting of halogen, —OR$^3$, =O, —NO$_2$, —C(O)R$^3$, —C(O)NR$^3$R$^4$, —NR$^3$R$^4$, —SR$^3$, —S(O)$_2$R$^3$, and substituted or unsubstituted C$_{1-8}$ alkyl. In other embodiments, $X^a$ or $X^2$ is selected from the group consisting of halogen, cyano and C$_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is a 4- to 7-membered heterocyclyl, optionally having from 1 to 3 substituents independently selected from the group consisting of substituted or unsubstituted C$_{1-8}$ alkyl, —OR$^3$, —OH, —NR$^5$C(O)R$^3$, —OC(O)R$^3$, —CO$_2$R$^3$, —C(O)R$^3$, —C(O)NR$^3$R$^4$, —NR$^3$R$^4$, —S(O)$_2$R$^3$, —SR$^3$ and —NR$^5$S(O)$_2$R$^3$. In other embodiments, $X^a$ or $X^2$ is selected from the group consisting of halogen, cyano and C$_{1-8}$ haloalkyl.

In one embodiment, in each of formulae (II, IV, V, VII, IX and XX-CXXXVI), each of $X^a$, $X^2$, $X^3$, $X^4$ and $X^5$ is hydrogen, and $X^1$ or $X^b$ is a 5- or 6-membered heterocyclyl, optionally having 1 to 2 substituents independently selected from the group consisting of substituted or unsubstituted $C_{1-8}$ alkyl, —$OR^3$, —$C(O)R^3$, —$C(O)NR^3R^4$, —$NR^3R^4$, and —$S(O)_2R^3$. In other embodiments, $X^a$ or $X^2$ is selected from the group consisting of halogen, cyano and $C_{1-8}$ haloalkyl.

In one embodiment, in each of formulae (II, IV, V, VII, IX, X, XII, and XX-CXXXVI), each of $Y^a$, $Y^2$, $Y^3$, and $Y^3$ is hydrogen, and $Y^1$ or $Y^a$ is other than hydrogen.

In one embodiment of any of formulae (II, IV, V, VII, IX, X, XII, and XX-CXXXVI), $Y^3$ is hydrogen, $Y^1$ is other than hydrogen, and one of $Y^2$ and $Y^4$ is hydrogen and the other is other than hydrogen. In a preferred embodiment, $Y^1$, $Y^2$, $Y^3$, $Y^4$, $Y^a$ and $Y^b$ are selected from the group consisting of halogen, —$CF_3$, $C_{1-8}$ alkyl, $C(O)R^1$, —$SO_2R^1$, —$C(O)NR^1R^2$.

In one embodiment of any of formulae (II, IV, V, VII, IX, X, XII, and XX-CXXXVI), at least one of $Y^1$, $Y^2$, $Y^3$, $Y^4$, $Y^a$ and $Y^b$ is halogen, —CN, —$NO_2$, —$OR^6$, —$C(O)R^6$, —$SR^6$, —$CF_3$, —$S(O)R^6$, —$S(O)_2R^6$ or substituted or unsubstituted $C_{1-4}$ alkyl.

In one embodiment of any of formulae (II, IV, V, VII, IX, X, XII, and XX-CXXXVI), at least one of $Y^1$, $Y^2$, $Y^3$, $Y^4$, $Y^a$ and $Y^b$ is halogen, —CN, —$NO_2$, —$C(O)R^6$, —$SR^6$, —$CF_3$, —$S(O)R^6$, —$S(O)_2R^6$ or substituted or unsubstituted $C_{1-4}$ alkyl.

In one embodiment of any of formulae (II, IV, V, VII, IX, X, XII, and XX-CXXXVI), $Y^1$ or $Y^b$ is hydrogen and $Y^a$, $Y^2$, $Y^3$, and $Y^4$ is other than hydrogen.

In one embodiment of any of formulae (II, IV, V, VII, IX, X, XII, and XX-CXXXVI), $Y^1$, $Y^a$ and $Y^b$ represent from 1 to 3 substituents independently selected from the group consisting of hydrogen, halogen, —CN, —$NO_2$, —$OR^6$, —$C(O)R^6$, —$SR^6$, —$CF_3$, —$S(O)R^6$, and —$S(O)_2R^6$ and substituted or unsubstituted $C_{1-6}$ alkyl.

In one embodiment of any of formulae (II, IV, V, VII, IX, X, XII, and XX-CXXXVI), $Y^1$, $Y^a$ and $Y^b$ represent from 1 to 3 substituents independently selected from the group consisting of hydrogen, halogen, —CN, —$NO_2$, —$C(O)R^6$, —$SR^6$, —$CF_3$, —$S(O)R^6$, and —$S(O)_2R^6$ and substituted or unsubstituted $C_{1-6}$ alkyl.

In one embodiment of any of formulae (I-IX, X, XII and XX-CXXXVI), $Y^1$, $Y^a$ and $Y^b$ represent from 1 to 3 substituents independently selected from the group consisting of hydrogen, halogen, —CN, —$NO_2$, —$CF_3$, and —$S(O)_2Me$.

In one embodiment of any of formulae (I-IX, X, XII and XX-CXXXVI), one of $Y^1$, $Y^a$ and $Y^b$ is halogen and one of the others is selected from the group consisting of hydrogen, halogen, —CN, —$NO_2$, —OH, —$OR^6$, —$C(O)R^6$, —$CO_2R^6$, —$SR^6$, —$S(O)R^6$, —$S(O)_2R^6$ and substituted or unsubstituted $C_{1-4}$ alkyl.

In one embodiment of any of formulae (I-IX, X, XII, and XX-CXXXVI), one of $Y^1$, $Y^a$ and $Y^b$ is halogen and one of the others is selected from the group consisting of hydrogen, halogen, —CN, —$NO_2$, —$C(O)R^6$, —$CO_2R^6$, —$SR^6$, —$S(O)R^6$, —$S(O)_2R^6$ and substituted or unsubstituted $C_{1-4}$ alkyl.

In one embodiment, in each of formulae (V and XX-CXXXVI), one of $Y^1$, $Y^a$ and $Y^b$ is substituted alkyl, having from 1 to 3 substituents independently selected from the group consisting of halogen, —OH, —$OR^m$, —CN, —$NO_2$, =O, —$OC(O)R^m$, —$CO_2R^m$, —$C(O)R^m$, —$C(O)NHR^n$, —$C(O)NH_2$, —$C(O)NR^mR^n$, —$NR^mC(O)R^n$, —$NHC(O)R^n$, —$NR^mR^n$, —$NHR^m$, —$NH_2$, —$SR^m$, —$S(O)R^m$, —$S(O)_2R^m$, —$NR^mS(O)_2R^n$, and —$NHS(O)_2R^m$, where $R^m$ and $R^n$ are each independently unsubstituted $C_{1-6}$ alkyl.

In one embodiment of any of formulae (V and XX-CXXXVI), $Y^1$, $Y^a$ and $Y^b$ are each independently selected from the group consisting of hydrogen, halogen, —CN, —$NO_2$, —OH, —$OR^6$, —$C(O)R^6$, —$CO_2R^6$, —$SR^6$, —$S(O)R^6$, —$S(O)_2R^6$, and substituted or unsubstituted $C_{1-4}$ alkyl, with the proviso that $Y^1$ and $Y^a$ or $Y^b$ and $Y^a$ cannot both be hydrogen simultaneously.

In one embodiment of any of formulae (V and XX-CXXXVI), $Y^1$, $Y^a$ and $Y^b$ are each independently selected from the group consisting of hydrogen, halogen, —CN, —$NO_2$, —$C(O)R^6$, —$CO_2R^6$, —$SR^6$, —$S(O)R^6$, —$S(O)_2R^6$, and substituted or unsubstituted $C_{1-4}$ alkyl, with the proviso that $Y^1$ and $Y^a$ or $Y^b$ and $Y^a$ cannot both be hydrogen simultaneously.

In one embodiment of any of formulae (V and XX-CXXXVI), $Y^1$ or $Y^b$, and $Y^a$ are each independently hydrogen or halogen, with the proviso that one or both are halogen.

In one embodiment of any of formulae (V and XX-CXXXVI), $Y^1$ or $Y^b$ is hydrogen and $Y^a$ is chloro, fluoro or bromo; in another embodiment, $Y^a$ is hydrogen and $Y^1$ or $Y^b$ is chloro, fluoro or bromo; in another embodiment $Y^1$ or $Y^b$ and $Y^a$ are both chloro, fluoro, or bromo (particularly fluoro).

In one embodiment, in each of formulae (V and XX-CXXXVI), $Y^1$, $Y^a$, and $Y^b$ are each independently selected from the group consisting of hydrogen, halogen, —CN, —$NO_2$, —$OR^6$, —$C(O)R^6$, —$SR^6$, —$S(O)R^6$, —$S(O)_2R^6$ and substituted or unsubstituted $C_{1-6}$ alkyl.

In one embodiment, in each of formulae (V and XX-CXXXVI), $Y^1$, $Y^a$, and $Y^b$ are each independently selected from the group consisting of hydrogen, halogen, —CN, —$NO_2$, —$C(O)R^6$, —$SR^6$, —$S(O)R^6$, —$S(O)_2R^6$ and substituted or unsubstituted $C_{1-6}$ alkyl.

In one embodiment, in each of formulae (V and XX-CXXXVI), $Y^1$, $Y^a$, and $Y^b$ are each independently selected from the group consisting of hydrogen, halogen, —CN, —$NO_2$, —$CF_3$, and —$SO_2Me$.

In one embodiment of any of formulae (V and XX-CXXXVI), one of $Y^1$, $Y^a$, and $Y^b$ is halogen and the other is selected from the group consisting of hydrogen, halogen, —CN, —$NO_2$, —OH, —$OR^6$, —$C(O)R^6$, —$CO_2R^6$, —$SR^6$, —$S(O)R^6$, —$S(O)_2R^6$ and substituted or unsubstituted $C_{1-4}$ alkyl.

In one embodiment, in each of formulae (V and XX-CXXXVI), one of $Y^1$, $Y^a$, and $Y^b$ is halogen and the other is selected from the group consisting of hydrogen, halogen, —CN, —$NO_2$, —$C(O)R^6$, —$CO_2R^6$, —$SR^6$, —$S(O)R^6$, —$S(O)_2R^6$ and substituted or unsubstituted $C_{1-4}$ alkyl.

In one embodiment, in each of formulae (V and XX-CXXXVI), one of $Y^1$, $Y^a$, and $Y^b$ is substituted alkyl, having from 1 to 3 substituents independently selected from the group consisting of halogen, —OH, —$OR^m$, —CN, —$NO_2$, =O, —$OC(O)R^m$, —$CO_2R^m$, —$C(O)R^m$, —$C(O)NHR^n$, —$C(O)NH_2$, —$C(O)NR^mR^n$, —$NR^mC(O)R^n$, —$NHC(O)R^n$, —$NR^mR^n$, —$NHR^m$, —$NH_2$, —$SR^m$, —$S(O)R^m$, —$S(O)_2R^m$, —$NR^mS(O)_2R^n$, and —$NHS(O)_2R^m$, where $R^m$ and $R^n$ are each independently unsubstituted $C_{1-6}$ alkyl.

In one embodiment of any of formulae (V and XX-CXXXVI), $Y^1$, $Y^a$, and $Y^b$ are each independently selected from the group consisting of hydrogen, halogen, —CN, —$NO_2$, —OH, —$OR^6$, —$C(O)R^6$, —$CO_2R^6$, —$SR^6$, —$S(O)R^6$, —$S(O)_2R^6$, and substituted or unsubstituted $C_{1-4}$ alkyl, with the proviso that $Y^1$ and $Y^a$, or $Y^a$ and $Y^b$ cannot both be hydrogen simultaneously.

In one embodiment of any of formulae (V and XX-CXXXVI), $Y^1$, $Y^a$, and $Y^b$ are each independently selected from the group consisting of hydrogen, halogen, —CN, —NO$_2$, —C(O)R$^6$, —CO$_2$R$^6$, —SR$^6$, —S(O)R$^6$, —S(O)$_2$R$^6$, and substituted or unsubstituted C$_{1-4}$ alkyl, with the proviso that Y$^1$ and Y$^a$, or Y$^a$ and Y$^b$ cannot both be hydrogen simultaneously.

In one embodiment, in each of formulae (V and XX-CXXXVI), Y$^1$, Y$^a$, and Y$^b$ are each independently hydrogen or halogen, with the proviso that one or both of Y$^1$ and Y$^a$, or Y$^a$ and Y$^b$ are halogen.

In one embodiment of any of formulae (V and XX-CXXXVI), Y$^1$ or Y$^b$ is hydrogen and Y$^a$ is chloro, fluoro or bromo; Y$^a$ is hydrogen and Y$^1$ or Y$^b$ is chloro, fluoro or bromo; or Y$^1$, Y$^a$, Y$^b$ are each independently chloro, fluoro, or bromo (particularly fluoro).

In one embodiment, in each of formulae (V and XX-CXXXVI), Y$^1$ or Y$^b$ is hydrogen and Y$^a$ is chloro, fluoro or bromo; or Y$^a$ is hydrogen and Y$^1$ or Y$^b$ is chloro, fluoro or bromo; or Y$^1$, Y$^b$ and Y$^a$ are each independently selected from the group consisting of chloro, fluoro, and bromo (and in one particular embodiment, both Y$^1$ and Y$^a$ are fluoro or both Y$^b$ and Y$^a$ are fluoro).

In one embodiment of any of formulae (I-IV, VI-IX, X, and XII), at least one of Y$^1$ to Y$^4$ is other than hydrogen. Preferably one or two of Y$^1$ to Y$^4$ are other than hydrogen. More preferably, Y$^3$ is hydrogen.

In one embodiment of any of formulae (I-IV, VI-IX, X, and XII), at least one of Y$^1$ to Y$^4$ is halogen, —CN, —NO$_2$, —OR$^6$, —C(O)R$^6$, —SR$^6$, —CF$_3$, —S(O)R$^6$, —S(O)$_2$R$^{13}$ or substituted or unsubstituted C$_{1-4}$ alkyl.

In one embodiment of any of formulae (I-IV, VI-X, X, and XII), at least one of Y$^1$ to Y$^4$ is halogen, —CN, —NO$_2$, —C(O)R$^6$, —SR$^6$, —CF$_3$, —S(O)R$^6$, —S(O)$_2$R$^{13}$ or substituted or unsubstituted C$_{1-4}$ alkyl.

In one embodiment of formula (I-IV, VI-IX, X, and XII), Y$^3$ is hydrogen and Y$^1$ is chlorine or fluorine, and when Y$^1$ is chlorine, both Y$^2$ and Y$^4$ are hydrogen or when Y$^1$ is fluorine, either Y$^2$ or Y$^4$ is also fluorine or halogen.

In one embodiment of formula (I-IV, VI-IX, X, and XII), Y$^3$ is hydrogen and Y$^1$ is chlorine or fluorine, with the following provisos: when Y$^1$ is chlorine, both Y$^2$ and Y$^4$ are hydrogen; and when Y$^1$ is fluorine, either Y$^2$ or Y$^4$ are fluorine, the other being hydrogen.

In one embodiment of formulae (I-IV, VI-IX, X, and XII), Y$^2$ is chlorine and Y$^1$, Y$^3$, and Y$^4$ are hydrogen.

In one embodiment of formulae (I-IV, VI-IX, X, and XII), Y$^2$ is halogen and Y$^3$ is hydrogen, Y$^1$ and Y$^4$ are each independently selected from the group consisting of halogen and hydrogen.

In one embodiment of formulae (I-IV, VI-IX, X, and XII),
Y$^3$ is hydrogen;
Y$^1$ is chlorine or fluorine, with the proviso that when Y$^1$ is chlorine, both Y$^2$ and Y$^4$ are hydrogen or when Y$^1$ is fluorine, either Y$^2$ or Y$^4$ is also fluorine; and
Ar$^2$ is selected from the group consisting of:

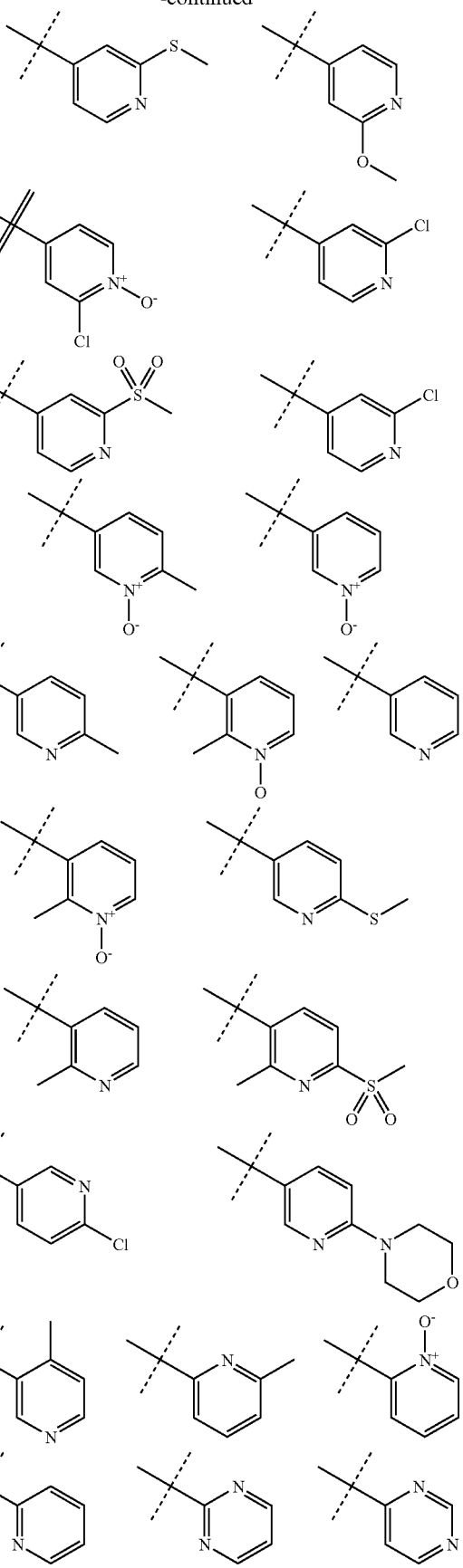

-continued
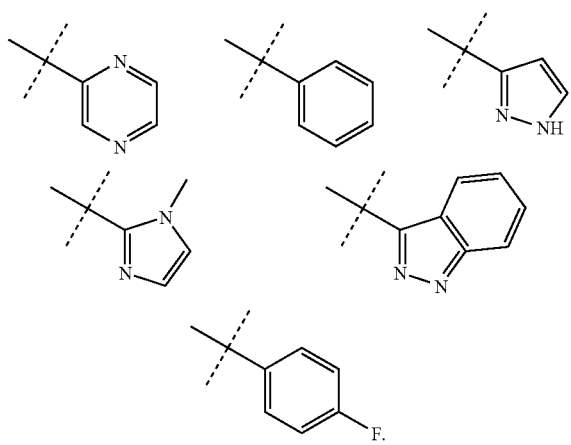
In one embodiment of formulae (I-IV, VI-IX, X, and XII),
$Y^3$ is hydrogen;
$Y^2$ is halogen;
$Y^1$ and $Y^4$ are each independently hydrogen or halogen; and
$Ar^2$ is selected from the group consisting of:
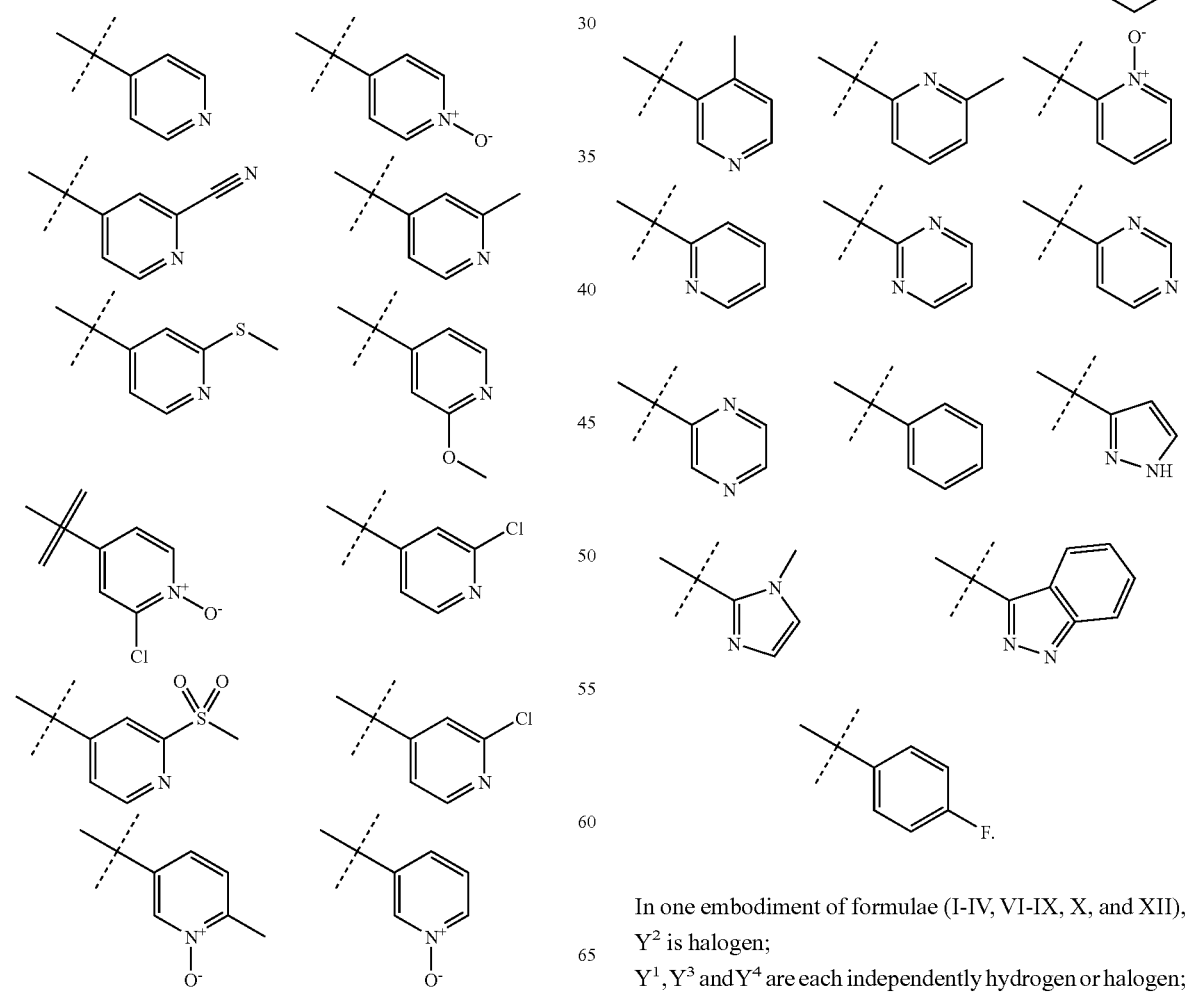
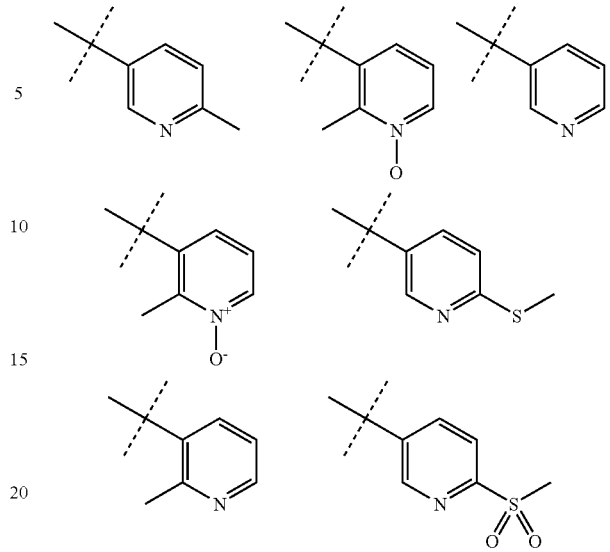
In one embodiment of formulae (I-IV, VI-IX, X, and XII),
$Y^2$ is halogen;
$Y^1, Y^3$ and $Y^4$ are each independently hydrogen or halogen; and Ar² is selected from the group consisting of:
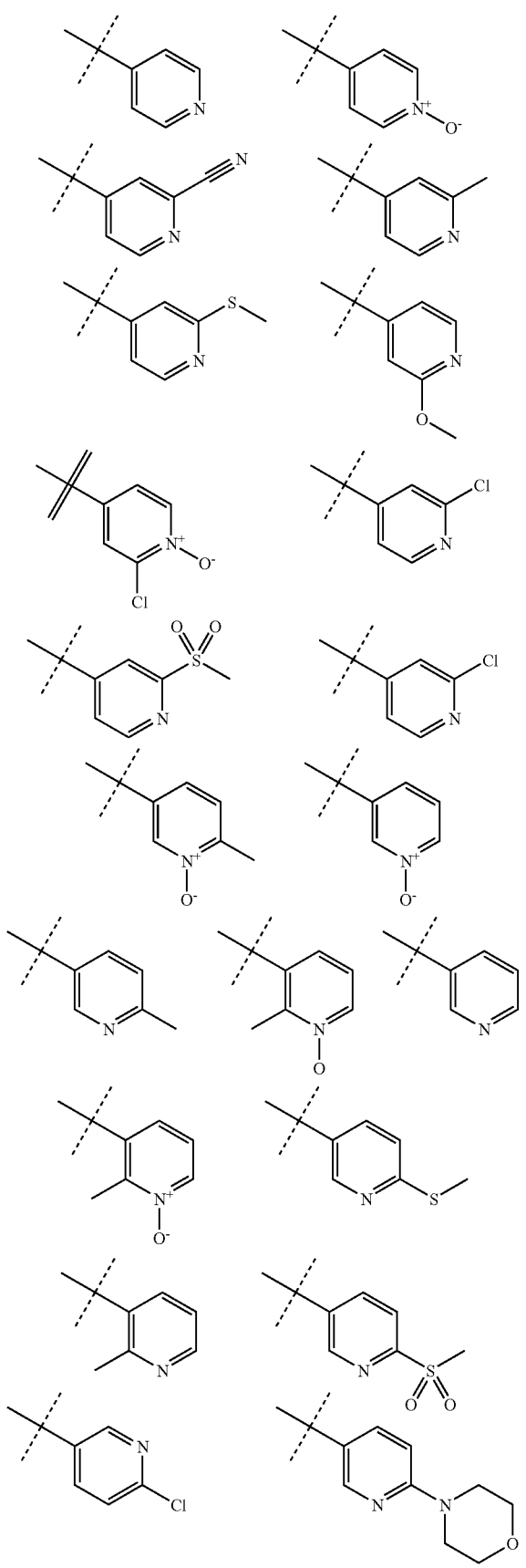
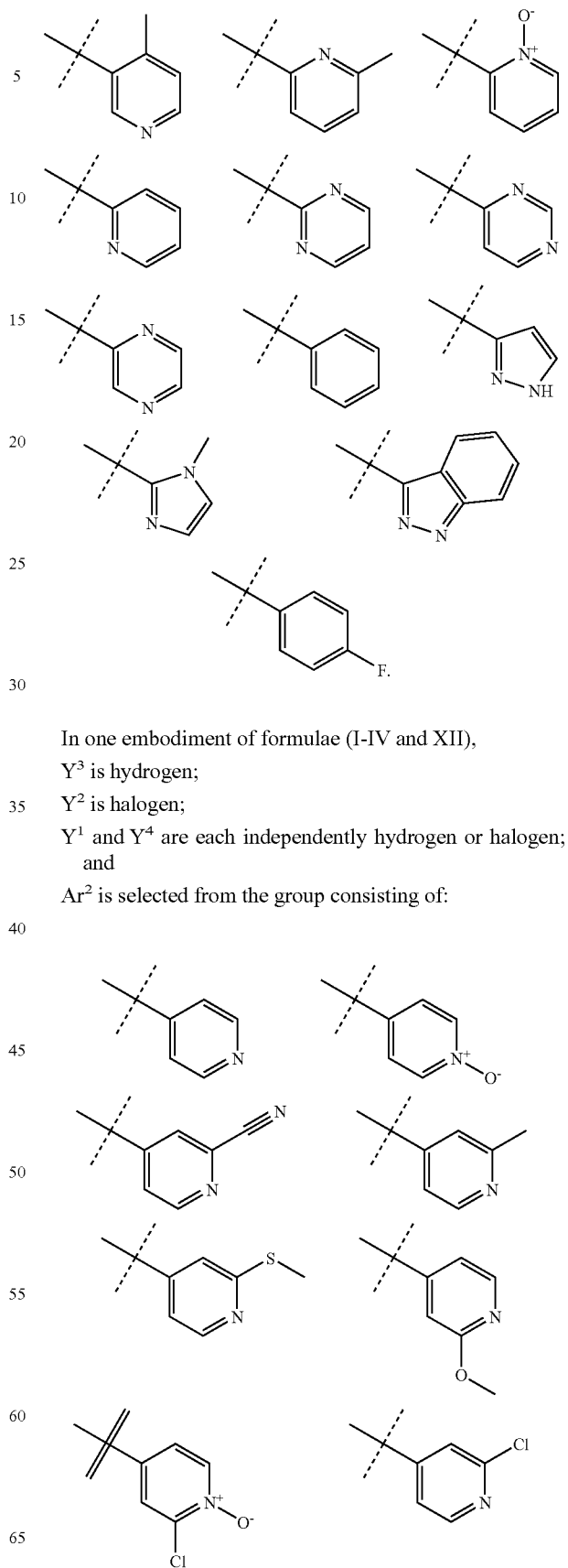
In one embodiment of formulae (I-IV and XII),
Y³ is hydrogen;
Y² is halogen;
Y¹ and Y⁴ are each independently hydrogen or halogen; and
Ar² is selected from the group consisting of:

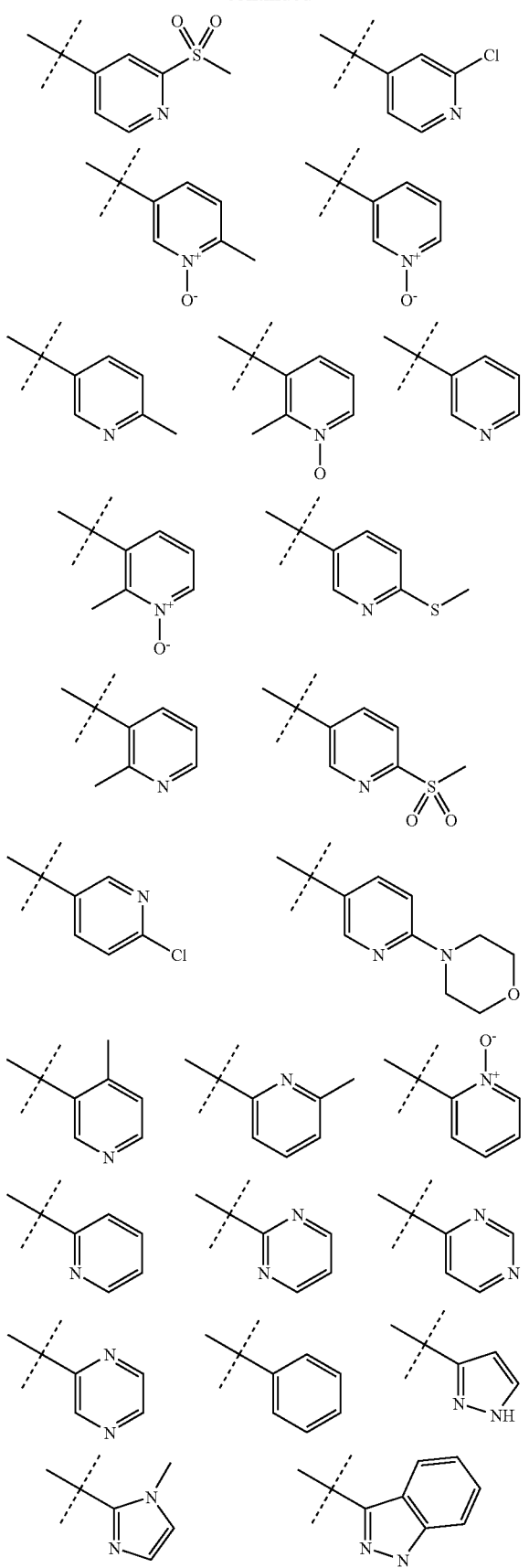
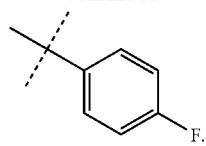
In one embodiment of formula (II):
$Y^3$ is hydrogen;
$Y^1$ is chlorine or fluorine, with the proviso that when $Y^1$ is chlorine, both $Y^2$ and $Y^4$ are hydrogen or alternatively, if $Y^1$ is fluorine, then either $Y^2$ or $Y^4$ is also fluorine;
$X^1$ is selected from the group consisting of:
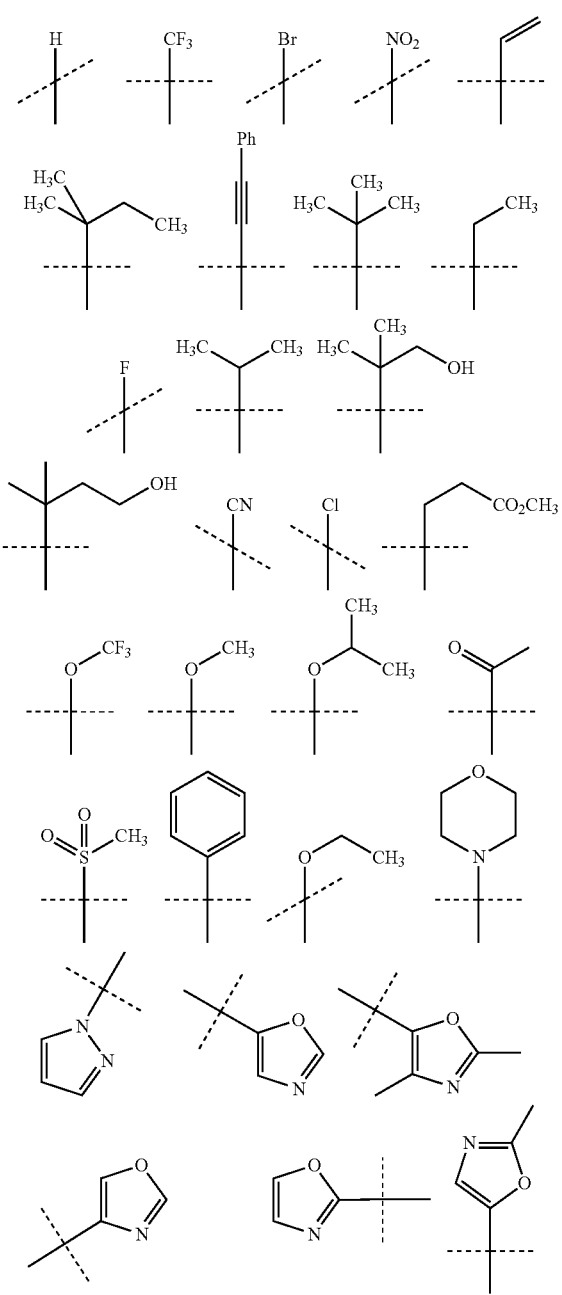

-continued
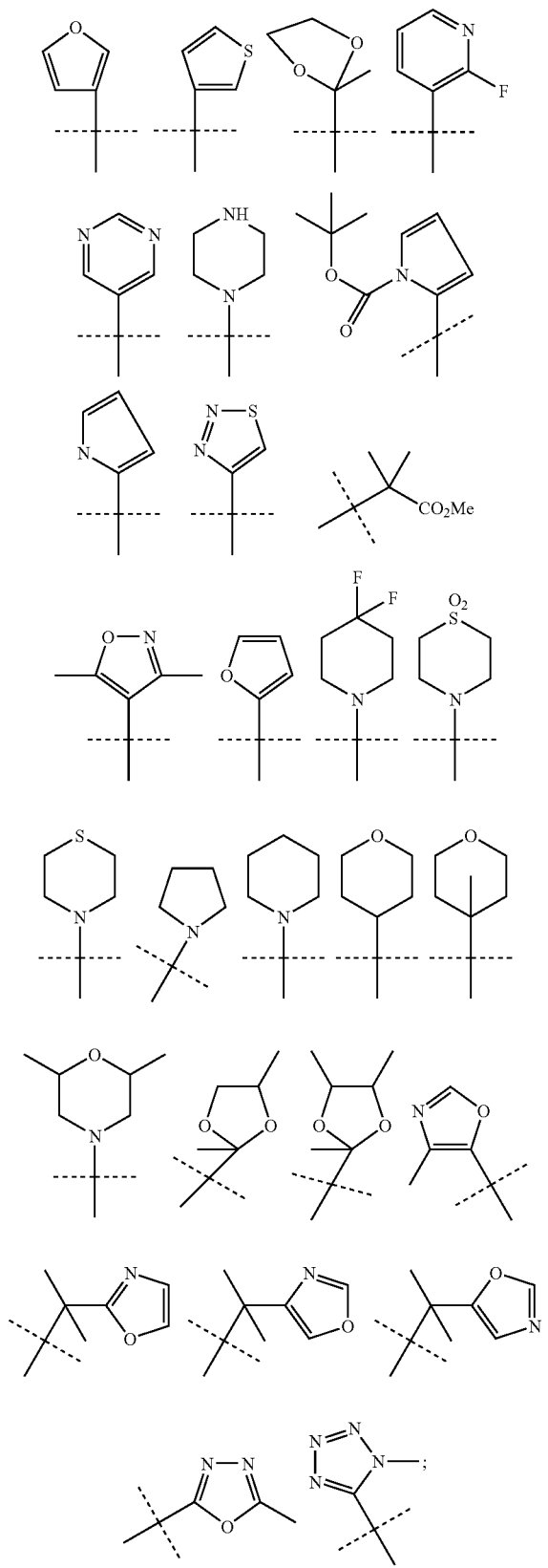
$X^2$, $X^3$, and $X^5$ are hydrogen;
$X^4$ is halogen, —CN, $CF_3$, or hydrogen;
$Ar^2$ is selected from the group consisting of:
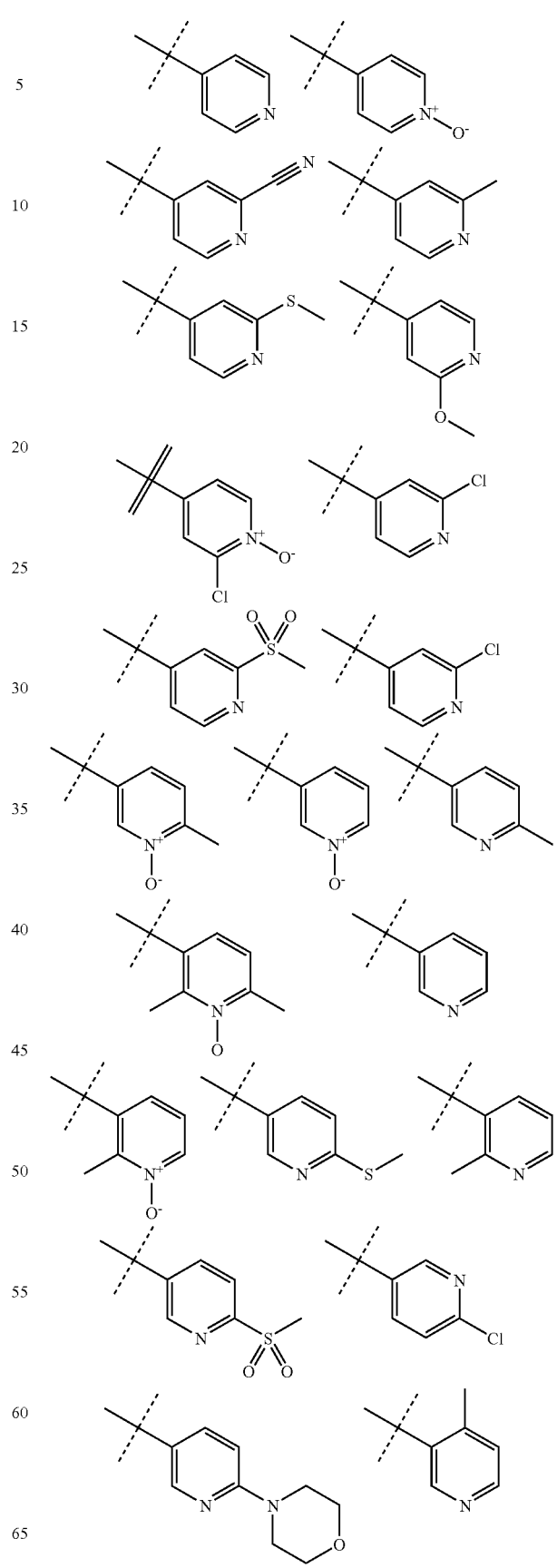

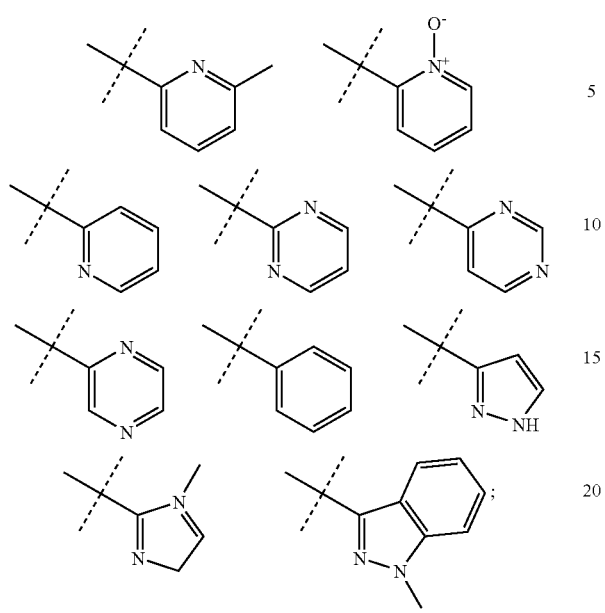
and $R^a$ and $R^b$ are hydrogen, halogen or $OR^1$, preferably both halogen.
In one embodiment of formula (II):
$Y^2$ is halogen;
$Y^1, Y^3$ and $Y^4$ are each independently hydrogen or halogen;
$X^1$ is selected from the group consisting of:
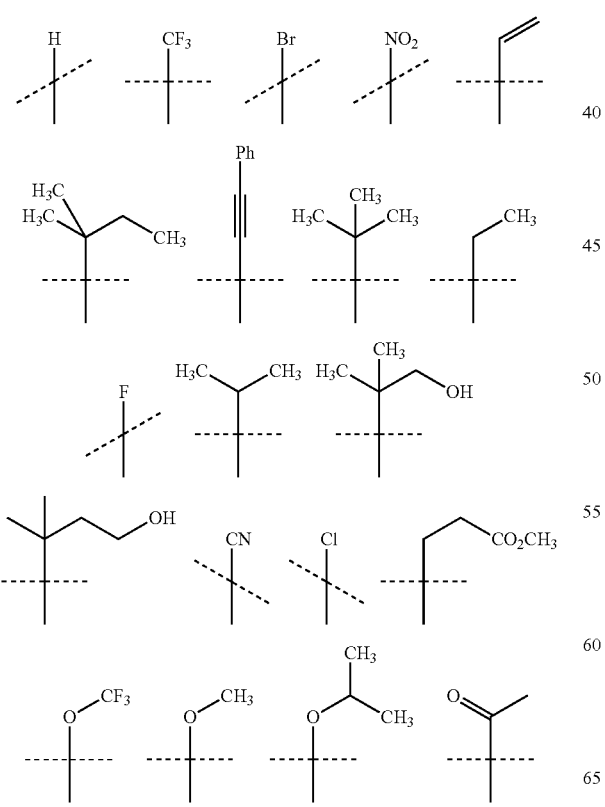
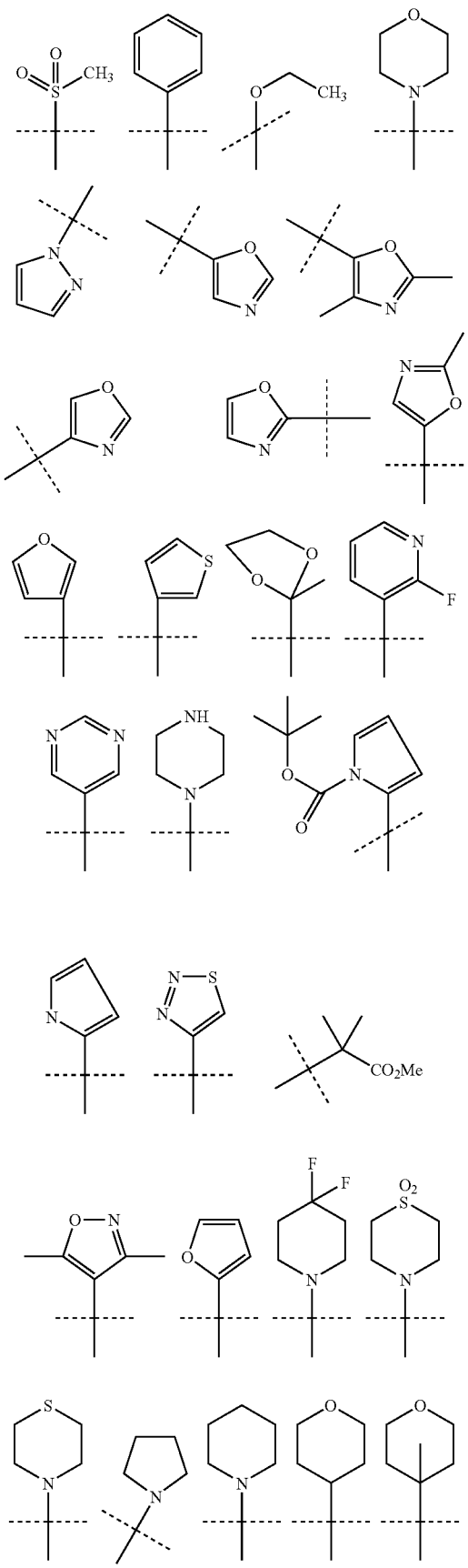

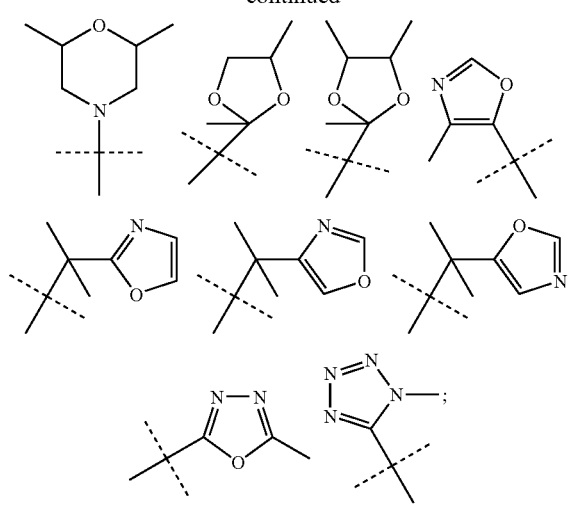

$X^2$, $X^3$, and $X^5$ are hydrogen;
$X^4$ is halogen, —CN, $CF_3$, or hydrogen;
$Ar^2$ is selected from the group consisting of:

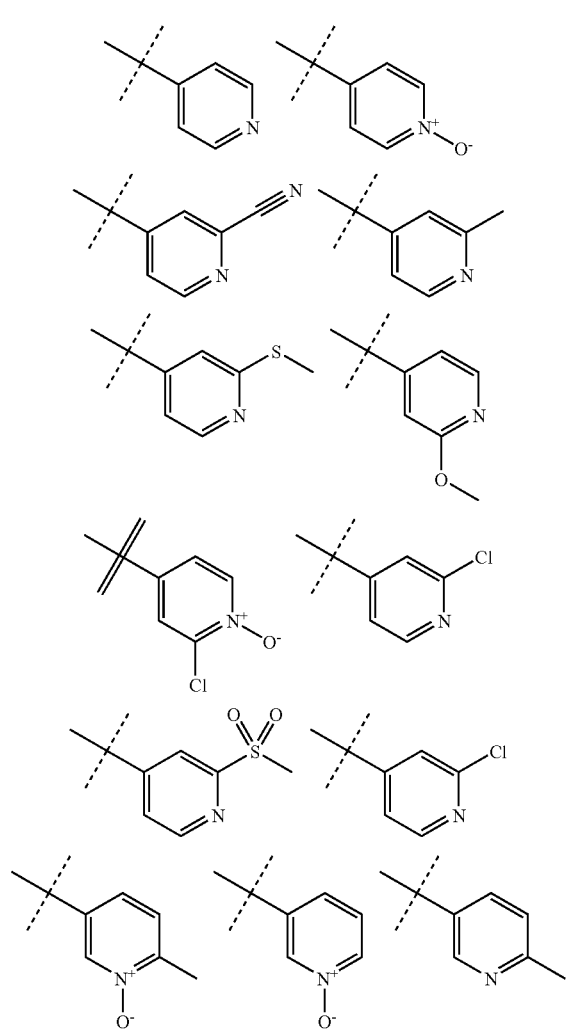

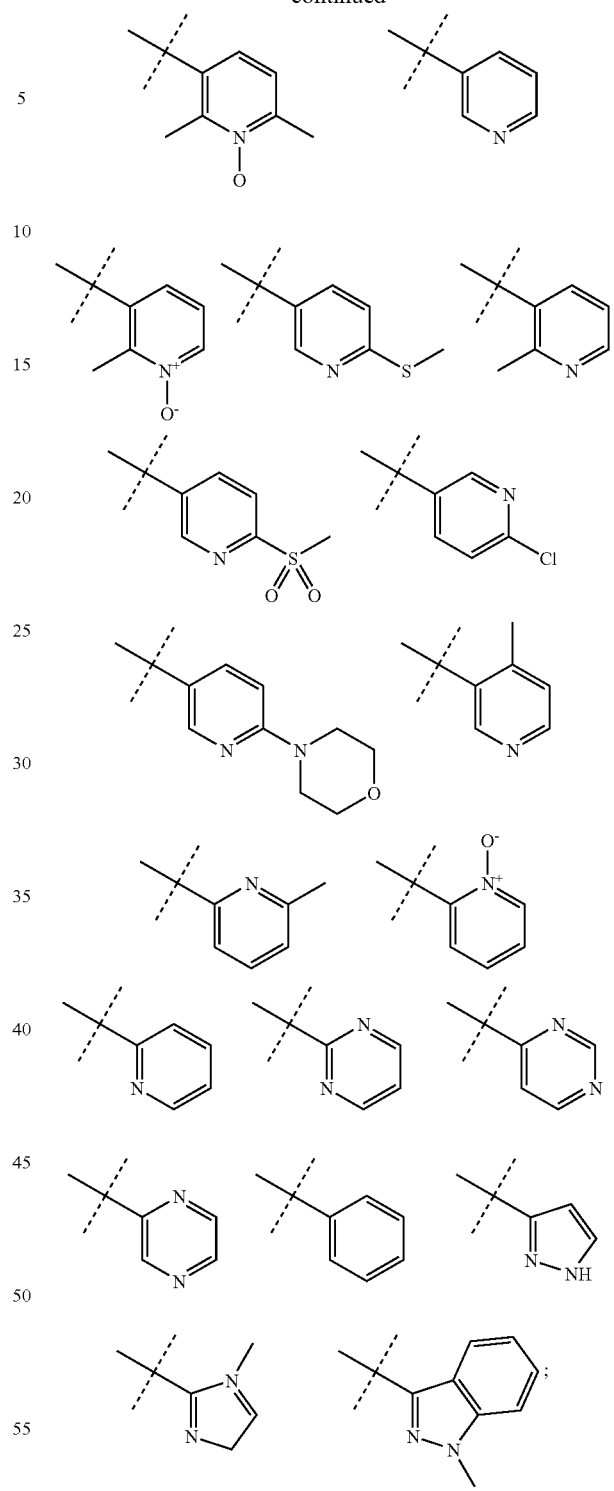

and $R^a$ and $R^b$ are hydrogen, halogen or $OR^1$, preferably both halogen.

In one embodiment of formula (II):

$Y^3$ is hydrogen;
$Y^1$ is chlorine or fluorine, with the proviso that when $Y^1$ is chlorine, both $Y^2$ and $Y^4$ are hydrogen or alternatively, if $Y^1$ is fluorine, then either $Y^2$ or $Y^4$ is also fluorine;

$X^1$ is selected from the group consisting of:
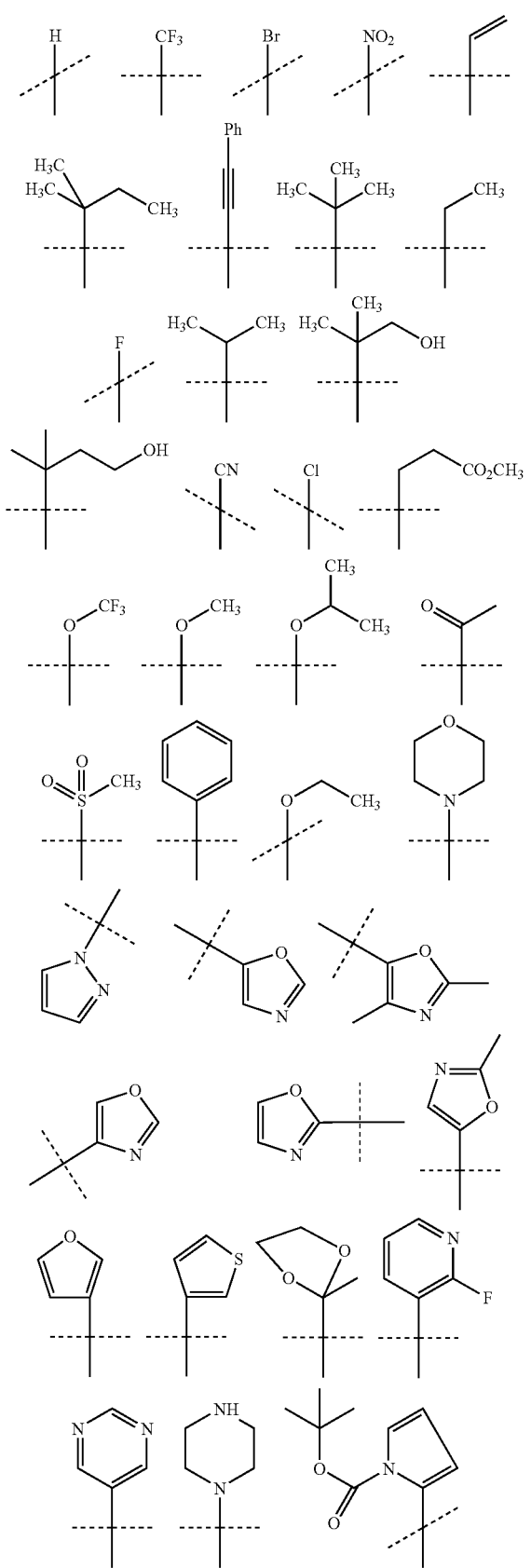
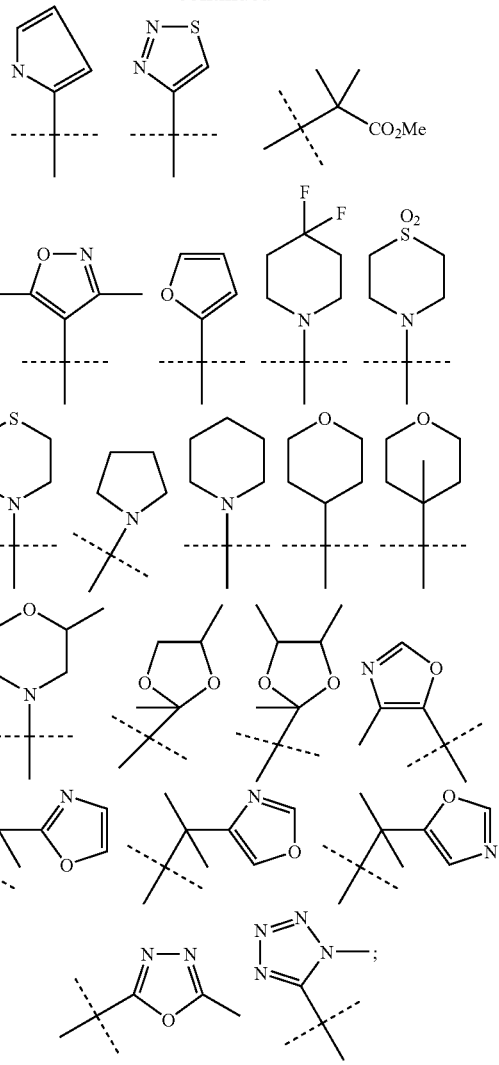
$X^2$, $X^3$, and $X^5$ are hydrogen;
$X^4$ is halogen, —CN, $CF_3$, or hydrogen;
$Ar^2$ is selected from the group consisting of:
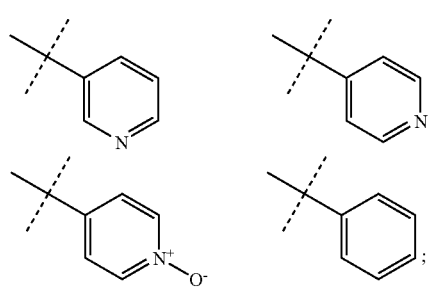
and $R^a$ and $R^b$ are both fluorine.
In one embodiment of formula (II):
$Y^2$ is halogen;
$Y^3$ is hydrogen;
$Y^1$ and $Y^4$ are each independently hydrogen or halogen;

$X^1$ is selected from the group consisting of:

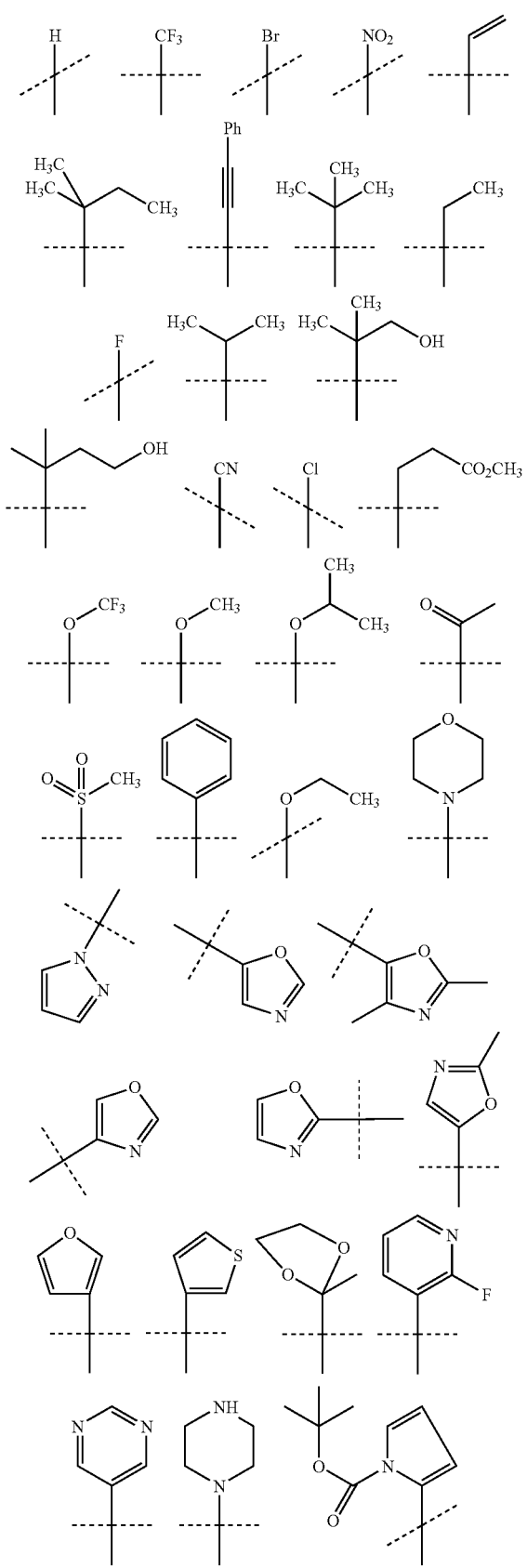

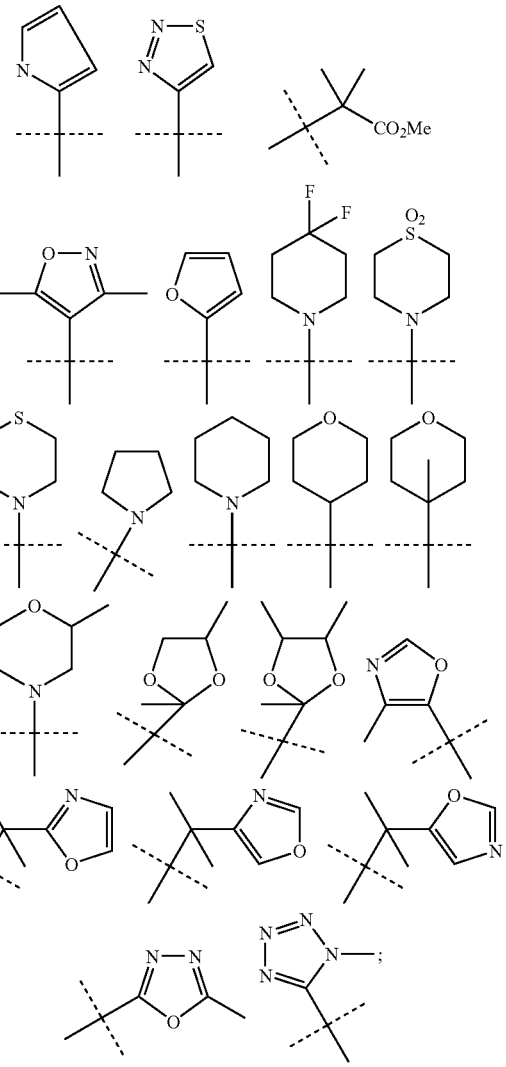

$X^2$, $X^3$, and $X^5$ are hydrogen;
$X^4$ is halogen, —CN, $CF_3$, or hydrogen;
$Ar^2$ is selected from the group consisting of:

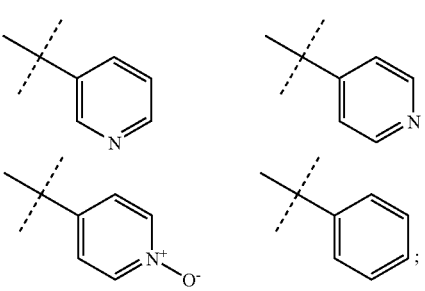

and $R^a$ and $R^b$ are both fluorine.

In one embodiment of formula (IV),
$Y^3$ is hydrogen;
$Y^1$ is chlorine or fluorine, with the following provisos:
when $Y^1$ is chlorine, both $Y^2$ and $Y^4$ are hydrogen; and
when $Y^1$ is fluorine, either $Y^2$ or $Y^4$ are fluorine, the other being hydrogen; and Ar² is selected from the group consisting of:

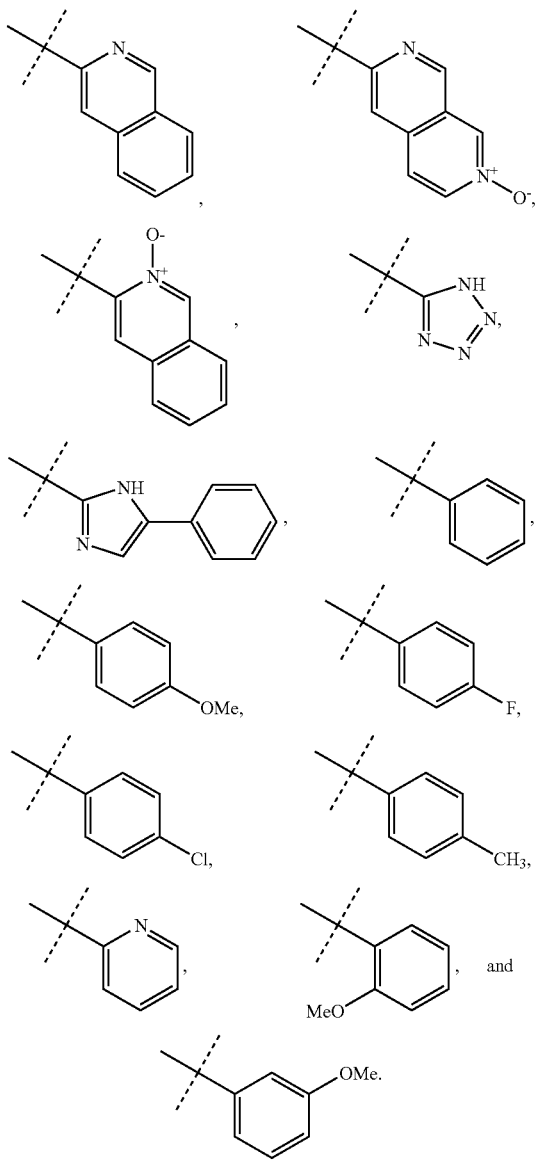

In one embodiment of formula (IV),
Y² is halogen;
Y³ is hydrogen;
Y¹ and Y⁴ are each independently hydrogen or halogen; and
Ar² is selected from the group consisting of:

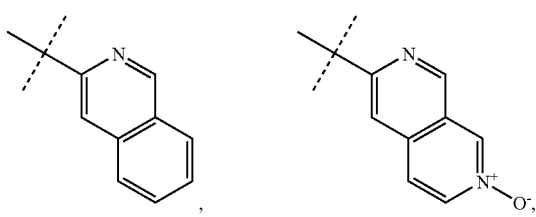

-continued

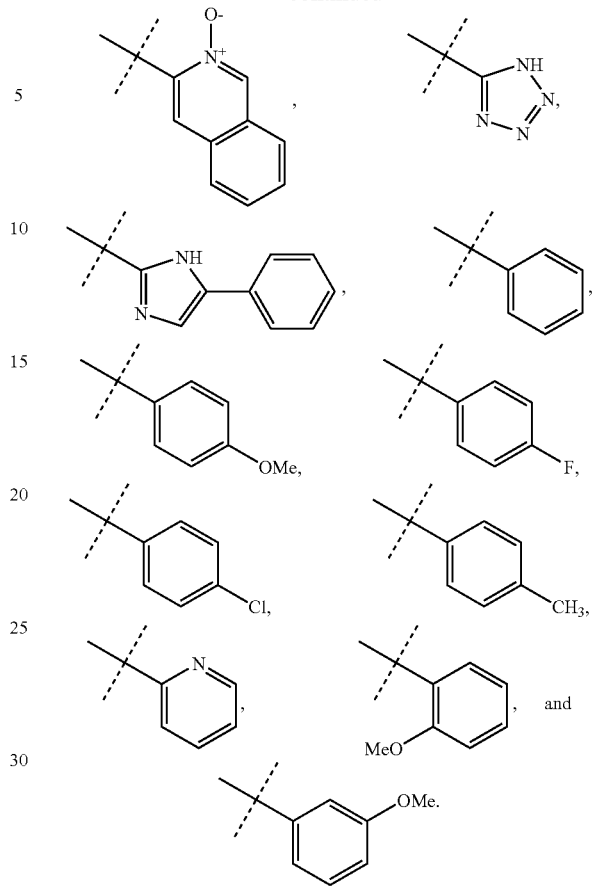

In one embodiment of formula (IV),
Y³ is hydrogen;
Y¹ is chlorine or fluorine, with the following provisos: when Y¹ is chlorine, both Y² and Y⁴ are hydrogen; and when Y¹ is fluorine, either Y² or Y⁴ are fluorine, the other being hydrogen;
Ar² is selected from the group consisting of:

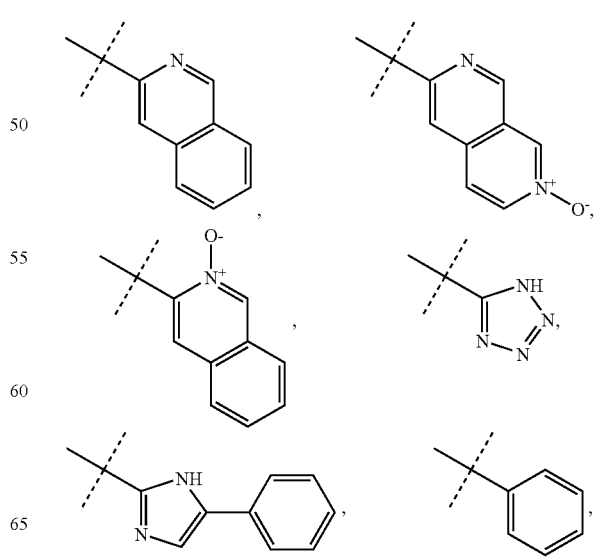

-continued

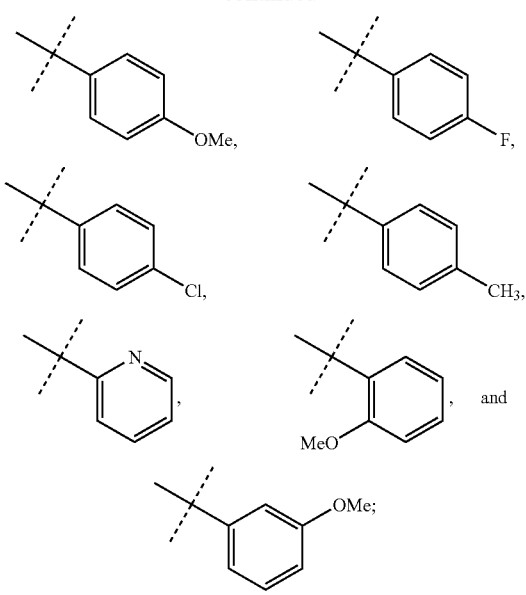

and $X^2$, $X^3$ and $X^5$ are hydrogen.

In one embodiment of formula (IV), $Y^2$ is halogen;

$Y^3$ is hydrogen;

$Y^1$ and $Y^4$ are each independently hydrogen or halogen;

$Ar^2$ is selected from the group consisting of:

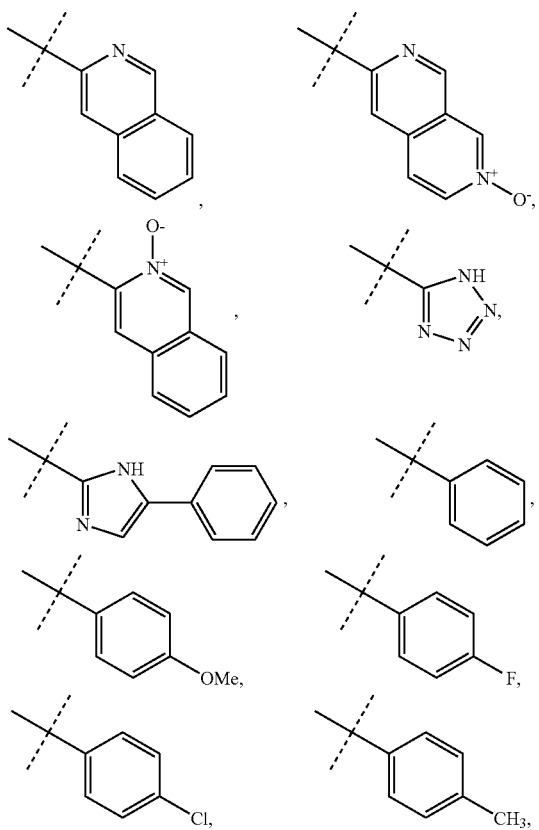

-continued

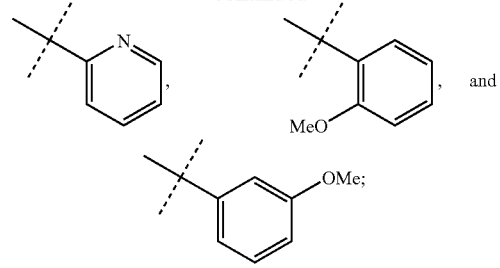

and $X^2$, $X^3$ and $X^5$ are hydrogen.

In one embodiment of formula (IV), $Y^3$ is hydrogen;

$Y^1$ is chlorine or fluorine, with the following provisos: when $Y^1$ is chlorine, both $Y^2$ and $Y^4$ are hydrogen; and when $Y^1$ is fluorine, either $Y^2$ or $Y^4$ are fluorine, the other being hydrogen;

$Ar^2$ is selected from the group consisting of:

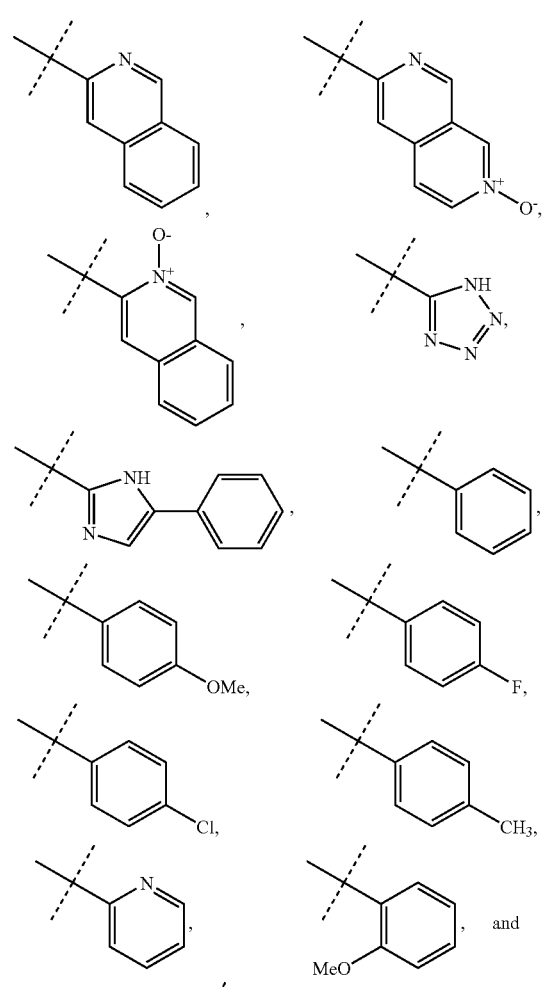

101
$X^2$, $X^3$ and $X^5$ are hydrogen; and
$X^1$ is selected from the group consisting of:
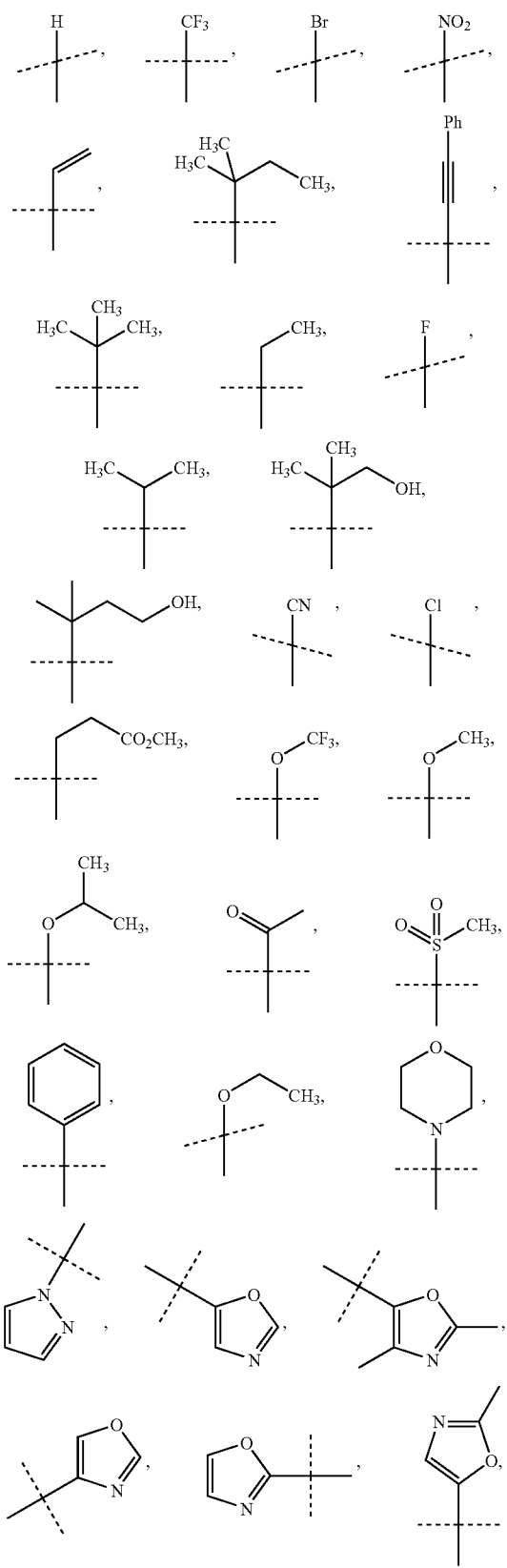
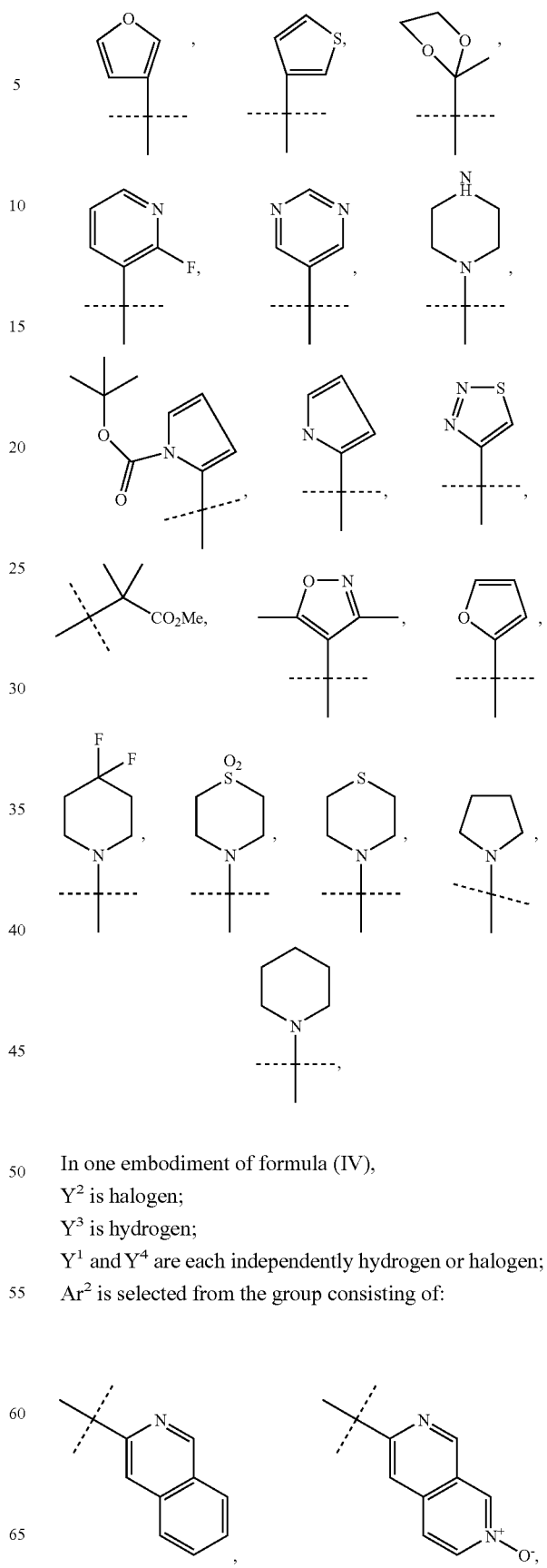
In one embodiment of formula (IV),
$Y^2$ is halogen;
$Y^3$ is hydrogen;
$Y^1$ and $Y^4$ are each independently hydrogen or halogen;
$Ar^2$ is selected from the group consisting of:

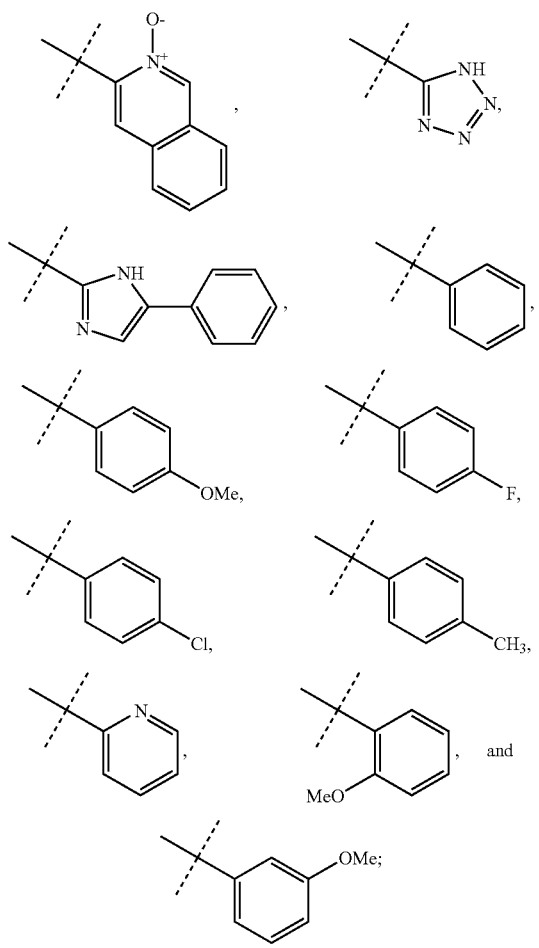
$X^2$, $X^3$ and $X^5$ are hydrogen; and
$X^1$ is selected from the group consisting of:
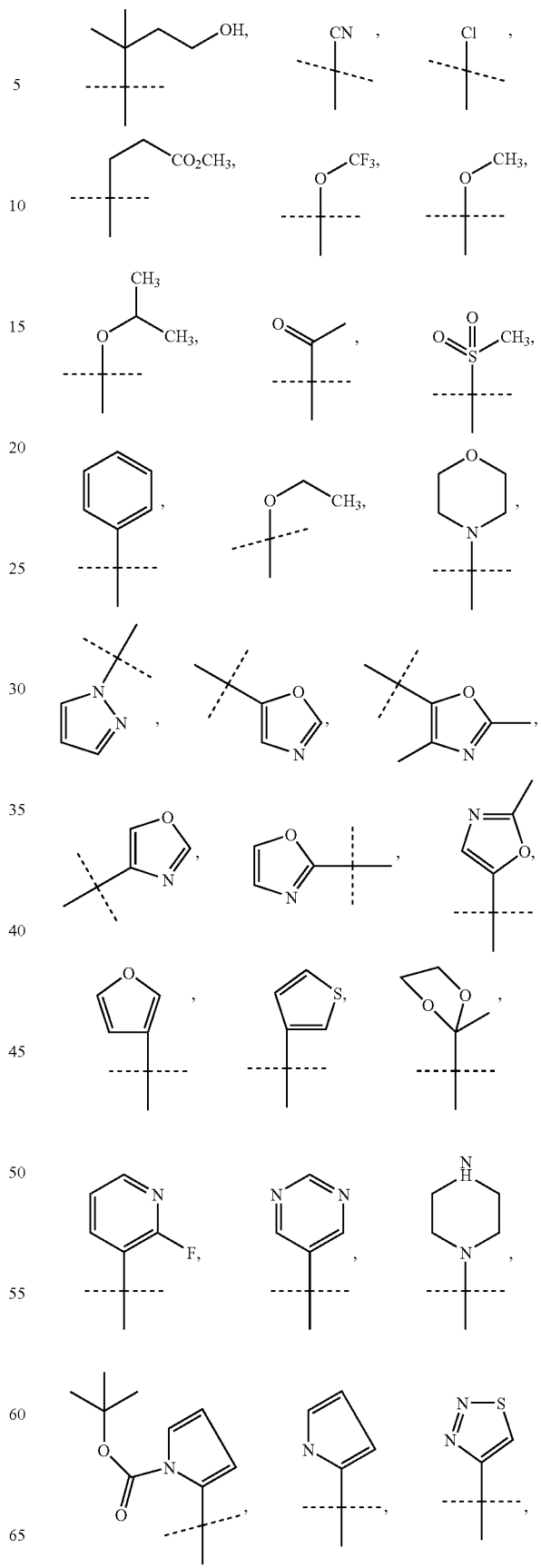

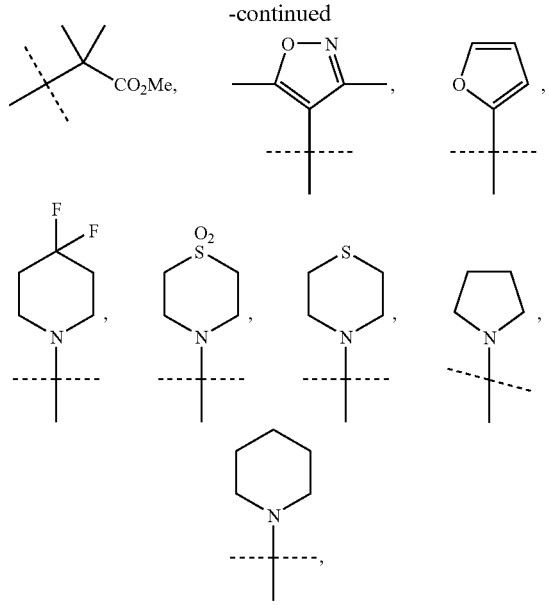

In one embodiment of formula (IV),

Y³ is hydrogen;

Y¹ is chlorine or fluorine, with the following provisos: when Y¹ is chlorine, both Y² and Y⁴ are hydrogen; and when Y¹ is fluorine, either Y² or Y⁴ are fluorine, the other being hydrogen;

Ar² is selected from the group consisting of:

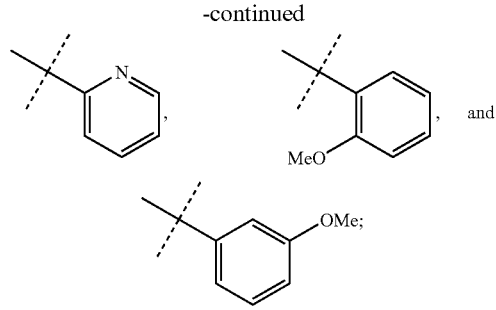

$X^2$, $X^3$ and $X^5$ are hydrogen;

$X^4$ is halogen, —CN, or —CF$_3$; and $X^1$ is selected from the group consisting of:

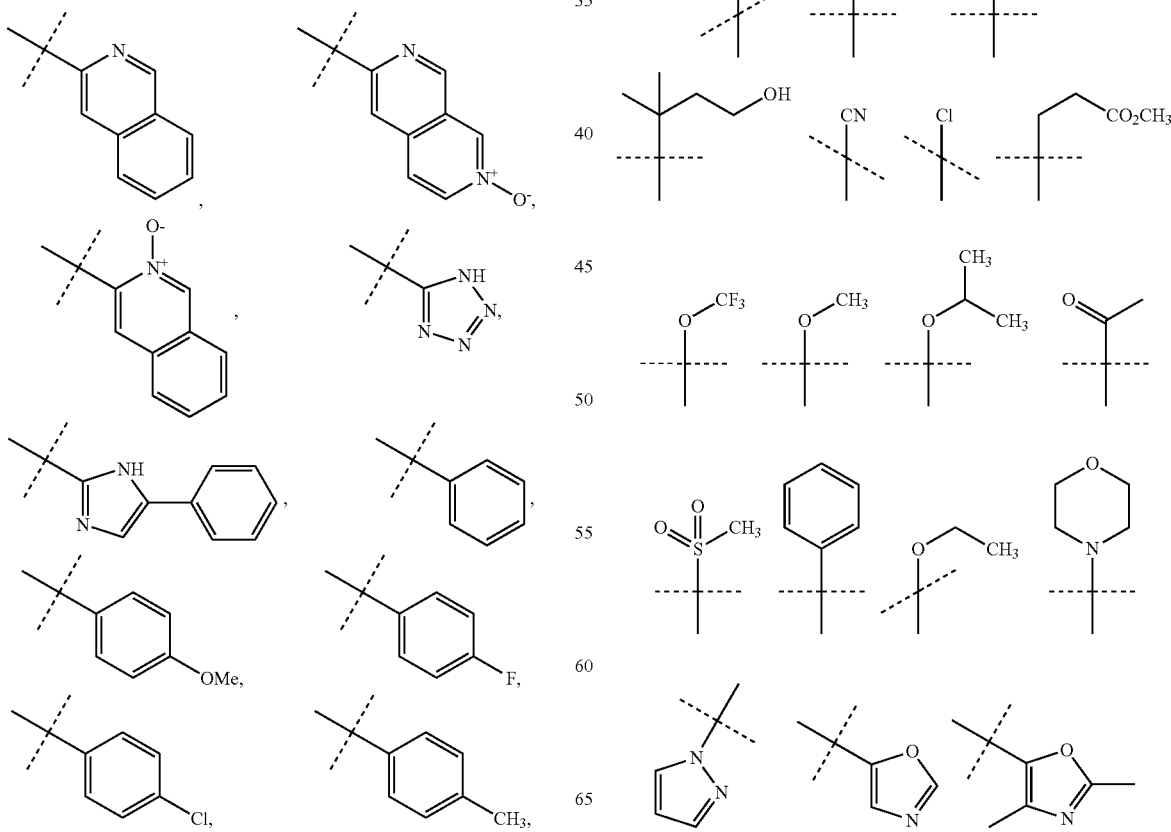

-continued
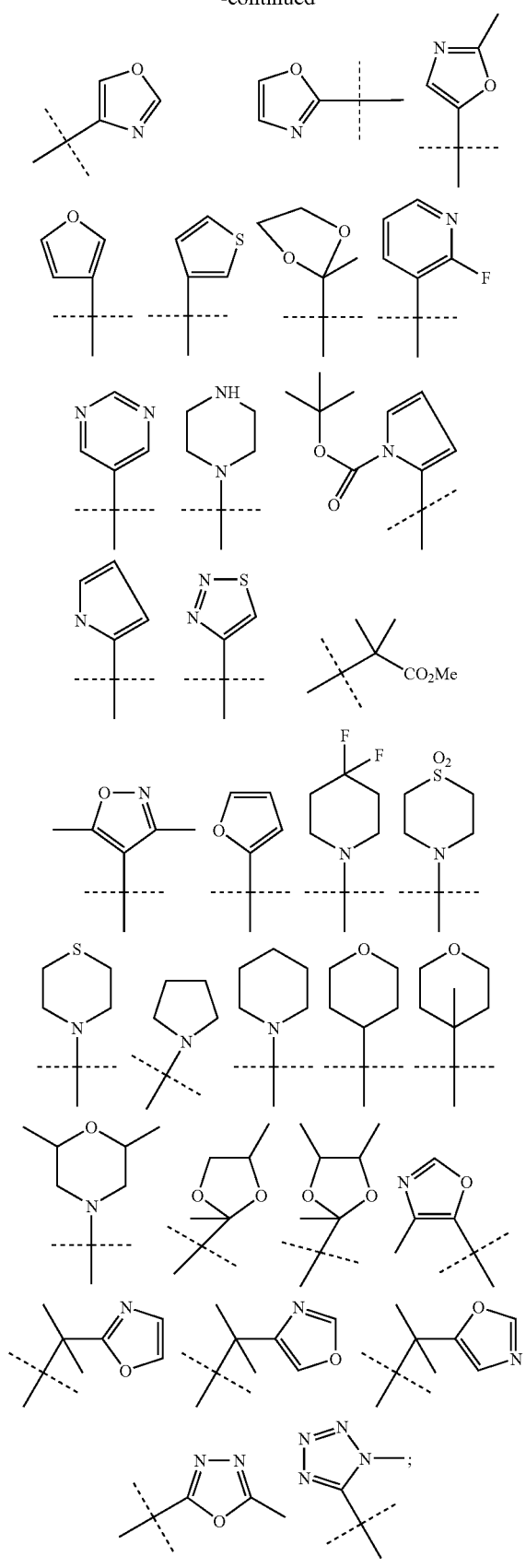
In one embodiment of formula (IV),
$Y^2$ is halogen;
$Y^3$ is hydrogen;
$Y^1$ and $Y^4$ are each independently hydrogen or halogen;
$Ar^2$ is selected from the group consisting of:
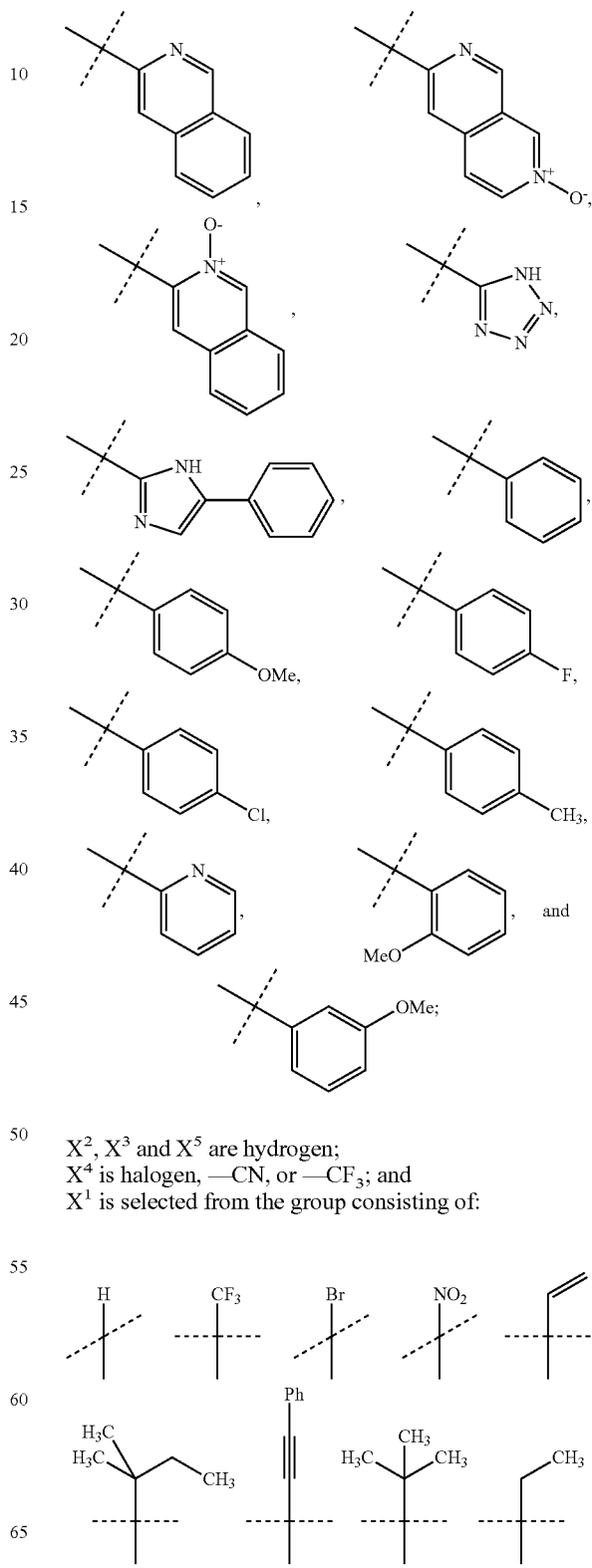
$X^2$, $X^3$ and $X^5$ are hydrogen;
$X^4$ is halogen, —CN, or —CF$_3$; and
$X^1$ is selected from the group consisting of:

-continued
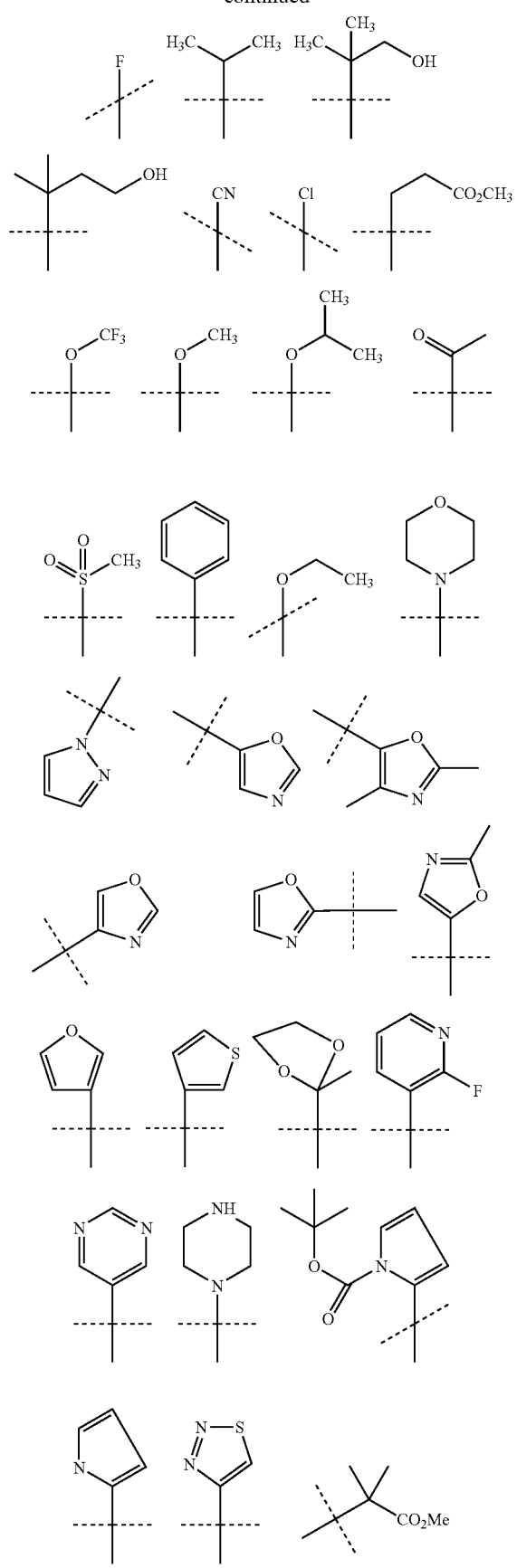
-continued
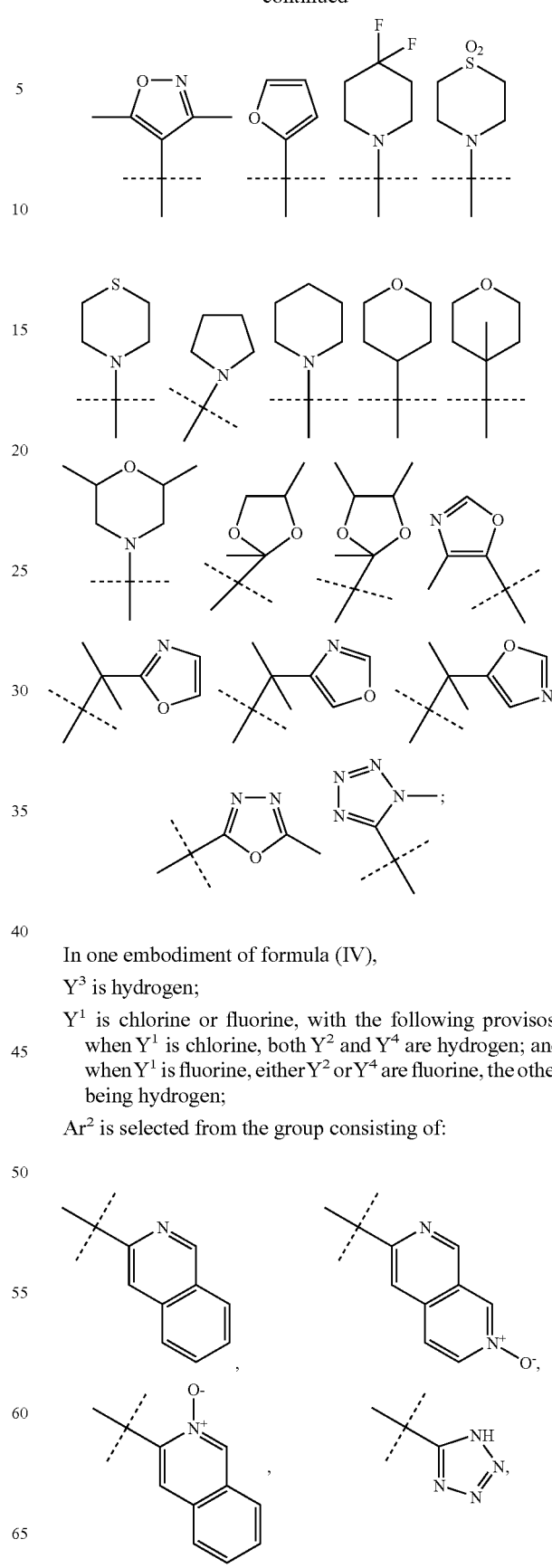
In one embodiment of formula (IV),
$Y^3$ is hydrogen;
$Y^1$ is chlorine or fluorine, with the following provisos: when $Y^1$ is chlorine, both $Y^2$ and $Y^4$ are hydrogen; and when $Y^1$ is fluorine, either $Y^2$ or $Y^4$ are fluorine, the other being hydrogen;
$Ar^2$ is selected from the group consisting of:
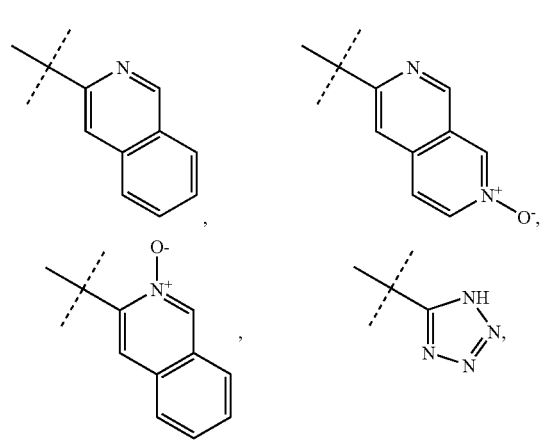

111
-continued
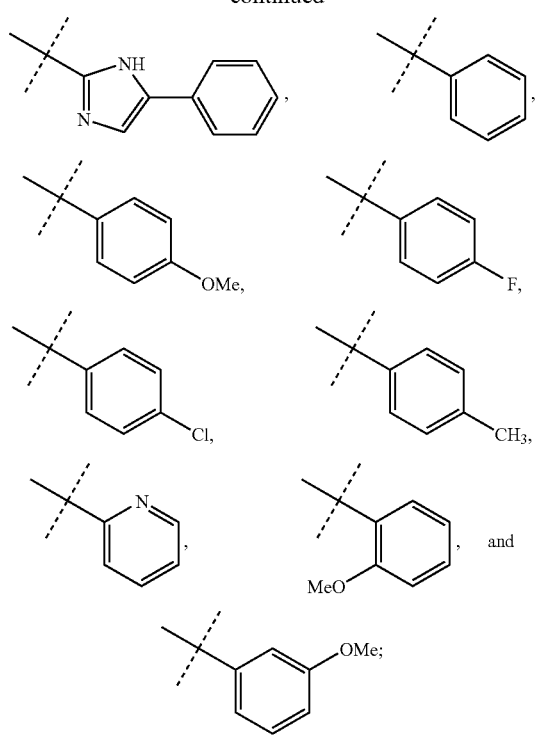
$X^2$, $X^3$ and $X^5$ are hydrogen;
$X^4$ is hydrogen; and
$X^1$ is selected from the group consisting of:
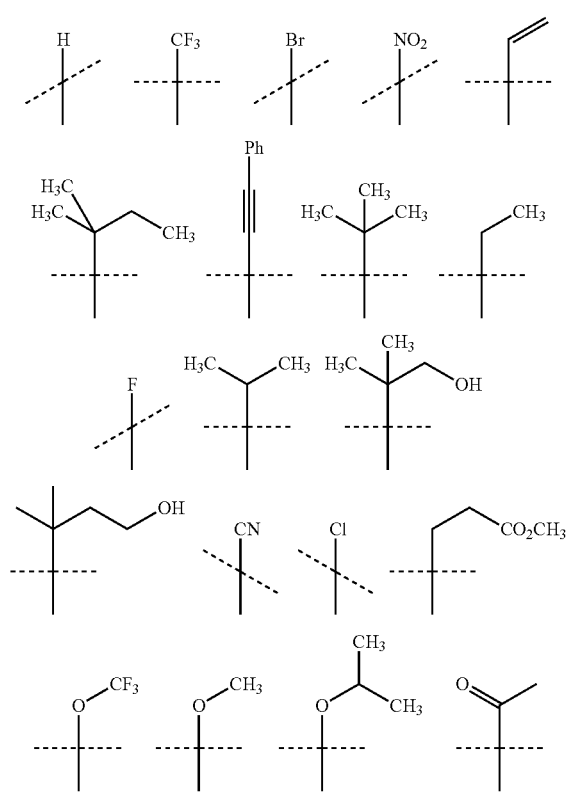
112
-continued
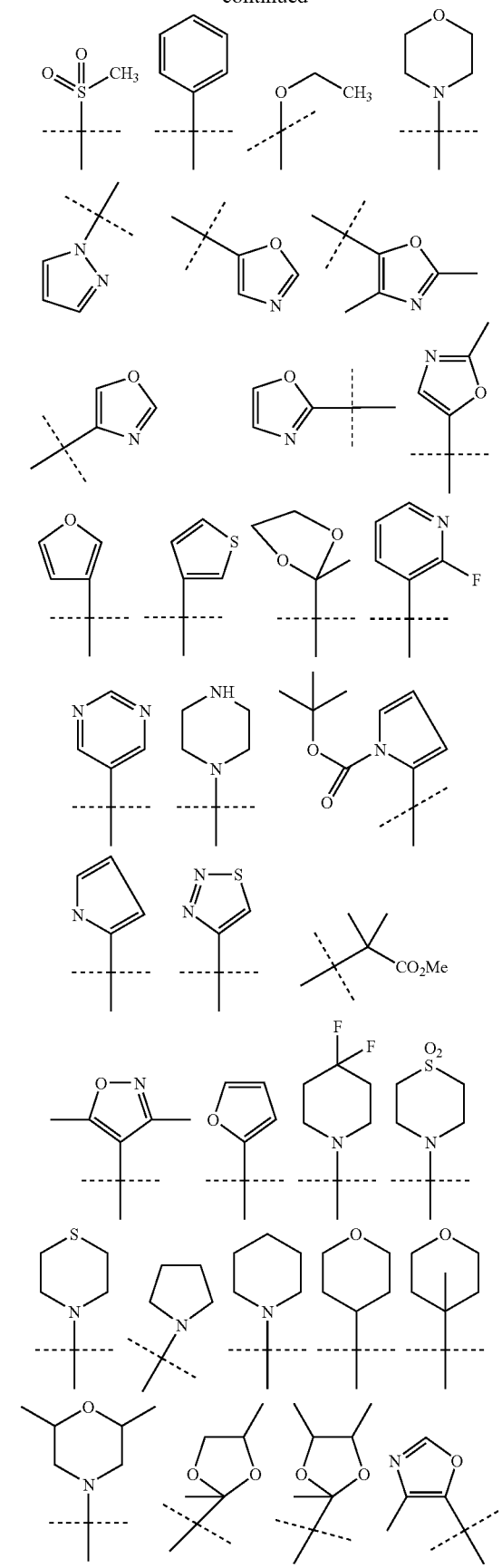

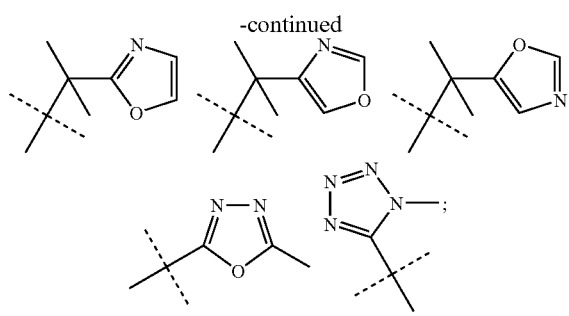
In one embodiment of formula (IV),
Y² is halogen;
Y³ is hydrogen;
Y¹ and Y⁴ are each independently hydrogen or halogen;
Ar² is selected from the group consisting of:
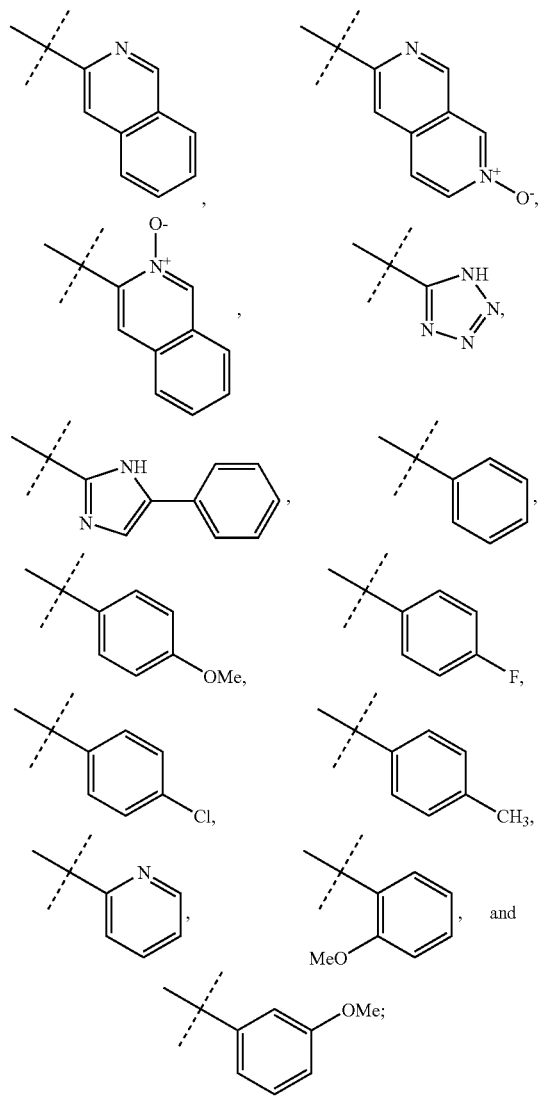
X², X³ and X⁵ are hydrogen;
X⁴ is hydrogen; and
X¹ is selected from the group consisting of:
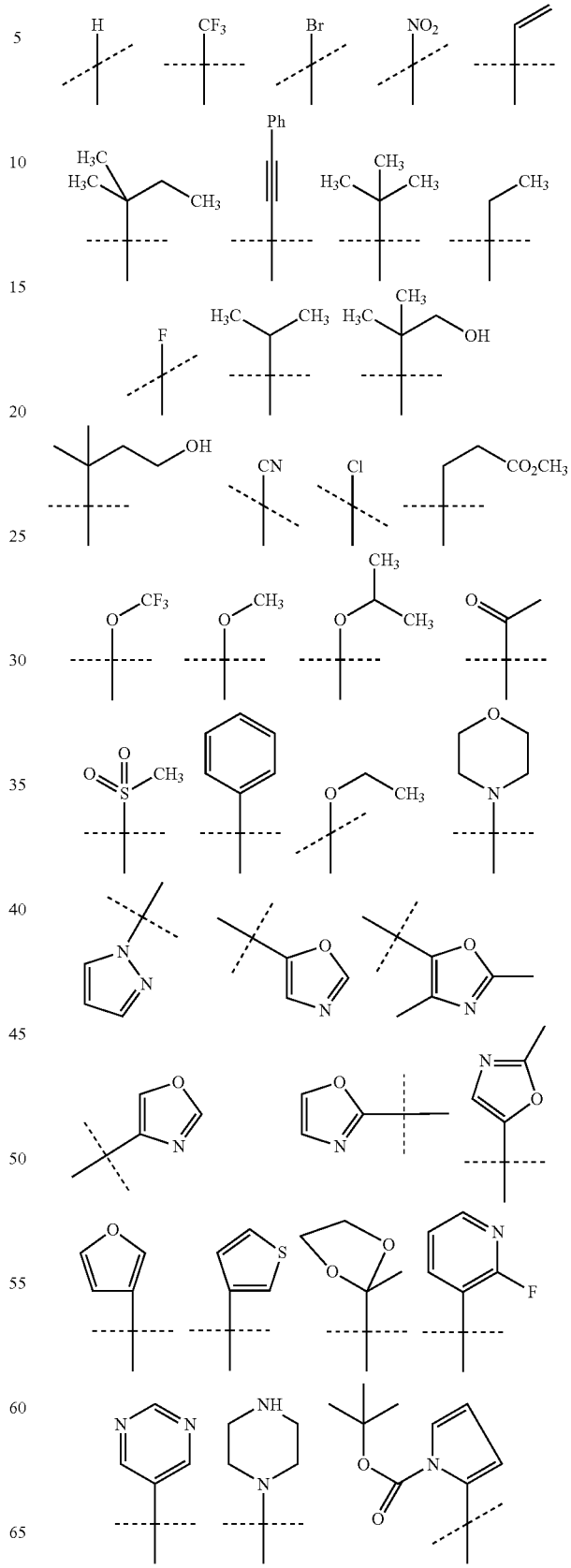

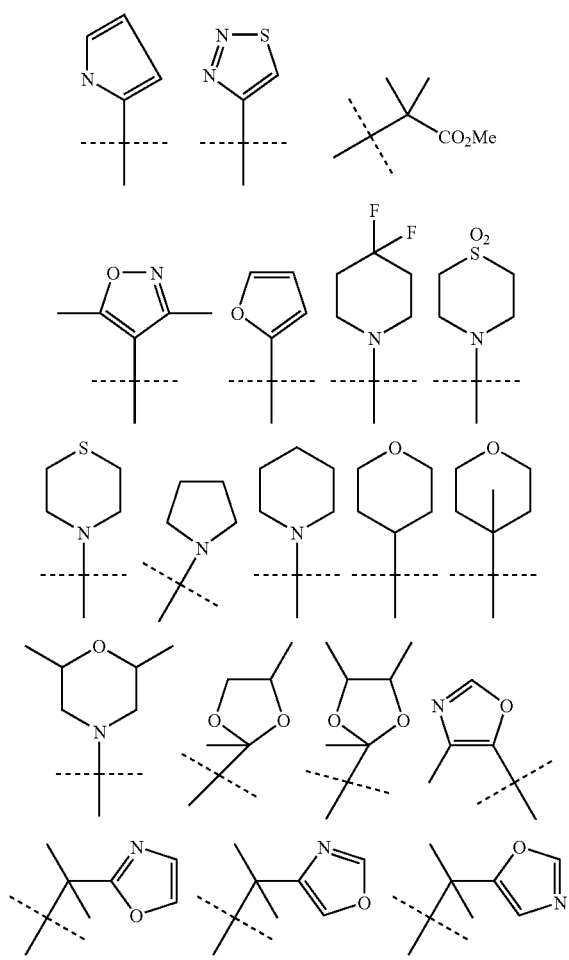
In one embodiment of formula (VII, IX),
$Y^3$ is hydrogen;
$Y^1$ is chlorine or fluorine, with the proviso that when $Y^1$ is chlorine, both $Y^2$ and $Y^4$ are hydrogen or when $Y^1$ is fluorine, either $Y^2$ or $Y^4$ is also fluorine;
$X^2$, $X^3$ and $X^5$ are hydrogen; and
$Ar^2$ is selected from the group consisting of:
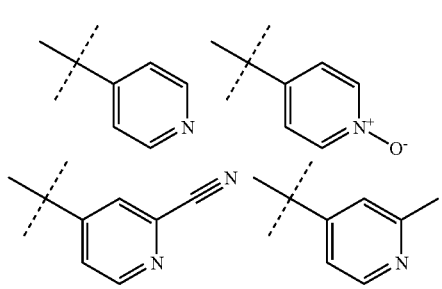
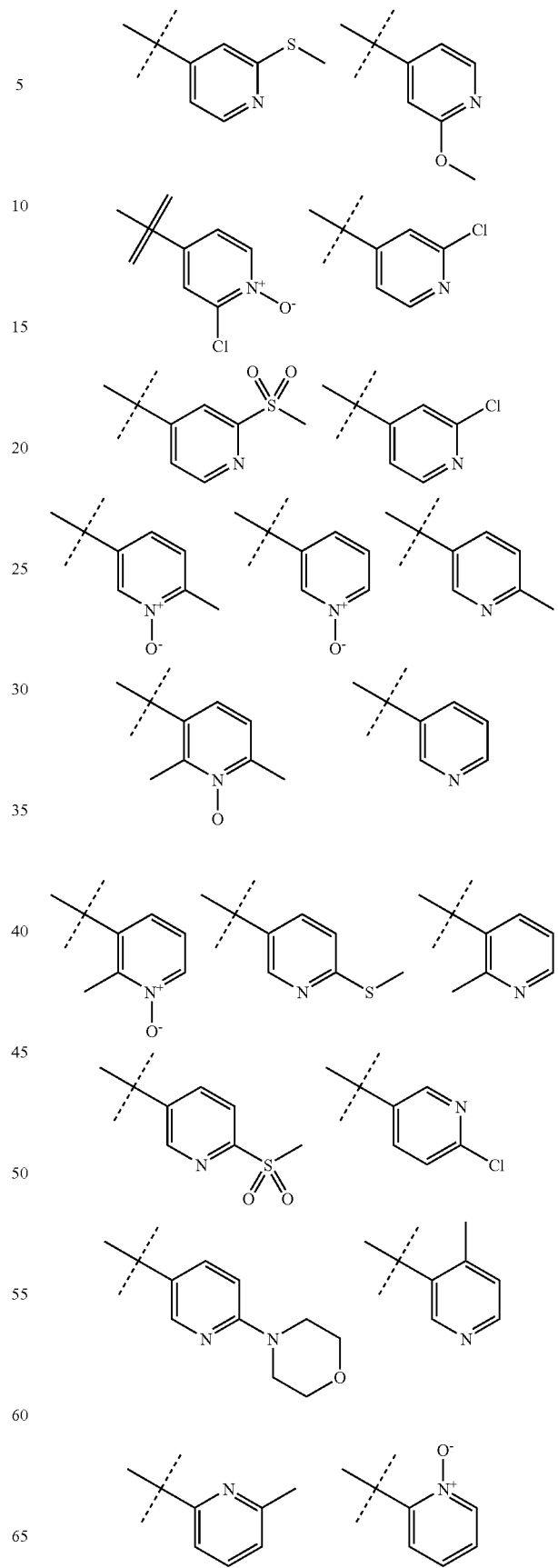

-continued

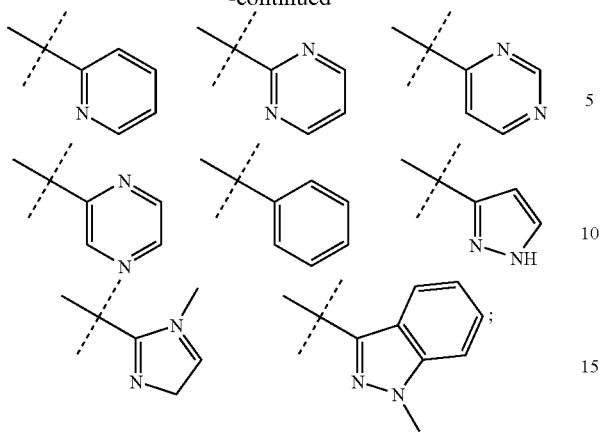

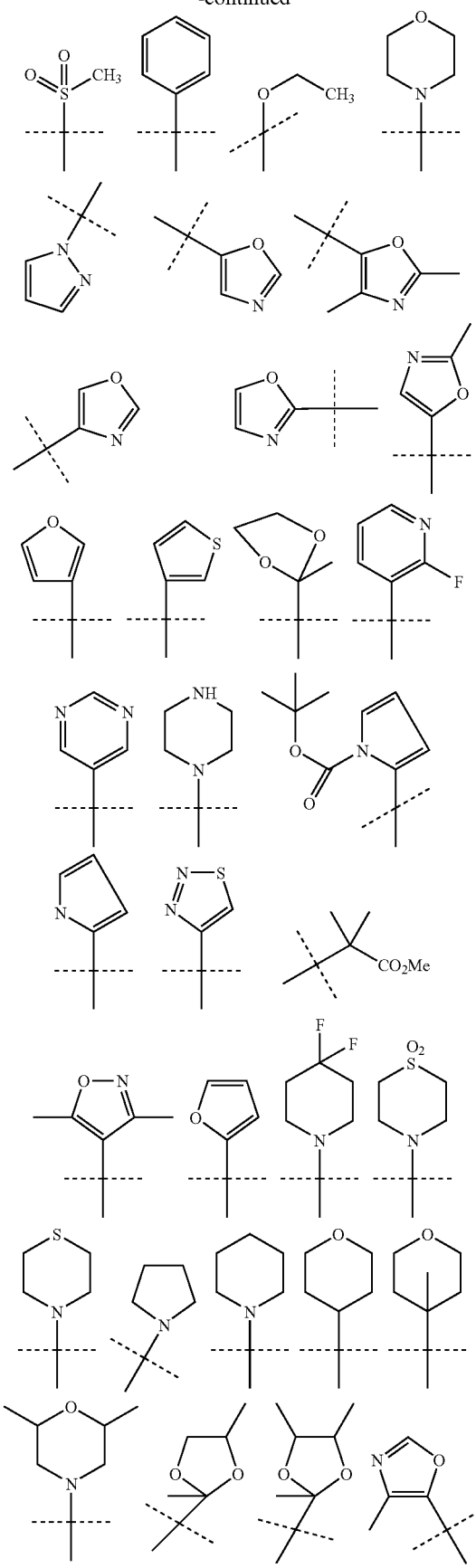

R$^c$ when present is as defined for formula (VI), preferably R$^c$ is hydrogen or —C(O)R, more preferably COMe;

T when present is as defined for formula (VIII), preferably T is =CHC(O)R$^{41}$, =CHC(O)$_2$R$^{41}$, =CH$_2$ or =NOMe, more preferably =CHC(O)Me, =CHC(O)$_2$Me.

In other embodiments Y$^2$ is halogen; Y$^3$ is hydrogen; and Y$^1$ and Y$^4$ are each independently hydrogen or halogen.

In one embodiment of formula (VII),

Y$^3$ is hydrogen;

Y$^1$ is chlorine or fluorine, with the proviso that when Y$^1$ is chlorine, both Y$^2$ and Y$^4$ are hydrogen or when Y$^1$ is fluorine, either Y$^2$ or Y$^4$ is also fluorine;

and X$^1$ is selected from the group consisting of:

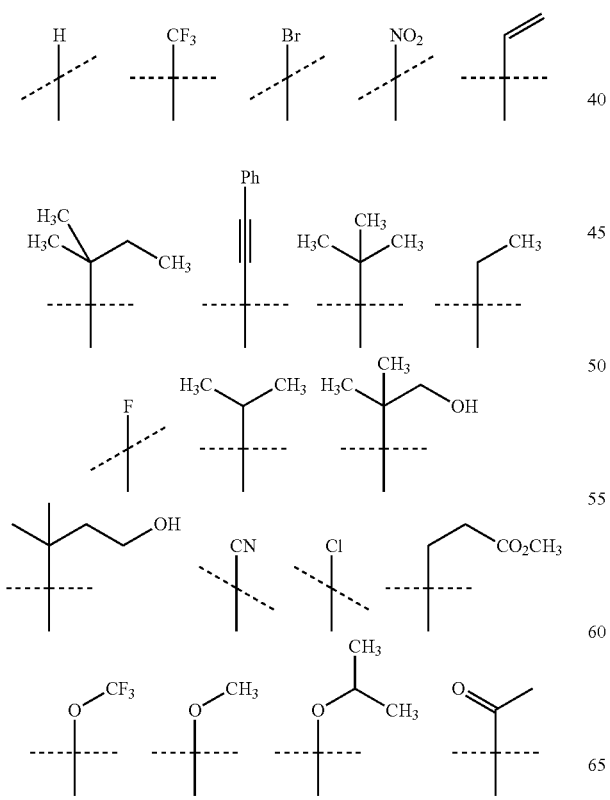

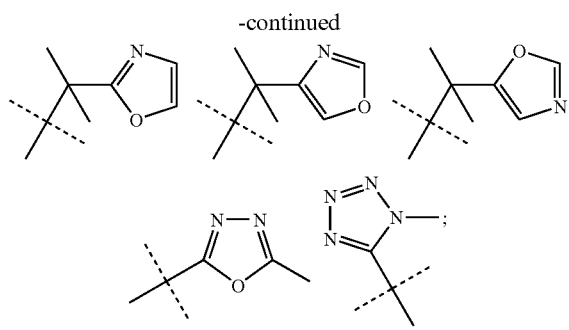

$X^2$, $X^3$ and $X^5$ are hydrogen;
and $Ar^2$ is selected from the group consisting of:

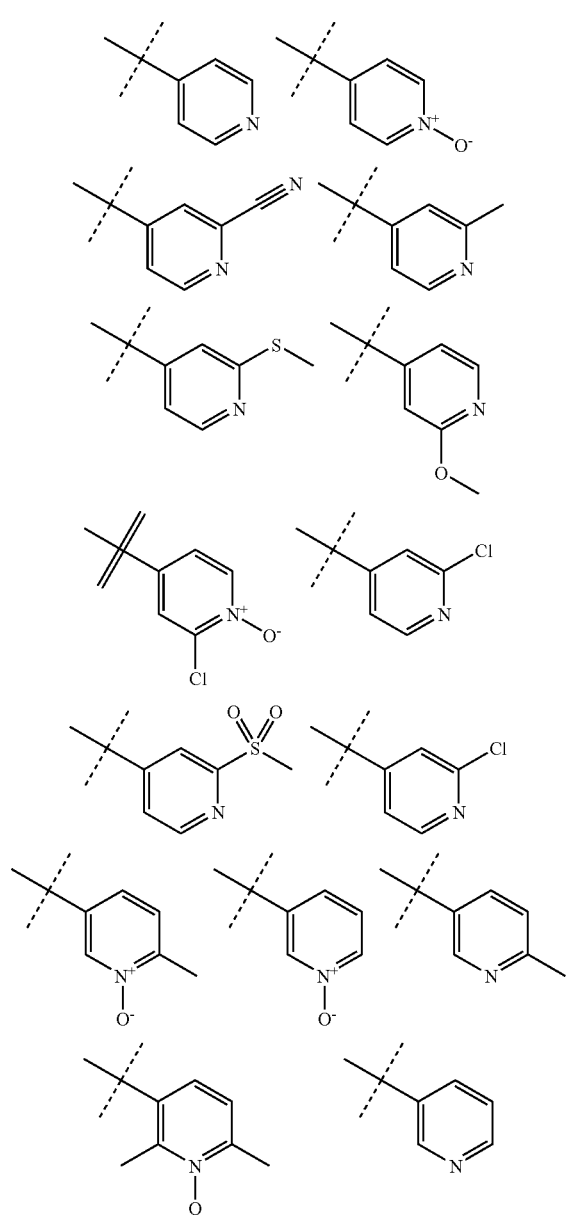

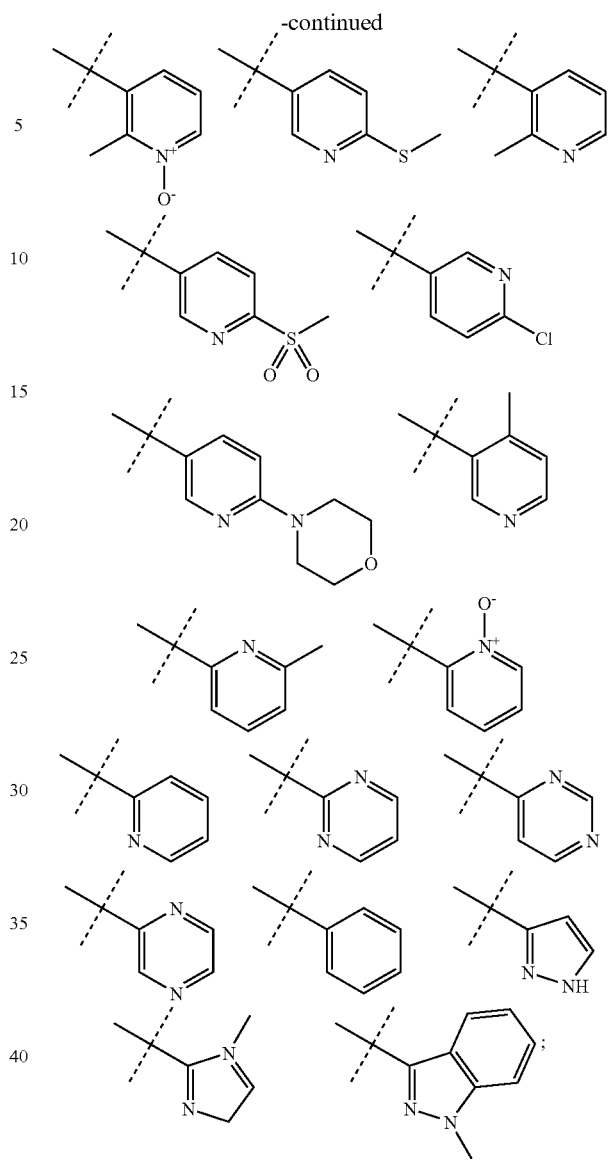

$R^c$ when present is as defined for formula (VI), preferably $R^c$ is hydrogen or —C(O)R, more preferably COMe;

T when present is as defined for formula (VIII), preferably T is =CHC(O)R$^{41}$, =CHC(O)$_2$R$^{41}$, =CH$_2$ or =NOMe, more preferably =CHC(O)Me, =CHC(O)$_2$Me.

In other embodiments $Y^2$ is halogen; $Y^3$ is hydrogen; and $Y^1$ and $Y^4$ are each independently hydrogen or halogen.

In one embodiment of formula (VII and IX),
$Y^3$ is hydrogen;
$Y^1$ is chlorine or fluorine, with the proviso that when $Y^1$ is chlorine, both $Y^2$ and $Y^4$ are hydrogen or when $Y^1$ is fluorine, either $Y^2$ or $Y^4$ is also fluorine;
$X^1$ is selected from the group consisting of:

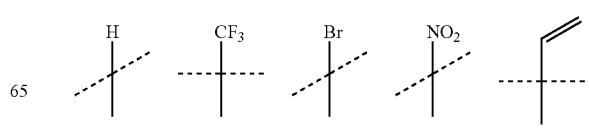

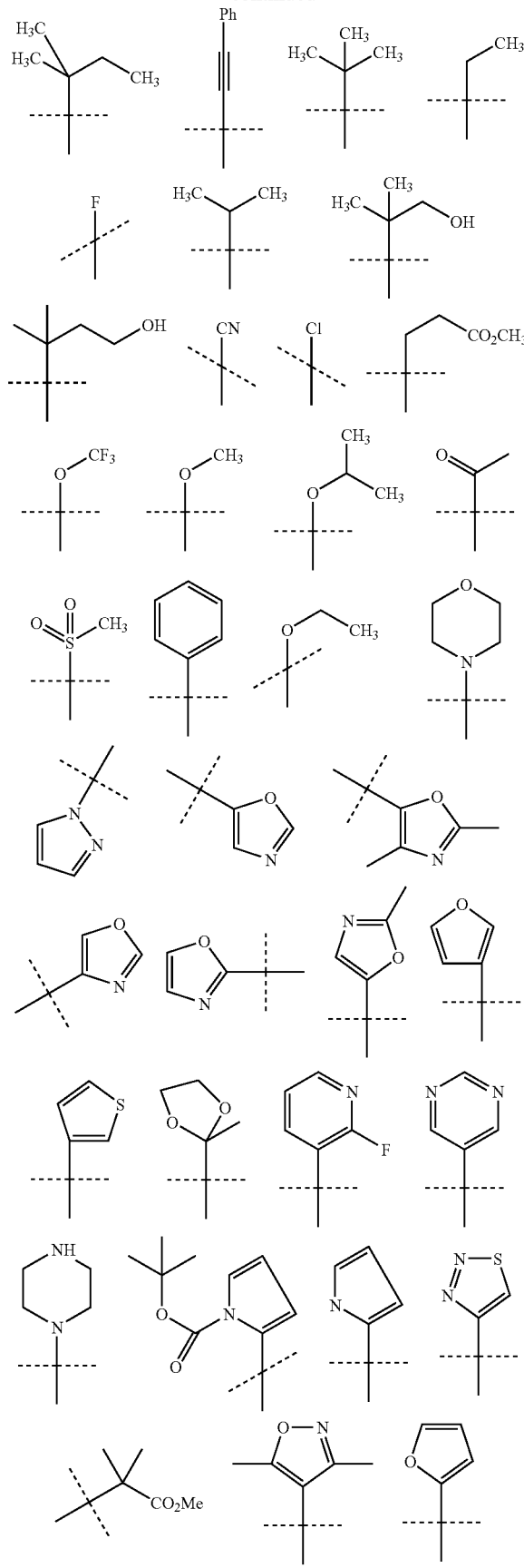
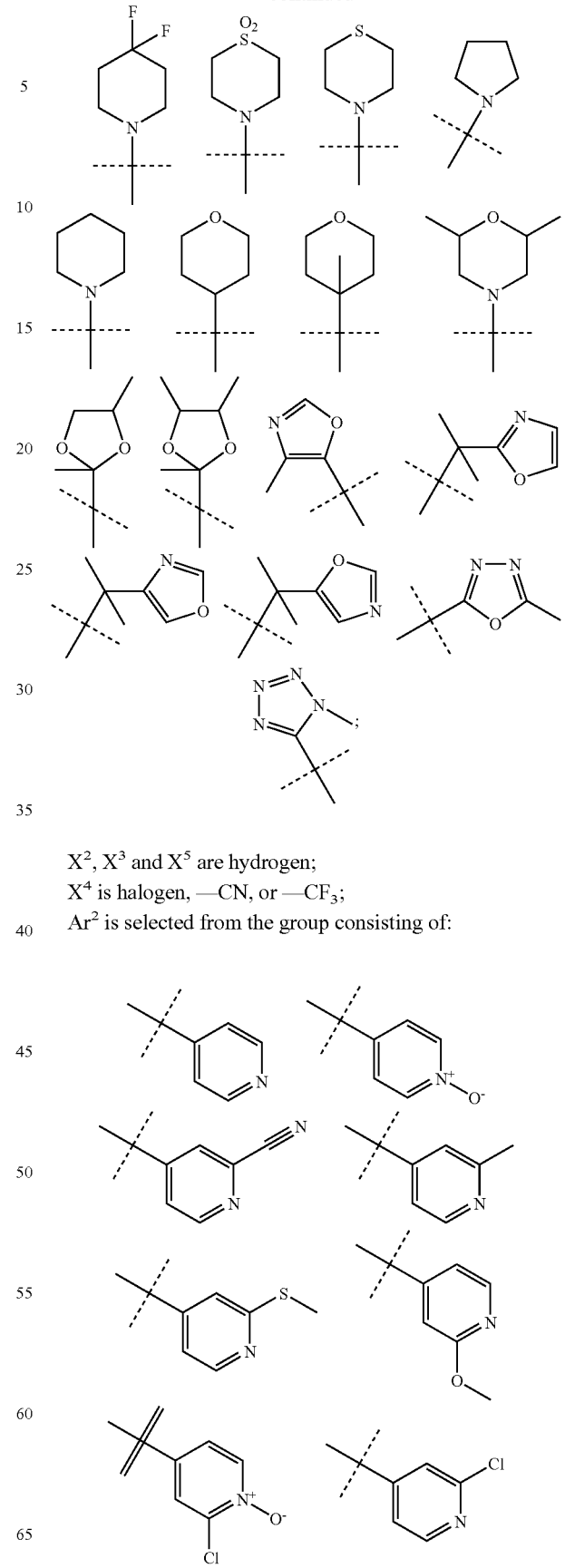
$X^2$, $X^3$ and $X^5$ are hydrogen;
$X^4$ is halogen, —CN, or —CF$_3$;
Ar$^2$ is selected from the group consisting of:

-continued

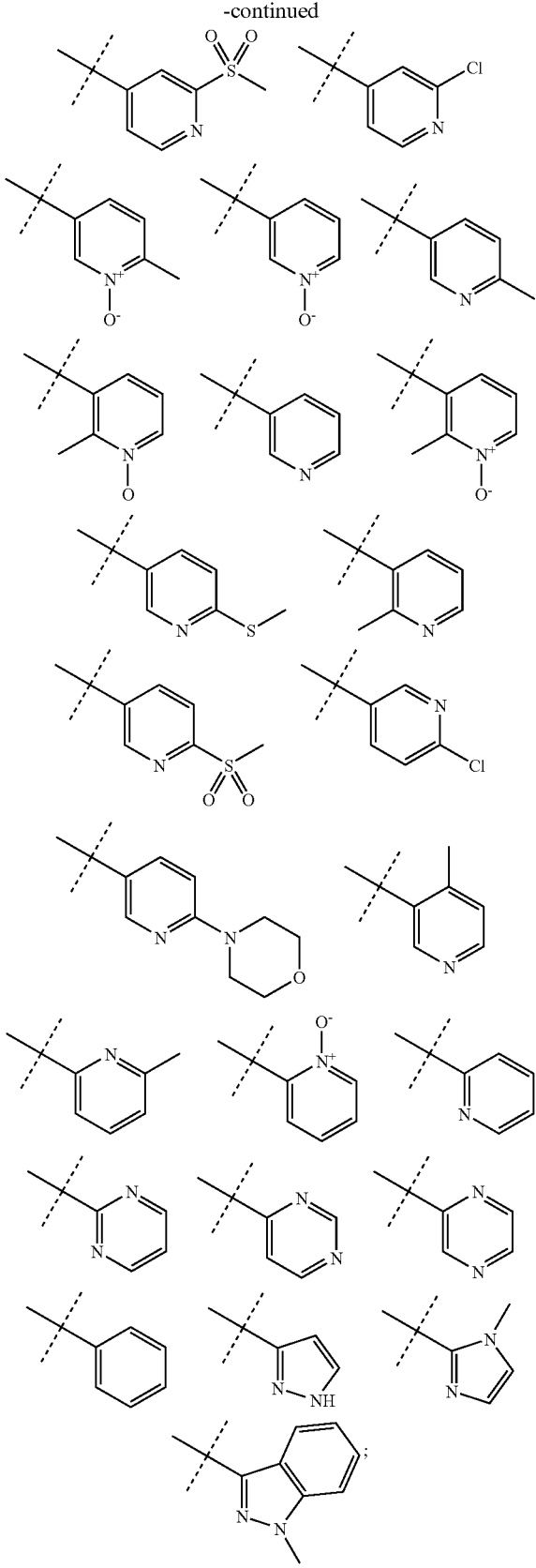

$R^c$ when present is as defined for formula (VI), preferably $R^c$ is hydrogen or —C(O)R, more preferably COMe;

T when present is as defined for formula (VIII), preferably T is =CHC(O)$R^{41}$, =CHC(O)$_2$$R^{41}$, =CH$_2$ or =NOMe, more preferably =CHC(O)Me, =CHC(O)$_2$Me.

In other embodiments $Y^2$ is halogen; $Y^3$ is hydrogen; and $Y^1$ and $Y^4$ are each independently hydrogen or halogen.

In one embodiment of formula (VII and IX), $Y^3$ is hydrogen;

$Y^1$ is chlorine or fluorine, with the proviso that when $Y^1$ is chlorine, both $Y^2$ and $Y^4$ are hydrogen or when $Y^1$ is fluorine, either $Y^2$ or $Y^4$ is also fluorine;

$X^1$ is selected from the group consisting of:

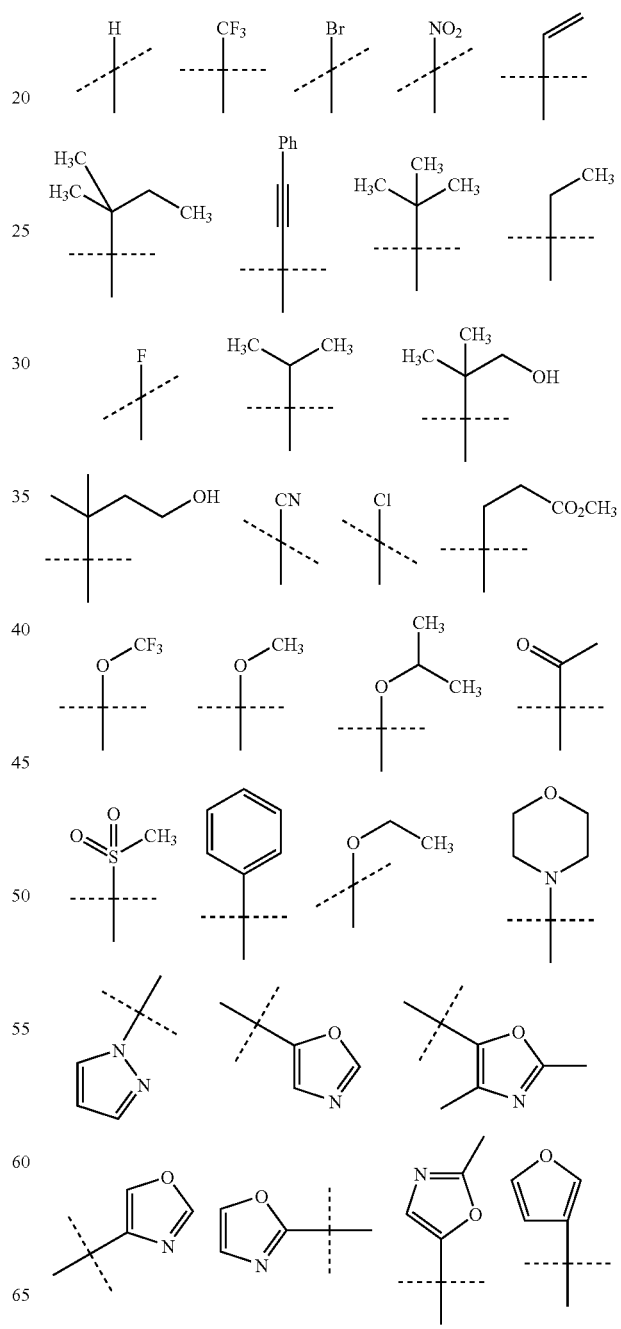

-continued
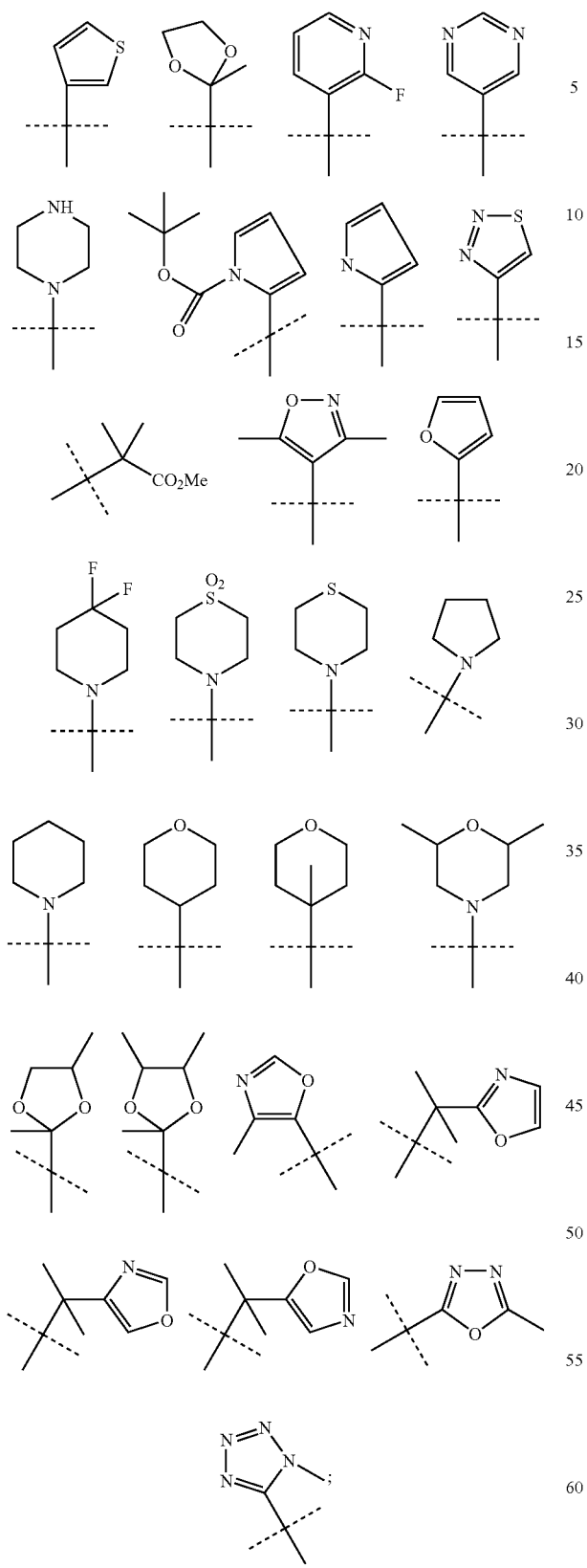
$X^2$, $X^3$ and $X^5$ are hydrogen;
$X^4$ is hydrogen;
and $Ar^2$ is selected from the group consisting of:
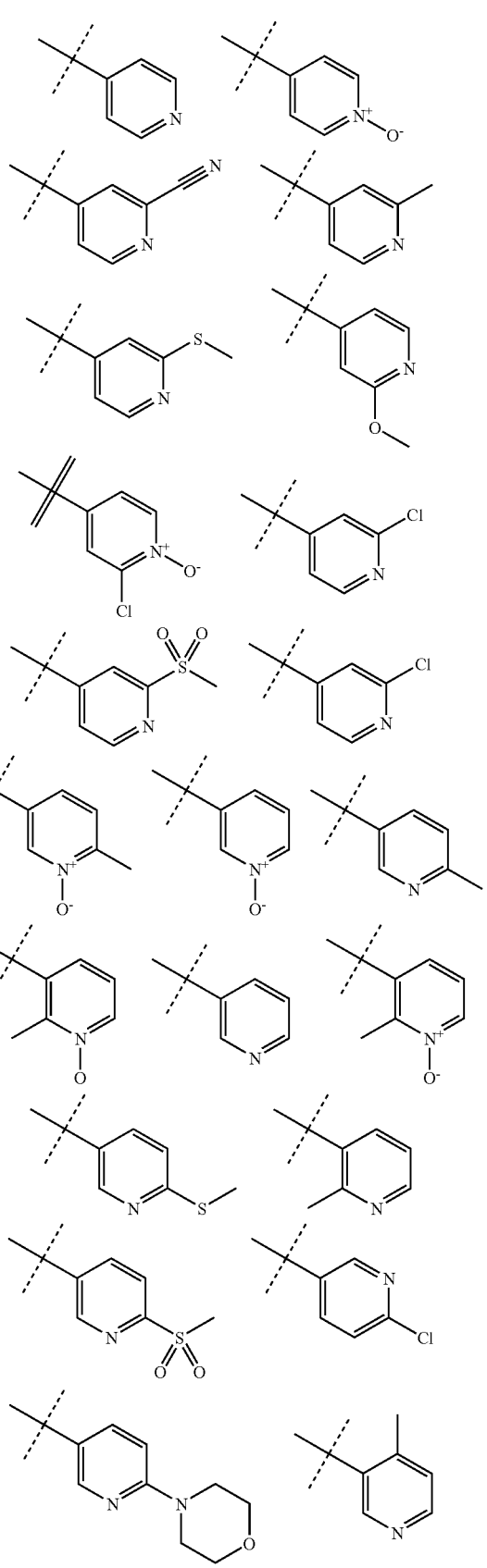

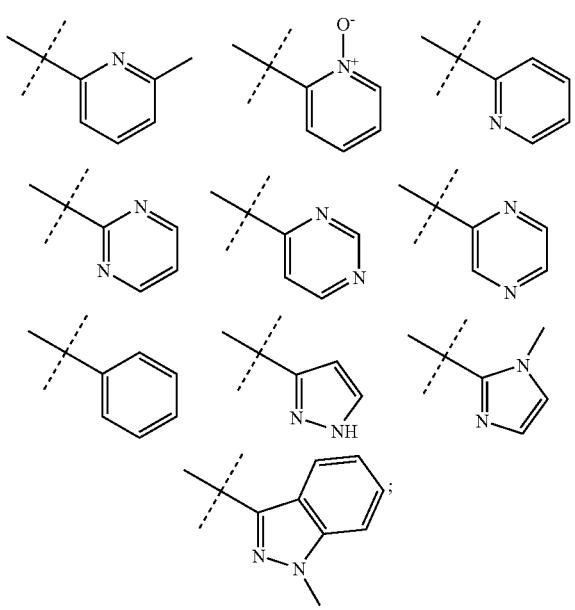

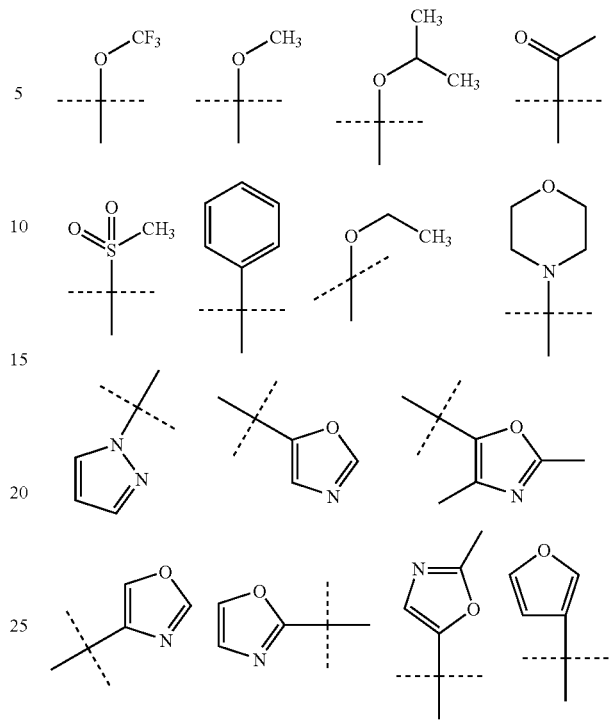

R$^c$ when present is as defined for formula (VI), preferably R$^c$ is hydrogen or —C(O)R, more preferably COMe;

T when present is as defined for formula (VIII), preferably T is =CHC(O)R$^{41}$, =CHC(O)$_2$R$^{41}$, =CH$_2$ or =NOMe, more preferably =CHC(O)Me, =CHC(O)$_2$Me.

In other embodiments Y$^2$ is halogen; Y$^3$ is hydrogen; and Y$^1$ and Y$^4$ are each independently hydrogen or halogen.

In one embodiment of formula (VII),

Y$^3$ is hydrogen;

Y$^1$ is chlorine or fluorine, with the proviso that when Y$^1$ is chlorine, both Y$^2$ and Y$^4$ are hydrogen or when Y$^1$ is fluorine, either Y$^2$ or Y$^4$ is also fluorine;

X$^1$ is selected from the group consisting of:

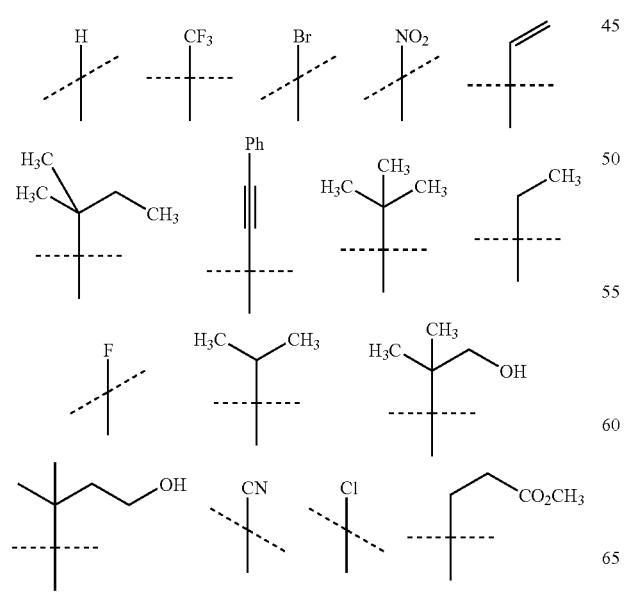

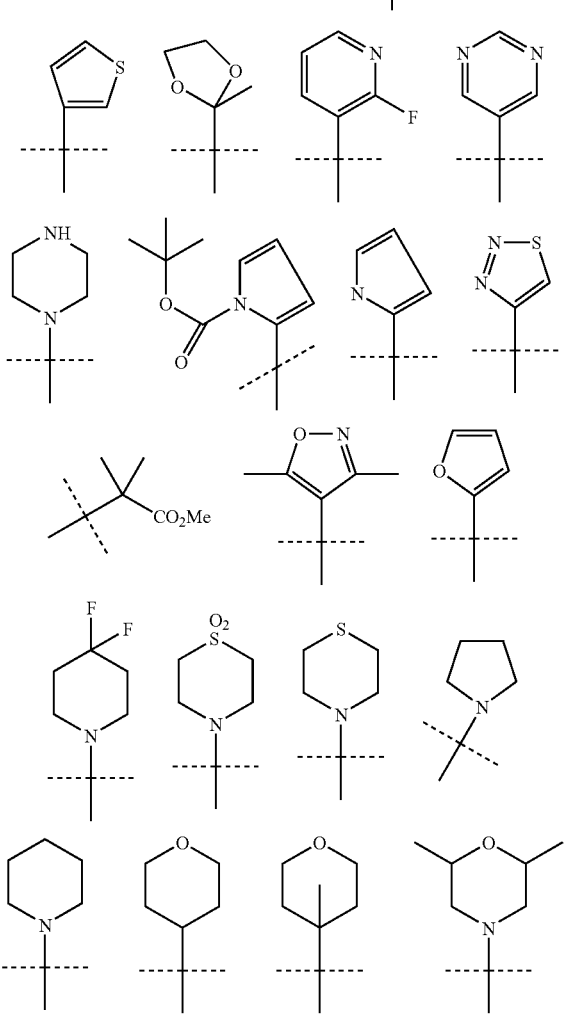

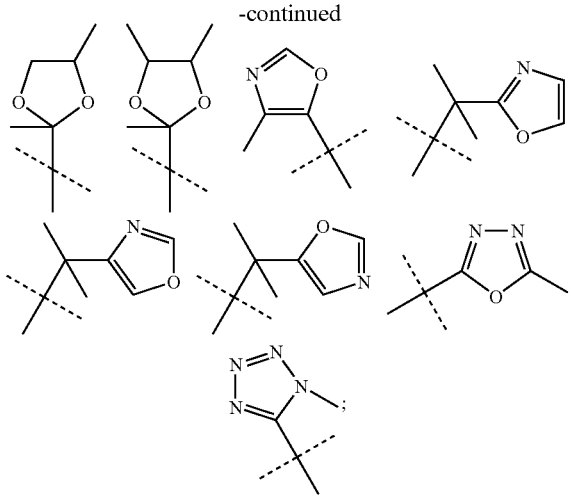

$X^2$, $X^3$ and $X^5$ are hydrogen;
$X^4$ is hydrogen;
and $Ar^2$ is selected from the group consisting of:

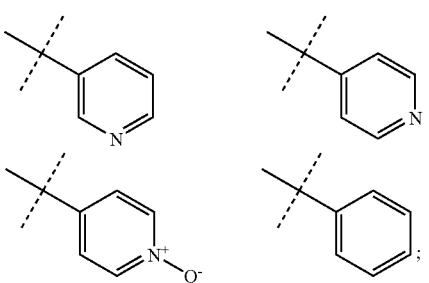

$R^c$ when present is as defined for formula (VI), preferably $R^c$ is hydrogen or —C(O)R, more preferably COMe;
T when present is as defined for formula (VIII), preferably T is =CHC(O)$R^{41}$, =CHC(O)$_2R^{41}$, =CH$_2$ or =NOMe, more preferably =CHC(O)Me, =CHC(O)$_2$Me.

In other embodiments $Y^2$ is halogen; $Y^3$ is hydrogen; and $Y^1$ and $Y^4$ are each independently hydrogen or halogen.

In one embodiment for any of formulae (XX-CXXXVI) where, $Z^1$, $Z^a$ and $Z^b$ are all simultaneously hydrogen.

In one embodiment, in each of the formula (XX-CXXXVI), $Z^1$, $Z^a$, $Z^b$ or $Z^c$ are independently selected from the group consisting of hydrogen, halogen —OR$^{10}$, —CN, —NO$_2$, =O, —OC(O)R$^{10}$, —CO$_2$R$^{10}$, —C(O)R$^{10}$, —CONR$^{11}$R$^{12}$, —NR$^{10}$C(O)R$^{12}$, —NR$^{11}$R$^{12}$, —SR$^{10}$, —S(O)R$^{10}$, —S(O)$_2$R$^{10}$, —NR$^{10}$S(O)$_2$R$^{11}$, substituted or unsubstituted C$_{1-8}$ alkyl, substituted or unsubstituted 4- to 7-membered heterocyclyl, substituted or unsubstituted 5 or 6 ring heteroaryl, substituted or unsubstituted phenyl, substituted or unsubstituted C$_{1-8}$ alkenyl and substituted or unsubstituted C$_{1-8}$ alkynyl;

suitable substituted C$_{1-8}$ alkyl, C$_{2-8}$ alkenyl and C$_{2-8}$ alkynyl may have from 1 to 3 substituents independently selected from the group consisting of halogen, —OR$^{10}$, —CN, —NO$_2$, =O, —OC(O)R$^{10}$, —CO$_2$R$^{10}$, —C(O)R$^{10}$, —CONR$^{10}$R$^{11}$, —OC(O)NR$^{10}$R$^{11}$, —NR$^{10}$C(O)R$^{11}$, —NR$^{10}$C(O)NR$^{11}$R$^{12}$, —NR$^{10}$R$^{11}$, —NR$^{10}$CO$_2$R$^{11}$, —SR$^{10}$, —SOR$^{10}$, —SO$_2$R$^{10}$, —SO$_2$NR$^{10}$R$^{11}$, —NR$^{10}$SO$_2$R$^{11}$, unsubstituted or substituted phenyl, unsubstituted or substituted C$_{5-6}$ heteroaryl, and unsubstituted or substituted C$_{3-6}$ heterocyclyl;

suitable substituted aryl, heteroaryl and heterocycle substituents may have from 1 to 3 substituents independently selected from the group consisting of halogen, —OR$^{10}$, —CN, —NO$_2$, =O, —OC(O)R$^{10}$, —OC(O)R$^{10}$,
—CO$_2$R$^{10}$, —C(O)R$^{10}$, —CONR$^{10}$R$^{11}$, —OC(O)NR$^{10}$R$^{11}$, —NR$^{10}$C(O)R$^{11}$, —NR$^{10}$C(O)NR$^{11}$R$^{12}$, —NR$^{10}$R$^{11}$, —NR$^{10}$CO$_2$R$^{11}$, —SR$^{10}$, —SOR$^{10}$, —SO$_2$R$^{10}$, —SO$_2$NR$^{10}$R$^{11}$, —NR$^{10}$SO$_2$R$^{11}$ and unsubstituted 4- to 7-membered heterocyclyl, unsubstituted C$_{1-8}$ alkyl and unsubstituted C$_{1-8}$ haloalkyl; with the proviso that where the substituent $Z^1$, $Z^a$, $Z^b$ and $Z^c$ is a heterocycle, suitable substituents on this heterocycle preferably do not include another heterocycle.

$R^{10}$, $R^{11}$ and $R^{12}$ are each independently hydrogen, C$_{1-8}$ alkyl, C$_{2-8}$ alkenyl, C$_{2-8}$ alkynyl, aryl, or heteroaryl, or where $R^{10}$ and $R^{11}$, or $R^{11}$ and $R^{12}$, or $R^{10}$ and $R^{12}$, together with the atom(s) to which they are attached, form an substituted or unsubstituted 5-, 6-, or 7-membered ring, and and the aromatic and aliphatic portions of $R^{10}$, $R^{11}$ and $R^{12}$ are optionally further substituted with from one to three members selected from the group consisting of halogen, —OH, —OR$^m$, —OC(O)NHR$^m$, —OC(O)NR$^m$R$^n$, —SH, —SR$^m$, —S(O)R$^m$, —S(O)$_2$R$^m$, —S(O)$_2$NH$_2$, —S(O)$_2$NHR$^m$, —S(O)$_2$NR$^m$R$^n$, —NHS(O)$_2$R$^m$, —NR$^m$S(O)$_2$R$^n$, —C(O)NH$_2$, —C(O)NHR$^m$, —C(O)N(R$^m$)$_2$, —C(O)R$^m$, —NHC(O)R$^m$, —NR$^m$C(O)R$^n$, —NHC(O)NH$_2$, —NR$^m$C(O)NH$_2$, —NR$^m$C(O)NHR$^n$, —NHC(O)NHR$^m$, —NR$^o$C(O)NR$^m$R$^n$, —NHC(O)N(R$^m$)$_2$, —CO$_2$H, —CO$_2$R$^m$, —NHCO$_2$R$^m$, —NR$^m$CO$_2$R$^n$, —CN, —NO$_2$, —NH$_2$, —NHR$^n$, —NR$^m$R$^n$, —NR$^m$S(O)NH$_2$, and —NR$^m$S(O)$_2$NHR$^n$, where R$^m$, R$^n$, and R$^o$ are each independently unsubstituted C$_{1-6}$ alkyl.

In one embodiment, any of formulae (XX-CXXXVI), $Z^1$, $Z^a$, $Z^b$ and $Z^c$ are independently selected from the group consisting of unsubstituted C$_{1-6}$ alkyl (not —Me), =O, C$_{1-6}$ haloalkyl (not —CF$_3$), —COOH, —NO$_2$, or —OR$^{10}$ (not —OMe). In this embodiment, $Ar^2$ can be any chemically allowed regioisomer of pyridyl, pyrimidinyl, pyridazinyl, pyrazinyl and the like, and their respective N-oxides.

In one embodiment, any of formulae (XX-CXXXVI), $Z^1$, $Z^a$, $Z^b$ and $Z^c$ are independently selected from the group consisting of —CH$_3$, =O, —CF$_3$, —OCH$_3$. In this embodiment, $Ar^2$ can be any chemically allowed regioisomer of pyridyl, pyrimidinyl, pyridazinyl, pyrazinyl and the like, and their respective N-oxides.

In one embodiment, any of formulae (XX-CXXIX), $Z^1$, $Z^a$, $Z^b$ and $Z^c$ are independently selected from the group consisting of halogen, substituted C$_{1-6}$ alkyl (but not C$_{1-6}$ haloalkyl), unsubstituted or substituted C$_{1-6}$ alkenyl, unsubstituted or substituted C$_{1-6}$ alkynyl, =O, —CN, —C(O)R$^{10}$, —C(O)NR$^{10}$R$^{11}$, —NR$^{10}$C(O)R$^{11}$, —NR$^{11}$R$^{12}$, —SR$^{10}$, —S(O)R$^{10}$, —S(O)$_2$R$^{10}$, —S(O)$_2$NR$^{11}$R$^{12}$, —NR$^{10}$S(O)$_2$R$^{11}$, —OC(O)R$^{10}$, —CO$_2$R$^{10}$ (but not —CO$_2$H), —OC(O)NR$^{11}$R$^{12}$, —NR$^{10}$C(O)NR$^{11}$R$^{12}$, —NR$^{10}$CO$_2$R$^{11}$, unsubstituted or substituted 5- or 6-membered heteroaryl and a unsubstituted or substituted 4- to 7-membered heterocyclyl. Preferred substituents include chlorine, =O, —CN, —SCH$_3$, —SO$_2$CH$_3$. In this embodiment, $Ar^2$ can be any chemically allowed regioisomer of pyridyl, pyrimidinyl, pyridazinyl, pyrazinyl and the like, and their respective N-oxides.

In one embodiment of any of formulae (XX-CXXIX) where L is a bond or $NR^c$, when $Z^1$, $Z^a$, $Z^b$ or $Z^c$ are substituted $C_{1-8}$ alkyl, substituted $C_{2-6}$ alkenyl, substituted $C_{2-8}$ alkynyl or substituted $C_{1-8}$ alkoxy groups, it preferably has from 1 to 3 substituents independently selected from the group consisting of halogen, —OH, —$OR^{10}$, =O, —$CO_2R^{10}$, —$C(O)R^{10}$, —$C(O)NR^{11}R^{12}$, —$NR^{10}C(O)R^{11}$, —$NR^{11}R^{12}$, —$SR^{10}$, —$S(O)R^{10}$, —$S(O)_2R^{10}$, —$NR^{10}S(O)_2R^{11}$, substituted or unsubstituted phenyl, substituted or unsubstituted 5- or 6-membered heteroaryl, and substituted or unsubstituted 4- to 7-membered heterocyclyl. More preferably, it has from 1 to 3 substituents independently selected from the group consisting of halogen, —OH, —$OR^{10}$, =O, —$C(O)R^{10}$, —$CO_2R^{10}$, —$C(O)NR^{11}R^{12}$, —$NR^{10}C(O)R^{11}$, —$NR^{11}R^{12}$, —$SR^{10}$, —$S(O)R^{10}$, —$S(O)_2R^{10}$, —$S(O)_2NR^{11}R^{12}$, —$NR^{10}S(O)_2R^{11}$, and 4- to 7-membered heterocyclyl.

In one embodiment, in each of the formula (XX-CXXXVI), when one of $Z^1$, $Z^a$, $Z^b$, $Z^c$, and $Z^d$ is a substituted $C_{1-8}$ alkyl, substituted $C_{2-8}$ alkenyl, substituted $C_{2-8}$ alkynyl, it preferably has from 1 to 3 substituents independently selected from the group consisting of halogen, —$OR^{10}$, =O, —$CO_2R^{10}$, —$C(O)R^{10}$, —$C(O)NR^{11}R^{12}$, —$NR^{10}C(O)R^{11}$, —$NR^{11}R^{12}$, —$SR^{10}$, —$S(O)R^{10}$, —$S(O)_2R^{10}$, —$NR^{10}S(O)_2R^{11}$, substituted or unsubstituted phenyl, substituted or unsubstituted 5- or 6-membered heteroaryl, and substituted or unsubstituted 4- to 7-membered heterocyclyl. More preferably, it has from 1 to 3 substituents independently selected from the group consisting of halogen, —$OR^{10}$, =O, —$C(O)R^{10}$, —$CO_2R^{10}$, —$CONR^{11}R^{12}$, —$NR^{10}C(O)R^{11}$, —$NR^{11}R^{12}$, —$SR^{10}$, —$S(O)R^{10}$, —$S(O)_2R^{10}$, —$S(O)_2NR^{11}R^{12}$, —$NR^{10}S(O)_2R^{11}$, and 4- to 7-membered heterocyclyl.

In one embodiment of any of formulae (XX-CXXXVI), when $Z^1$, $Z^a$, $Z^b$ or $Z^c$ is substituted heterocyclyl, it preferably has from 1 to 2 substituents independently selected from the group consisting of substituted or unsubstituted $C_{1-8}$ alkyl, —$OR^{10}$, —OH, —$C(O)R^{10}$, —$C(O)NR^{11}R^{12}$, —$NR^{11}R^{12}$, and —$S(O)_2R^{10}$.

In one embodiment of any of formulae (XX-CXXXVI), when $Z^1$, $Z^a$, $Z^b$, $Z^c$, and $Z^d$ is substituted heterocyclyl, it preferably has from 1 to 2 substituents independently selected from the group consisting of substituted or unsubstituted $C_{1-8}$ alkyl, —$OR^{10}$, —OH, —$C(O)R^{10}$, —$C(O)NR^{11}R^{12}$, —$NR^{11}R^{12}$, and —$S(O)_2R^{10}$.

In one embodiment of any of formulae (XX-CXXXVI), at least one of $Z^1$, $Z^a$, $Z^b$ and $Z^c$ is a unsubstituted or substituted heterocyclyl selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of any of formulae (XX-CXXXVI), $Z^1$, $Z^a$, $Z^b$ and $Z^c$ are independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{1-8}$ alkoxy, =O, —CN, —$NO_2$, —$OR^{10}$, —$OC(O)R^{10}$, —$CO_2R^{10}$, —$C(O)R^{10}$, —$C(O)NR^{11}R^{12}$, —$NR^{10}C(O)R^1$, —$NR^{11}R^{12}$, —$SR^{10}$, —$S(O)R^{10}$, —$S(O)_2R^{10}$, —$S(O)_2NR^{11}R^{12}$, —$NR^{10}S(O)_2R^{11}$, —$OC(O)NR^{11}R^{12}$, —$NR^{10}C(O)NR^{11}R^{12}$, substituted or unsubstituted phenyl, substituted or unsubstituted 5- or 6-membered heteroaryl, and substituted or unsubstituted 4- to 7-membered heterocyclyl. If present, one substituent is preferably located ortho to one of the heteroatoms in the heteroaryl $Ar^2$ ring. Alternatively, one substituent, =O, may be directly connected to a ring heteroatom in the heteroaryl $Ar^2$ ring.

In one embodiment of any of formulae (XX-CXXXVI), when $Z^1$, $Z^a$, $Z^b$ or $Z^c$ are substituted $C_{1-8}$ alkyl, substituted $C_{2-8}$ alkenyl, substituted $C_{2-8}$ alkynyl or substituted $C_{1-8}$ alkoxy groups, it preferably has from 1 to 3 substituents independently selected from the group consisting of halogen, —OH, —$OR^{10}$, =O, —$CO_2R^{10}$, —$C(O)R^{10}$, —$C(O)NR^{11}R^{12}$, —$NR^{10}C(O)R^{11}$, —$NR^{11}R^{12}$, —$SR^{10}$, —$S(O)R^{10}$, —$S(O)_2R^{10}$, —$NR^{10}S(O)_2R^{11}$, substituted or unsubstituted phenyl, substituted or unsubstituted 5- or 6-membered heteroaryl, and substituted or unsubstituted 4- to 7-membered heterocyclyl. More preferably, it has from 1 to 3 substituents independently selected from the group consisting of halogen, —OH, —$OR^{10}$, =O, —$C(O)R^{10}$, —$CO_2R^{10}$, —$C(O)NR^{11}R^{12}$, —$NR^{10}C(O)R^{11}$, —$NR^{11}R^{12}$, —$SR^{10}$, $S(O)R^{10}$, —$S(O)_2R^{10}$, —$S(O)_2NR^{11}R^{12}$, —$NR^{10}S(O)_2R^{11}$, and 4- to 7-membered heterocyclyl.

In one embodiment of each of the formulae (XX-CXXXVI) when at least one of $Z^1$, $Z^a$, $Z^b$ and $Z^c$ is a substituted $C_{1-8}$ alkyl, at least one substituent is a substituted or unsubstituted 4- to 7-membered heterocyclyl represented by formula (AA) as defined in [0029], [0030], and [0031]. Preferably, $R^{20}$, $R^{21}$, $R^{22}$, $R^{23}$, $R^{24}$, $R^{25}$, and $R^{26}$ are independently hydrogen or $C_{1-4}$alkyl. In another preferred embodiment, at least three of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4. In another preferred embodiments, at least five of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4.

In one embodiment of each of the formulae (XX-CXXXVI) when at least one of $Z^1$, $Z^a$, $Z^b$ and $Z^c$ is a substituted $C_{1-8}$ alkyl, at least one substituent is selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of each of the formulae (XX-CXXXVI) when at least one of $Z^1$, $Z^a$, $Z^b$ and $Z^c$ is a substituted $C_{1-8}$ alkyl, at least one substituent is a substituted or unsubstituted 5- or 6-membered heteroaryl selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl.

In one embodiment of any of formulae (XX-CXXXVI), when $Z^1$, $Z^a$, $Z^b$ or $Z^c$ is substituted heterocyclyl, it preferably has from 1 to 2 substituents independently selected from the group consisting of substituted, or unsubstituted $C_{1-8}$ alkyl, —$OR^{10}$, —OH, —$C(O)R^{10}$, —$C(O)NR^{11}R^{12}$, —$NR^{11}R^{12}$, and —$S(O)_2R^{10}$.

In one embodiment of any of formulae (XX-CXXXVI), $Z^1$, $Z^a$, $Z^b$ and $Z^c$ are independently selected from the group consisting of halogen, —OH, —$OR^{10}$, —CN, —$NO_2$, =O, —$OC(O)R^{10}$, —$CO_2R^{10}$, —$C(O)R^{10}$, —$C(O)NR^{11}R^{12}$, —$NR^{10}C(O)R^{12}$, —$NR^{11}R^{12}$, —$SR^{10}$, —$S(O)R^{10}$, —$S(O)_2R^{10}$, —$NR^{10}S(O)_2R^{11}$, substituted or unsubstituted $C_{1-8}$ alkyl, substituted or unsubstituted 4- to 7-membered heterocyclyl, substituted or unsubstituted 5 or 6 ring heteroaryl, substituted or unsubstituted phenyl, substituted or unsubstituted $C_{1-8}$ alkenyl and substituted or unsubstituted $C_{1-8}$ alkynyl.

In one embodiment of any of formulae (XX-CXXXVI), at least one of $Z^1$, $Z^a$, $Z^b$ and $Z^c$ is a substituted or unsubstituted 5- or 6-membered heteroaryl selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl.

In one embodiment of any of formulae (XCII and XCIII) where L is $NR^c$, $Z^a$, and $Z^b$ are independently selected from the group consisting of halogen, —OH, —$OR^{10}$, —CN, —$NO_2$, =O, —$OC(O)R^{10}$, —$CO_2R^{10}$, —$C(O)R^{10}$, —$C(O)NR^{11}R^{12}$, —$NR^{10}C(O)R^{12}$, —$NR^{11}R^{12}$, —$SR^{10}$, —$S(O)R^{10}$, —$S(O)_2R^{10}$, —$NR^{10}S(O)_2R^{11}$, substituted or unsubstituted $C_{1-8}$ alkyl, substituted or unsubstituted 4- to 7-membered heterocyclyl, substituted or unsubstituted 5 or 6 ring heteroaryl, substituted or unsubstituted phenyl, substituted or unsubstituted $C_{1-8}$ alkenyl, and substituted or unsubstituted $C_{1-8}$ alkynyl.

In one embodiment of the formulae (XX-CXXXVI), $Z^1$, $Z^a$, $Z^b$ or $Z^c$ are each hydrogen.

In one embodiment in any of the formulae (XX-CXXXVI), at least one substituent $Z^1$, $Z^a$, $Z^b$ and $Z^c$ is cyano.

In one embodiment in any of the formulae (XX-CXXXVI), at least one substituent $Z^1$, $Z^a$, $Z^b$ and $Z^c$ is —$S(O)_2R^7$. In one particular embodiment, $R^7$ is methyl.

In one embodiment in any of the formulae (XX-CXXXVI), at least one substituent $Z^1$, $Z^a$, $Z^b$ and $Z^c$ is halogen (in particular chlorine).

In one embodiment in any of the formulae (XX-CXXXVI), at least one substituent $Z^1$, $Z^a$, $Z^b$ and $Z^c$ is —$OR^7$. In one particular embodiment, $R^7$ is methyl.

In one embodiment in any of the formulae (XX-CXXXVI), at least one substituent $Z^1$, $Z^a$, $Z^b$ and $Z^c$ is —$SR^7$. In one particular embodiment, $R^7$ is methyl.

In one embodiment of any of formulae (XX-CXXXVI), any one of $Z^1$, $Z^a$, $Z^b$, and $Z^c$ may be a heterocyclic group represented by formula (AA) below, where formula (AA) is attached via a free valence on either $M^1$ or $M^2$, and where formula (AA) and the substituents therein are defined in [0029].

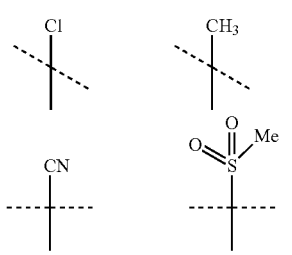

(AA)

In one embodiment of the formulae (XX-CXXXVI), $Z^1$, $Z^a$, $Z^b$ or $Z^c$ are selected from one of the following residues

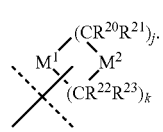

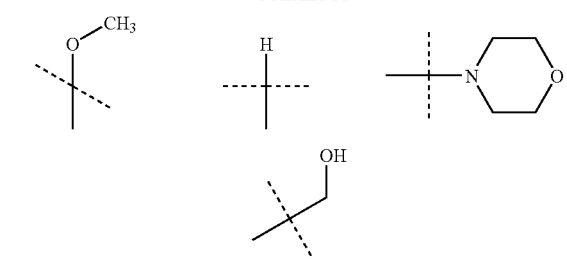

with the proviso that at least one of Z', $Z^1$, $Z^a$, $Z^b$ or $Z^c$ are other than hydrogen.

In one embodiments for each of the formulae (VIII, IX, XX-CXXIX, CXXXIII, and CXXXIV) where L is C=T, T is =$CR^dR^e$ or =$NOR^d$.

In other embodiments for each of the formulae (VIII, IX, XX-CXXIX, CXXXIII, and CXXXIV) where L is C=T, T is =$CR^dR^e$ or =$NOR^d$ and $R^d$ and $R^e$ are each independently selected from the group consisting of hydrogen, substituted or unsubstituted $C_{1-8}$ alkyl, —$C(O)R^{41}$ and —$C(O)_2R^{41}$.

In other preferred embodiments for each of the formulae (VIII, IX, XX-CXXIX, CXXXIII, and CXXXIV) where L is C=T, T is =$NOR^d$ and $R^d$ is a substituted or unsubstituted $C_{1-8}$ alkyl, more preferably methyl.

In other preferred embodiments for each of the formulae (VIII, IX, XX-CXXIX, CXXXIII, and CXXXIV) where L is C=T, T is =$CR^dR^e$, and $R^d$ and $R^e$ are each independently selected from the group consisting of hydrogen, —$C(O)R^{41}$ and —$C(O)_2R^{41}$. More preferably, $R^d$ and $R^e$ are each independently selected from the group consisting of hydrogen, —C(O)Me and —$C(O)_2$Me.

In one embodiment of formula (IX), T is =CHC(O)Me, =$CHCO_2$Me, =$CH_2$ or =NOMe; $X^2$, $X^3$ and $X^5$ are hydrogen; $X^4$ is selected from the group consisting of hydrogen, fluorine, chlorine, —CN and trifluoromethoxy; and $X^1$ is selected from one of the residues shown below:

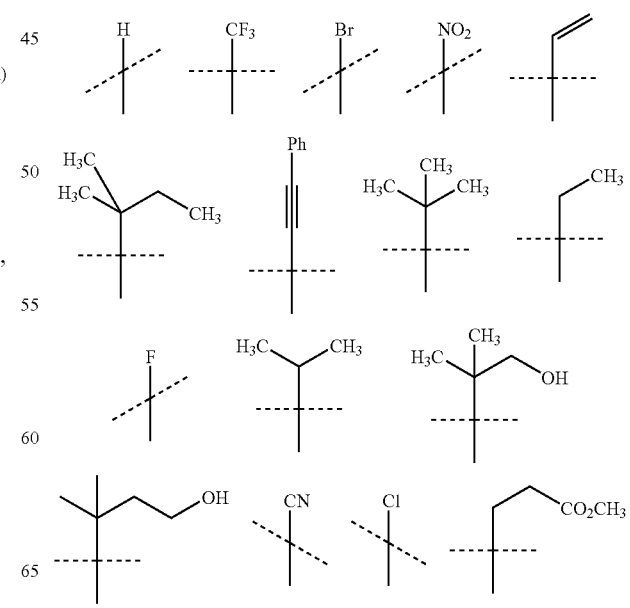

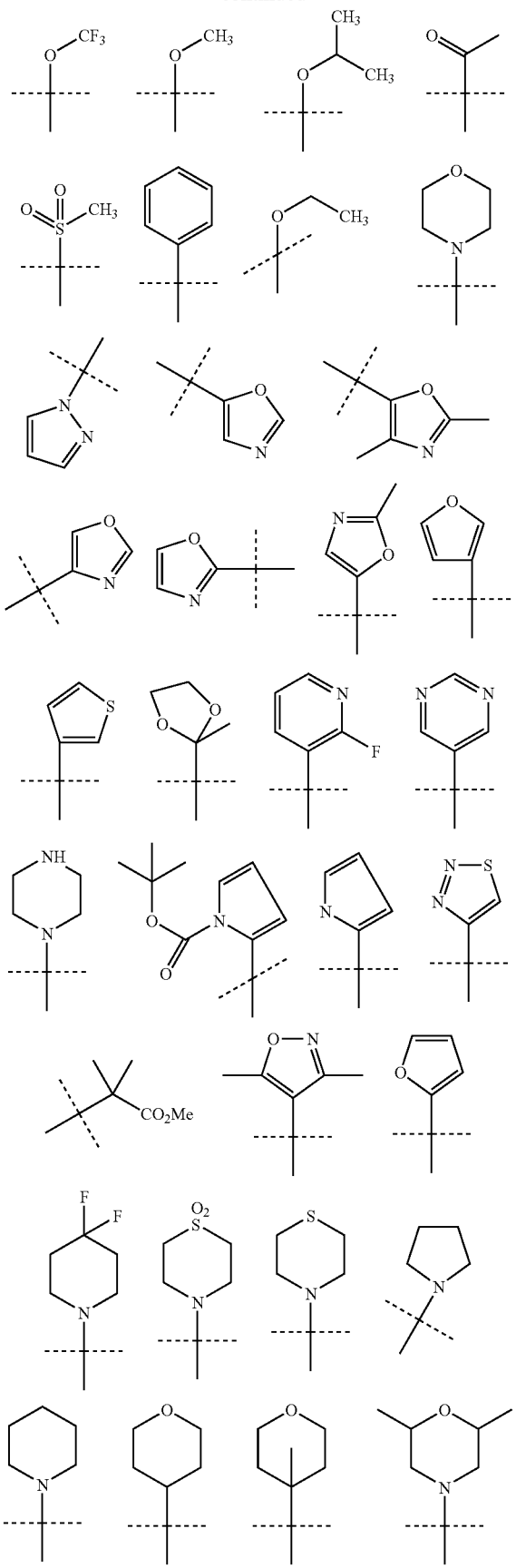

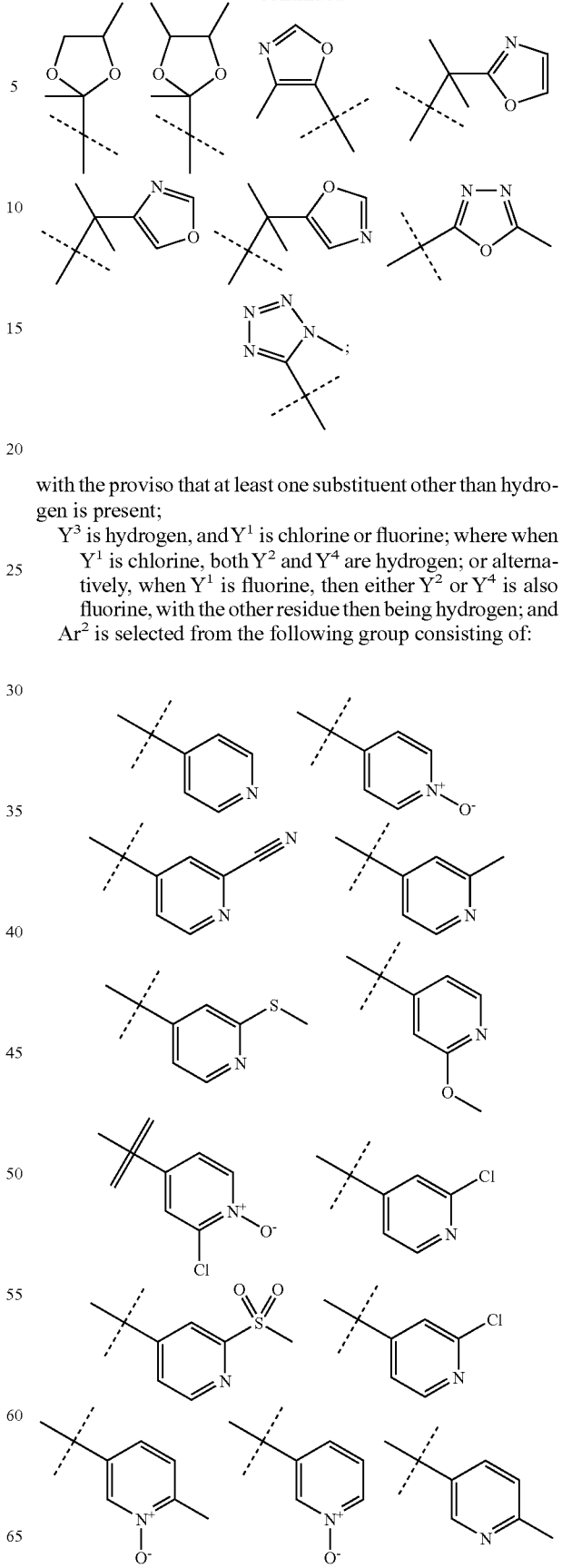

with the proviso that at least one substituent other than hydrogen is present;

$Y^3$ is hydrogen, and $Y^1$ is chlorine or fluorine; where when $Y^1$ is chlorine, both $Y^2$ and $Y^4$ are hydrogen; or alternatively, when $Y^1$ is fluorine, then either $Y^2$ or $Y^4$ is also fluorine, with the other residue then being hydrogen; and $Ar^2$ is selected from the following group consisting of:

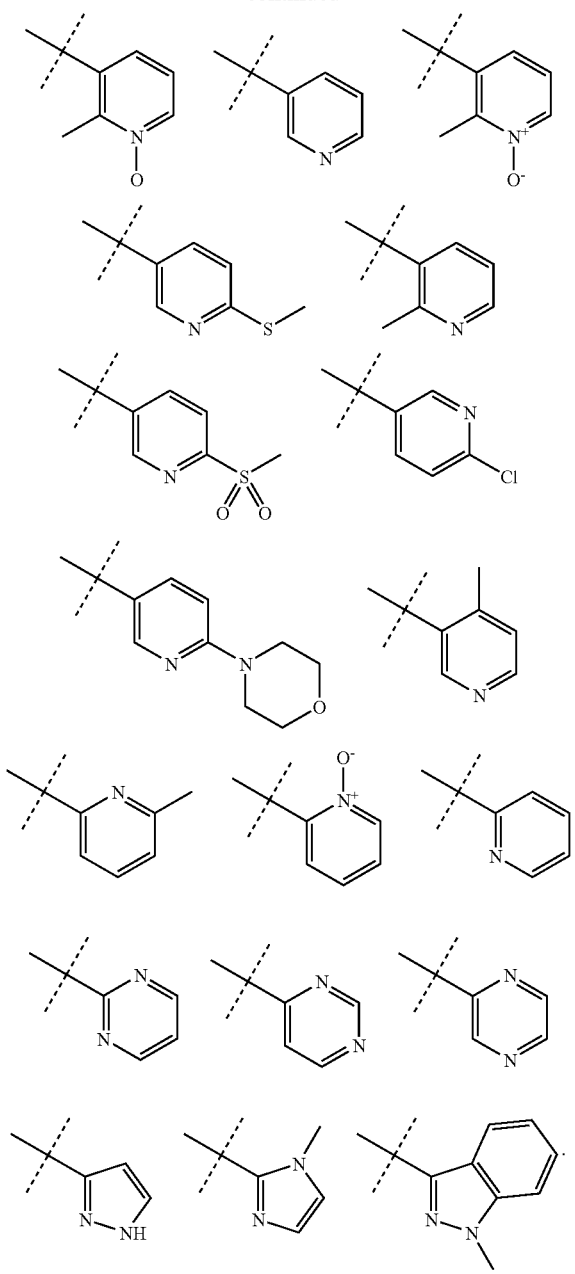

In other embodiments $Y^2$ is halogen; $Y^3$ is hydrogen; and $Y^1$ and $Y^4$ are each independently hydrogen or halogen.

In one embodiment for any of formulae (XX-CXXIX, CXXXIII, and CXXXIV) where L is C=T, T is =CHC(O)Me, =CHCO$_2$Me, =CH$_2$ or =NOMe; $X^2$, $X^3$ and $X^5$ are hydrogen; $X^4$ is selected from the group consisting of hydrogen, fluorine, chlorine, —CN and trifluoromethoxy; $X^1$ is selected from one of the residues shown below:

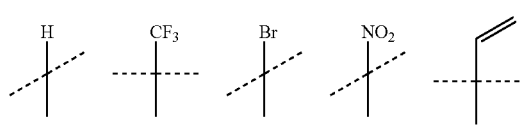

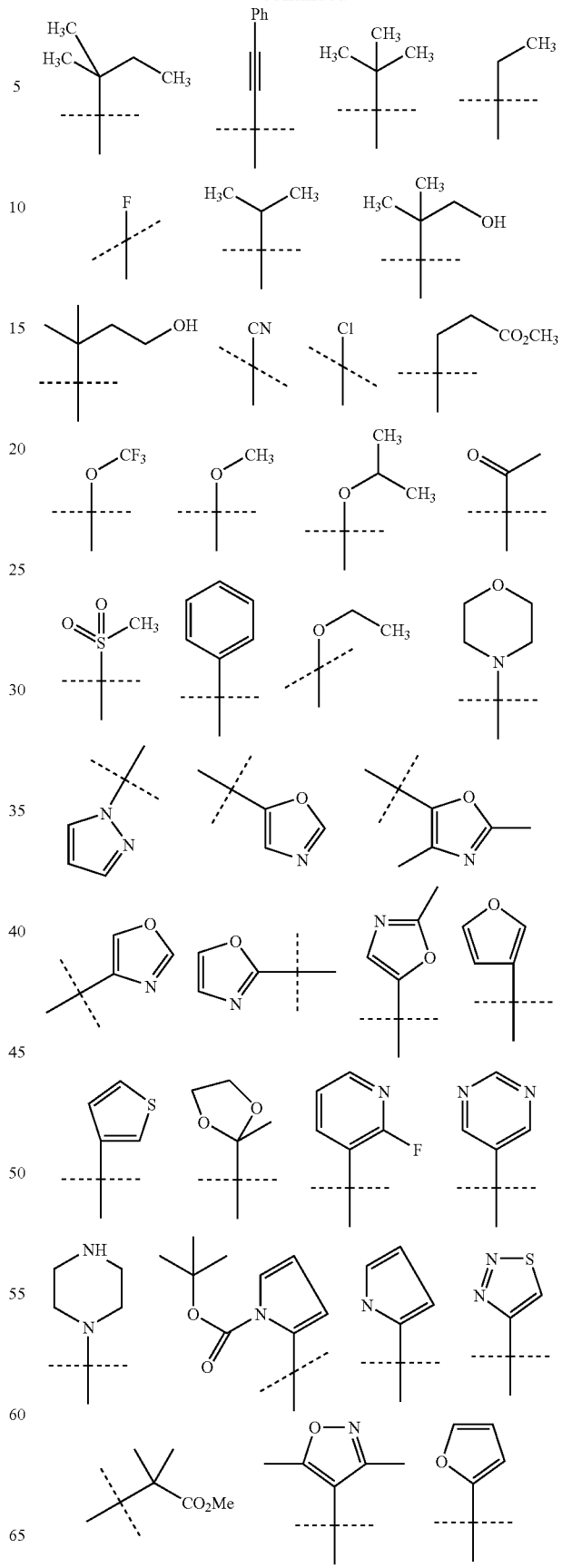

-continued

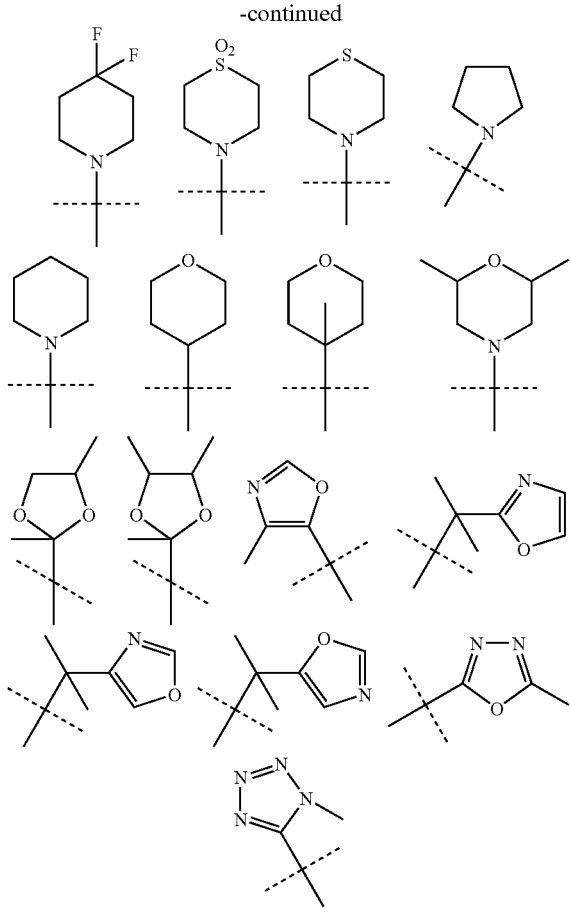

with the proviso that at least one substituent other than hydrogen is present;
Y3 is hydrogen, and Y1 is chlorine or fluorine; where when Y1 is chlorine, both Y2 and Y4 are hydrogen; or alternatively, if Y1 is fluorine, then either $Y_2$ or $Y_4$ is also fluorine, with the other residue then being hydrogen;
$Z^a$ is hydrogen, and $Z^1$ or $Z^b$ is selected from the group consisting of:

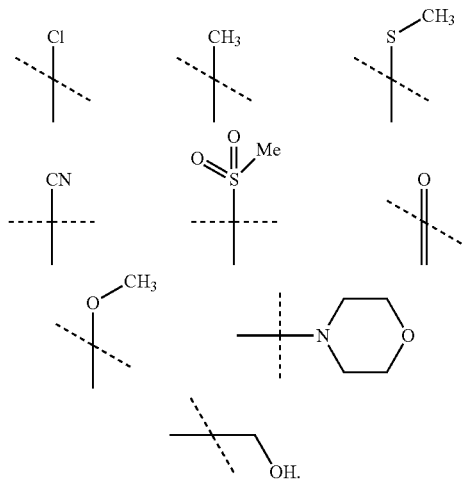

In other embodiments $Y^2$ is halogen; $Y^3$ is hydrogen; and $Y^1$ and $Y^4$ are each independently hydrogen or halogen.

In one highly preferred embodiment of formulae (II, IV, VII, and IX), $X^2$, $X^3$ and $X^5$ are hydrogen, $X^4$ is selected from the group consisting of hydrogen, fluorine, chlorine, —CN and trifluoromethoxy and $X^1$ is selected from one of the residues shown below:

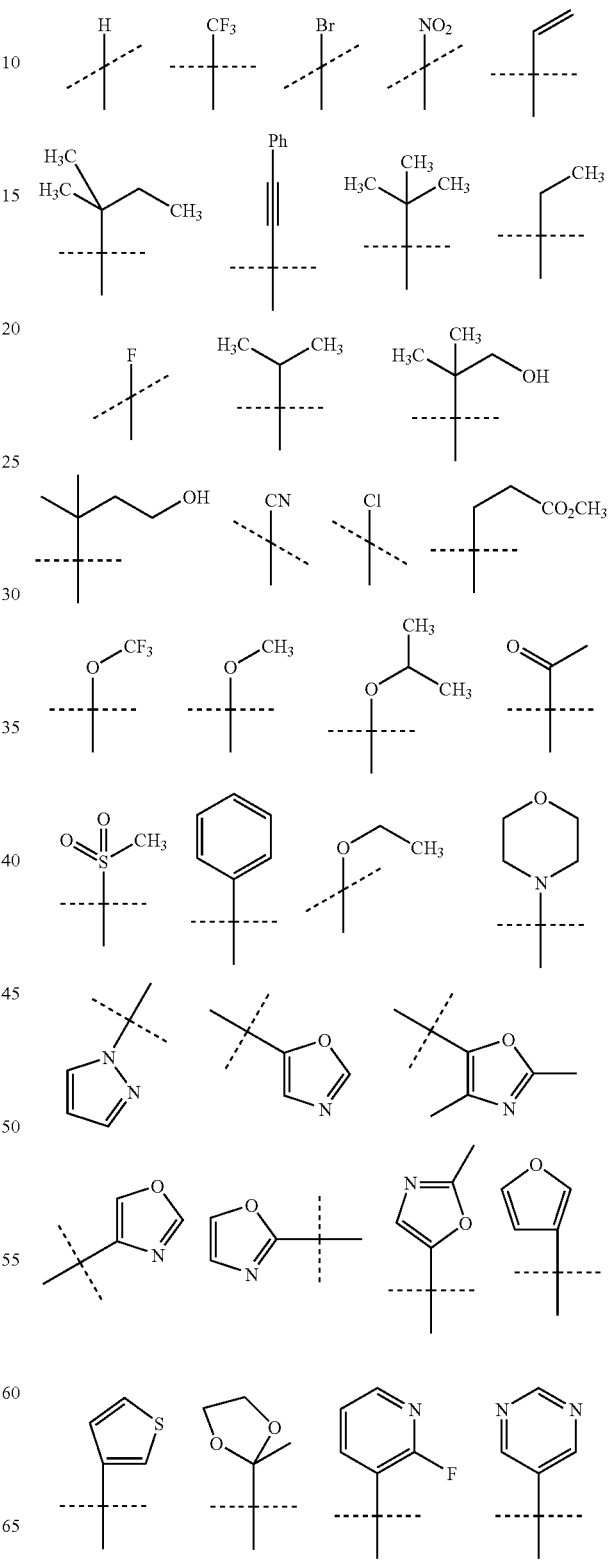

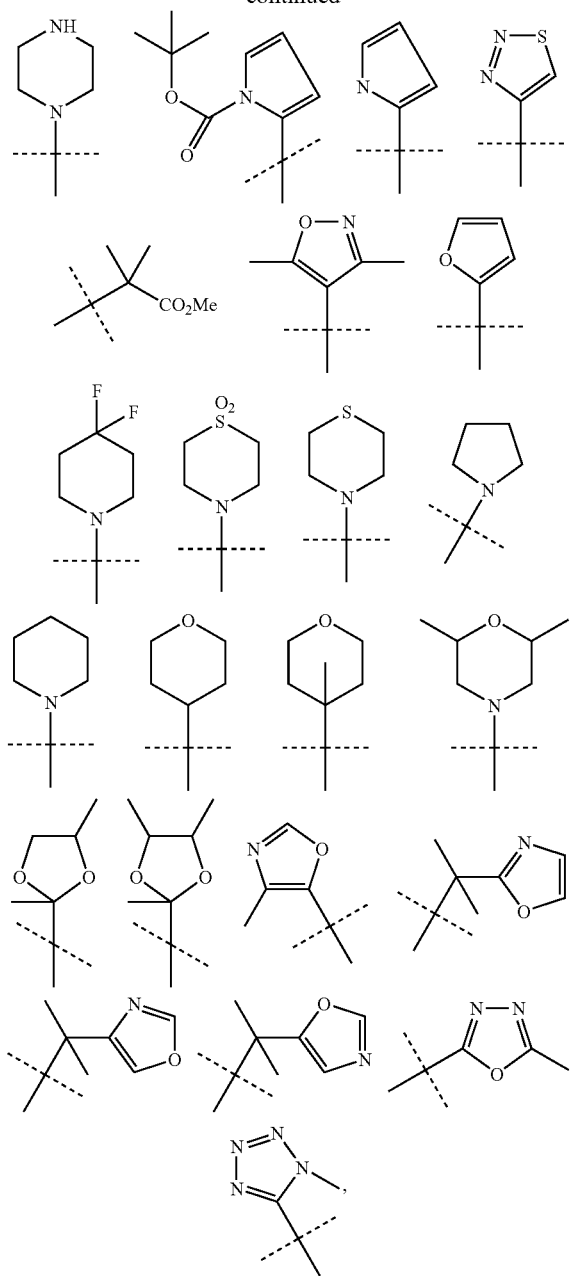
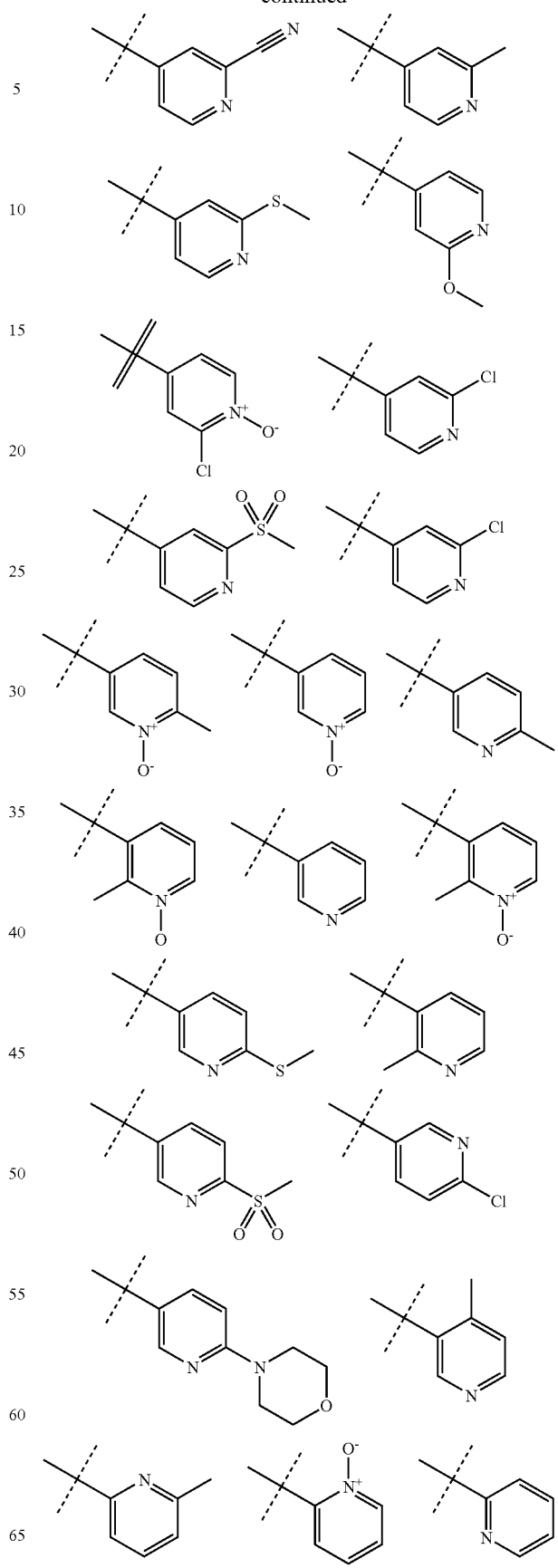
with the proviso that at least one of the substituents is other than hydrogen;
when $Y_3$ is hydrogen, $Y_1$ is chlorine or fluorine; when $Y_1$ is chlorine, both $Y_2$ and $Y_4$ are hydrogen also; or when $Y_1$ is fluorine, either $Y_2$ or $Y_4$ is also fluorine, with the other residue being hydrogen;
$Ar^2$ is selected from the group consisting of:
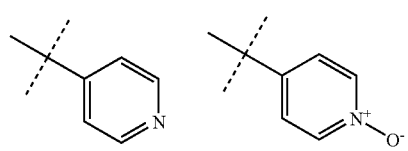

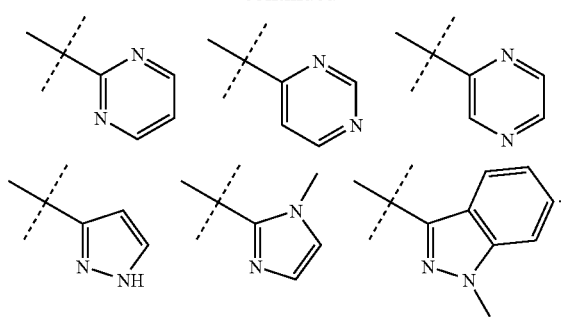

In other embodiments $Y^2$ is halogen; $Y^3$ is hydrogen; and $Y^1$ and $Y^4$ are each independently hydrogen or halogen.

In other highly preferred embodiments, in each of formulae (XX-CXXIX, CXXXI, CXXXII, CXXXV, and CXXXVI) where L is $CR^aR^b$ or $NR^c$, $X^2$, $X^3$ and $X^5$ are hydrogen; $X^4$ is selected from the group consisting of hydrogen, fluorine, chlorine, —CN and trifluoromethoxy; and $X^1$ is selected from the group consisting of:

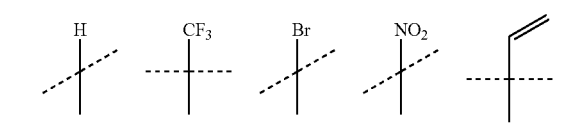
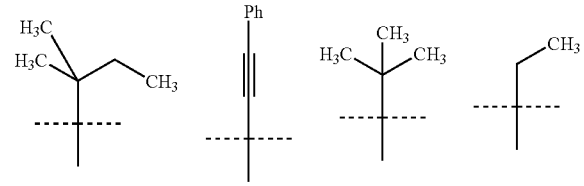
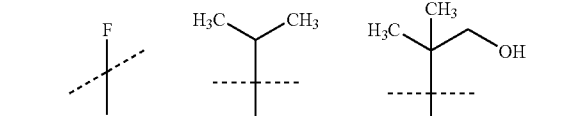
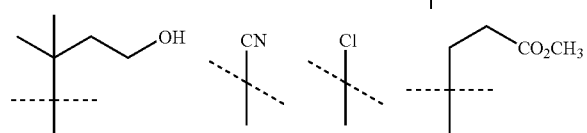
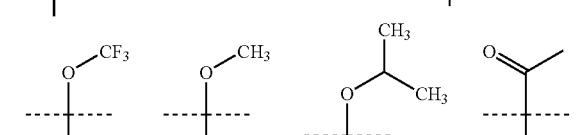
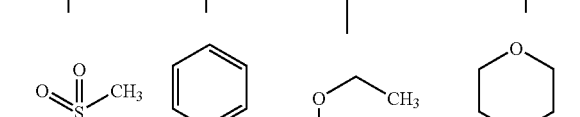
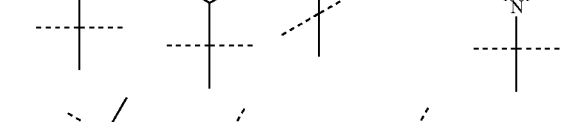
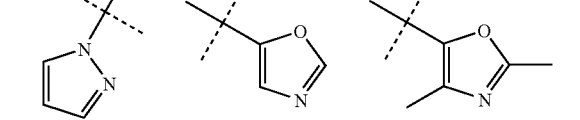

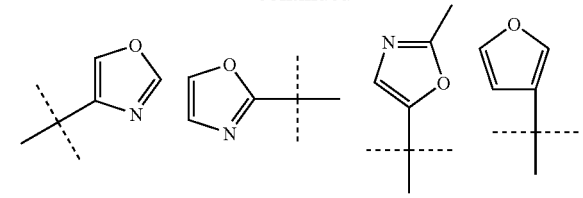

with the proviso that at least one substituent other than hydrogen is present;

when $Y^1$ or $Y^b$ is chlorine, then $Y^a$ is hydrogen; or alternatively, when $Y^1$ or $Y^b$ is fluorine, then $Y^a$ is hydrogen or fluorine;

$Z^a$ is hydrogen, and $Z^1$ or $Z^b$ are selected from the group consisting of:

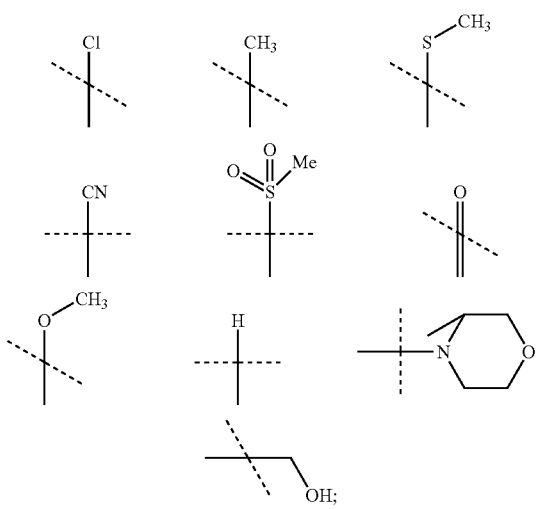

or $Z^1$, $Z^a$ and $Z^b$ are all simultaneously hydrogen.

In other embodiments $Y^2$ is halogen; $Y^3$ is hydrogen; and $Y^1$ and $Y^4$ are each independently hydrogen or halogen.

In one highly preferred embodiment of formula (IV), $X^2$, $X^3$ and $X^5$ are hydrogen, $X^4$; is selected from the group consisting of hydrogen, fluorine, chlorine, —CN and trifluoromethoxy; and $X^1$ is selected from group consisting of:

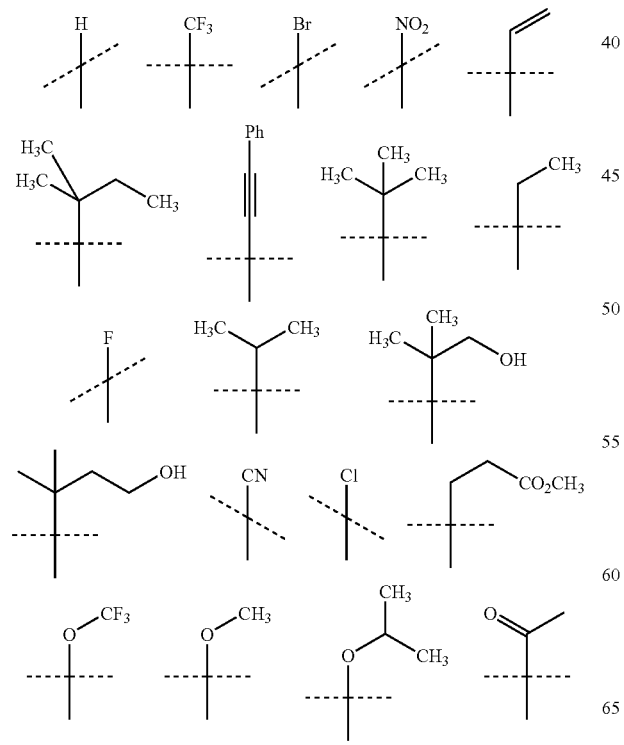

-continued

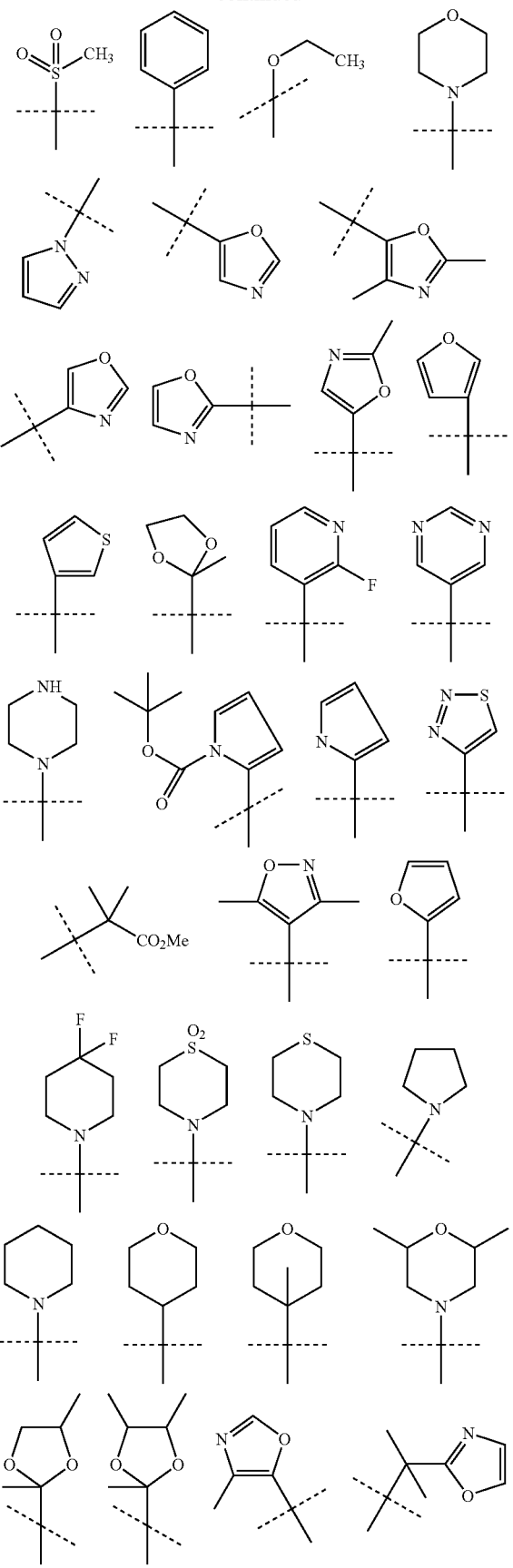

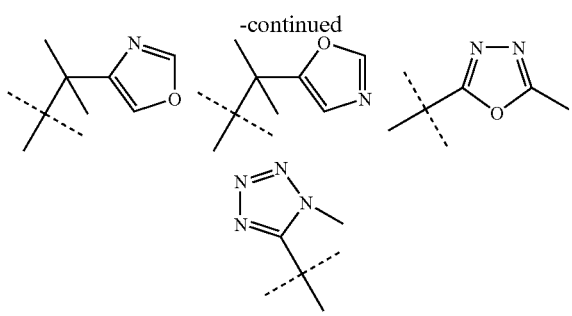

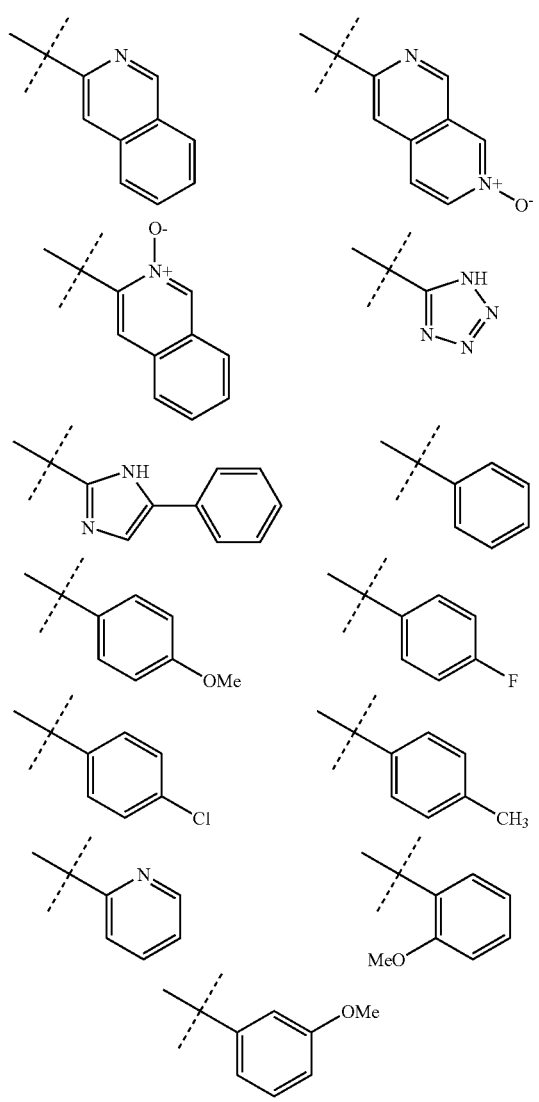

with the proviso that at least one of the substituents is other than hydrogen;

Y³ is hydrogen, and Y¹ is chlorine or fluorine, but when Y¹ is chlorine, both Y² and Y⁴ are hydrogen; alternatively, when Y¹ is fluorine, then either Y² or Y⁴ is also fluorine, with the other residue then being hydrogen; and $Ar_2$ is selected from the group consisting of:

In other embodiments $Y^2$ is halogen; $Y^3$ is hydrogen; and $Y^1$ and $Y^4$ are each independently hydrogen or halogen.

In other highly preferred embodiments, in each of formulae (IV, V, XX-CXXIX and CXXX) where L is a bond, $X^2$, $X^3$ and $X^5$ are hydrogen, $X^4$ is selected from the group consisting of hydrogen, fluorine, chlorine, —CN and trifluoromethoxy, and $X^1$ is selected from the group consisting of:

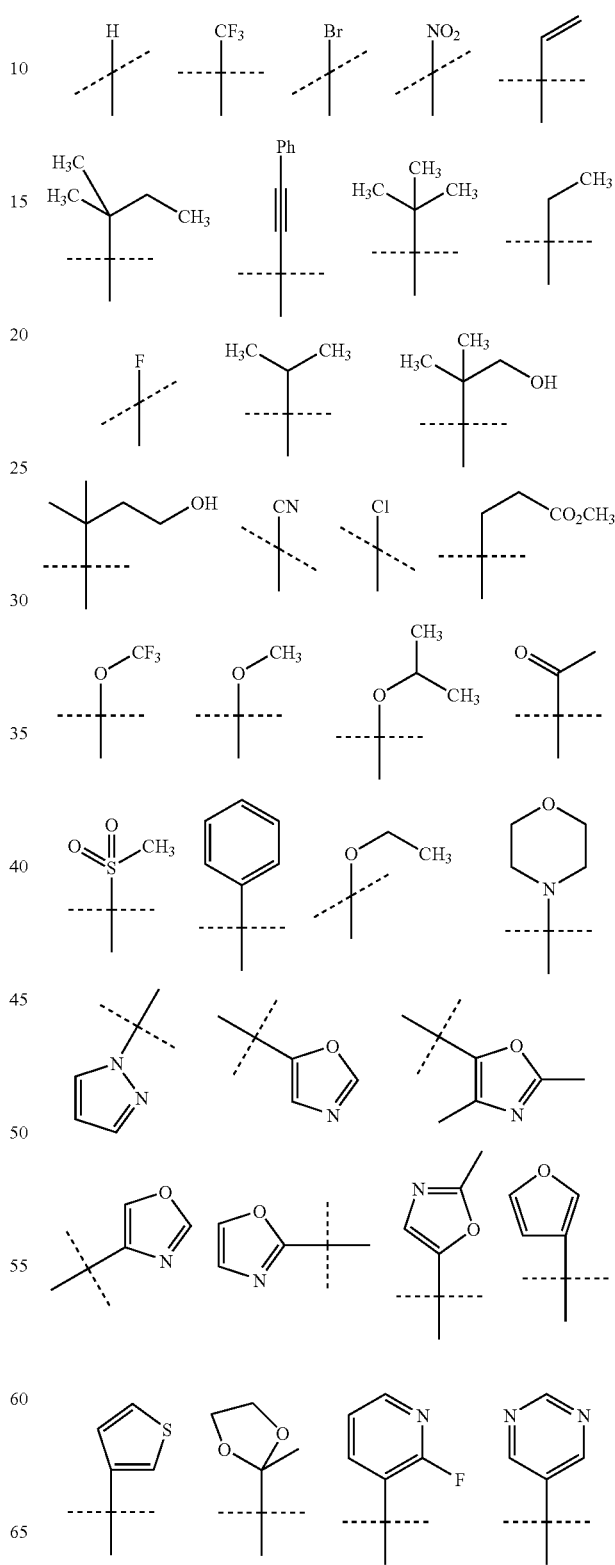

-continued

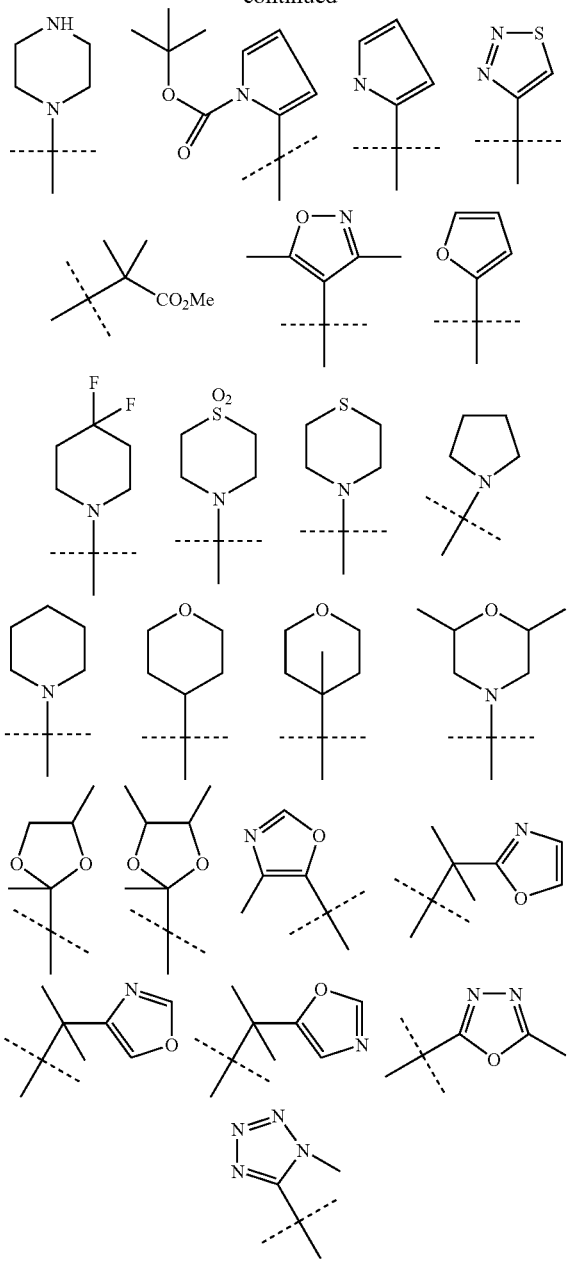

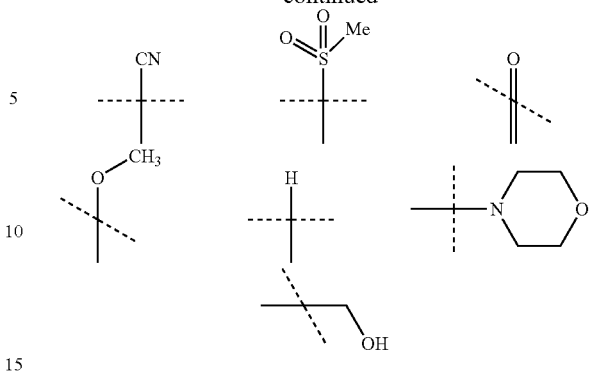

with the proviso that:
at least one of $X^1$ and $X^4$ is other than hydrogen;
when $Y^1$ or $Y^b$ is chlorine, $Y^a$ is hydrogen; alternatively when $Y^1$ or Yb is fluorine, then $Y^a$ is hydrogen or fluorine;
when $Z^1$, $Z^a$ and $Z^b$ or any combination thereof are present, $Z^a$ is hydrogen, and $Z^1$ or $Z^b$ are selected from the following group consisting of:

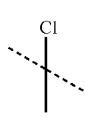 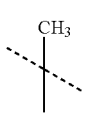 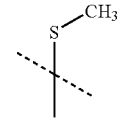

or $Z^1$, $Z^a$ and $Z^b$ are all simultaneously hydrogen;
or $Z^1$, $Z^a$ and $Z^b$ are all selected from the group consisting of hydrogen, =O, —OCH$_3$, —Cl, —F, and —CH$_3$.

In other embodiments $Y^2$ is halogen; $Y^3$ is hydrogen; and $Y^1$ and $Y^4$ are each independently hydrogen or halogen.

Compositions that Modulate CCR9 Activity

In another aspect, the present invention provides compositions that modulate CCR9 activity. Generally, the compositions for modulating chemokine receptor activity in humans and animals will comprise a pharmaceutically acceptable excipient or diluent and a compound having the formula provided above as any of formulae (I, III, VI, and VIII).

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oil and stabilized with surfactants such as monodiglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose, any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

Methods of Treating CCR9-Mediated Conditions or Diseases

In yet another aspect, the present invention provides methods of treating or preventing a CCR9-mediated condition or disease by administering to a subject having such a condition or disease a therapeutically effective amount of any compound of formulae (I, III, VI and VIII) above. Compounds for use in the present methods include those compounds according to formulae (I, III, VI and VIII), those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR9-mediated condition or disease" and related phrases and terms refer to a condition or disease characterized by inappropriate, i.e., less than or greater than normal, CCR9 functional activity. Inappropriate CCR9 functional activity might arise as the result of CCR9 expression in cells which normally do not express CCR9, increased CCR9 expression (leading to, e.g., inflammatory and immunoregulatory disorders and diseases) or decreased CCR9 expression. Inappropriate CCR9 functional activity might also arise as the result of TECK secretion by cells which normally do not secrete TECK, increased TECK expression (leading to, e.g., inflammatory and immunoregulatory disorders and diseases) or decreased TECK expression. A CCR9-mediated condition or disease may be completely or partially mediated by inappropriate CCR9 functional activity. However, a CCR9-mediated condition or disease is one in which modulation of CCR9 results in some effect on the underlying condition or disease (e.g., a CCR9 antagonist results in some improvement in patient well-being in at least some patients).

The term "therapeutically effective amount" means the amount of the subject compound that will elicit the biological or medical response of a cell, tissue, system, or animal, such as a human, that is being sought by the researcher, veterinarian, medical doctor or other treatment provider.

Diseases and conditions associated with inflammation, immune disorders, infection and cancer can be treated or prevented with the present compounds, compositions, and methods. In one group of embodiments, diseases or conditions, including chronic diseases, of humans or other species can be treated with inhibitors of CCR9 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) immune mediated food allergies such as Coeliac (Celiac) disease (14) pulmonary fibrosis and other fibrotic diseases, and (15) irritable bowel syndrome.

In another group of embodiments, diseases or conditions can be treated with modulators and agonists of CCR9 function. Examples of diseases to be treated by modulating CCR9 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is means to include bone marrow transplant conditions and solid organ (e.g., kidney, liver, lung, heart, pancreas or combination thereof) transplant conditions.

Preferably, the present methods are directed to the treatment of diseases or conditions selected from inflammatory bowel disease including Crohn's disease and Ulcerative Colitis, allergic diseases, psoriasis, atopic dermatitis and asthma, autoimmune disease such as rheumatoid arthritis and immune-mediated food allergies such as Coelaic disease.

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds and compositions of the present invention in a depot formulation.

In the treatment or prevention of conditions which require chemokine receptor modulation, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In still other embodiments, the present methods are directed to the treatment of allergic diseases, wherein a compound or composition of the invention is administered either alone or in combination with a second therapeutic agent, wherein said second therapeutic agent is an antihistamine. When used in combination, the practitioner can administer a combination of the compound or composition of the present invention and a second therapeutic agent. Also, the compound or composition and the second therapeutic agent can be administered sequentially, in any order.

In yet other embodiments, the present methods are directed to the treatment of psoriasis wherein a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

The compounds and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

EXAMPLES

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as the delivery system.

Compounds within the scope of this invention can be synthesized as described below, using a variety of reactions known to the skilled artisan. A sample of useful routes to both the benzophenone and heteroaryl derived subunits and to fully elaborated sulfonamide molecules of formulae (I, III, VI and VIII) within this claim are provided below. In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the invention can be prepared using conventional synthetic methodology. Examples of approaches that may be taken to synthesize these compounds are shown below. Nonetheless, one skilled in the art will recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are within the scope of the invention.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Preparation of CCR 9 Modulators

The following examples are offered to illustrate, but not to limit, the claimed invention.

Additionally, those skilled in the art will recognize that the molecules claimed in this patent may be synthesized using a variety of standard organic chemistry transformations.

Certain general reaction types employed widely to synthesize target compounds in this invention are summarized in the examples. Specifically, generic procedures for sulfonamide formation, pyridine N-oxide formation and 2-aminophenyl-arylmethanone synthesis via Friedel-Crafts type approaches are given, but numerous other standard chemistries are described within and were employed routinely.

While not intended to be exhaustive, representative synthetic organic transformations which can be used to prepare compounds of the invention are included below.

These representative transformations include: standard functional group manipulations; reduction such as nitro to amino; oxidations of functional groups including alcohols and pyridines; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Stille, Ullmann, Harwig, Buckvald, Suzuki and Sonigashira reactions and variants thereof; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nuclephilic substitution reactions; alkylations; acylations; sulfonamide formation; chlorosulfonylations; ester and related hydrolyses; Wittig, Peterson, Julia, Grubb olefinations and standard olefinations; and the like.

Examples

Scheme I: General Procedure for the Synthesis of (2-Amino-phenyl)-pyridinyl-methanones and (2-Amino-phenyl)-heteroaryl-methanones

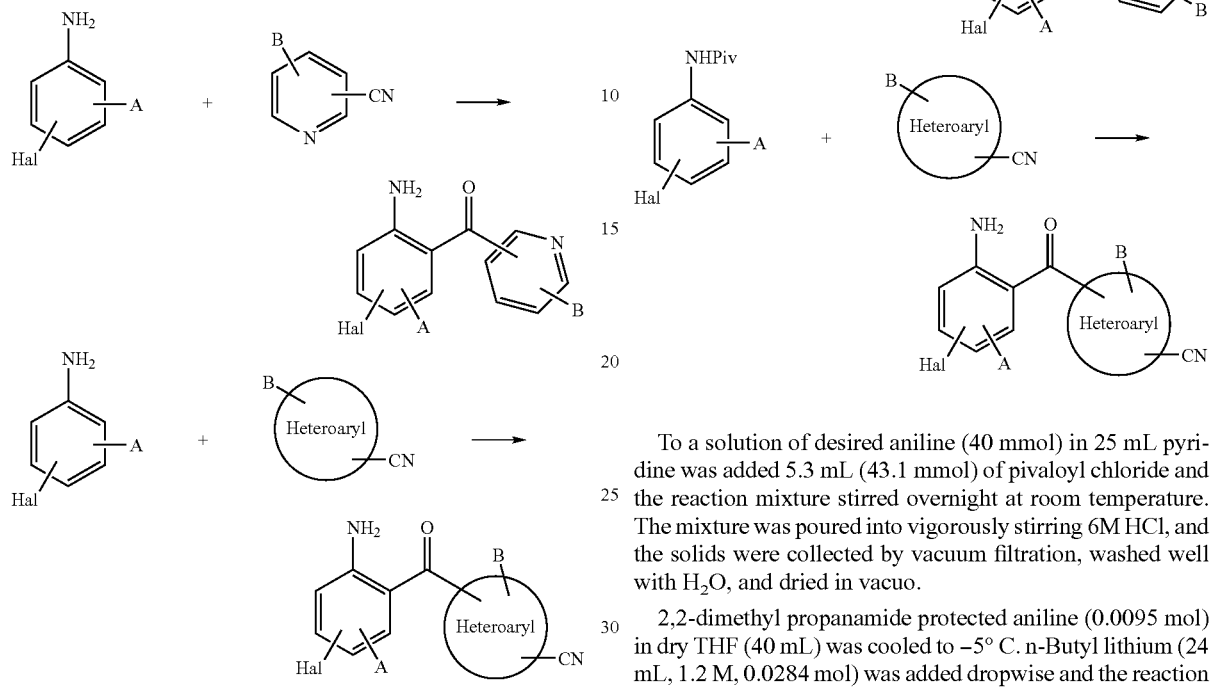

To 12.5 mL 1 M BCl$_3$ (12 mmol, 1.2 eq.) in methylene chloride stirred at 0° C. was added a solution of the desired haloaniline (10 mmol, 1.0 eq.) in 15 mL of TCE drop wise over 20 minutes. After 10 minutes the desired cyanopyridine (11 mmol, 1.1 eq.) was added followed by AlCl$_3$ (15 mmol, 1.5 eq.). The reaction was brought to RT, stirred for an hour then heated at 80-90° C. until all of the DCM was distilled off. The reaction mixture was then refluxed at 160° C. for 4 hours, cooled to RT and stirred overnight. 10 mL 3 M HCl were carefully added and the mixture was refluxed at 120° C. for 2-3 hours while reaction progress was monitored by LC/MS. The crude reaction was cooled to RT and 100 mL water were added. The crude mixture was extracted with DCM (2×50 mL), the aqueous layer was set aside and the organic layer was back extracted with 50 mL 1 M HCl (aq.). All aqueous layers were combined, brought to pH 12 with 3 M NaOH (aq.) and extracted with DCM (4×50 mL). The DCM layer was dried on Na$_2$SO$_4$, filtered and concentrated by rotary evaporation. The crude product was washed liberally with Et$_2$O and dried under vacuum, and further purified by conventional techniques such as column chromatography when necessary.

Scheme II: Alternate General Procedure (2) for the Synthesis of (2-Amino-phenyl)- pyridinyl-methanones and (2-Amino-phenyl)-heteroaryl-methanones

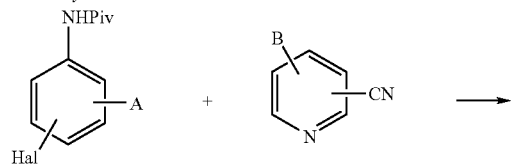

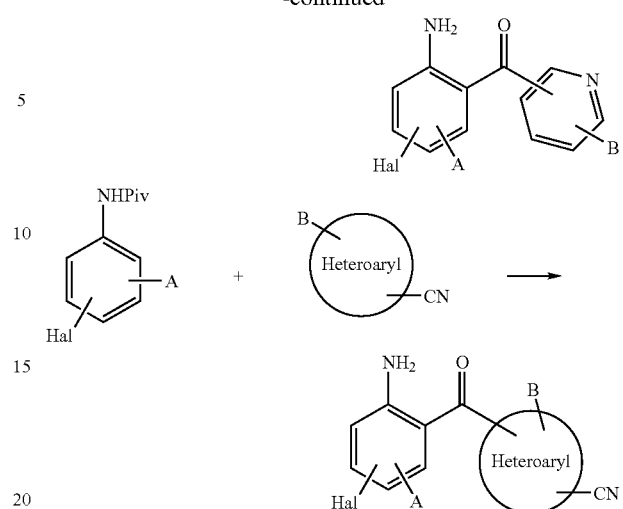

To a solution of desired aniline (40 mmol) in 25 mL pyridine was added 5.3 mL (43.1 mmol) of pivaloyl chloride and the reaction mixture stirred overnight at room temperature. The mixture was poured into vigorously stirring 6M HCl, and the solids were collected by vacuum filtration, washed well with H$_2$O, and dried in vacuo.

2,2-dimethyl propanamide protected aniline (0.0095 mol) in dry THF (40 mL) was cooled to −5° C. n-Butyl lithium (24 mL, 1.2 M, 0.0284 mol) was added dropwise and the reaction stirred at the same temperature for 2 h. The reaction mixture was cooled to −70° C. and to this was added the desired aryl or heteroaryl carboxylic acid (0.0142 mol), dissolved in dry THF (10 mL), dropwise. The mixture was stirred at room temperature for 18 h, quenched with water and extracted with ethyl acetate. The extract was washed with brine solution and concentrated. The product was purified by column using 5-10% of ethyl acetate in pet ether as eluent.

Removal of the pivaloyl protecting group form the amino ketone (0.4 g, 0.0013 mol) in 2 mL of methanol was effected via addition of potassium hydroxide (0.48 g, 0.00857 mol) in 1.2 mL of water. The reaction mixture was heated at 70° C. for 6 h, diluted with water and extracted with ethyl acetate. The extract was washed with water, brine and concentrated. The crude material was purified by column chromatography.

Alternatively, 6N HCl (10 mL) and intermediate pivaloyl protected aminoketone (1.2 g, 3.755 mmol) were heated at 90° C. overnight, cooled to room temperature, the reaction mixture basified by adding saturated sodium bicarbonate solution and extracted with ether. The organic layer was washed with brine, dried over sodium sulfate and concentrated. The product was purified by column chromatography.

Scheme III: Alternate General Procedure (3) for the Synthesis of (2-Amino-phenyl)- pyridinyl-methanones and (2-Amino-phenyl)-heteroaryl-methanones

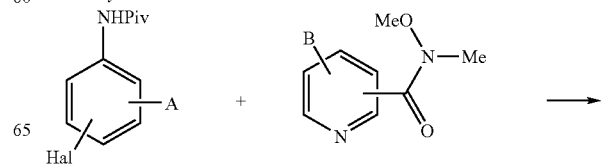

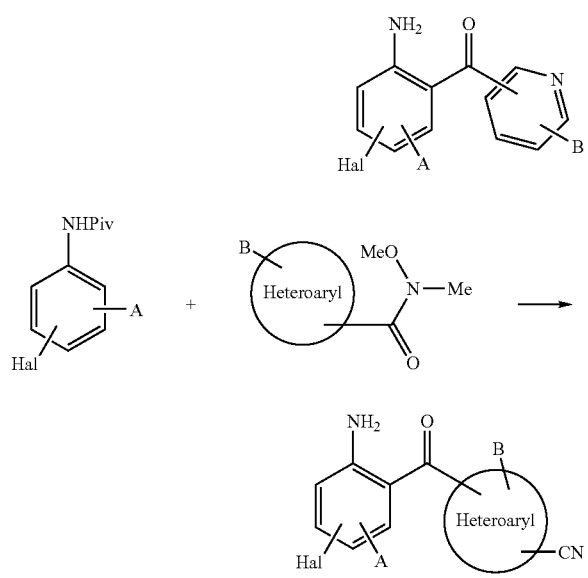

Trimethylacetyl chloride was added drop wise to a solution of desired aniline in dry pyridine and the reaction was stirred under nitrogen overnight. About half of the pyridine was removed by rotary evaporation, then the mixture was treated with 6M hydrochloric acid and extracted with ethyl acetate. The extracts were washed with saturated aqueous $NaHCO_3$ and with water, then were dried ($MgSO_4$), filtered and concentrated by rotary evaporation.

EDC and desired heteroaryl carboxylic acid were stirred in acetonitrile-THF with N,O-dimethylhydroxylamine hydrochloride and triethylamine. After stirring overnight at ambient temperature, the resulting reaction mixture was added to ice water and extracted with ethyl acetate (3×100 mL). The extracts were dried, filtered, and concentrated.

To a stirred solution of the pivaloyl protected intermediate in dry THF was added 2.5M n-butyllithium in hexane at −40° C. and the mixture was stirred at 0° C. for 2 h. A solution of the Weinreb amide in dry THF was added dropwise and the reaction was stirred at ambient temp overnight. The mixture was diluted with water and extracted with ethyl acetate and the organic layer was dried ($MgSO_4$), filtered and concentrated, to yield, after purification by HPLC or column chromatography, the pivaloyl protected aminoketone intermediate.

Deprotection with 70% sulfuric acid was carried out at 75° C. and progress monitored by LC/MS. The reaction was allowed to cool to ambient temperature, and was washed with ether-hexane. The acidic aqueous layer was cooled in an ice bath and aqueous NaOH was added drop wise to basify the mixture. The product was extracted with ethyl acetate and the extracts were washed with saturated aqueous NaHCO3 (2×100 mL), with saturated aqueous sodium chloride, dried ($MgSO_4$), filtered and concentrated, yielding the desired (2-Amino-phenyl)-heteroaryl-methanone.

Scheme IV: General Procedure for the preparation of N-Aryl-benzenesulfonamides

To the desired aniline (0.5 mmol) dissolved in pyridine and cooled in an ice-water bath was added a solution of an aryl sulfonyl chloride (0.5 mmol) dissolved in cold pyridine. The reaction mixture was then heated to 60° C. with gentle shaking for 16 h. Evaporation of the solvent with standard workup followed by either flash chromatography or reversed phase HPLC yielded the corresponding N-aryl-benzenesulfonamides.

Scheme V: General Procedure for the Synthesis of Sulfonamide Pyridine-N-Oxides

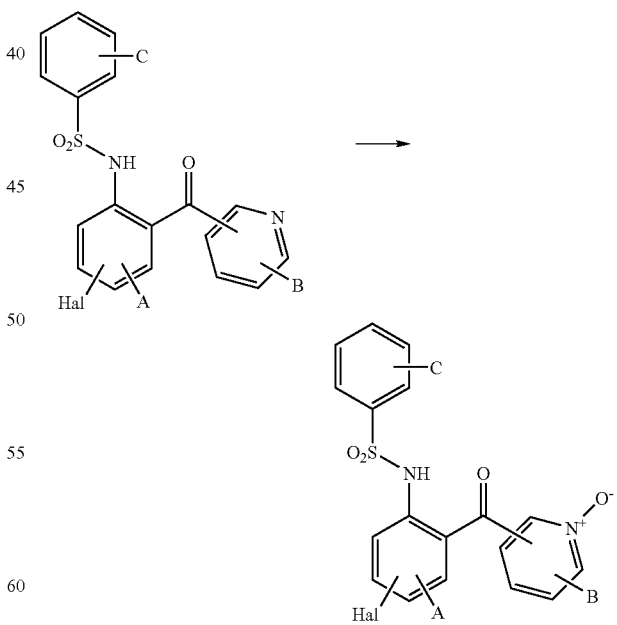

The desired N-Aryl-benzenesulfonamide (250 μmol) was dissolved in 2 mL DCM and m-CPBA (1.0-1.5 eq) was then added. The reaction was shaken at RT and monitored by LC-MS. Additional m-CPBA was added as needed in aliquots until the reaction was complete. In most cases the reaction required 15-24 h reaction time. Standard workup led to the required products.

Synthesis of 4-tert-Butyl-N-[4-chloro-2-(1-oxy-pyridine-4-carbonyl)-phenyl]-benzenesulfonamide

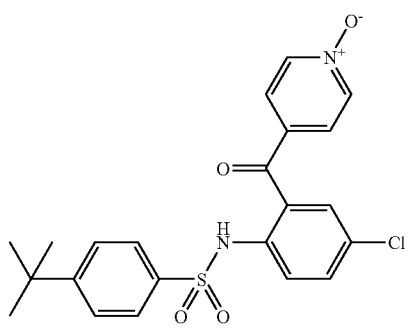

The title compound was prepared according to the procedure described in patent application Ser. No. 10/716,170 (filed Nov. 17, 2003, pending), following the above general procedures.

Synthesis of 4-Chloro-2-(difluoro-pyridin-4-yl-methyl)-phenylamine

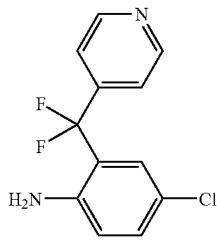

4-tert-butyl-N-[4-chloro-2-(1-oxy-pyridine-4-carbonyl)-phenyl]-benzenesulfonamide (444 mg, 1 mmol) suspended in DCM was cooled to 0° C. and treated with DAST (1 mL). The mixture was stirred at 0° C. for 30 min and then at room temperature overnight. After evaporating the volatiles the residue was dissolved in ethyl acetate (50 mL) and washed with ice-cold saturated sodium bicarbonate solution (50 mL). The aqueous phase was washed with ethyl acetate (2×20 mL) and the combined organic extract was dried and concentrated. Purification by preparative HPLC afforded title compound as off-white solid. MS: (M+H)/z=255.

Synthesis of 4-tert-Butyl-N-[4-chloro-2-(difluoro-pyridin-4-yl-methyl)-phenyl]-benzenesulfonamide

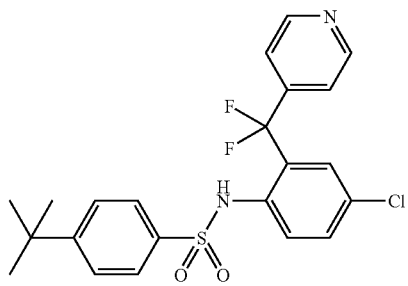

The title compound was prepared according to the general procedure for the preparation of N-Aryl-benzenesulfonamides using 4-chloro-2-(difluoro-pyridin-4-yl-methyl)-phenylamine and 4-tert-butyl-benzenesulfonyl chloride. MS: (M+H)=451.

Synthesis of 4-tert-Butyl-N-{4-chloro-2-[difluoro-(1-oxy-pyridin-4-yl)-methyl]-phenyl}-benzenesulfonamide

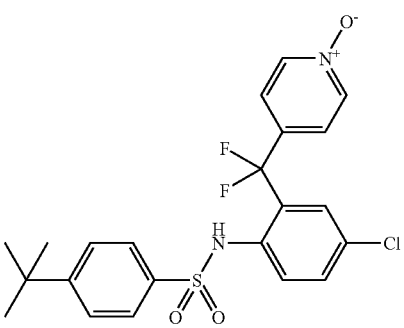

The title compound was prepared by treatment of 4-tert-butyl-N-{4-chloro-2-[difluoro-(1-oxy-pyridin-4-yl)-methyl]-phenyl}-benzenesulfonamide with mCPBA following the procedure described for the synthesis of pyridine N-oxides. MS: (M+H)=467.

Synthesis of 4-tert-Butyl-N-{4-chloro-2-[hydroxy-(1-oxy-pyridin-4-yl)-methyl]-phenyl}-benzenesulfonamide

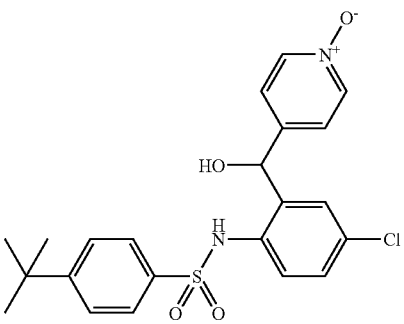

4-tert-Butyl-N-[4-chloro-2-(1-oxy-pyridine-4-carbonyl)-phenyl]-benzenesulfonamide (111 mg, 0.25 mmol) was suspended in ethanol (4 mL) and NaBH$_4$ (38 mg, 1 mmol) was carefully added, and the reaction mixture, which turned to a solution, was stirred for one hour. The reaction mixture was diluted with 10% HCl (10 mL) and the product was extracted with ethyl acetate (2×10 mL). The organic extract was dried over MgSO$_4$ and concentrated to afford the 92 mg of the title compound. MS: (M+H)=447.

Synthesis of 4-tert-Butyl-N-[4-chloro-2-(hydroxy-pyridin-4-yl-methyl)-phenyl]-benzenesulfonamide

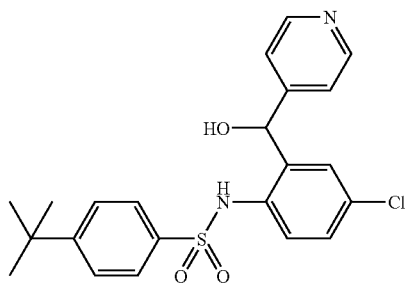

The title compound was prepared by the reduction of 4-tert-Butyl-N-[4-chloro-2-(pyridine-4-carbonyl)-phenyl]-benzenesulfonamide with NaBH$_4$ according to the procedure described in the preceding example. MS: (M+H)=431.

Scheme VI: Synthesis of 4-tert-Butyl-N-{4-chloro-2-[1-hydroxy-1-(1-oxy-pyridin-4-yl)-allyl]-phenyl}-benzenesulfonamide

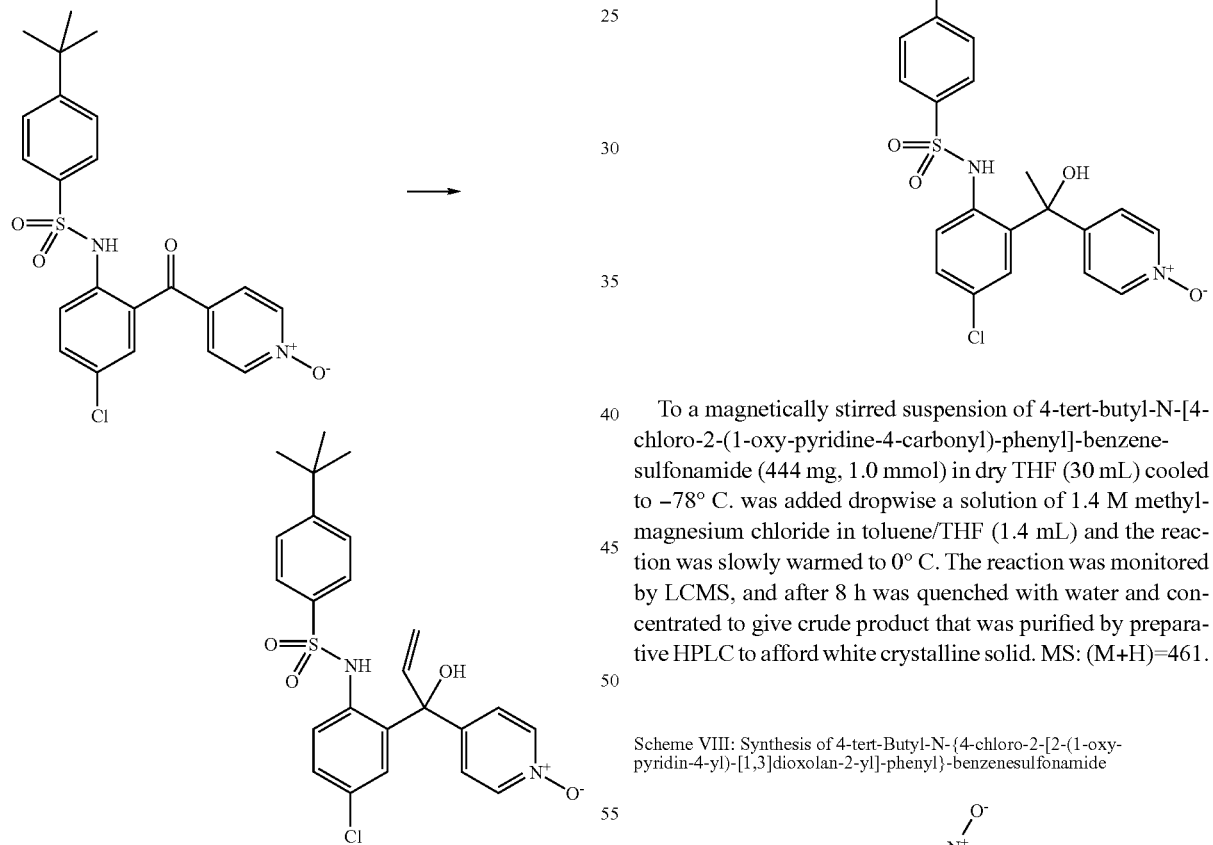

To a magnetically stirred suspension of 4-tert-butyl-N-[4-chloro-2-(1-oxy-pyridine-4-carbonyl)-phenyl]-benzenesulfonamide (444 mg, 1.0 mmol) in dry THF (30 mL) cooled to −78° C., was added dropwise a solution of 1.0 M vinylmagnesium chloride in THF (2.5 mL) and the reaction was slowly allowed to warm to 0° C. The reaction was monitored by LCMS, and after 16 h was concentrated to give a crude product which was separated by purified by HPLC to afford white crystalline solid: MS: (M+H)=473.

Scheme VII: Synthesis of 4-tert-Butyl-N-{4-chloro-2-[1-hydroxy-1-(1-oxy-pyridin-4-yl)-ethyl]-phenyl}-benzenesulfonamide

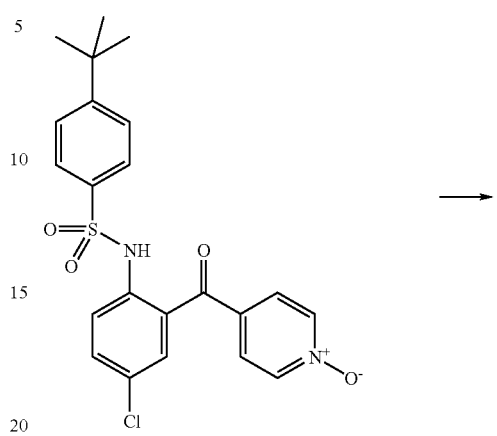

To a magnetically stirred suspension of 4-tert-butyl-N-[4-chloro-2-(1-oxy-pyridine-4-carbonyl)-phenyl]-benzenesulfonamide (444 mg, 1.0 mmol) in dry THF (30 mL) cooled to −78° C. was added dropwise a solution of 1.4 M methylmagnesium chloride in toluene/THF (1.4 mL) and the reaction was slowly warmed to 0° C. The reaction was monitored by LCMS, and after 8 h was quenched with water and concentrated to give crude product that was purified by preparative HPLC to afford white crystalline solid. MS: (M+H)=461.

Scheme VIII: Synthesis of 4-tert-Butyl-N-{4-chloro-2-[2-(1-oxy-pyridin-4-yl)-[1,3]dioxolan-2-yl]-phenyl}-benzenesulfonamide

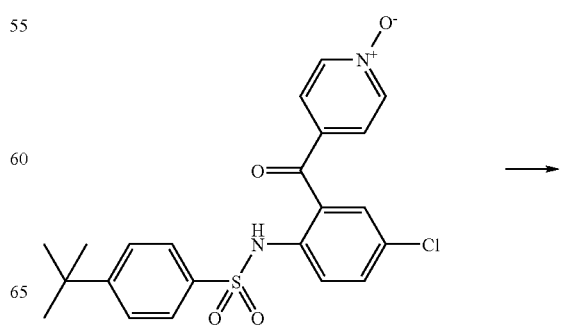

166
Synthesis of 4-tert-Butyl-N-[4-chloro-2-(chloro-pyridin-4-yl-methyl)-phenyl]-benzenesulfonamide

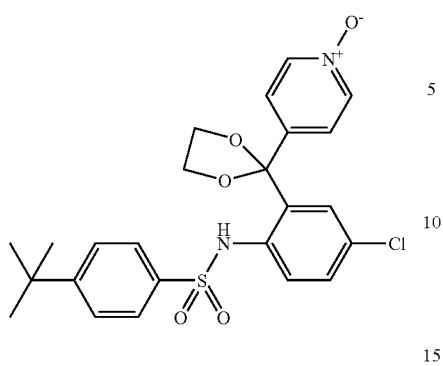

4-tert-Butyl-N-[4-chloro-2-(1-oxy-pyridine-4-carbonyl)-phenyl]-benzenesulfonamide (444 mg, 1.0 mmol) was dissolved in $SOCl_2$ (10 mL) and heated at 80° C. for 1 h. Excess $SOCl_2$ was removed by rotary evaporation. The residue was dissolved in dry THF (5 mL) and was slowly added to an ice cold solution of ethylene glycol (5 mmol) and TEA (5 mmol) in 5 mL THF. After stirring for 2 h the solvent was evaporated and the product was purified by flash chromatography on silica gel column using 10-30 mL ethyl acetate in hexane as the mobile phase. MS: (M+H)=489.

Scheme IX: General approaches to alkyl derivatives

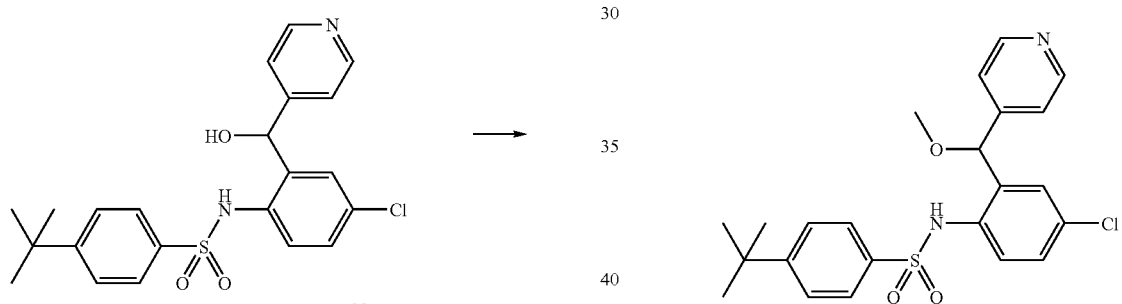

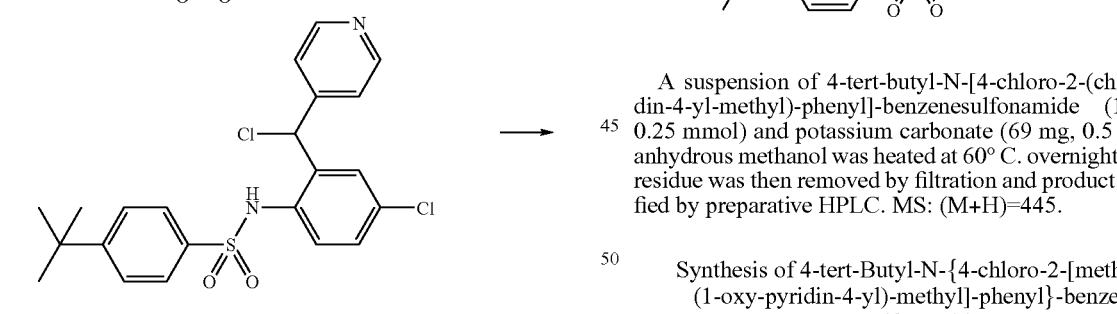

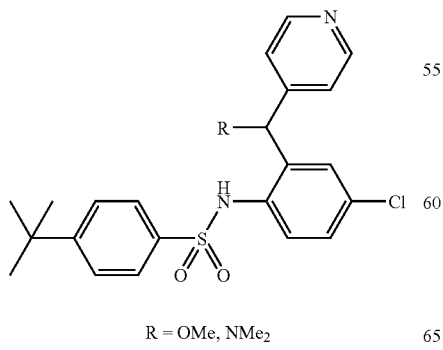

R = OMe, NMe$_2$

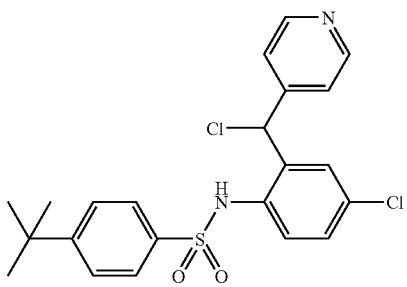

4-tert-Butyl-N-[4-chloro-2-(hydroxy-pyridin-4-yl-methyl)-phenyl]-benzenesulfonamide (1.1 g, 2.5 mmol) was dissolved in $SOCl_2$ and heated at 80° C. overnight. Excess $SOCl_2$ was removed by rotary evaporation. The residue suspended in 50 mL DCM was washed with saturated sodium bicarbonate solution (50 mL) and dried over $MgSO_4$. Evaporation of solvent gave white crystalline solid. MS: (M+H)=450.

Synthesis of 4-tert-Butyl-N-[4-chloro-2-(methoxy-pyridin-4-yl-methyl)-phenyl]-benzenesulfonamide A suspension of 4-tert-butyl-N-[4-chloro-2-(chloro-pyridin-4-yl-methyl)-phenyl]-benzenesulfonamide (113 mg, 0.25 mmol) and potassium carbonate (69 mg, 0.5 mmol) in anhydrous methanol was heated at 60° C. overnight, the solid residue was then removed by filtration and product was purified by preparative HPLC. MS: (M+H)=445.

Synthesis of 4-tert-Butyl-N-{4-chloro-2-[methoxy-(1-oxy-pyridin-4-yl)-methyl]-phenyl}-benzenesulfonamide

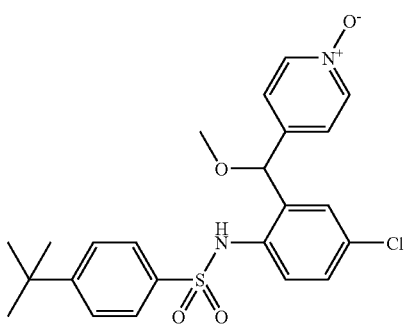

The title compound was prepared by the reaction of 4-tert-butyl-N-[4-chloro-2-(methoxy-pyridin-4-yl-methyl)-phenyl]-benzenesulfonamide with mCPBA according to the procedure described for the preparation of pyridine N-oxides and purified by HPLC. MS: (M+H)=461.

Scheme X: Synthesis of N-{2-[Amino-(1-oxy-pyridin-4-yl)-methyl]-4-chloro-phenyl}-4-tert-butyl-benzenesulfonamide

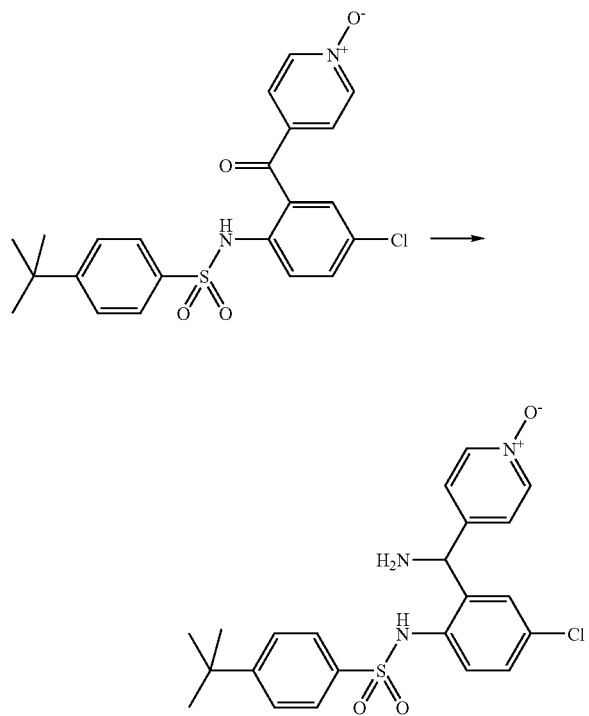

4-tert-Butyl-N-[4-chloro-2-(1-oxy-pyridine-4-carbonyl)-phenyl]-benzenesulfonamide (444 mg, 1 mmol) was treated with a solution of 4 M ammonia in dioxane (5 mL), acetic acid (0.25 mL) and finally NaCNBH₃ (315 mg). After stirring for 48 h the reaction mixture was diluted with 3 N HCl (10 mL) and the product was extracted with ethyl acetate (3×10 mL). The ethyl acetate was removed by rotary evaporation and product was purified by preparative HPLC to afford white crystalline solid. MS: (M+H)=446.

Scheme XI: General procedure for the synthesis of biarylamines

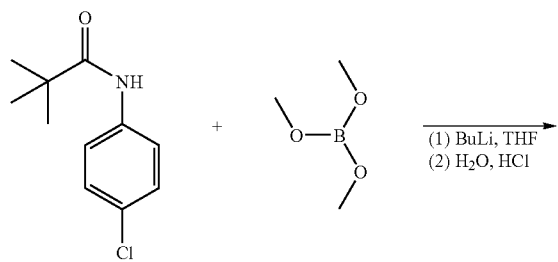

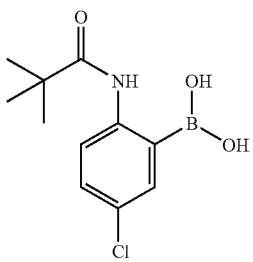

N-(4-Chloro-phenyl)-2,2-dimethyl-propionamide (2.11 g, 10 mmol) was dissolved in anhydrous THF (25 mL) and cooled to 0° C., then n-butyl lithium (22 mmol, 8.8 mL of 2.5 M solution in hexanes) was added dropwise over 30 minutes. The reaction mixture was stirred at this temperature for an additional 2 h and was then cooled to −78° C. A solution of trimethylborate (3.11 g, 30 mmol) in anhydrous THF was added and the mixture was allowed to warm to room temperature and stirred overnight. After concentrating by rotary evaporation the crude product was acidified with 3N HCl. The crystalline solid was collected by filtration, washed with water and dried to afford 1.2 g of the boronic acid MS: MS (M+H⁺): 256. The boronic acid (0.5 mmol), the appropriate aryl halide (0.5 mmol), tetrakis(triphenylphosophine)palladium(0) (0.025 mmol) and K₂CO₃ (1 mmol) were suspended DMF (5 mL) and heated at 100° C. overnight. After cooling to room temperature the reaction mixture was diluted with ether (20 mL) and washed twice with 10 mL portions of water. The organic extract was concentrated and product was purified by flash chromatography on silica gel column using 5-20% ethylacetate/hexane solvent mixture. The pivaloyl protected biaryl was suspended in 70% sulfuric acid and refluxed overnight. After cooling to room temperature the reaction was cautiously added to cold concentrated aqueous NaOH solution to achieve neutral pH and extracted with ethyl acetate.

The organic layer was dried over anhydrous magnesium sulfate and the solvent was evaporated to afford product.

4-Chloro-2-pyridin-2-yl-phenylamine

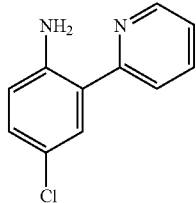

The title compound was prepared according to the general procedure described in Scheme XI using 2-chloropyridine as the aryl halide component. MS: (M+H)/z=205.

4-Chloro-2-isoquinolin-1-yl-phenylamine

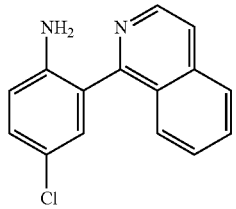

The title compound was prepared according to the general procedure described in Scheme XI using 1-chloroisoquinoline as the aryl halide component. MS: (M+H)/z=255.

4-Chloro-2-isoquinolin-3-yl-phenylamine

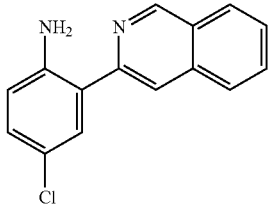

The title compound was prepared according to the general procedure described in Scheme XI using 3-bromoisoquinoline as the aryl halide component. MS: (M+H)/z=255.

Scheme XII: General procedure for the synthesis of sulfonamides

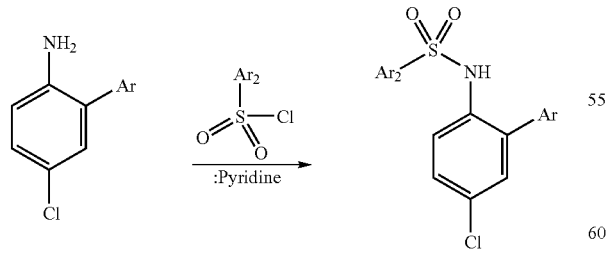

To the desired aniline (0.5 mmol) dissolved in pyridine and cooled in an ice-water bath was added a solution of an aryl sulfonyl chloride (0.5 mmol) dissolved in cold pyridine. The reaction mixture was then heated to 60° C. with gentle shaking for 16 h. Evaporation of the solvent with standard workup followed by either flash chromatography or reverse phase HPLC yielded the corresponding N-aryl-benzenesulfonamide.

4-tert-Butyl-N-(4-chloro-2-pyridin-2-yl-phenyl)-benzenesulfonamide

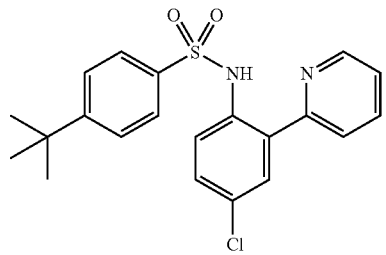

The title compound was prepared according to the general procedure using 4-tert-butyl-benzenesulfonyl chloride and 4-chloro-2-pyridin-2-yl-phenylamine and purified by preparative HPLC. MS: (M+H)/z=401.

4-tert-Butyl-N-(4-chloro-2-isoquinolin-1-yl-phenyl)-benzenesulfonamide

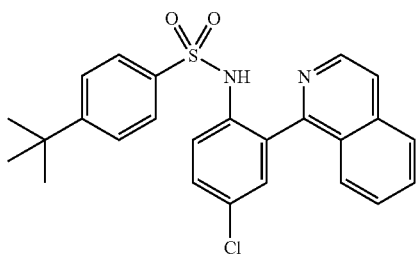

The title compound was prepared according to the general procedure using 4-tert-butyl-benzenesulfonyl chloride and 4-chloro-2-isoquinolin-1-yl-phenylamine and purified by preparative HPLC. MS: (M+H)/z=451.

4-tert-Butyl-N-(4-chloro-2-isoquinolin-3-yl-phenyl)-benzenesulfonamide

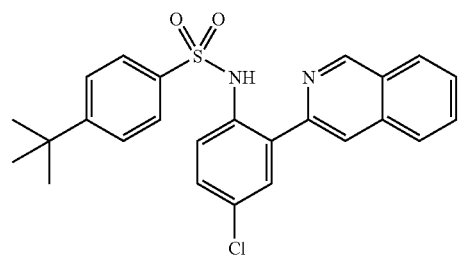

The title compound was prepared according to the general procedure using 4-tert-butyl-benzenesulfonyl chloride and 2-(5-Phenyl-1H-imidazol-2-yl)-phenylamine and purified by preparative HPLC. MS: (M+H)/z=432.

N-(4-Chloro-2-isoquinolin-1-yl-phenyl)-4-oxazol-5-yl-benzenesulfonamide

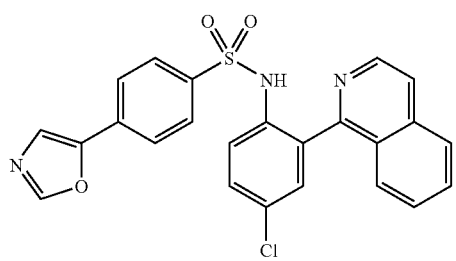

The title compound was prepared according to the general procedure using 4-oxazol-5-yl-benzenesulfonyl chloride and 4-chloro-2-isoquinolin-1-yl-phenylamine and purified by preparative HPLC. MS: (M+H)/z=462.

4-tert-Butyl-N-[2-(5-phenyl-1H-imidazol-2-yl)-phenyl]-benzenesulfonamide

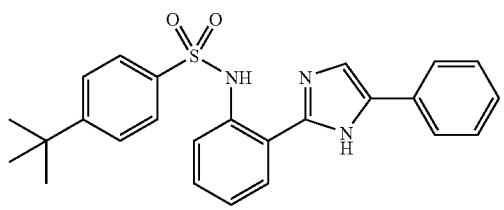

The title compound was prepared according to the general procedure using 4-tert-butyl-benzenesulfonyl chloride and 4-chloro-2-isoquinolin-3-yl-phenylamine and purified by preparative HPLC. MS: (M+H)/z=451.

Scheme XIII: General synthetic approach to biarylamies

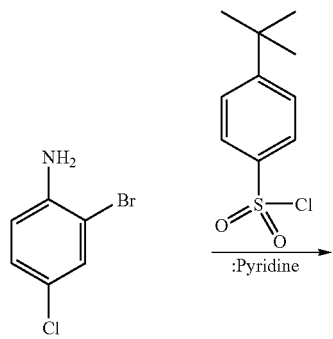

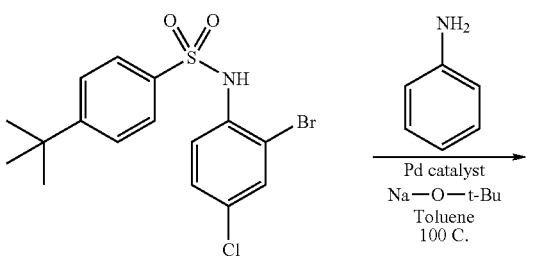

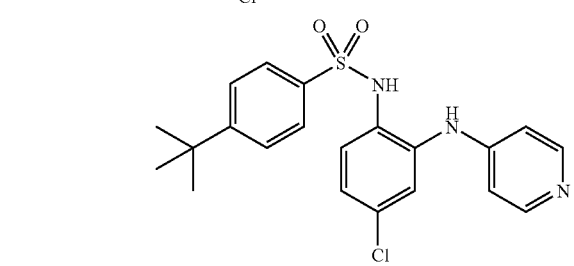

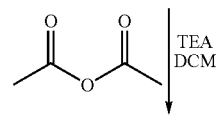

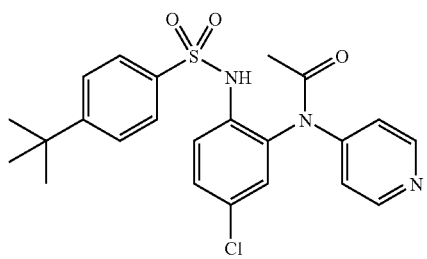

N-(2-Bromo-4-methyl-phenyl)-4-tert-butyl-benzenesulfonamide

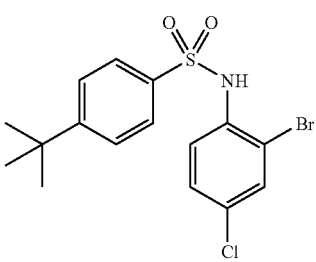

2-Bromo-4-chloro-phenylamine (2.06 g, 10 mmol) and 4-tert-butylbenzenesulfonyl chloride (2.55 g, 11 mmol) were suspended in anhydrous pyridine (10 mL) and heated at 60° C. for 4 h. After cooling to room temperature the reaction mixture was added to 6 M HCl (100 mL) and the product was extracted with ethyl acetate (3×50 mL). The combined organic extract was dried over MgSO₄, the solvent was evaporated, and the crude product was purified by flash chromatography to afford the title compound as a white solid. MS: (M+H)/z=403.

4-tert-Butyl-N-[4-chloro-2-(pyridin-4-ylamino)-phenyl]-benzenesulfonamide

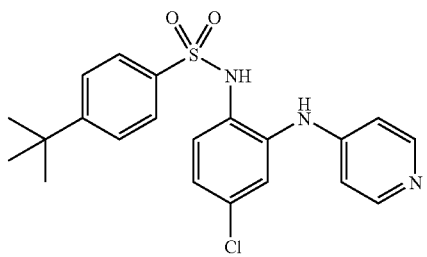

N-(2-Bromo-4-methyl-phenyl)-4-tert-butyl-benzenesulfonamide (416 mg, 1 mmol) Pd(dba)$_3$ (5 mol %), rac-2-2'-bis(diphenylphosphino)-1,1'-binaphtyl (3, mmol), 4-aminopyridine (3 mmol) and Na—O-t-Bu (3 mmol) were suspended in toluene (5 mL) and heated at 100° C. overnight. After cooling to room temperature the reaction mixture was filtered through a short plug of silica, washed with ethyl acetate, and the product purified by flash chromatography on a silica gel column using 10-30% ethyl acetate in hexanes as the mobile phase. Fractions containing product were combined and concentrated to yield product as a solid.

N-[2-(4-tert-Butyl-benzenesulfonylamino)-5-chloro-phenyl]-N-pyridin-4-yl-acetamide

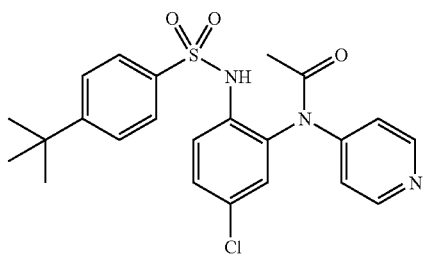

4-tert-Butyl-N-[4-chloro-2-(pyridin-4-ylamino)-phenyl]-benzenesulfonamide (103 mg, 0.25 mmol) dissolved in DCM (5 mL) was treated with acetic anhydride (26 mg, 0.25 mmol) and triethylamine (51 mg, 0.5 mmol), and the reaction mixture was allowed to stir overnight. The volatiles were evaporated and the product was purified by HPLC to afford the title compound. MS: (M+H)/z=458.

Scheme XIV: General Procedure for the Synthesis of Substituted Phenyl Sulfonyl Chlorides via Chlorosulfonation

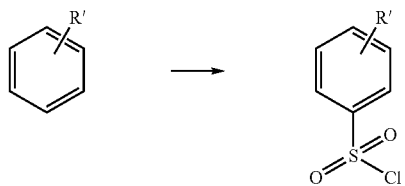

The desired benzene derivative (1.4 mmol) was dissolved in CHCl$_3$ (15 mL) at 0° C., and to this was added chlorosulfonic acid (4.2 mmol). After 30 minutes, the reaction mixture was warmed to room temperature, and additional chlorosulfonic acid (4.2 mmol) was added. After a further hour, the reaction mixture was cooled to 0° C., and crushed ice added to the reaction. The reaction mixture was partitioned between 1M pH7 phosphate buffer and ether, and the ether layer washed with saturated aqueous NaCl, dried over Na$_2$SO$_4$, filtered, and concentrated in vacuo to yield crude product.

Scheme XV: General Procedure for the Synthesis of Substituted Phenyl Sulfonyl Chlorides via diazonium salt intermediates

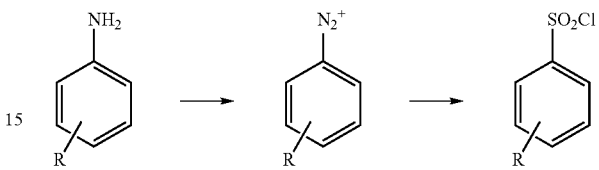

The desired aniline (0.0848 mol) was added slowly to concentrated HCl (109.2 mL), the reaction stirred at room temperature for 15 min, then cooled to 0° C., sodium nitrite (6.2 g, 0.1103 mol in 26 mL of water) added dropwise and the reaction stirred for 15 min.

Separately, distilled water (0.198 mL) was cooled to 0° C. and thionyl chloride (42.9 g, 0.3605 mol) was added dropwise, the mixture warmed to and stirred at room temperature for 17 h, then re-cooled to 0° C., and copper (I) chloride (0.120 g) added in small portions with further stirring for 30 mins to yield a yellowish green solution (Solution A).

This Cu(I) solution (A) was added dropwise to the aniline/HCl solution at −5° C., and stirring continued at 0° C. for 75 min. The reaction mixture was diluted with chloroform. The organic layer was separated, washed with brine, dried over sodium sulphate and concentrated in vacuo.

Scheme XVI: General procedure for the synthesis of heterocyclyl substituted phenylsulfonyl derivatives

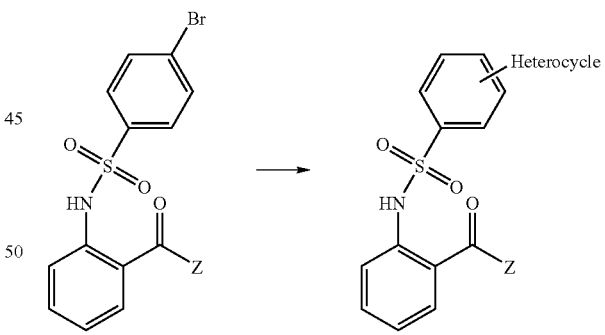

The desired bromobenzenesulfonamide derivative (0.22 mmol) was dissolved in 6 mL anhydrous dioxane, and to this solution was added potassium phosphate tribasic monohydrate (1.32 mmol), rac-2,2'-bis(diphenylphosphino)-1,1'-binaphthyl (0.032 mmol), followed by the desired heterocycle (1.1 mmol). The mixture was purged under nitrogen, and Pd(dba)$_3$ (0.01 mmol) was added. The reaction mixture was heated overnight at 90° C., cooled, water (5 mL) added, and extracted with ethyl acetate 3 times. The combined organic layer was washed with brine, dried over magnesium sulfate, filtered and concentrated. The crude reaction mixture was purified using HPLC.

Scheme XVII: General procedure for the synthesis of heteroaryl substituted phenylsulfonyl derivatives

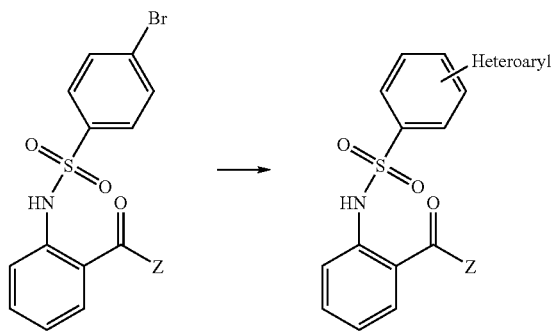

The desired bromobenzenesulfonamide derivative (0.25 g, 0.55 mmol) was dissolved in 2.5 mL of anhydrous dimethylformamide. To this solution was added 0.14 g (1.3 mmol) sodium carbonate, suitable heteroaryl-3-boronic acid (0.68 mmol), and Pd(PPh$_3$)$_4$ 19 mg (0.014 mmol). The reaction mixture was heated overnight at 80° C. under a nitrogen atmosphere. The mixture was quenched with water and extracted 3 times with dichloromethane. The organic layer was dried over magnesium sulfate, filtered, and concentrated, and the crude product purified by flash column chromatography.

Scheme XVIII: General procedures for the synthesis of N-{4-chloro-2-[1-(heteroaryl)-ethenyl]-phenyl}-arylsulfonamides and related derivatives

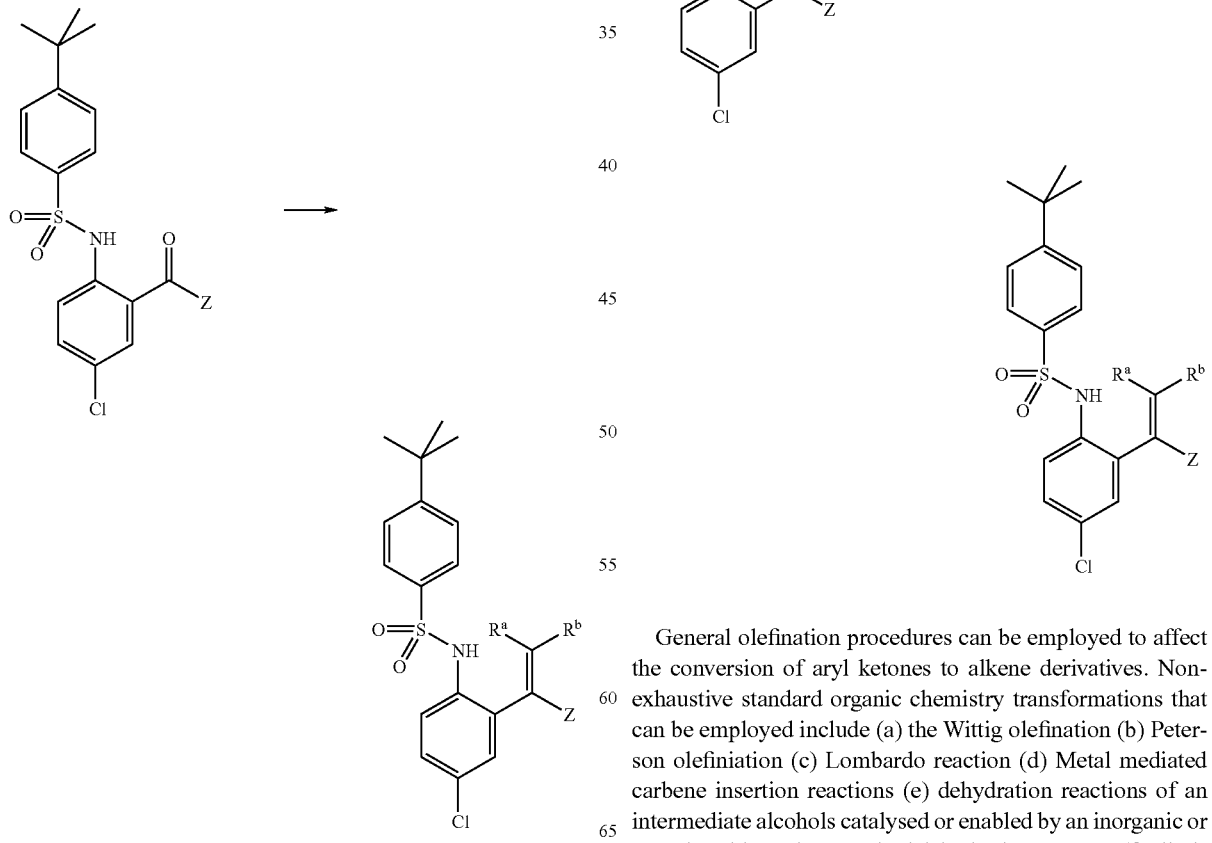

To a magnetically stirred suspension of arylketone (1.0 mmol) in dry THF (30 mL) cooled to −78° C. was added dropwise a solution of 1.4 M Grignard reagent in toluene/THF (1.4 mL) and the reaction was slowly warmed to 0° C. The reaction was monitored by LCMS, and after 8 h was quenched with water and concentrated to give crude alcohol intermediate that was purified by preparative HPLC or column chromatography.

To this alcohol (0.080 mmol) in dry toluene (10 mL) was added 5.0 mg of para-toluenesulfonic acid monohydrate and the reaction was heated at reflux under nitrogen. The reaction was monitored by LCMS, and after 72 h was concentrated to give crude olefin product, which was purified by preparative HPLC or column chromatography.

Scheme XIX: Alternate procedures for the synthesis of N-{4-chloro-2-[1-(heteroaryl)-ethenyl]-phenyl}-arylsulfonamides and related derivatives

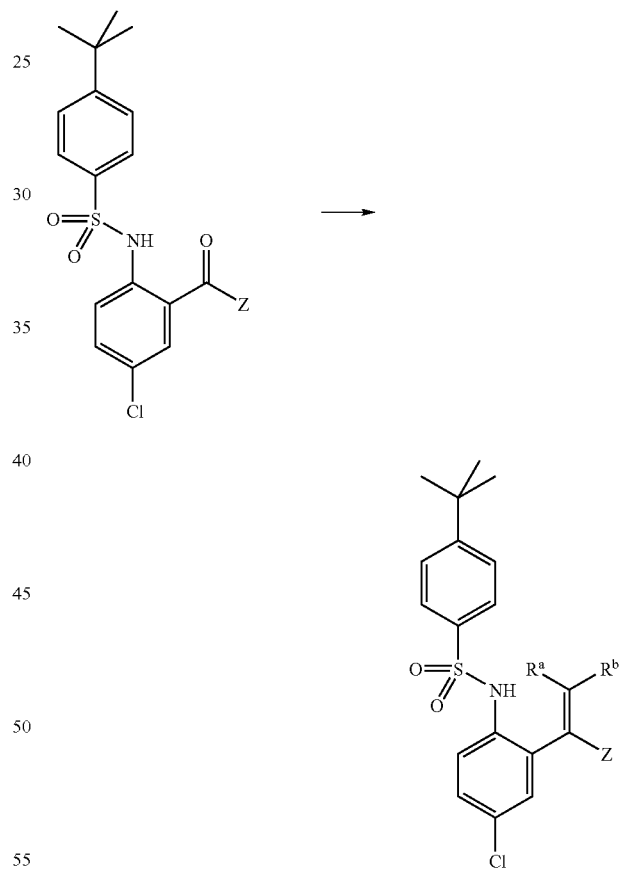

General olefination procedures can be employed to affect the conversion of aryl ketones to alkene derivatives. Non-exhaustive standard organic chemistry transformations that can be employed include (a) the Wittig olefination (b) Peterson olefiniation (c) Lombardo reaction (d) Metal mediated carbene insertion reactions (e) dehydration reactions of an intermediate alcohols catalysed or enabled by an inorganic or organic acid or other standard dehydrating reagents (f) elimination of an active intermediate such as a mesylate or tosylate.

Scheme XX: General procedure for the synthesis of N-(4-chloro-2-[(E)-alkoxyimino]-heteroaryl-methyl}-phenyl)-benzenesulfonamides and benzenesulfonamide and N-(4-chloro-2-[(Z)-alkoxyimino]-heteroaryl-methyl}-phenyl)-benzenesulfonamides and benzenesulfonamide

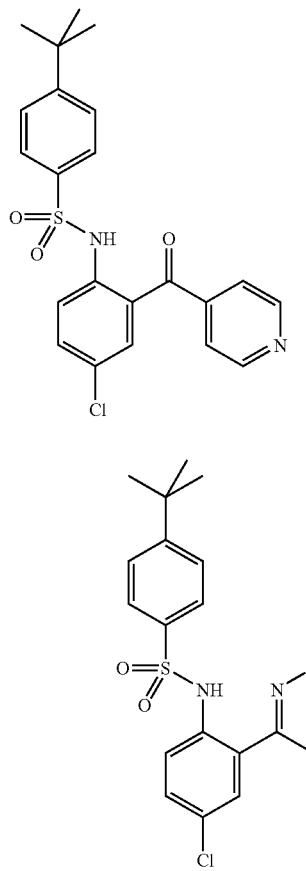

Scheme XXI: Examples of alternate approaches towards the Syntheses of Functionalized Alkyl Phenyl Sulfonyl Chlorides and Alkylsulfonyl Phenyl Sulfonyl Chlorides

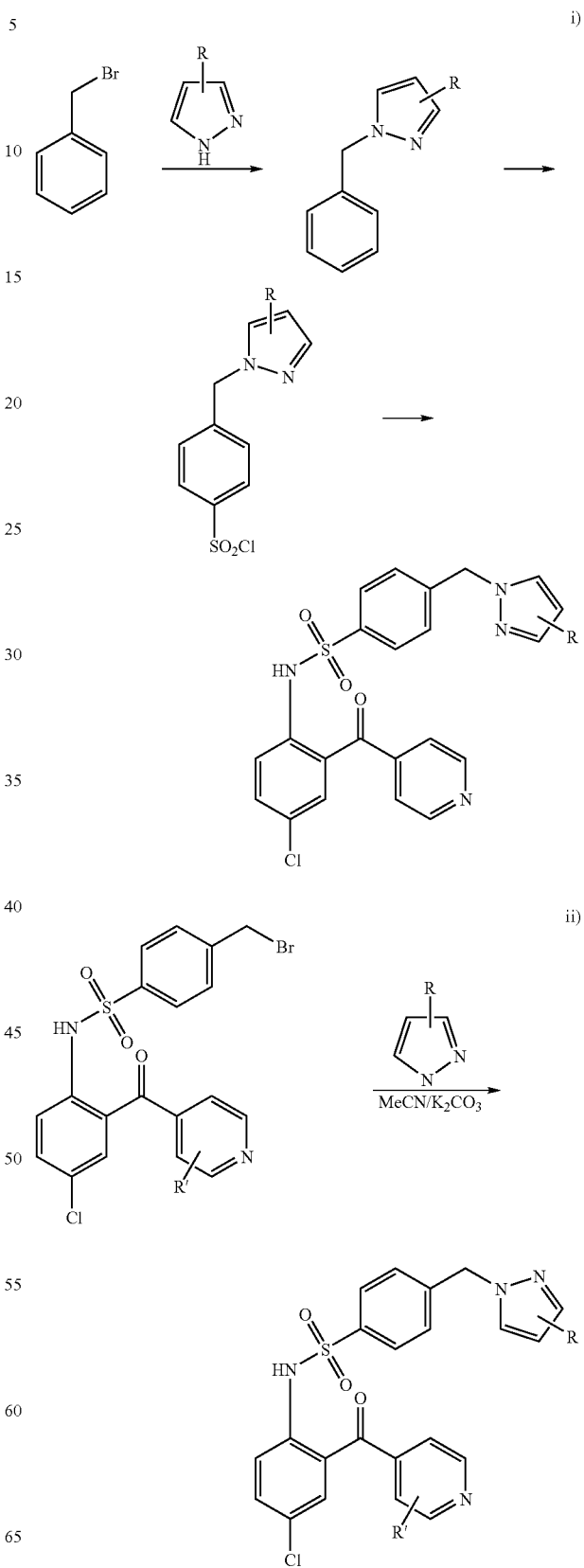

Aryl ketone (1 mmol), O-alkylhydroxylamine hydrochloride (835 mg, 10 mmol), anhydrous pyridine (1.6 mL) and absolute ethanol (5 mL) were placed in a vial. The vial was capped, placed in a 70° C. sand-bath and shaken for 20 h. After cooling to room temperature the crude reaction mixture was diluted with ethyl acetate (20 mL) and washed twice with 20 mL portions of water. The organic layer was concentrated and the isomeric products were isolated by preparative HPLC.

179
-continued
180
-continued
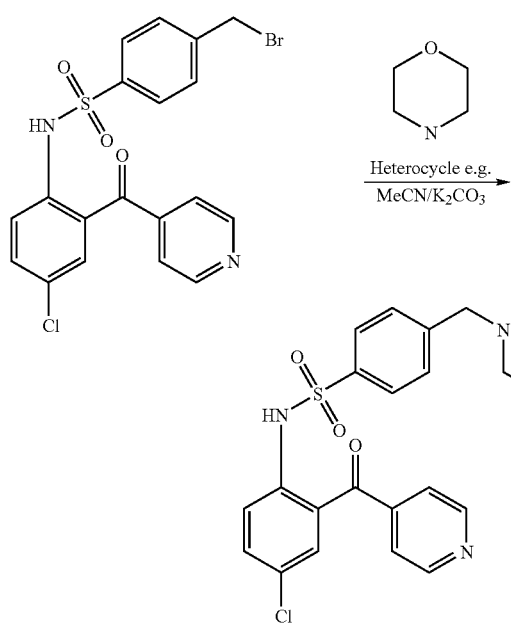
iii)
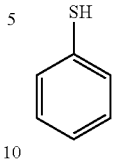
Heterocycle e.g.
MeCN/K₂CO₃
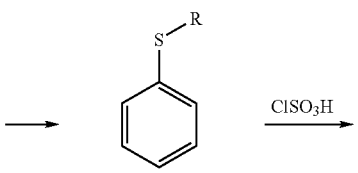
iv)
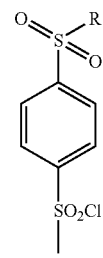
Scheme XXII: Examples of alternate approaches towards the synthesis of (2-Amino-phenyl)-hetrtoaryl-methanones
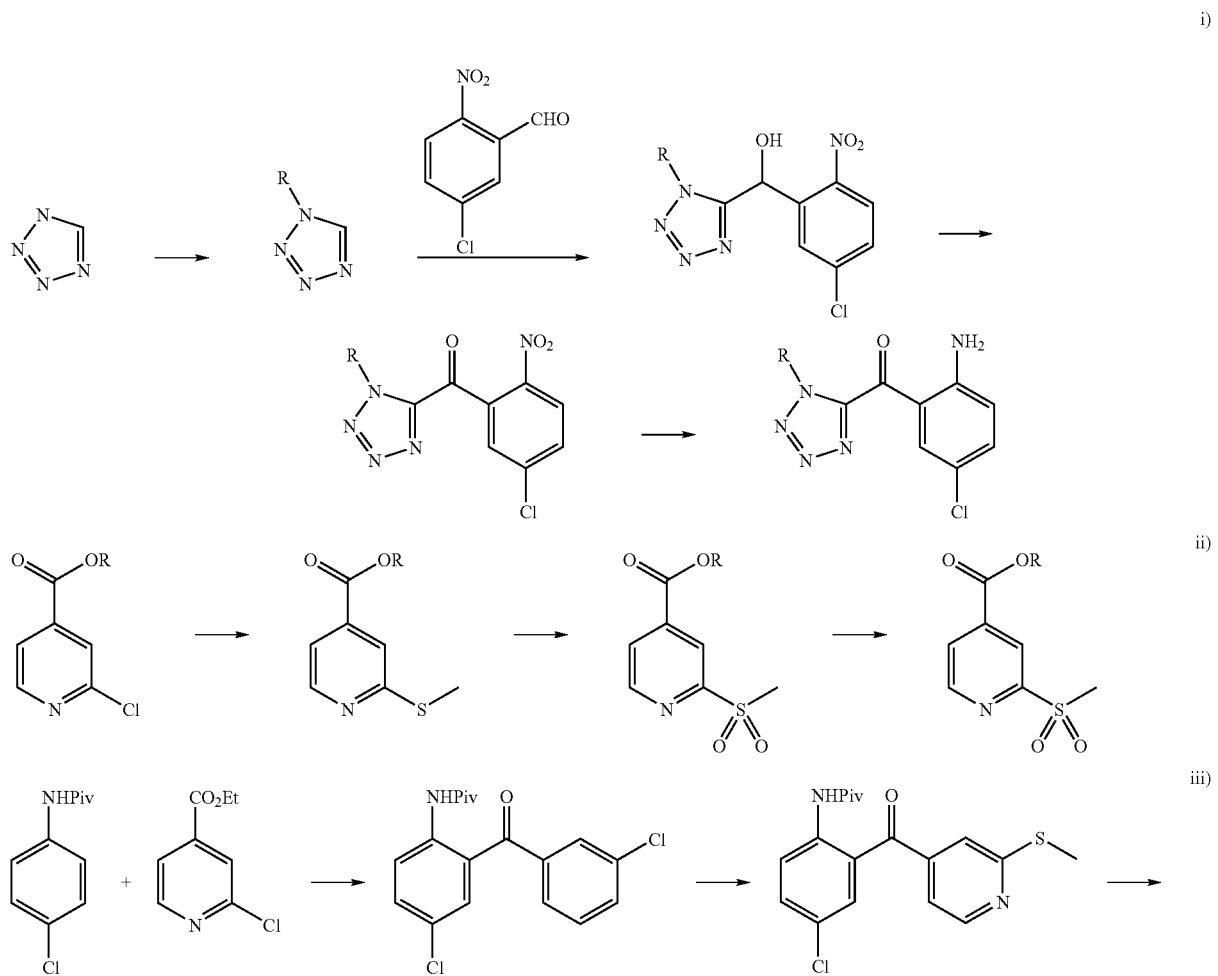

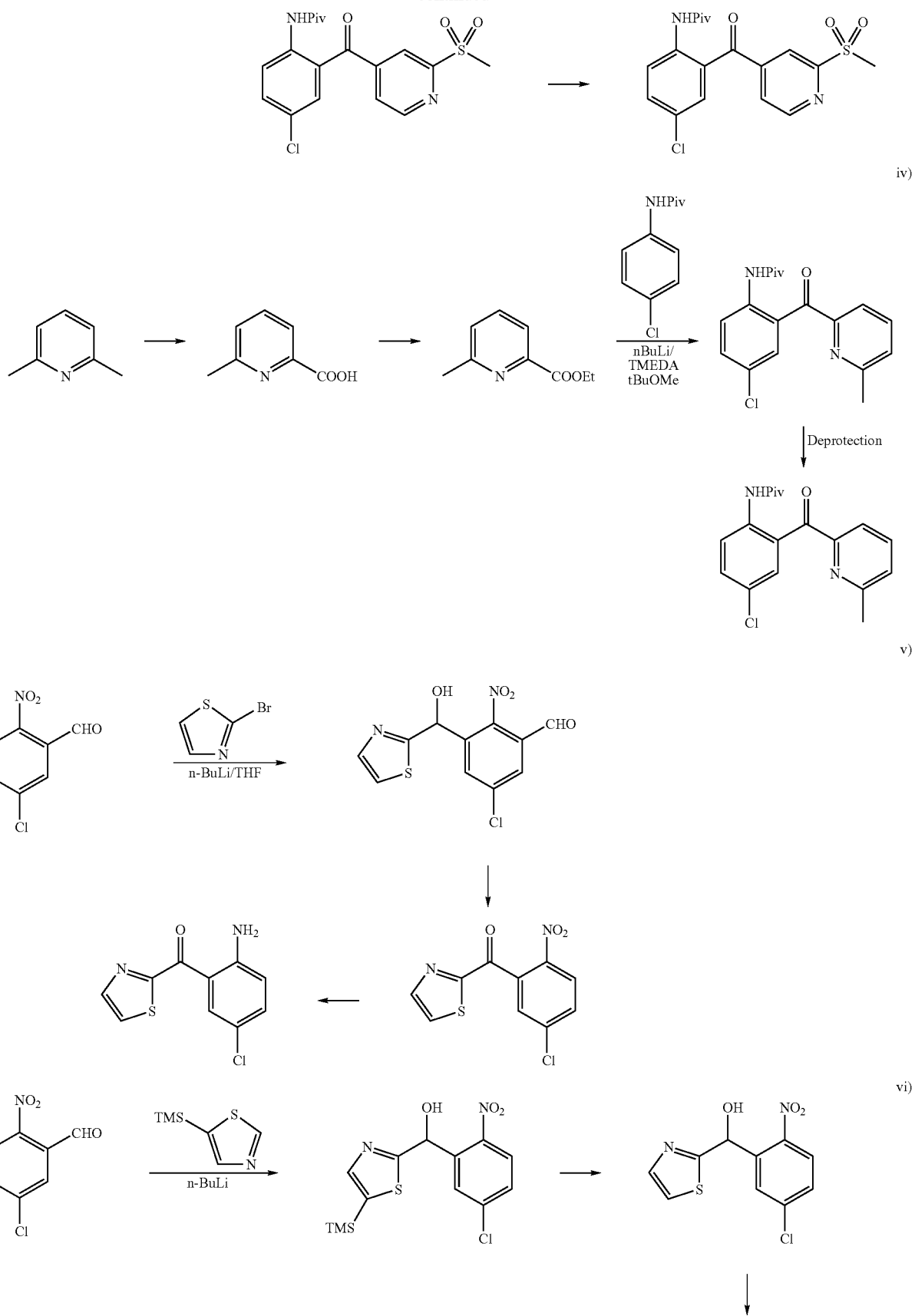

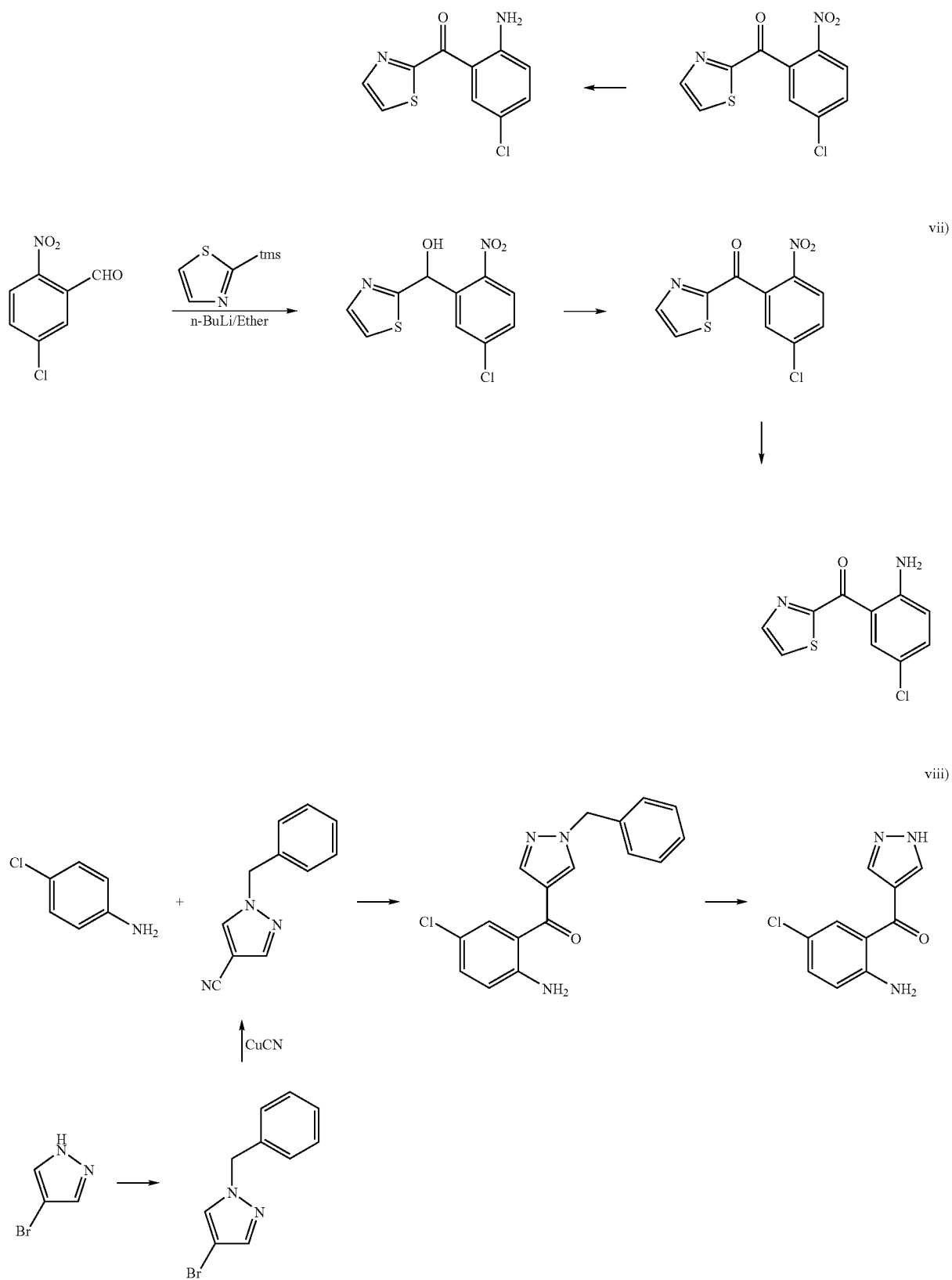

185

Synthesis of 4-tert-Butyl-N-[4-chloro-2-(1-oxy-pyridine-4-carbonyl)-phenyl]-benzenesulfonamide

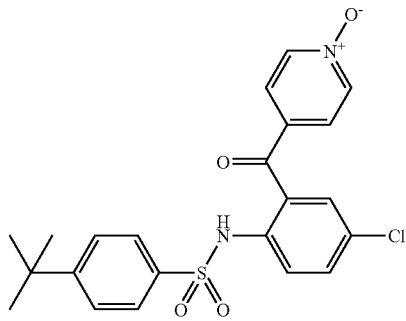

The title compound was prepared according to the procedure described in patent application Ser. No. 10/716,170 (filed Nov. 17, 2003; pending) following the above general procedures.

Scheme XXIII: Synthesis of 4-tert-Butyl-N-{4-chloro-2-[1-hydroxy-1-(1-oxy-pyridin-4-yl)-ethyl]-phenyl}-benzenesulfonamide

186

To a magnetically stirred suspension of 4-tert-butyl-N-[4-chloro-2-(1-oxy-pyridine-4-carbonyl)-phenyl]-benzenesulfonamide (444 mg, 1.0 mmol) in dry THF (30 mL) cooled to −78° C. was added dropwise a solution of 1.4 M methylmagnesium chloride in toluene/THF (1.4 mL) and the reaction was slowly warmed to 0° C. The reaction was monitored by LCMS, and after 8 h was quenched with water and concentrated to give crude product that was purified by preparative HPLC to afford white crystalline solid. MS: (M+H)=461.

Scheme XXIV: Synthesis of 4-tert-butyl-N-{4-chloro-2-[1-(1-oxy-pyridin-4-yl)-ethenyl]-phenyl}-benzenesulfonamide

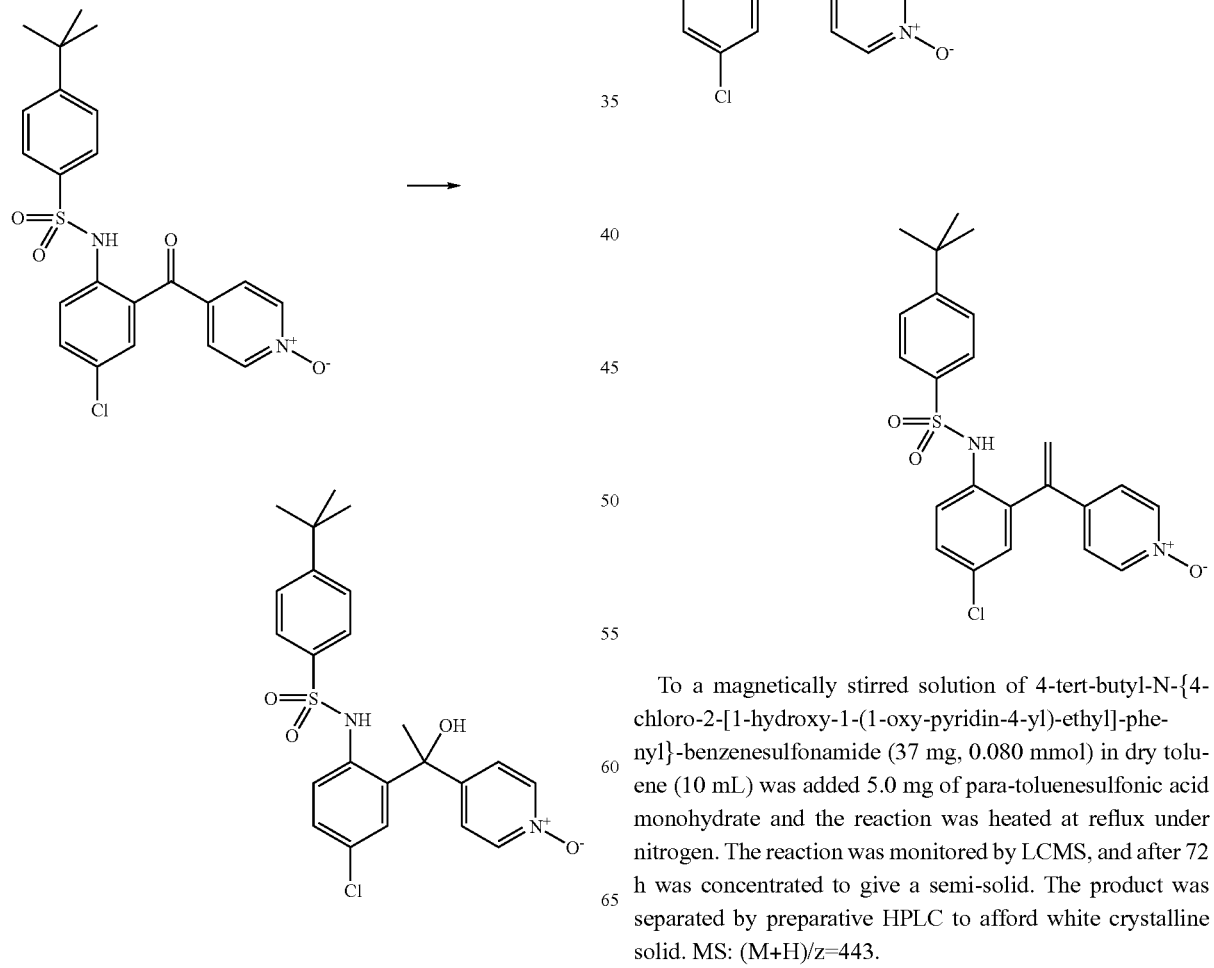

To a magnetically stirred solution of 4-tert-butyl-N-{4-chloro-2-[1-hydroxy-1-(1-oxy-pyridin-4-yl)-ethyl]-phenyl}-benzenesulfonamide (37 mg, 0.080 mmol) in dry toluene (10 mL) was added 5.0 mg of para-toluenesulfonic acid monohydrate and the reaction was heated at reflux under nitrogen. The reaction was monitored by LCMS, and after 72 h was concentrated to give a semi-solid. The product was separated by preparative HPLC to afford white crystalline solid. MS: (M+H)/z=443.

Scheme XXV: Synthesis of 4-tert-Butyl-N-(4-chloro-2-[(E)-methoxyimino]-pyridin-4-yl-methyl}-phenyl)benzenesulfonamide and 4-tert-butyl-N-(4-chloro-2-{[(Z)-methoxyimino]-pyridin-4-yl-methyl}-phenyl)-benzenesulfonamide

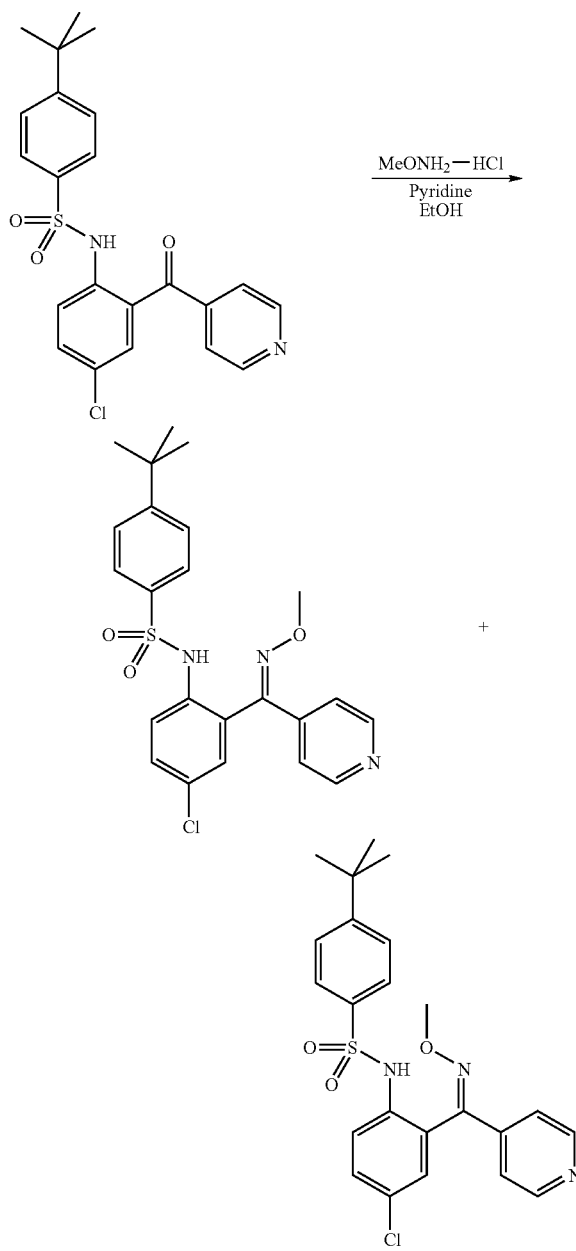

4-tert-Butyl-N-[4-chloro-2-(pyridine-4-carbonyl)-phenyl]-benzenesulfonamide (428, 1 mmol), O-methylhydroxylamine hydrochloride (835 mg, 10 mmol), anhydrous pyridine (1.6 mL) and absolute ethanol (5 mL) were placed in a vial. The vial was capped, placed in a 70° C. sand-bath and shaken for 20 h. After cooling to room temperature the crude reaction mixture was diluted with ethyl acetate (20 mL) and washed twice with 20 mL portions of water. The organic layer was concentrated and the isomeric products were isolated by preparative HPLC. MS: (M+H)/z=458.

Measuring Efficacy of CCR9 Modulators
In Vitro Assays

A variety of assays can be used to evaluate the compounds provided herein, including signaling assays, migration assays, and other assays of cellular response. CCR9 receptor signaling assays can be used to measure the ability of a compound, such as a potential CCR9 antagonist, to block CCR9 ligand- (e.g. TECK)-induced signaling. A migration assay can be used to measure the ability of a compound of interest, such as a possible CCR9 antagonist, to block CCR9-mediated cell migration in vitro. The latter is believed to resemble chemokine-induced cell migration in vivo.

In a suitable assay, a CCR9 protein (whether isolated or recombinant) is used which has at least one property, activity, or functional characteristic of a mammalian CCR9 protein. The property can be a binding property (to, for example, a ligand or inhibitor), a signaling activity (e.g., activation of a mammalian G protein, induction of rapid and transient increase in the concentration of cytosolic free calcium $[Ca^{++}]$), cellular response function (e.g., stimulation of chemotaxis or inflammatory mediator release by leukocytes), and the like.

The assay can be a cell based assay that utilizes cells stably or transiently transfected with a vector or expression cassette having a nucleic acid sequence which encodes the CCR9 receptor. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., TECK) as a competitor.

Binding inhibition assays can be used to evaluate the present compounds. In these assays, the compounds are evaluated as inhibitors of ligand binding using, for example, TECK. In this embodiment, the CCR9 receptor is contacted with a ligand such as TECK and a measure of ligand binding is made. The receptor is then contacted with a test agent in the presence of a ligand (e.g., TECK) and a second measurement of binding is made. A reduction in the extent of ligand binding is indicative of inhibition of binding by the test agent. The binding inhibition assays can be carried out using whole cells which express CCR9, or a membrane fraction from cells which express CCR9.

The binding of a G protein coupled receptor by, for example, an agonist, can result in a signaling event by the receptor. Accordingly, signaling assays can also be used to evaluate the compounds of the present invention and induction of signaling function by an agent can be monitored using any suitable method. For example, G protein activity, such as hydrolysis of GTP to GDP, or later signaling events triggered by receptor binding can be assayed by known methods (see, for example, PCT/US97/15915; Neote, et al., *Cell*, 72:415425 (1993); Van Riper, et al., *J. Exp. Med.*, 177:851-856 (1993) and Dahinden, et al., *J. Exp. Med.*, 179:751-756 (1994)).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. A variety of chemotaxis assays are known in the art, and any suitable assay can be used to evaluate the compounds of the present invention. Examples of suitable assays include those described in PCT/US97/15915; Springer, et al., WO 94/20142; Berman et al., *Immunol. Invest.*, 17:625-677 (1988); and Kavanaugh et al., *J. Immunol.*, 146:4149-4156 (1991)).

Calcium signaling assays measure calcium concentration over time, preferably before and after receptor binding. These assays can be used to quantify the generation of a receptor signaling mediator, $Ca^{++}$, following receptor binding (or absence thereof). These assays are useful in determining the ability of a compound, such as those of the present invention, to generate the receptor signaling mediator by binding to a receptor of interest. Also, these assays are useful in determining the ability of a compound, such as those of the present invention, to inhibit generation of the receptor signaling mediator by interfering with binding between a receptor of interest and a ligand.

In calcium signaling assays used to determine the ability of a compound to interfere with binding between CCR9 and a known CCR9 ligand, CCR9-expressing cells (such as a T cell line MOLT-4 cells) are first incubated with a compound of interest, such as a potential CCR9 antagonist, at increasing concentrations. The cell number can be from $10^5$ to $5 \times 10^5$ cells per well in a 96-well microtiter plate. The concentration of the compound being tested may range from 0 to 100 µM. After a period of incubation (which can range from 5 to 60 minutes), the treated cells are placed in a Fluorometric Imaging Plate Reader (FLIPR®) (available from Molecular Devices Corp., Sunnyvale, Calif.) according to the manufacturer's instruction. The FLIPR® system is well known to those skilled in the art as a standard method of performing assays. The cells are then stimulated with an appropriate amount of the CCR9 ligand TECK (e.g. 5-100 nM final concentration) and the signal of intracellular calcium increase (also called calcium flux) is recorded. The efficacy of a compound as an inhibitor of binding between CCR9 and the ligand can be calculated as an $IC_{50}$ (the concentration needed to cause 50% inhibition in signaling) or $IC_{90}$ (at 90% inhibition).

In vitro cell migration assays can be performed (but are not limited to this format) using the 96-well microchamber (called ChemoTX™). The ChemoTX™ system is well known to those skilled in the art as a type of chemotactic/cell migration instrument. In this assay, CCR9-expressing cells (such as MOLT-4) are first incubated with a compound of interest, such as a possible CCR9 antagonist, at increasing concentrations. Typically, fifty thousand cells per well are used, but the amount can range from $10^3$-$10^6$ cells per well. CCR9 ligand TECK, typically at 50 nM (but can range from 5-100 nM), is placed at the lower chamber and the migration apparatus is assembled. Twenty microliters of test compound-treated cells are then placed onto the membrane. Migration is allowed to take place at 37° C. for a period of time, typically 2.5 hours. At the end of the incubation, the number of cells that migrated across the membrane into the lower chamber is then quantified. The efficacy of a compound as an inhibitor of CCR9-mediated cell migration is calculated as an $IC_{50}$ (the concentration needed to reduce cell migration by 50%) or $IC_{90}$ (for 90% inhibition).

In Vivo Efficacy Models for Human IBD

T cell infiltration into the small intestine and colon have been linked to the pathogenesis of human inflammatory bowel diseases which include Coeliac disease, Crohn's disease and ulcerative colitis. Blocking trafficking of relevant T cell populations to the intestine is believed to be an effective approach to treat human IBD. CCR9 is expressed on gut-homing T cells in peripheral blood, elevated in patients with small bowel inflammation such as Crohn's disease and Coeliac disease. CCR9 ligand TECK is expressed in the small intestine. It is thus believed that this ligand-receptor pair plays a role in IBD development by mediating migration of T cells to the intestine. Several animal models exist and can be used for evaluating compounds of interest, such as potential CCR9 antagonists, for an ability to affect such T cell migration and/or condition or disease, which might allow efficacy predictions of antagonists in humans.

Animal Models with Pathology Similar to Human Ulcerative Colitis

A murine model described by Panwala and coworkers (Panwala, et al., *J Immunol.*, 161(10):5733-44 (1998)) involves genetic deletion of the murine multi-drug resistant gene (MDR). MDR knockout mice (MDR−/−) are susceptible to developing a severe, spontaneous intestinal inflammation when maintained under specific pathogen-free facility conditions. The intestinal inflammation seen in MDR−/− mice has a pathology similar to that of human inflammatory bowel disease (IBD) and is defined by Th1 type T cells infiltration into the lamina propria of the large intestine.

Another murine model was described by Davidson et al., *J Exp Med.*, 184(1):241-51 (1986). In this model, the murine IL-10 gene was deleted and mice rendered deficient in the production of interleukin 10 (IL-10−/−). These mice develop a chronic inflammatory bowel disease (IBD) that predominates in the colon and shares histopathological features with human IBD.

Another murine model for IBD has been described by Powrie et al., *Int Immunol.*, 5(11):1461-71 (1993), in which a subset of CD4+ T cells (called CD45RB (high)) from immunocompetent mice are purified and adoptively transferred into immunodeficient mice (such as C.B-17 scid mice). The animal restored with the CD45RBhighCD430 T cell population developed a lethal wasting disease with severe mononuclear cell infiltrates in the colon, pathologically similar with human IBD.

Murine Models with Pathology Similar to Human Crohn's Disease

The TNF ARE(−/−) model. The role of TNF in Crohn's disease in human has been demonstrated more recently by success of treatment using anti-TNF alpha antibody by Targan et al., *N Engl J Med.*, 337(15):1029-35 (1997). Mice with aberrant production of TNF-alpha due to genetic alteration in the TNF gene (ARE−/−) develop Crohn's-like inflammatory bowel diseases (see Kontoyiannis et al., *Immunity*, 10(3):387-98 (1999)).

The SAMP/yit model. This is model described by Kosiewicz et al., *J Clin Invest.*, 107(6):695-702 (2001). The mouse strain, SAMP/Yit, spontaneously develops a chronic inflammation localized to the terminal ileum. The resulting ileitis is characterized by massive infiltration of activated T lymphocytes into the lamina propria, and bears a remarkable resemblance to human Crohn's disease.

Materials and Methods (In Vitro Assays)

Reagents and Cells

MOLT-4 cells were obtained from the American Type Culture Collection (Manassas, Va.) and cultured in RPMI tissue culture medium supplemented with 10% fetal calf serum (FCS) in a humidified 5% $CO_2$ incubator at 37° C. Recombinant human chemokine protein TECK was obtained from R&D Systems (Minneapolis, Minn.). ChemoTX® chemotaxis microchambers were purchased from Neuro Probe (Gaithersburg, Md.). CyQUANT® cell proliferation kits were purchased from Molecular Probes (Eugene, Oreg.). Calcium indicator dye Fluo-4 AM was purchased from Molecular Devices (Mountain View, Calif.).

Conventional Migration Assay

Conventional migration assay was used to determine the efficacy of potential receptor antagonists in blocking migration mediated through CCR9. This assay was routinely performed using the ChemoTX® microchamber system with a 5-μm pore-sized polycarbonate membrane. To begin such an assay, MOLT-4 cells were harvested by centrifugation of cell suspension at 1000 PRM on a GS-6R Beckman centrifuge. The cell pellet was resuspended in chemotaxis buffer (HBSS with 0.1% BSA) at 5×10$^6$ cells/mL. Test compounds at desired concentrations were prepared from 10 mM stock solutions by serial dilutions in chemotaxis buffer. An equal volume of cells and compounds were mixed and incubated at room temperature for 15 minutes. Afterwards, 20 μL of the mixture was transferred onto the porous membrane of a migration microchamber, with 29 μL of 50 nM chemokine TECK protein placed at the lower chamber. Following a 150-minute incubation at 37° C., during which cells migrated against the chemokine gradient, the assay was terminated by removing the cell drops from atop the filter. To quantify cells migrated across the membrane, 5 μL of 7× CyQUANT® solution was added to each well in the lower chamber, and the fluorescence signal measured on a Spectrafluor Plus fluorescence plate reader (TECAN, Durham, N.C.). The degree of inhibition was determined by comparing migration signals between compound-treated and untreated cells. IC50 calculation was further performed by non-linear squares regression analysis using Graphpad Prism (Graphpad Software, San Diego, Calif.).

RAM Assay

The primary screen to identify CCR9 antagonists was carried out using RAM assay (WO 02101350), which detects potential hits by their ability to activate cell migration under inhibitory TECK concentration. To begin such an assay, MOLT-4 cells were harvested by centrifugation of cell suspension at 1000 RPM on a GS-6R Beckman centrifuge. The cell pellet was resuspended in chemotaxis buffer (HBSS/ 0.1% BSA) at 5×10$^6$ cells/mL. Twenty-five microliters of cells was mixed with an equal volume of a test compound diluted to 20 μM in the same buffer. Twenty microliters of the mixture was transferred onto the filter in the upper chemotaxis chamber, with 29 μL of 500 nM chemokine protein TECK placed in the lower chamber. Following a 150-minute incubation at 37° C., the assay was terminated by removing the cell drops from atop the filter. To quantify cells migrated across the membrane, 5 μL of 7× CyQUANT® solution was added to each well in the lower chamber, and the fluorescence signal measured on a Spectrafluor Plus fluorescence plate reader (TECAN, Durham, N.C.).

For selection of potential hits, the level of migration activation was calculated as a RAM index—the ratio between the signal of a particular well and the median signal of the whole plate. Compounds with a RAM index of greater than 1.8 were regarded as RAM positive, and were selected for IC$_{50}$ determinations in conventional functional assays.

Calcium Flux Assay

Calcium flux assay measures an increase in intracellular calcium following ligand-induced receptor activation. In the screen of CCR9 antagonists, it was used as a secondary assay carried out on a FLIPR® machine (Molecular Devices, Mountain View, Calif.). To begin an assay, MOLT-4 cells were harvested by centrifugation of cell suspension, and resuspended to 1.5×10$^6$ cells/mL in HBSS (with 1% fetal calf serum). Cells were then labeled with a calcium indicator dye Fluo-4 AM for 45 minutes at 37° C. with gentle shaking. Following incubation, cells were pelleted, washed once with HBSS and resuspended in the same buffer at a density of 1.6×10$^6$ cells/mL. One hundred microliters of labeled cells were mixed with 10 μL of test compound at the appropriate concentrations on an assay plate. Chemokine protein TECK was added at a final concentration of 25 nM to activate the receptor. The degree of inhibition was determined by comparing calcium signals between compound-treated and untreated cells. IC$_{50}$ calculations were further performed by non-linear squares regression analysis using Graphpad Prism (Graphpad Software, San Diego, Calif.).

Discovery of CCR9 Antagonists

The discovery of CCR9 antagonists was carried out in two steps: First, RAM assay was used to screen a compound library in a high-throughput manner. The assay detected compounds by their ability to cause a positive migration signal under RAM condition. Secondly, RAM positive compounds were tested to determine their IC$_{50}$s using the conventional migration and calcium flux assays.

For instance, in a screen of approximately 100,000 compounds, 2000 individual wells representing approximately 2% of total compounds showed a RAM index greater than 1.8. These compounds were cherry-picked and retested in duplicate wells by RAM assay. A total of 270 compounds, or 0.27% of the library, were confirmed RAM positives.

Since a RAM positive signal indicates only the presence of a receptor antagonist and not how strongly it blocks receptor functions, the RAM positive compounds were further tested for potency in calcium flux assay using MOLT-4 cells. IC$_{50}$ determinations on this subset discovered several compounds with IC$_{50}$s less than 1 μM and that did not inhibit other chemokine receptors examined at significant levels.

Additional CCR9 antagonists were discovered by varying and optimizing different structural elements into the compounds discovered in this assay, with regards to key pharmacokinetic, pharmacodynamic and toxicokinetic parameters, both in vitro and in vivo.

In the table below, structures and activity are provided for representative compounds described herein, demonstrating that compounds provided herein can significantly and specifically inhibit signaling from CCR9. Activity is provided as follows for either or both of the chemotaxis assay and/or calcium mobilization assays, described above.

TABLE 1

Compounds with activity in either or both of the chemotaxis assay and calcium mobilization assays, with IC$_{50}$ < 500 nM.

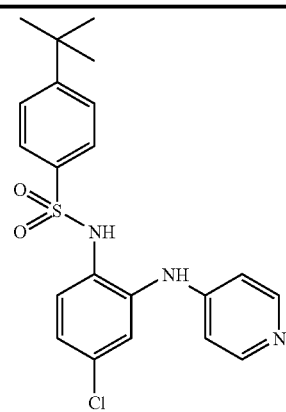

TABLE 1-continued
Compounds with activity in either
or both of the chemotaxis assay and calcium
mobilization assays, with IC$_{50}$ < 500 nM.
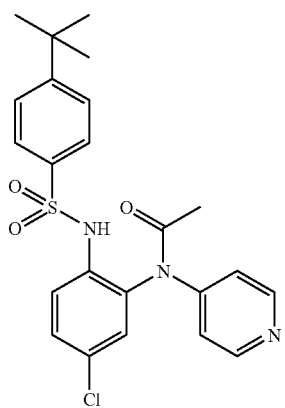
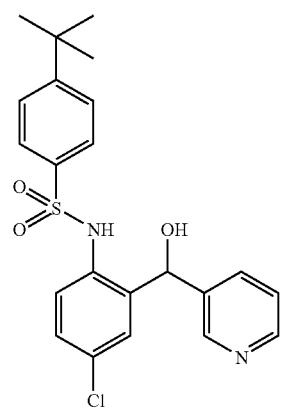
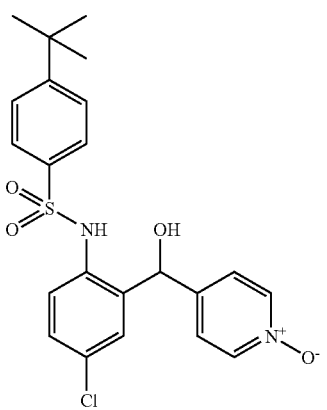
TABLE 1-continued
Compounds with activity in either
or both of the chemotaxis assay and calcium
mobilization assays, with IC$_{50}$ < 500 nM.
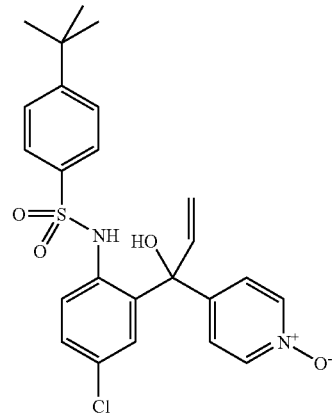
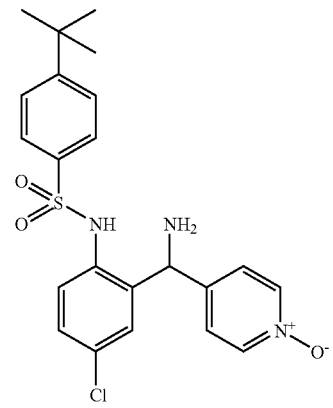
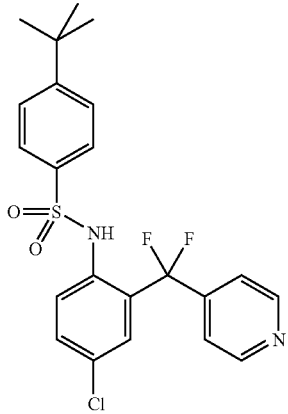

TABLE 1-continued
Compounds with activity in either or both of the chemotaxis assay and calcium mobilization assays, with IC$_{50}$ < 500 nM.
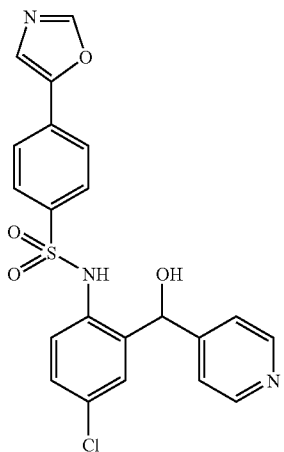
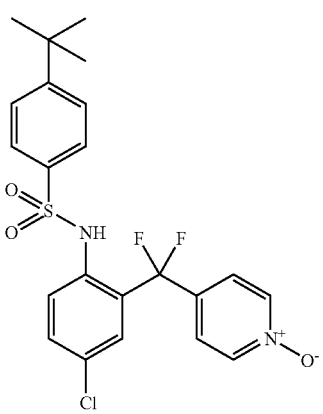
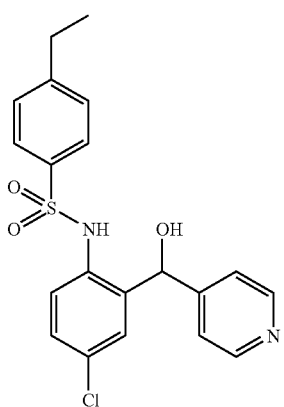
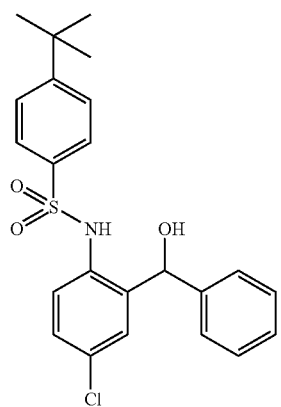
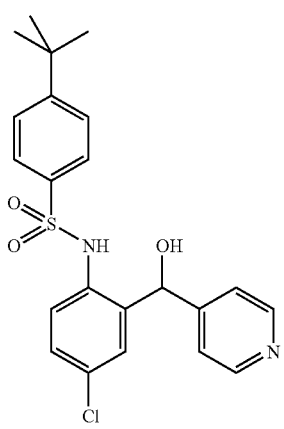
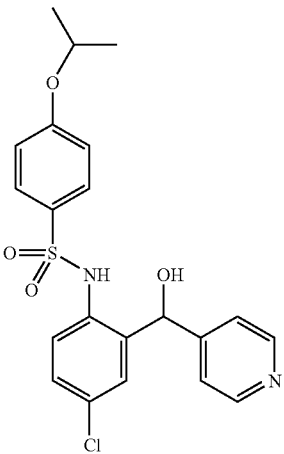

TABLE 1-continued
Compounds with activity in either or both of the chemotaxis assay and calcium mobilization assays, with IC$_{50}$ < 500 nM.
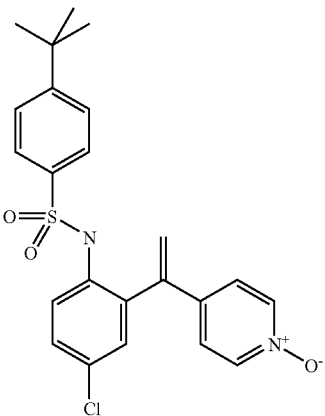
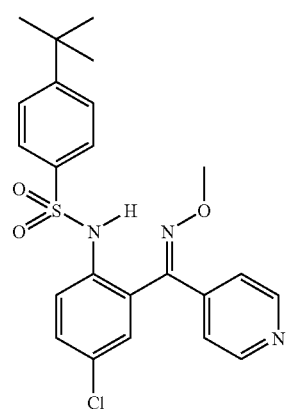
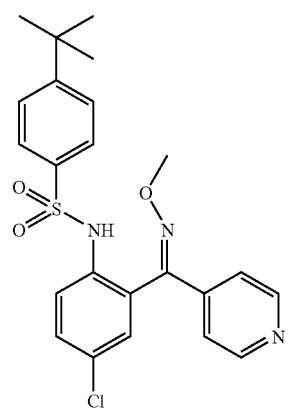
TABLE 2
Compounds with activity in either or both of the chemotaxis assay and calcium mobilization assays, with IC$_{50}$ < 2000 nM.
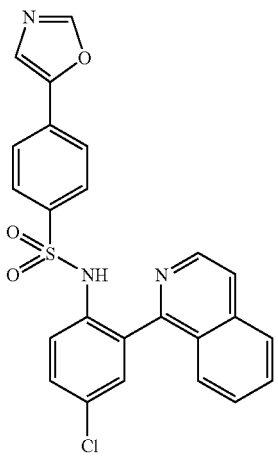
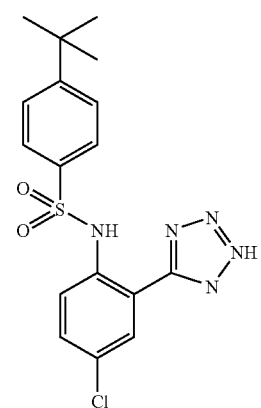
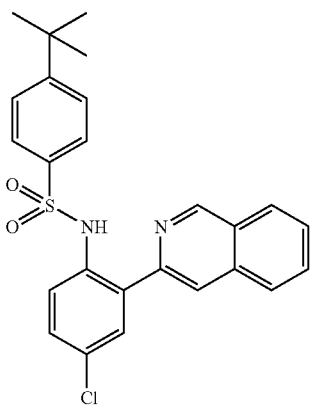

TABLE 2-continued

Compounds with activity in either or both of the chemotaxis assay and calcium mobilization assays, with IC$_{50}$ < 2000 nM.

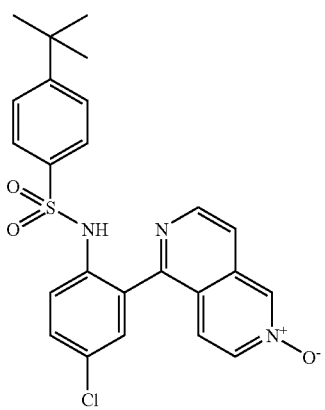

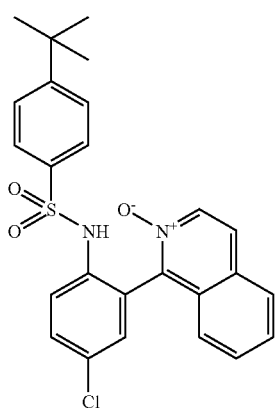

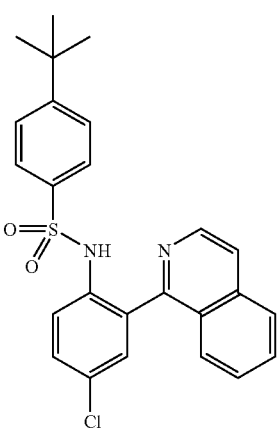

TABLE 2-continued

Compounds with activity in either or both of the chemotaxis assay and calcium mobilization assays, with IC$_{50}$ < 2000 nM.

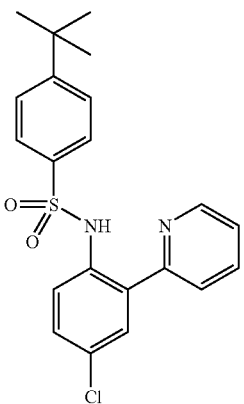

TABLE 3

Compounds with activity in either or both of the chemotaxis assay and calcium mobilization assays, with 500 nM < IC$_{50}$ < 5000 nM.

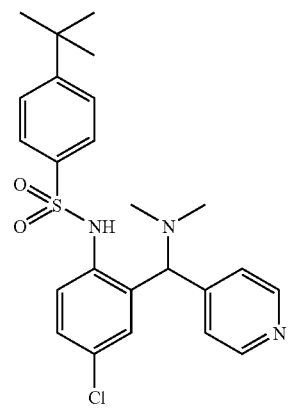

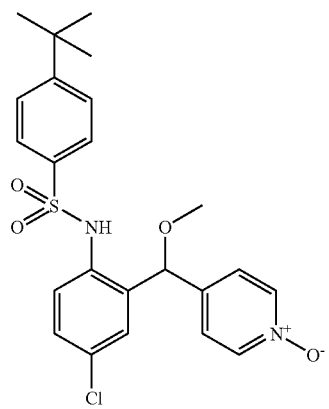

TABLE 3-continued
Compounds with activity in either or both of the chemotaxis assay and calcium mobilization assays, with 500 nM < IC$_{50}$ < 5000 nM.
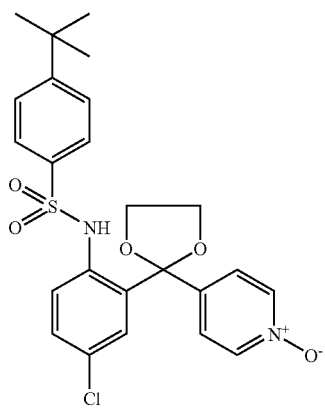
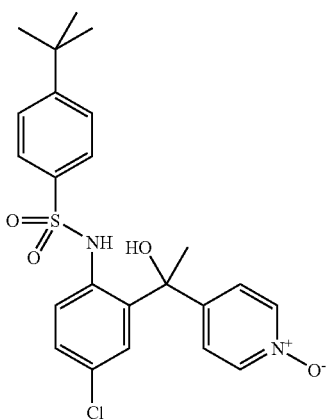
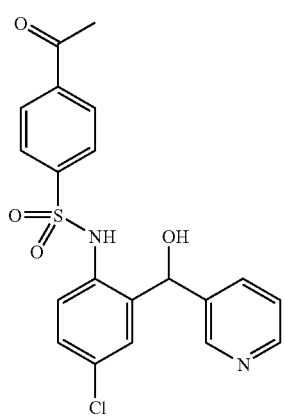
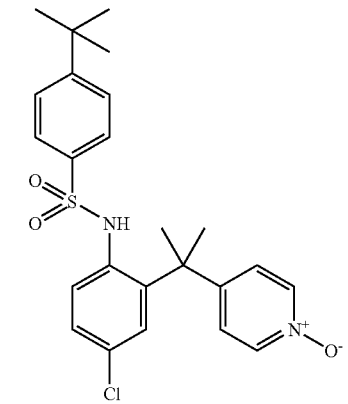
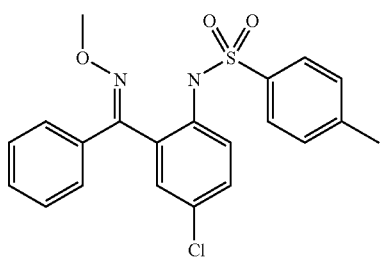
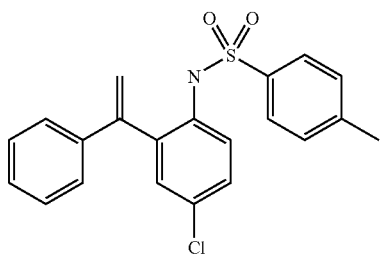
TABLE 4
Compounds with activity in either or both of the chemotaxis assay and calcium mobilization assays, with 2000 nM < IC$_{50}$ < 10000 nM (++)
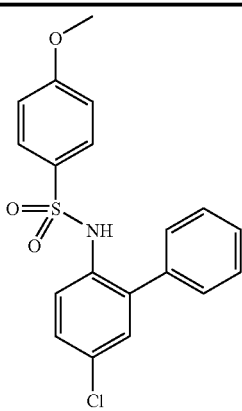

TABLE 4-continued

Compounds with activity in either
or both of the chemotaxis assay and calcium
mobilization assays, with 2000 nM < IC$_{50}$ < 10000 nM (++)

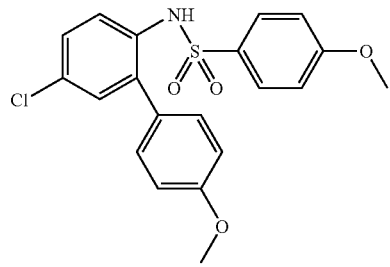

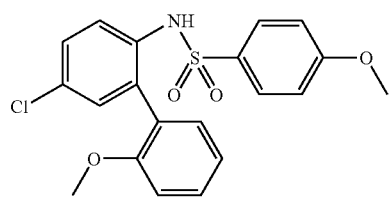

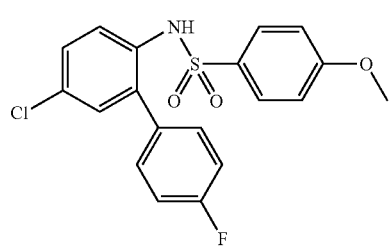

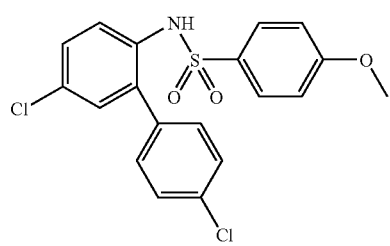

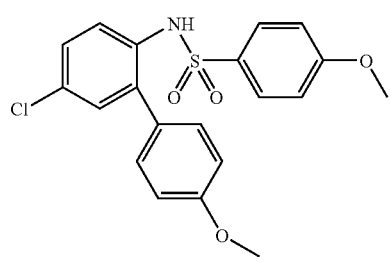

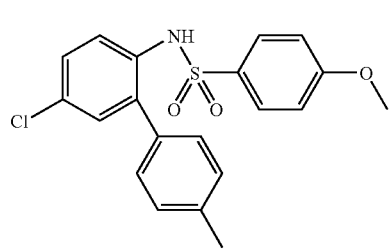

TABLE 4-continued

Compounds with activity in either
or both of the chemotaxis assay and calcium
mobilization assays, with 2000 nM < IC$_{50}$ < 10000 nM (++)

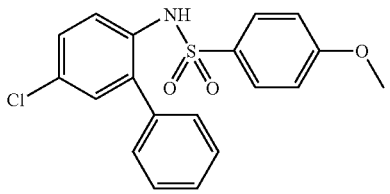

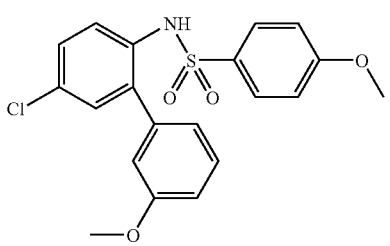

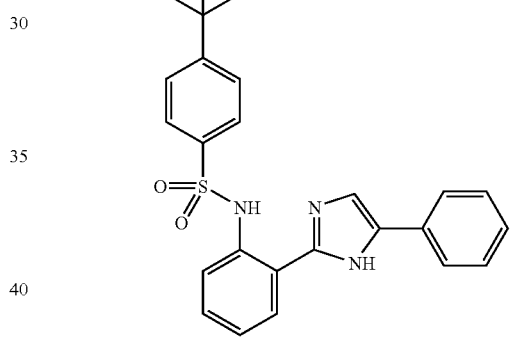

In Vivo Efficacy Studies

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However, the ages at which disease emerges and the ultimate penetrance level often vary considerably among different animal facilities. The compounds of the present invention will be tested using this model or in the TNF ARE(−/−) model described above.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of the formula (III), or a salt thereof:

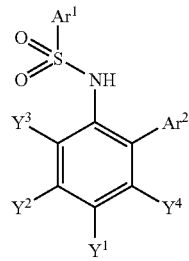

(III)

where
Ar$^1$ is a substituted or unsubstituted C$_{6-10}$ aryl or substituted or unsubstituted 5- to 10-membered heteroaryl; each having 0 to 5 substituents selected from the group consisting of halogen, substituted or unsubstituted C$_{1-8}$ alkyl, substituted or unsubstituted C$_{2-8}$ alkenyl, substituted or unsubstituted C$_{2-8}$ alkynyl, —CN, —C(O)R$^3$, —CO$_2$R$^3$, —C(O)NR$^3$R$^4$, —OR$^3$, —OC(O)R$^3$, —OC(O)NR$^3$R$^4$, —NO$_2$, —NR$^5$C(O)R$^3$, —NR$^5$C(O)NR$^3$R$^4$, —NR$^3$R$^4$, —NR$^5$CO$_2$R$^3$, —NR$^5$S(O)$_2$R$^3$, —SR$^3$, —S(O)R$^3$, —S(O)$_2$R$^3$, —S(O)$_2$NR$^3$R$^4$, substituted or unsubstituted C$_{6-10}$ aryl, substituted or unsubstituted 5- to 10-membered heteroaryl, and substituted or unsubstituted 3- to 10-membered heterocyclyl;

suitable substituted C$_{1-8}$ alkyl, substituted C$_{2-8}$ alkenyl, or substituted C$_{2-8}$ alkynyl may have from 1-5 substituents independently selected from the group consisting of halogen, —OH, —CN, —NO$_2$, ═O, —OC(O)R$^3$, —OR$^3$, —C(O)R$^3$, —C(O)NR$^3$R$^4$, —OC(O)NR$^3$R$^4$, —NR$^4$C(O)R$^3$, —NR$^3$C(O)NR$^4$R$^5$, —CO$_2$R$^3$, —NR$^3$R$^4$, —NR$^4$CO$_2$R$^3$, —SR$^3$, —S(O)R$^3$, —S(O)$_2$R$^3$, —S(O)$_2$NR$^3$R$^4$, —NR$^3$S(O)$_2$R$^4$, unsubstituted or substituted aryl, unsubstituted or substituted heteroaryl, and unsubstituted or substituted heterocyclyl;

suitable substituted C$_{6-10}$ aryl, substituted 5- to 10-membered heteroaryl, or substituted 3- to 10-membered heterocyclyl, may have from 1-4 substituents independently selected from the group consisting of halogen, unsubstituted C$_{1-8}$ alkyl, unsubstituted C$_{1-8}$ haloalkyl, —CN, —NO$_2$, —OR$^3$, ═O, —OC(O)R$^3$, —CO$_2$R$^3$, —C(O)R$^3$, —C(O)NR$^3$R$^4$, —OC(O)NR$^3$R$^4$, —NR$^4$C(O)R$^3$, —NR$^3$C(O)NR$^4$R$^5$, —NR$^3$R$^4$, —NR$^4$CO$_2$R$^3$, —SR$^3$, —S(O)R$^3$, —S(O)$_2$R$^3$, —S(O)$_2$NR$^3$R$^4$, and —NR$^3$S(O)$_2$R$^4$;

where R$^3$, R$^4$, and R$^5$ are each independently selected from the group consisting of hydrogen, C$_{1-8}$ alkyl, C$_{2-8}$ alkenyl, C$_{2-8}$ alkynyl, C$_{6-10}$ aryl, 5- to 10-membered heteroaryl, and 3- to 10-membered heterocycle, or where R$^3$ and R$^4$, together with the atom(s) to which they are attached, form an substituted or unsubstituted 5-, 6-, or 7-membered ring;

where the aliphatic and aromatic portions of R$^3$, R$^4$ and R$^5$ can be substituted with from 1 to 3 substituents selected from the group consisting of halogen, —OH, —OR$^m$, —OC(O)NHR$^m$, —OC(O)NR$^m$R$^n$, —SH, —SR$^m$, —S(O)R$^m$, —S(O)$_2$R$^m$, —S(O)$_2$NH$_2$, —S(O)$_2$NHR$^m$, —S(O)$_2$NR$^m$R$^n$, —NHS(O)$_2$R$^m$, —NR$^m$S(O)$_2$R$^n$, —C(O)NH$_2$, —C(O)NHR$^m$, —C(O)N(R$^m$)$_2$, —C(O)R$^m$, —NHC(O)R$^m$, —NR$^m$C(O)R$^n$, —NHC(O)NH$_2$, —NR$^m$C(O)NH$_2$, —NR$^m$C(O)NHR$^n$, —NHC(O)NHR$^m$, —NR$^o$C(O)NR$^m$R$^n$, —NHC(O)N(R$^m$)$_2$, —CO$_2$H, —CO$_2$R$^m$, —NHCO$_2$R$^m$, —NR$^m$CO$_2$R$^n$, —CN, —NO$_2$, —NH$_2$, —NHR$^n$, —NR$^m$R$^n$, —NR$^m$S(O)NH$_2$ and —NR$^m$S(O)$_2$NHR$^n$, where R$^m$,R$^n$, and R$^o$ are each independently unsubstituted C$_{1-6}$ alkyl;

Y$^1$,Y$^2$,Y$^3$, and Y$^4$ are each independently selected from the group consisting of hydrogen, halogen, substituted or unsubstituted C$_{1-4}$ alkyl, —CN, —C(O)R$^6$, —CO$_2$R$^6$, —OR$^6$, —NO$_2$, —SR$^6$, —S(O)R$^6$, and —S(O)$_2$R$^6$;

where substituted C$_{1-4}$ alkyl can have from 1 to 3 substituents independently selected from the group consisting of halogen, —OH, —OR$^6$, —CN, —NO$_2$, ═O, —OC(O)R$^6$, —CO$_2$R$^6$, —C(O)R$^6$, —C(O)NR$^6$R$^{13}$, —OC(O)NR$^6$R$^{13}$, —NR$^{13}$C(O)R$^6$, —NR$^6$C(O)NR$^{13}$R$^{14}$, —NR$^6$R$^{13}$, —NR$^{13}$CO$_2$R$^6$, —SR$^6$, —S(O)R$^6$, —S(O)$_2$R$^6$, —S(O)$_2$NR$^6$R$^{13}$, and —NR$^{13}$S(O)$_2$R$^6$;

where R$^6$, R$^{13}$, and R$^{14}$ are independently selected from the group consisting of hydrogen, C$_{1-8}$ alkyl, C$_{2-8}$ alkenyl, C$_{2-8}$ alkynyl, C$_{6-10}$ aryl, and 5- to 10-membered heteroaryl; and where the aliphatic and aromatic portions of R$^6$, R$^{13}$, and R$^{14}$ can be substituted with from 1 to 3 substituents selected from the group consisting of halogen, —OH, —OR$^m$, —OC(O)NHR$^m$, —OC(O)NR$^m$R$^n$, —SH, —SR$^m$, —S(O)R$^m$, —S(O)$_2$R$^m$, —S(O)$_2$NH$_2$, —S(O)$_2$NHR$^m$, —S(O)$_2$NR$^m$R$^n$, —NHS(O)$_2$R$^m$, —NR$^m$S(O)$_2$R$^n$, —C(O)NH$_2$, —C(O)NHR$^m$, —C(O)N(R$^m$)$_2$, —C(O)R$^m$, —NHC(O)R$^m$, —NR$^m$C(O)R$^n$, —NHC(O)NH$_2$, —NR$^m$C(O)NH$_2$, —NR$^m$C(O)NHR$^n$, —NHC(O)NHR$^m$, —NR$^o$C(O)NR$^m$R$^n$, —NHC(O)N(R$^m$)$_2$, —CO$_2$H, —CO$_2$R$^m$, —NHCO$_2$R$^m$, —NR$^m$CO$_2$R$^n$, —CN, —NO$_2$, —NH$_2$, —NHR$^n$, —NR$^m$R$^n$, —NR$^m$S(O)NH$_2$ and —NR$^m$S(O)$_2$NHR$^n$, where R$^m$, R$^n$, and R$^o$ are each independently unsubstituted C$_{1-6}$ alkyl;

Ar$^2$ is a substituted or unsubstituted isoquinolinyl, quinolizinyl, pyrrolizinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, pyrazolopyridinyl, imidazopyridinyl, pyridinopyridinyl, pyridinopyrimidinyl, pyridinopyridizinyl, pyridinopyrazinyl, triazolopyridinyl, pyrrolopyrazinyl, imidazotriazinyl, imidazopyrimidinyl, naphthyridinyl, benzothiazolyl, benzofuranyl, benzothienyl, indolyl, azaindolyl, benzopyrrolyl, quinolyl, isoquinolyl, indazolyl, pteridinyl, or benzisothiazolyl having 0 to 4 substituents selected from the group consisting of halogen, substituted or unsubstituted C$_{1-8}$ alkyl, substituted or unsubstituted C$_{2-8}$ alkenyl, substituted or unsubstituted C$_{2-8}$ alkynyl, —CN, ═O, —NO$_2$, —OR$^7$, —OC(O)R$^7$, —CO$_2$R$^7$, —C(O)R$^7$, —C(O)NR$^8$R$^9$, —OC(O)NR$^8$R$^9$, —NR$^7$C(O)R$^8$, —NR$^7$C(O)NR$^8$R$^9$, —NR$^8$R$^9$, —NR$^7$CO$_2$R$^8$, —SR$^7$, —S(O)R$^7$, —S(O)$_2$R$^7$, —S(O)$_2$NR$^8$R$^9$, —NR$^7$S(O)$_2$R$^8$, substituted or unsubstituted C$_{6-10}$ aryl, substituted or unsubstituted 5- to 10-membered heteroaryl and substituted or unsubstituted 3- to 10-membered heterocyclyl;

suitable substituted C$_{1-8}$ alkyl, C$_{2-8}$ alkenyl, C$_{2-8}$ alkynyl may have from 1 to 5 substituents independently selected from the group consisting of halogen, —OH, —OR$^7$, —CN, —NO$_2$, ═O, —OC(O)R$^7$, —CO$_2$R$^7$, —C(O)R$^7$, —C(O)NR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —S(O)R$^7$, —S(O)$_2$R$^7$, —S(O)$_2$NR$^7$R$^8$, —NR$^7$S(O)$_2$R$^8$, unsubstituted or substituted phenyl, unsubstituted or substituted C$_{5-6}$ heteroaryl, or unsubstituted or substituted C$_{3-6}$ heterocyclyl;

suitable substituted aryl, heteroaryl and heterocyclyl substituents may have from 1 to 5 substituents independently selected from the group consisting of halogen, —$OR^7$, —CN, —$NO_2$, =O, —OC(O)$R^7$, —$CO_2R^7$, —C(O)$R^7$, —C(O)$NR^7R^8$, —OC(O)$NR^7R^8$, —$NR^7$C(O)$R^8$, —$NR^7$C(O)$NR^8R^9$, —$NR^7R^8$, —$NR^7CO_2R^8$, —$SR^7$, —S(O)$R^7$, —$S(O)_2R^7$, —$S(O)_2NR^7R^8$, —$NR^7S(O)_2R^8$, unsubstituted $C_{3-6}$ heterocyclyl, unsubstituted $C_{1-8}$ alkyl, and unsubstituted $C_{1-8}$ haloalkyl;

where $R^7$, $R^8$ and $R^9$ are each independently selected from the group consisting of hydrogen, $C_{1-8}$ alkyl, $C_{2-8}$ alkenyl, $C_{2-8}$ alkynyl, $C_{6-10}$ aryl, 5 to 10 membered heteroaryl and 3- to 10-membered heterocycle, or $R^7$, $R^8$ and $R^9$, may together with the atom(s) to which they are attached, form a substituted or unsubstituted 5-, 6-, or 7-membered ring, and where the aliphatic and aromatic portions of $R^7$, $R^8$ and $R^9$ can be substituted with 1 to 3 substituents selected from the group consisting of halogen, —OH, —$OR'''$, —OC(O)$NHR'''$, —OC(O)$NR'''R''$, —SH, —$SR'''$, —S(O)$R'''$, —$S(O)_2R'''$, —$S(O)_2NH_2$, —$S(O)_2NHR'''$, —$S(O)_2NR'''R''$, —$NHS(O)_2R'''$, —$NR'''S(O)_2R''$, —C(O)$NH_2$, —C(O)$NHR'''$, —C(O)N($R'''$)$_2$, —C(O)$R'''$, —NHC(O)$R'''$, —$NR'''$C(O)$R''$, —NHC(O)$NH_2$, —$NR'''$C(O)$NH_2$, —$NR'''$C(O)$NHR''$, —NHC(O)$NHR'''$, —$NR'''$C(O)$NHR''$, —$NR°$C(O)$NR'''R''$, —NHC(O)N($R'''$)$_2$, —$CO_2H$, —$CO_2R'''$, —$NHCO_2R'''$, —$NR'''CO_2R''$, —CN, —$NO_2$, —$NH_2$, —$NHR''$, —$NR'''R''$, —$NR'''S(O)NH_2$ and —$NR'''S(O)_2NHR''$, where $R'''$, $R''$, and $R°$ are each independently unsubstituted $C_{1-6}$ alkyl.

2. A composition comprising a pharmaceutically acceptable carrier and a compound of claim 1.

3. The compound of claim 1, wherein $Ar^1$ is substituted or unsubstituted phenyl.

4. The compound of claim 1, wherein $Ar^2$ has 0 to 4 substituents independently selected from the group consisting of halogen, unsubstituted or substituted $C_{1-6}$ alkyl, unsubstituted or substituted $C_{2-6}$ alkenyl, unsubstituted or substituted $C_{2-6}$ alkynyl, =O, —CN, —$NO_2$, —$OR^7$, —C(O)$R^7$, —C(O)$NR^8R^9$, —$NR^7$C(O)$R^8$, —$NR^8R^9$, —S(O)$R^7$, —$S(O)_2R^7$, —$S(O)_2NR^8R^9$, —$NR^7S(O)_2R^8$, —OC(O)$R^7$, —$CO_2R^7$, —OC(O)$NR^8R^9$, —$NR^7$C(O)$NR^8R^9$, —$NR^7CO_2R^8$, unsubstituted or substituted 5- or 6-membered heteroaryl and a unsubstituted or substituted 3- to 7-membered heterocyclyl.

* * * * *

UNITED STATES PATENT AND TRADEMARK OFFICE
CERTIFICATE OF CORRECTION

PATENT NO. : 7,932,252 B2  Page 1 of 1
APPLICATION NO. : 11/596147
DATED : April 26, 2011
INVENTOR(S) : Solomon Ungashe et al.

It is certified that error appears in the above-identified patent and that said Letters Patent is hereby corrected as shown below:

On the Title Page

In item (75), after "Jessen Wright," replace "Sandringham" with --Victoria--.

In the Claims

In column 205, claim 1, line 56, after "attached, form" replace "an" with --a--.

In column 206, claim 1, line 17, after "$C_{2-8}$ alkynyl," replace "$C_{6-10\ aryl,\ and}$" with --$C_{6-10}$ aryl, and--.

In column 207, claim 1, line 13, after "$C_{2-8}$ alkynyl," replace "$C_{6-10\ aryl,}$" with --$C_{6-10}$ aryl,--.

In column 208, claim 4, line 18, before "$S(O)R^7$," insert -- -$SR^7$,--.

Signed and Sealed this
Twenty-eighth Day of August, 2012

David J. Kappos
*Director of the United States Patent and Trademark Office*